US011091794B2

(12) United States Patent
Lo et al.

(10) Patent No.: US 11,091,794 B2
(45) Date of Patent: Aug. 17, 2021

(54) DETERMINATION OF BASE MODIFICATIONS OF NUCLEIC ACIDS

(71) Applicant: The Chinese University of Hong Kong, New Territories (HK)

(72) Inventors: Yuk-Ming Dennis Lo, Hong Kong (CN); Rossa Wai Kwun Chiu, Hong Kong (CN); Kwan Chee Chan, Hong Kong (CN); Peiyong Jiang, Hong Kong (CN); Suk Hang Cheng, Hong Kong (CN); Wenlei Peng, Hong Kong (CN); On Yee Tse, Hong Kong (CN)

(73) Assignee: The Chinese University of Hong Kong, New Territories (HK)

( * ) Notice: Subject to any disclaimer, the term of this patent is extended or adjusted under 35 U.S.C. 154(b) by 0 days.

(21) Appl. No.: 16/995,607

(22) Filed: Aug. 17, 2020

(65) Prior Publication Data

US 2021/0047679 A1 Feb. 18, 2021

Related U.S. Application Data

(60) Provisional application No. 63/051,210, filed on Jul. 13, 2020, provisional application No. 63/019,790, filed on May 4, 2020, provisional application No. 62/991,891, filed on Mar. 19, 2020, provisional application No. 62/970,586, filed on Feb. 5, 2020, provisional application No. 62/887,987, filed on Aug. 16, 2019.

(51) Int. Cl.
| | |
|---|---|
| *C12Q 1/6816* | (2018.01) |
| *G16B 30/00* | (2019.01) |
| *G16B 20/00* | (2019.01) |
| *C12N 9/22* | (2006.01) |
| *C12Q 1/6851* | (2018.01) |

(52) U.S. Cl.
CPC ............. *C12Q 1/6816* (2013.01); *C12N 9/22* (2013.01); *C12Q 1/6851* (2013.01); *G16B 20/00* (2019.02); *G16B 30/00* (2019.02)

(58) Field of Classification Search
CPC combination set(s) only.
See application file for complete search history.

(56) References Cited

U.S. PATENT DOCUMENTS

| | | | |
|---|---|---|---|
| 8,467,976 B2 | 6/2013 | Lo et al. | |
| 9,116,118 B2 | 8/2015 | Turner et al. | |
| 9,175,338 B2 * | 11/2015 | Flusberg | C12Q 1/6869 |
| 9,175,341 B2 | 11/2015 | Flusberg et al. | |
| 10,438,691 B2 | 10/2019 | Kim et al. | |
| 10,465,232 B1 | 11/2019 | Wu et al. | |
| 10,468,121 B2 | 11/2019 | Kermani et al. | |
| 10,590,484 B2 | 3/2020 | Korlach et al. | |
| 2011/0183320 A1 | 7/2011 | Flusberg et al. | |
| 2013/0230909 A1 | 9/2013 | Pan et al. | |
| 2014/0004511 A1 | 1/2014 | Korlach et al. | |
| 2016/0017419 A1 | 1/2016 | Chiu et al. | |
| 2017/0037464 A1 | 2/2017 | Turner et al. | |
| 2017/0159132 A1 | 6/2017 | Okino et al. | |
| 2017/0233802 A1 | 8/2017 | Flusberg et al. | |
| 2018/0201993 A1 | 7/2018 | Turner et al. | |
| 2019/0024162 A1 | 1/2019 | Korlach et al. | |

FOREIGN PATENT DOCUMENTS

| | | |
|---|---|---|
| AU | 2012380221 B2 | 9/2016 |
| CN | 104053789 A | 9/2014 |
| CN | 104053789 B | 2/2016 |
| KR | 101896167 B1 | 9/2018 |
| WO | 2009013492 A1 | 1/2009 |
| WO | 2010027484 A2 | 3/2010 |
| WO | 2010068289 A2 | 6/2010 |
| WO | 2013170429 A1 | 11/2013 |
| WO | 2013188846 A1 | 12/2013 |
| WO | 2014153757 A1 | 10/2014 |
| WO | 2017012544 A1 | 1/2017 |

OTHER PUBLICATIONS

Flusberg etal (Nature Methods, 2010, 7:461-465).*
Sugai et al (Clinical Epigtenetics, 2017, 9:55, internet pp. 1-10).*
Kile etal (PLoS ONE, 2010, 5:e13730, internet pp. 1-9).*
Flusberg etal (Nature Methods, 2010, 7:461-465) Supplemental Data.*
Flusberg, Benjamin A. et al.; "Direct detection of DNA methylation during single-molecule, real-time sequencing"; Nature Methods; Jun. 2010; vol. 7, No. 6; pp. 461-465 (7 pages).
Liu, Qian et al.; "Detection of DNA base modifications by deep recurrent neural network on Oxford Nanopore sequencing data"; Nature Communications; 2019; 10(1):2449; doi: 10.1038/s41467-019-10168-2; 11 pages.
Ni, Peng et al.; "DeepSignal: detecting DNA methylation state from Nanopore sequencing reads using deep-learning"; Bioinformatics; 2019; vol. 35, No. 22; doi: 10.1093/bioinformatics/btz276; 10 pages.
Suzuki, Yuta et al.; "Agin: measuring the landscape of CpG methylation of individual repetitive elements"; Bioinformatics; 2016; vol. 32, No. 19; pp. 2911-2919.

(Continued)

*Primary Examiner* — Laura B Goddard
(74) *Attorney, Agent, or Firm* — Kilpatrick Townsend & Stockton LLP

(57) ABSTRACT

Systems and methods for using determination of base modification in analyzing nucleic acid molecules and acquiring data for analysis of nucleic acid molecules are described herein. Base modifications may include methylations. Methods to determine base modifications may include using features derived from sequencing. These features may include the pulse width of an optical signal from sequencing bases, the interpulse duration of bases, and the identity of the bases. Machine learning models can be trained to detect the base modifications using these features. The relative modification or methylation levels between haplotypes may indicate a disorder. Modification or methylation statuses may also be used to detect chimeric molecules.

19 Claims, 145 Drawing Sheets
(85 of 145 Drawing Sheet(s) Filed in Color)
Specification includes a Sequence Listing.

(56) References Cited

OTHER PUBLICATIONS

Blow, Matthew J. et al.; "The Epigenomic Landscape of Prokaryotes"; PLOS Genetics; Feb. 12, 2016; 12(2): e1005854; doi:10.1371/journal.pgen.1005854; 28 pages.

Clark, Tyson A. et al.; "Enhanced 5-methylcytosine detection in single-molecule, real-time sequencing via Tet1 oxidation"; BMC Biology; 2013; vol. 11, No. 4; http://www.biomedcentral.com/1741-7007/11/4; 10 pages.

Clark, Tyson A et al.; "Characterization of DNA methyltransferase specificities using single-molecule, real-time DNA sequencing"; Nucleic Acids Research; 2012; vol. 40, No. 4; e29; https://doi.org/10.1093/nar/gkr1146; 12 pages.

Eid, John et al.; "Real-Time DNA Sequencing from Single Polymerase Molecules"; Science; Jan. 2, 2009; vol. 323, Issue 5910; DOI: 10.1126/science.1162986; p. 133-138 (7 pages).

Feng, Zhixing et al.; "Detecting DNA Modifications from SMRT Sequencing Data by Modeling Sequence Context Dependence of Polymerase Kinetic"; PLOS Computational Biology; Mar. 2013; vol. 9, Issue 3; e1002935; https://doi.org/10.1371/journal.pcbi.1002935; 10 pages.

Liu, Yibin et al.; "Bisulfite-free direct detection of 5-methylcytosine and 5-hydroxymethylcytosine at base resolution"; Nature Biotechnology Letters; Apr. 2019; vol. 37; pp. 424-429 (11 pages).

Schadt, Eric E. et al.; "Modeling kinetic rate variation in third generation DNA sequencing data to detect putative modifications to DNA bases"; Genome Research; 2013; vol. 23, No. 1; doi: 10.1101/gr.136739.111; pp. 129-141.

Feng, Zhixing et al.; "qDNAmod: a statistical model-based tool to reveal intercellular heterogeneity of DNA modification from SMRT sequencing data"; Nucleic Acids Research; 2014; vol. 42, No. 22; doi: 10.1093/nar/gku1097; pp. 13488-13499.

Suzuki, Yuta; "Observing comprehensive DNA methylomes via single molecule real-time sequencing: application to diploid and centromeric methylation"; dissertation submitted to the Graduate School of Frontier Sciences, The University of Tokyo, on Dec. 13, 2017; 118 pages.

International Search Report and Written Opinion dated Nov. 19, 2020 in International Patent Application No. PCT/CN2020/109602. 11 pages.

Combined Search and Examination Report under Sections 17 & 18(3) dated Mar. 29, 2021 in GB Patent Application No. 2103003.6. 5 pages.

Examination Report under Section 18(3) dated Apr. 12, 2021 in GB Patent Application No. 2102808.9. 6 pages.

Combined Search and Examination Report under Sections 17 & 18(3) dated Apr. 15, 2021 in GB Patent Application No. 2103010.1. 4 pages.

He, Jing et al.; "Tet1 promotes leukemic growth of AML1-ETO+ AML via 5-hydroxymethylcytosine marks and its oncogenic role and high expression can be antagonized using Olaparib, an inhibitor of its binding partner PARP1 " Experimental Hematology; 2017; vol. 53, Supplement; pp. S92-S93.

* cited by examiner (I)

5'— mA — T — mA — C — G — T — mA — C — G — T —3'

3'— T — mA — T — G — C — mA — T — G — C — mA —5'

(II)

5'— uA — C — G — T — mA — C — G — T —3'

3'— T — G — C — mA — T — G — C — mA —5'

(III)

5'— uA — C — G — T — uA — C — G — T —3'

3'— T — G — C — mA — T — G — C — mA —5'

(IV)

5'— uA — C — G — T — uA — C — G — T —3'

3'— T — G — C — uA — T — G — C — uA —5'

Whole-genome amplified DNA products

| Categories | Training dataset | Testing dataset |
|---|---|---|
| Fully-unmethylated | 283 (7.0%) | 276 (7.0%) |
| Hemi-methylated | 401 (10.0%) | 389 (9.8%) |
| Fully-methylated | 3194 (79.4%) | 3142 (79.4%) |
| Interlacing methylation patterns | 145 (3.6%) | 148 (3.7%) |

FIG. 45

| Chromosomes | Start | End | Imprinted gene names | Length of CpG islands | Molecules sequenced by PacBio SMRT sequencing and methylation states determined according to embodiments present in this disclosure | Methylation call for a molecule |
|---|---|---|---|---|---|---|
| chr11 | 2013333 | 2013617 | H19 | 284 | -U----------M------------M-M----------U---U-------M------M-<br>-U-----------------M--------------U----------M-<br>M-------M-M-------U---------[T]------M-<br>--M--- | Methylated |
| chr11 | 2019565 | 2019863 | H19 | 298 | -M-M--------M-----------M-----------[C]-M-M------M-<br>M----M-M-M---------M------M-M------M-<br>| Methylated |
| chr11 | 32460586 | 32461004 | WT1-AS/WT1 | 418 | -U-M----U-M---------U-------U--<br>-U-----U-U-U-----U------U-U-U----U-U--<br>-U-U-U-------U-U-U---U---M | Unmethylated |
| chr14 | 101192851 | 101193499 | DLK1 | 648 | -U----U-------U-U---------U----<br>-U-----------U-U-U-U-U-U-U-U--U-U-<br>-U-U-U-------U-U-U-U-U-U-U-U-<br>M-- | Unmethylated |
| chr14 | 101201559 | 101201763 | DLK1 | 204 | -M-M---------U--------M------M---[T]--M-<br>--M--------M------M------M-- | Methylated |
| chr14 | 101292863 | 101293101 | MEG3 | 238 | --------M------U---M-<br>----M-M-----M-- | Methylated |
| chr15 | 25981176 | 25981392 | ATP10A | 216 | --*----M------M---------M-<br>M-M-------M---------[T]----M-M-------U- | Methylated |
| chr2 | 805311367 | 80531719 | LRRTM1 | 352 | --*--[G]--------U------U---M------U-<br>-U------U-------M------M-----U-<br>-U-U------------------U-U-U--- | Unmethylated |
| chr7 | 79082174 | 79082427 | MAGI2 | 253 | -*-U--------[A]-M-U-----U---U---U---U--<br>------U----------*--- | Unmethylated |

FIG. 48

| Groups | Samples | Total subreads | Mapped subreads | Subread mappability (%) | Mean subread depth per SMRT well (x) | No. of SMRT wells | Mappable wells | Mappable well rate (%) |
|---|---|---|---|---|---|---|---|---|
| Maternal buffy coat | M1315Sw | 39,006,460 | 30,673,525 | 78.6 | 13.4 | 3,157,310 | 2,295,002 | 72.7 |
| Placenta | N1315S | 23,013,428 | 16,374,758 | 71.2 | 10.4 | 2,393,400 | 1,573,540 | 65.7 |
| HCC tissues | TBR3032T | 20,164,513 | 15,232,744 | 75.5 | 13.1 | 1,742,890 | 1,147,985 | 64.8 |
|  | TBR3033T | 22,699,890 | 17,479,024 | 77.2 | 8.1 | 2,652,627 | 2,157,196 | 79.2 |
| Adjacent normal tissues | TBR3033N | 73,118,110 | 56,446,202 | 77.2 | 12.6 | 6,881,142 | 4,471,370 | 65.0 |
|  | TBR3032N | 76,652,680 | 60,145,452 | 78.3 | 12.8 | 6,000,227 | 4,702,130 | 78.4 |
| Buffy coat (healthy control subjects) | M1 | 44,777,423 | 28,325,597 | 63.3 | 7.7 | 7,316,000 | 3,859,866 | 50.0 |
|  | F2 | 49,840,758 | 32,984,845 | 66.2 | 8.8 | 7,215,112 | 3,823,329 | 53.0 |
|  | F1 | 40,012,804 | 24,717,288 | 61.8 | 6.5 | 7,301,760 | 3,800,392 | 52.0 |
|  | M2 | 152,530,411 | 88,596,520 | 58.1 | 7.7 | 21,794,600 | 11,563,500 | 53.1 |
| HCC cell line | HepG2 | 47,308,680 | 34,581,721 | 73.1 | 7.3 | 6,220,000 | 4,750,581 | 76.4 |

FIG. 60

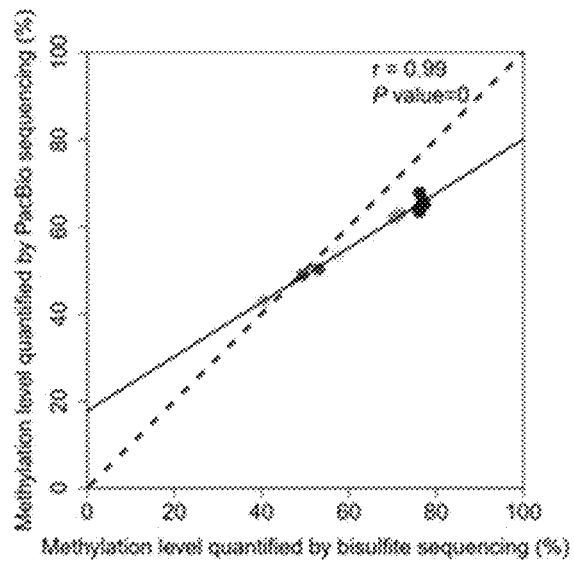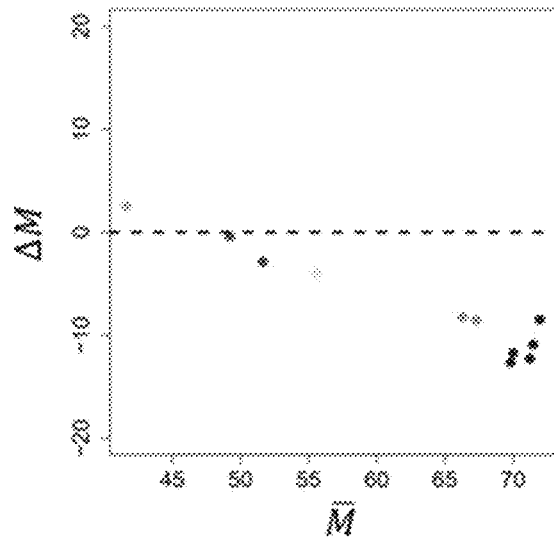
FIG. 63A  FIG. 63B
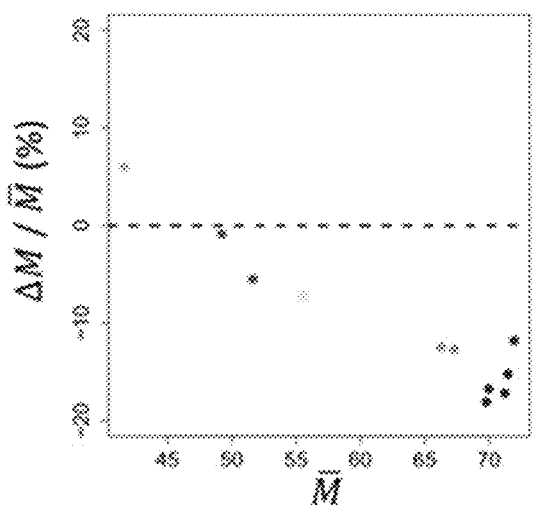
- Placenta
- Adjacent normal tissue
- HCC tumor tissue
- Buffy coat
- HepG2 (HCC cell line)
FIG. 63C

HBV in 4 cirrhotic liver tissues: a median of 25 X depth

HBV in 15 HCC tumor tissues: a median of 14 X depth

|  | Gene | Allele 1 | Allele 2 | Methylation level (%) | |
|---|---|---|---|---|---|
|  |  |  |  | Allele 1 | Allele 2 |
| Imprinted genes | SNURF | T | C | 15.73 | 89.37 |
|  | PLAGL1 | T | C | 7.56 | 89.41 |
|  | NAP1L5 | C | T | 12.5 | 91.07 |
|  | ZIM2 | C | T | 13 | 84.64 |
| Randomly selected regions | Region 01 | G | A | 71.79 | 69.17 |
|  | Region 02 | T | G | 63.22 | 65.22 |
|  | Region 03 | C | T | 73.33 | 74.9 |
|  | Region 04 | C | T | 10.83 | 8.51 |

FIG. 81

| Tissues | Methylation level of Alu (%) |
|---|---|
| Buffy coat | 89.54 |
| Liver | 88.18 |
| Colon | 89.56 |
| Lung | 91.52 |
| Small intestine | 86.56 |
| Adrenal gland | 89.07 |
| Adipose | 91.44 |
| Pancreas | 85.82 |
| Brain | 91.79 |
| HCC | 76.74 |
| Placenta | 73.04 |

FIG. 96

| Subread depth cutoffs ≥ | Pearson's r (SMRT-seq vs BS-seq) | No. of CpG sites |
|---|---|---|
| 1 | 0.797 | 25,606,068 (23,949,832-27,008,582) |
| 10 | 0.873 | 21,668,418 (18,263,886-23,515,147) |
| 20 | 0.933 | 14,276,212 (10,526,406-16,736,887) |
| 30 | 0.952 | 6,736,890 (4,255,452-10,449,814) |
| 40 | 0.948 | 3,420,790 (2,232,511-5,792,825) |
| 50 | 0.941 | 1,684,871 (1,278,475-3,055,876) |
| 60 | 0.929 | 911,961 (707,295-1,581,313) |
| 70 | 0.917 | 532,422 (350,001-866,045) |
| 80 | 0.907 | 284,375 (177,698-534,540) |
| 90 | 0.906 | 150,974 (98,000-333,933) |
| 100 | 0.875 | 89,788 (58,552-182,861) |

```
┌─────────────────────────────────────────────────────────────────┐
│ Receiving a plurality of first data structures, each first data │
│ structure of the first plurality of first data structures       │
│ corresponding to a respective window of nucleotides sequenced   │
│ in a respective nucleic acid molecule of a plurality of first   │── 1022
│ nucleic acid molecules, where each of the first nucleic acid    │
│ molecules is sequenced by measuring pulses in a signal          │
│ corresponding to the nucleotides, where a modification has a    │
│ known first state in the nucleotide at a target position in     │
│ each window of each first nucleic acid molecule, each first     │
│ data structure comprising values for certain properties         │
└─────────────────────────────────────────────────────────────────┘
                                │
                                ▼
┌─────────────────────────────────────────────────────────────────┐
│ Storing a plurality of first training samples, each including   │
│ one of the first plurality of first data structures and a first │── 1024
│ label indicating the first state for the modification of the    │
│ nucleotide at the target position                               │
└─────────────────────────────────────────────────────────────────┘
                                │
                                ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ Receiving a second plurality of second data structures, each   │
│ second data structure of the second plurality of second data    │
│ structures corresponding to a respective window of nucleotides  │
│ sequenced in a respective nucleic acid molecule of a plurality  │── 1026
│ of second nucleic acid molecules, where the modification has a  │
│ known second state in a nucleotide at a target position within  │
│ each window of each second nucleic acid molecule, each second   │
│ data structure comprising values for the same properties as the │
│ first plurality of first data structures                        │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                │
                                ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ Storing a plurality of second training samples, each including  │── 1028
│ one of the second plurality of second data structures and a    │
│ second label indicating the second state for the modification   │
│ of the nucleotide at the target position                        │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                │
                                ▼
┌─────────────────────────────────────────────────────────────────┐
│ Training a model using the plurality of first training samples  │
│ and optionally the plurality of second training samples, where  │── 1029
│ an output of the model specifies whether the nucleotide at the  │
│ target position in the respective window has the modification   │
└─────────────────────────────────────────────────────────────────┘
```

FIG. 102

1030

Receiving an input data structure, the input data structure corresponding to a window of nucleotides sequenced in a sample nucleic acid molecule, wherein the sample nucleic acid molecule is sequenced by measuring pulses in an optical signal corresponding to the nucleotide, the input data structure comprising values for the following properties:
for each nucleotide within the window:
an identity of the nucleotide,
a position of the nucleotide with respect to a target position within the respective window,
a width of the pulse corresponding to the nucleotide, and
an interpulse duration representing a time between the pulse corresponding to the nucleotide and a pulse corresponding to a neighboring nucleotide

— 1032

Inputting the input data structure into a model — 1034

Determining, using the model, whether the modification is present in a nucleotide at the target position within the window in the input data structure — 1036

FIG. 103

Relative haplotype-based methylation imbalance index e.g. Methylation level of Hap I − Methylation level of Hap II

| Chr | start | end | Length | Haplotype block id | PacBio sequencing | | | |
|---|---|---|---|---|---|---|---|---|
| | | | | | Methylation level in adjacent non-tumoral tissue | | Methylation level in tumor tissue | |
| | | | | | Hap I | Hap II | Hap I | Hap II |
| chr1 | 56312395 | 56347696 | 35301 | hap1927 | 68.2 | 67.4 | 60.3 | 23.5 |
| chr1 | 194413819 | 194424806 | 10987 | hap5953 | 52.8 | 49.5 | 48.8 | 9.3 |
| chr1 | 220674478 | 220699011 | 24533 | hap6863 | 63.0 | 64.5 | 50.4 | 17.3 |
| chr10 | 113088792 | 113124248 | 35456 | hap11838 | 62.7 | 63.4 | 38.1 | 5.7 |
| chr11 | 5482746 | 5498801 | 16055 | hap12904 | 70.3 | 75.0 | 16.3 | 51.7 |
| chr11 | 42819351 | 42852772 | 33421 | hap14385 | 54.6 | 54.9 | 65.3 | 17.8 |
| chr11 | 57983961 | 58051078 | 67117 | hap14930 | 67.3 | 66.4 | 58.2 | 18.6 |
| chr11 | 60174708 | 60204209 | 29501 | hap14990 | 58.4 | 59.8 | 49.6 | 10.8 |
| chr12 | 128079419 | 128114656 | 35237 | hap22249 | 60.0 | 58.3 | 12.1 | 45.2 |
| chr15 | 20480575 | 20533464 | 52889 | hap29631 | 64.7 | 69.1 | 27.7 | 59.3 |
| chr15 | 94902853 | 94946231 | 43378 | hap32161 | 74.1 | 74.5 | 74.9 | 15.8 |
| chr15 | 96526684 | 96549225 | 22541 | hap32221 | 70.8 | 68.8 | 28.9 | 64.4 |
| chr16 | 31595372 | 31613277 | 17905 | hap33499 | 55.9 | 59.3 | 46.3 | 14.4 |
| chr16 | 80151778 | 80182097 | 30319 | hap34821 | 71.1 | 71.0 | 11.5 | 51.8 |
| chr16 | 82519715 | 82554191 | 34476 | hap34920 | 71.3 | 66.5 | 47.4 | 13.0 |
| chr17 | 21668593 | 21685572 | 16979 | hap36049 | 50.3 | 47.8 | 67.4 | 19.6 |
| chr17 | 44999177 | 45012087 | 12910 | hap36640 | 47.1 | 45.2 | 81.6 | 35.1 |
| chr17 | 69911623 | 69926625 | 15002 | hap37435 | 67.3 | 63.0 | 37.8 | 5.2 |
| chr18 | 11441122 | 11458521 | 17399 | hap38335 | 65.5 | 66.8 | 65.9 | 22.4 |
| chr18 | 23405569 | 23423387 | 17818 | hap38673 | 66.3 | 61.7 | 3.3 | 48.1 |
| chr18 | 68887284 | 68925031 | 37747 | hap40390 | 63.0 | 61.0 | 22.0 | 53.4 |
| chr18 | 69487809 | 69505470 | 17661 | hap40414 | 74.5 | 74.1 | 33.3 | 72.2 |
| chr2 | 41480394 | 41514135 | 33741 | hap43972 | 54.0 | 54.0 | 14.9 | 77.8 |
| chr2 | 114171214 | 114182880 | 11666 | hap46226 | 72.4 | 68.8 | 79.7 | 16.7 |
| chr2 | 123762541 | 123797629 | 35088 | hap46589 | 66.7 | 68.1 | 24.0 | 54.5 |
| chr2 | 125236882 | 125241950 | 5068 | hap46673 | 58.9 | 59.2 | 10.7 | 46.4 |
| chr2 | 130016110 | 130040331 | 24221 | hap46835 | 54.6 | 50.8 | 5.6 | 41.6 |
| chr2 | 137757638 | 137783716 | 26078 | hap47090 | 61.8 | 61.4 | 13.5 | 69.2 |
| chr2 | 144128597 | 144160845 | 32248 | hap47343 | 65.8 | 66.6 | 9.3 | 50.3 |
| chr20 | 15736792 | 15753459 | 16667 | hap51505 | 78.9 | 74.3 | 45.8 | 77.3 |
| chr20 | 26167979 | 26177235 | 9256 | hap51868 | 55.0 | 52.2 | 38.5 | 68.6 |
| chr20 | 44255808 | 44264190 | 8382 | hap52246 | 57.4 | 56.1 | 9.7 | 50.6 |
| chr20 | 59518410 | 59559273 | 40863 | hap52761 | 61.0 | 62.4 | 30.0 | 72.8 |
| chr21 | 21402034 | 21424129 | 22095 | hap53197 | 63.5 | 67.3 | 25.0 | 75.5 |
| chr21 | 24750027 | 24768793 | 18766 | hap53333 | 68.2 | 64.6 | 3.4 | 38.9 |
| chr21 | 26666833 | 26701575 | 34742 | hap53418 | 62.1 | 66.5 | 47.6 | 16.7 |
| chr3 | 2364024 | 2387896 | 23872 | hap55539 | 67.4 | 67.8 | 54.9 | 10.9 |
| chr3 | 21036965 | 21049451 | 12486 | hap56223 | 54.8 | 51.4 | 53.1 | 21.1 |
| chr3 | 56011690 | 56046642 | 34952 | hap57346 | 64.2 | 61.2 | 71.2 | 22.6 |

FIG. 105A

| | | | | | | | |
|---|---|---|---|---|---|---|---|
| chr3 | 73330942 | 73371216 | 40274 | hap57939 | 60.9 | 62.9 | 9.4 | 42.9 |
| chr3 | 106372440 | 106401301 | 28861 | hap59077 | 67.8 | 67.9 | 13.8 | 53.2 |
| chr3 | 107772994 | 107807482 | 34488 | hap59122 | 69.6 | 73.5 | 30.4 | 66.4 |
| chr3 | 116742501 | 116776747 | 34246 | hap59493 | 64.3 | 69.1 | 14.1 | 51.6 |
| chr3 | 171076306 | 171100102 | 23796 | hap61495 | 68.0 | 66.0 | 80.6 | 48.8 |
| chr3 | 193058272 | 193080344 | 22072 | hap62231 | 65.5 | 64.7 | 54.6 | 20.0 |
| chr4 | 30411613 | 30432317 | 20704 | hap63589 | 59.3 | 60.6 | 53.4 | 14.6 |
| chr4 | 31304718 | 31338193 | 33475 | hap63633 | 60.2 | 60.0 | 7.2 | 55.0 |
| chr4 | 92003467 | 92030505 | 27038 | hap65794 | 65.3 | 65.1 | 54.1 | 21.7 |
| chr4 | 155224697 | 155250915 | 26218 | hap68104 | 60.5 | 57.5 | 57.3 | 25.0 |
| chr5 | 2281802 | 2299281 | 17479 | hap69632 | 71.5 | 66.9 | 69.9 | 6.6 |
| chr5 | 4624948 | 4664704 | 39756 | hap69739 | 62.8 | 61.0 | 14.0 | 52.0 |
| chr5 | 89593236 | 89606080 | 12844 | hap72628 | 76.6 | 74.0 | 20.3 | 78.4 |
| chr5 | 119214026 | 119233058 | 19032 | hap73698 | 62.8 | 61.2 | 57.6 | 13.1 |
| chr5 | 119940397 | 119972658 | 32261 | hap73720 | 59.1 | 54.7 | 53.8 | 12.2 |
| chr5 | 132859668 | 132877415 | 17747 | hap74150 | 62.5 | 66.6 | 59.5 | 28.3 |
| chr6 | 26914610 | 26936918 | 22308 | hap76887 | 41.9 | 40.9 | 71.9 | 32.6 |
| chr6 | 66879106 | 66957243 | 78137 | hap78266 | 61.6 | 59.6 | 25.4 | 62.0 |
| chr6 | 77349083 | 77377529 | 28446 | hap78674 | 64.5 | 66.4 | 27.0 | 62.9 |
| chr6 | 159738794 | 159751033 | 12239 | hap81616 | 79.6 | 79.0 | 21.2 | 59.8 |
| chr7 | 26585255 | 26641907 | 56652 | hap83161 | 66.2 | 64.7 | 49.4 | 13.3 |
| chr7 | 48214640 | 48248036 | 33396 | hap84003 | 76.0 | 76.7 | 78.0 | 32.3 |
| chr7 | 88558182 | 88575482 | 17300 | hap85335 | 63.8 | 59.6 | 63.8 | 22.9 |
| chr7 | 96588562 | 96607580 | 19018 | hap85620 | 60.4 | 63.1 | 19.7 | 50.0 |
| chr7 | 122942180 | 122956897 | 14717 | hap86454 | 42.3 | 39.0 | 19.2 | 50.0 |
| chr7 | 132321970 | 132344802 | 22832 | hap86807 | 61.4 | 60.7 | 52.5 | 11.5 |
| chr7 | 153296219 | 153302441 | 6222 | hap87487 | 48.7 | 53.7 | 64.4 | 19.3 |
| chr7 | 156356247 | 156371897 | 15650 | hap87631 | 74.9 | 71.6 | 87.5 | 56.6 |
| chr7 | 159091986 | 159119486 | 27500 | hap87738 | 54.0 | 49.1 | 52.0 | 13.2 |
| chr8 | 51530582 | 51550889 | 20307 | hap89477 | 66.4 | 65.7 | 68.0 | 19.9 |
| chr8 | 63513932 | 63537543 | 23611 | hap89942 | 62.0 | 63.3 | 11.6 | 48.4 |
| chr8 | 72373321 | 72398122 | 24801 | hap90226 | 58.0 | 54.9 | 71.6 | 32.0 |
| chr8 | 94100451 | 94141855 | 41404 | hap90991 | 65.2 | 65.7 | 36.2 | 68.7 |
| chr8 | 109300499 | 109326404 | 25905 | hap91510 | 63.6 | 67.7 | 29.5 | 65.8 |

FIG. 105B

| Chr | start | end | Length | Haplotype block id | PacBio sequencing | | | |
|---|---|---|---|---|---|---|---|---|
| | | | | | Methylation level in adjacent non-tumoral tissue | | Methylation level in tumor tissue | |
| | | | | | Hap I | Hap II | Hap I | Hap II |
| chr9 | 27803548 | 27888202 | 84654 | hap58508 | 64.2 | 60.9 | 20.6 | 75.4 |
| chr6 | 242149 | 386636 | 144487 | hap47880 | 62.3 | 63.3 | 77.4 | 32.2 |
| chr5 | 28219159 | 28302858 | 83699 | hap44666 | 59.3 | 58.0 | 16.8 | 58.2 |
| chr5 | 18119943 | 18153743 | 33800 | hap44475 | 61.6 | 65.0 | 53.2 | 21.7 |
| chr7 | 24906307 | 25046195 | 139888 | hap52069 | 69.3 | 68.7 | 44.0 | 76.2 |
| chr15 | 27689897 | 27752573 | 62676 | hap18337 | 65.9 | 61.9 | 64.8 | 20.5 |
| chr12 | 42183870 | 42212433 | 28563 | hap12045 | 63.5 | 68.4 | 19.4 | 51.2 |
| chr21 | 9825597 | 9935752 | 110155 | hap34175 | 54.3 | 53.5 | 60.9 | 29.1 |
| chr2 | 118813055 | 118893366 | 80311 | hap30060 | 62.6 | 62.3 | 77.0 | 38.6 |
| chr6 | 90307702 | 90344869 | 37167 | hap49779 | 69.1 | 66.4 | 84.7 | 53.9 |
| chr7 | 107932914 | 108049376 | 116462 | hap53838 | 67.2 | 62.9 | 43.8 | 76.4 |
| chr7 | 137039327 | 137160933 | 121606 | hap54447 | 59.5 | 60.9 | 22.9 | 72.0 |
| chr17 | 21193754 | 21254930 | 61176 | hap22633 | 59.2 | 54.3 | 69.7 | 31.6 |
| chr12 | 11473697 | 11644714 | 171017 | hap11451 | 62.8 | 66.4 | 35.5 | 75.9 |
| chr5 | 129212299 | 129353349 | 141050 | hap46632 | 50.9 | 54.5 | 45.5 | 14.0 |
| chr11 | 93910738 | 94028887 | 118149 | hap10288 | 67.6 | 63.6 | 36.6 | 74.2 |
| chr3 | 131707434 | 132003636 | 296202 | hap38642 | 57.8 | 55.9 | 17.9 | 60.2 |
| chr3 | 43024004 | 43161785 | 137781 | hap36769 | 69.1 | 66.5 | 46.1 | 80.2 |
| chr3 | 190403156 | 190606658 | 203502 | hap39947 | 60.9 | 61.6 | 36.9 | 72.7 |
| chr15 | 40218970 | 40279780 | 60810 | hap18606 | 53.4 | 57.5 | 79.1 | 47.4 |

FIG. 106

| Tissue types | No. of haplotype blocks showing methylation imbalance between two haplotypes in tumor tissues | No. of haplotype blocks showing methylation imbalance between two haplotypes in paired adjacent non-tumoral tissues |
|---|---|---|
| Colon | 92 | 47 |
| Breast | 57 | 13 |
| Kidney | 68 | 18 |
| Lung | 31 | 21 |
| Prostate | 26 | 19 |
| Stomach | 2 | 0 |

FIG. 107A

| Tissue types | No. of haplotype blocks showing methylation imbalance between two haplotypes in tumor tissues | Tumor Staging information (TNM) available |
|---|---|---|
| Breast | 18 | T2 |
| | 57 | T3 |
| Kidney | 68 | T3a |
| | 0 | T2 |

| | Bisulfite sequencing | | PacBio sequencing | |
|---|---|---|---|---|
| | No. of CG sites | Methylation density (%) | No. of CG sites | Methylation density (%) |
| 1) Human-only | 2,220,407 | 41.4 | 16,226,014 | 56.0 |
| 2) Mouse-only | 2,726,489 | 1.6 | 9,398,340 | 10.7 |
| 3) Human-mouse hybrid DNA — Human part | 73,780 | 46.8 | 4,838,454 | 57.4 |
| 3) Human-mouse hybrid DNA — Mouse part | 76,312 | 2.3 | 4,385,046 | 12.1 |

FIG. 119

| | Bisulfite sequencing | | PacBio sequencing | |
|---|---|---|---|---|
| | No. of CG sites | Methylation density (%) | No. of CG sites | Methylation density (%) |
| 1) Human-only | 2,938,088 | 1.6 | 14,503,548 | 11.6 |
| 2) Mouse-only | 1,513,971 | 62.4 | 11,348,555 | 71.5 |
| 3) Human-mouse hybrid DNA — Human part | 67,371 | 1.8 | 5,824,379 | 13.1 |
| 3) Human-mouse hybrid DNA — Mouse part | 58,242 | 67.4 | 5,093,097 | 72.2 |

```
1230
```

```
┌─────────────────────────────────────────────────────────────┐
│ Perform single molecule sequencing of a DNA molecule to     │
│ obtained a sequence read that provides a methylation status at │ ─ 1232
│ each of N sites, N being 5 or more, where the methylation statuses │
│ of the sequence read form a methylation pattern            │
└─────────────────────────────────────────────────────────────┘
                              ▼
┌─────────────────────────────────────────────────────────────┐
│ Slide the methylation pattern over one or more reference patterns │
│ that correspond to chimeric molecules that have two portions from │
│ two parts of a reference human genome, the one or more     │
│ reference patterns including a change between methylated   │ ─ 1234
│ statuses and unmethylated statuses                         │
└─────────────────────────────────────────────────────────────┘
                              ▼
┌─────────────────────────────────────────────────────────────┐
│ Identify a match position between the methylation pattern and a │
│ first reference pattern of the one or more reference patterns, the │ ─ 1236
│ match position identifying a junction between the two parts of the │
│ reference human genome in the sequence read                │
└─────────────────────────────────────────────────────────────┘
                              ▼
┌─────────────────────────────────────────────────────────────┐
│ Output the junction as a location of a gene fusion in a chimeric │ ─ 1238
│ molecule                                                    │
└─────────────────────────────────────────────────────────────┘
```

FIG. 123

| Size ranges (bp) | No. of molecules | Percentage of molecules within a size range relative to total fragments (%) | No. of molecules within a size range overlapping CpG islands | Percentage of molecules within a size range overlapping CpG islands (%) | No. of CpG sites being sequenced | No. of CpG sites falling within CpG islands | Percentage of CpG sites targeted by size selection and falling within CpG islands (%) |
|---|---|---|---|---|---|---|---|
| 50-200 | 526,543 | 23.03 | 104,059 | 19.76 | 2,358,020 | 885,041 | 37.53 |
| 200-400 | 269,562 | 11.79 | 23,927 | 8.88 | 1,781,556 | 353,087 | 19.82 |
| 400-600 | 177,776 | 7.77 | 7,369 | 4.15 | 1,468,561 | 107,130 | 7.29 |
| 600-800 | 133,927 | 5.86 | 3,673 | 2.74 | 1,326,544 | 48,851 | 3.68 |
| 800-1000 | 104,976 | 4.59 | 2,168 | 2.07 | 1,193,233 | 25,821 | 2.16 |
| 1000-2000 | 311,596 | 13.63 | 4,596 | 1.47 | 4,610,504 | 58,288 | 1.26 |
| 2000-3000 | 149,468 | 6.54 | 1,771 | 1.18 | 3,036,951 | 25,106 | 0.83 |
| 3000-4000 | 86,760 | 3.79 | 809 | 0.93 | 2,165,171 | 10,785 | 0.50 |
| 5000-6000 | 36,931 | 1.62 | 266 | 0.72 | 1,242,712 | 3,412 | 0.27 |
| 6000-7000 | 25,027 | 1.09 | 202 | 0.81 | 947,874 | 3,354 | 0.35 |
| 7000-8000 | 17,597 | 0.77 | 86 | 0.49 | 736,830 | 791 | 0.11 |
| 8000-9000 | 12,658 | 0.55 | 76 | 0.60 | 583,680 | 993 | 0.17 |
| 9000-10000 | 9,184 | 0.40 | 48 | 0.52 | 461,935 | 591 | 0.13 |
| 10000-15000 | 20,790 | 0.91 | 97 | 0.47 | 1,255,731 | 2,003 | 0.16 |
| 15000-20000 | 5,111 | 0.22 | 16 | 0.31 | 414,400 | 163 | 0.04 |
| 20000-25000 | 1,441 | 0.06 | 6 | 0.42 | 147,731 | 34 | 0.02 |

FIG. 128

SEQUENCE LISTING

```
<160> NUMBER OF SEQ ID NOS: 5

<210> SEQ ID NO 1
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gccuguaauc ccagcacuuu guuuuagagc uaugcu                                 36

<210> SEQ ID NO 2
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agcauagcaa guuaaaauaa ggcuaguccg uuaucaacuu gaaaagugg caccgagucg       60 gugcuuu                                                                 67
```

```
<210> SEQ ID NO 3
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
agggucucgc ucugucgccc guuuuagagc uaugcu                                 36

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atacgtacgt                                                              10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atacgtacgt                                                              10
```

DETERMINATION OF BASE MODIFICATIONS OF NUCLEIC ACIDS

CROSS-REFERENCES TO RELATED APPLICATIONS

The present application claims the benefit of priority to U.S. Provisional Application No. 63/051,210, entitled "DETERMINATION OF BASE MODIFICATIONS OF NUCLEIC ACIDS," filed on Jul. 13, 2020; U.S. Provisional Application No. 63/019,790, entitled "DETERMINATION OF BASE MODIFICATIONS OF NUCLEIC ACIDS," filed on May 4, 2020; U.S. Provisional Application No. 62/991,891, entitled "DETERMINATION OF BASE MODIFICATIONS OF NUCLEIC ACIDS," filed on Mar. 19, 2020; U.S. Provisional Application No. 62/970,586, entitled "DETERMINATION OF BASE MODIFICATIONS OF NUCLEIC ACIDS," filed on Feb. 5, 2020; and U.S. Provisional Application No. 62/887,987, entitled "DETERMINATION OF BASE MODIFICATIONS OF NUCLEIC ACIDS," filed on Aug. 16, 2019, the entire contents of all of which are herein incorporated by reference for all purposes.

REFERENCE TO A "SEQUENCE LISTING" SUBMITTED AS ASCII TEXT FILES VIA EFS-WEB

The instant application contains a Sequence Listing which has been filed electronically in ASCII format and is hereby incorporated by reference in its entirety. Said ASCII copy, created on Oct. 22, 2020, is named 080015-028410US-1199353_SL.txt and is 1,709 bytes in size.

BACKGROUND

The existence of base modifications in nucleic acids varies throughout different organisms including viruses, bacteria, plants, fungi, nematodes, insects, and vertebrates (e.g. humans), etc. The most common base modifications are the addition of a methyl group to different DNA bases at different positions, so-called methylation. Methylation has been found on cytosines, adenines, thymines and guanines, such as 5mC (5-methylcytosine), 4mC (N4-methylcytosine), 5hmC (5-hydroxymethylcytosine), 5fC (5-formylcytosine), 5caC (5-carboxylcytosine), 1 mA (N1-methyladenine), 3 mA (N3-methyladenine), 7 mA (N7-methyladenine), 3mC (N3-methylcytosine), 2mG (N2-methylguanine), 6mG (O6-methylguanine), 7mG (N7-methylguanine), 3mT (N3-methylthymine), and 4mT (O4-methylthymine). In vertebrate genomes, 5mC is the most common type of base methylation, followed by that for guanine (i.e. in the CpG context).

DNA methylation is essential for mammalian development and has notable roles in gene expression and silencing, embryonic development, transcription, chromatin structure, X chromosome inactivation, protection against activity of the repetitive elements, maintenance of genomic stability during mitosis, and the regulation of parent-of-origin genomic imprinting.

DNA methylation plays many important roles in the silencing of promoters and enhancers in a coordinated manner (Robertson, 2005; Smith and Meissner, 2013). Many human diseases have been found to be associated with aberrations of DNA methylation, including but not limited to the process of carcinogenesis, imprinting disorders (e.g. Beckwith-Wiedemann syndrome and Prader-Willi syndrome), repeat-instability diseases (e.g. fragile X syndrome), autoimmune disorders (e.g. systemic lupus erythematosus), metabolic disorders (e.g. type I and type II diabetes), neurological disorders, aging, etc.

The accurate measurement of methylomic modification on DNA molecules would have numerous clinical implications. One widely used method to measure DNA methylation is through the use of bisulfite sequencing (BS-seq) (Lister et al., 2009; Frommer et al., 1992). In this approach, DNA samples are first treated with bisulfite which converts unmethylated cytosine (i.e. C) to uracil. In contrast, the methylated cytosine remains unchanged. The bisulfite modified DNA is then analyzed by DNA sequencing. In another approach, following bisulfite conversion, the modified DNA is then subjected to polymerase chain reaction (PCR) amplification using primers that can differentiate bisulfite converted DNA of different methylation profiles (Herman et al., 1996). This latter approach is called methylation-specific PCR.

One disadvantage of such bisulfite-based approaches is that the bisulfite conversion step has been reported to significantly degrade the majority of the treated DNA (Grunau, 2001). Another disadvantage is that the bisulfite conversion step would create strong CG biases (Olova et al., 2018), resulting in the reduction of signal-to-noise ratios typically for DNA mixtures with heterogeneous methylation states. Furthermore, bisulfite sequencing would not be able to sequence long DNA molecules because of the degradation of DNA during bisulfite treatment. Thus, there is a need to determine the modification of bases of nucleic acids, without prior chemical (e.g. bisulfite conversion) and nucleic acid amplification (e.g. using the PCR).

BRIEF SUMMARY

We have developed a new method that, in one embodiment, allows the determination of base modifications, such as 5mC in nucleic acids without template DNA pre-treatment such as enzymatic and/or chemical conversions, or protein and/or antibody binding. While such template DNA pre-treatment is not necessary for the determination of the base modifications, in examples that are shown, certain pre-treatment (e.g. digestion with restriction enzymes) may serve to enhance aspects of the invention (e.g. allowing the enrichment of CpG sites for analysis). The embodiments present in this disclosure could be used for detecting different types of base modification, for example, including but not limited to 4mC, 5hmC, 5fC, and 5caC, 1 mA, 3 mA, 7 mA, 3mC, 2mG, 6mG, 7mG, 3mT, and 4mT, etc. Such embodiments can make use of features derived from sequencing, such as kinetic features, that are affected by the various base modifications, as well as an identity of nucleotides in a window around a target position whose methylation status is determined.

Embodiments of the present invention can be used for, but is not limited to, single molecule sequencing. One type of single molecule sequencing is single molecule, real-time sequencing in which the progress of the sequencing of a single DNA molecule is monitored in real-time. One type of single molecule, real-time sequencing is that commercialized by Pacific Biosciences using their Single Molecule, Real-Time (SMRT) system. Methods may use the pulse width of a signal from sequencing bases, the interpulse duration (IPD) of bases, and the identity of the bases in order to detect a modification in a base or in a neighboring base. Another single molecule system is that based on nanopore sequencing. One example of a nanopore sequencing system is that commercialized by Oxford Nanopore Technologies.

The methods we have developed can serve as tools to detect base modifications in biological samples to assess the methylation profiles in the samples for various purposes including but not limited to research and diagnostic purposes. The detected methylation profiles can be used for different analysis. The methylation profiles can be used to detect the origin of DNA (e.g., maternal or fetal, tissue, bacterial, or DNA obtained from tumor cells enriched from the blood of a cancer patient). Detection of aberrant methylation profiles in tissues aids the identification of developmental disorders in individuals, identify and prognosticate tumors or malignancies.

Embodiments of the present invention may include analyzing the relative methylation levels of haplotypes of an organism. An imbalance in the methylation levels between the two haplotypes may be used to determine a classification of a disorder. A higher imbalance may indicate the presence of a disorder or a more severe disorder. The disorder may include cancer.

Methylation patterns in a single molecule can identify chimera and hybrid DNA. Chimeric and hybrid molecules may include sequences from two different genes, chromosomes, organelles (e.g. mitochondria, nucleus, chloroplasts), organisms (mammals, bacteria, viruses, etc.), and/or species. Detecting junctions of chimeric or hybrid DNA molecules may allow for detecting gene fusions for various disorders or diseases, including cancer, prenatal, or congenital disorders.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 45 is a table showing the percentage of fully-unmethylated molecules, hemi-methylated molecules, fully-methylated molecules, and molecules with interlaced methyladenine patterns in training and testing datasets according to embodiments of the present invention.

FIG. 48 is a table showing that the 9 DNA molecules were sequenced by Pacific Biosciences SMRT sequencing and which overlapped with imprinted regions according to embodiments of the present invention.

FIG. 60 shows a table summarizing sequencing data from different human tissue DNA samples according to embodiments of the present invention.

FIGS. 63A, 63B, and 63C show different correlations of overall methylation levels quantified by bisulfite sequencing and single molecule, real-time sequencing according to embodiments of the present invention.

FIG. 81 shows a table of methylation levels of allele-specific fragments according to embodiments of the present invention.

FIG. 96 shows a table of tissues and the methylation levels of Alu regions in the tissues according to embodiments of the present invention.

FIG. 100 is a table showing the effect of the subread depth on the correlation of methylation levels between two measurements by SMRT-seq (Sequel II Sequencing Kit 2.0) and BS-seq according to embodiments of the present invention.

FIG. 102 shows a method of detecting a modification of a nucleotide in a nucleic acid molecule according to embodiments of the present invention.

FIG. 103 shows a method for detecting a modification of a nucleotide in a nucleic acid molecule according to embodiments of the present invention.

FIGS. 105A and 105B are a table of the haplotype blocks showing differential methylation levels between Hap I and Hap II in the tumor DNA compared with the adjacent non-tumoral tissue DNA for the case TBR3033 according to embodiments of the present invention.

FIG. 106 is a table of the haplotype blocks showing differential methylation levels between Hap I and Hap II in the tumor DNA compared with the adjacent normal tissue DNA for the case TBR3032 according to embodiments of the present invention.

FIG. 107A is a table summarizing the number of haplotype blocks showing methylation imbalance between two haplotypes between tumor and adjacent nontumoral tissues on the basis of data generated by Sequel II Sequencing Kit 2.0 according to embodiments of the present invention.

FIG. 107B is a table summarizing the number of haplotype blocks showing methylation imbalance between two haplotypes in tumor tissues for different tumor stages on the basis of data generated by Sequel II Sequencing Kit 2.0 according to embodiments of the present invention.

FIG. 114 illustrates methylation analysis for the DNA mixture according to embodiments of the present invention.

FIG. 115 shows a boxplot of the probabilities of being methylated for CpG sites in the sample MIX01 according to embodiments of the present invention.

FIG. 116 shows length distribution of DNA molecules in the DNA mixture after cross-ligation of sample MIX02 according to embodiments of the present invention.

FIG. 117 shows a boxplot of the probabilities of being methylated for CpG sites in the sample MIX02 according to embodiments of the present invention.

FIG. 118 is a table comparing methylation determined by bisulfite sequencing and Pacific Biosciences sequencing for MIX01 according to embodiments of the present invention.

FIG. 119 is a table comparing methylation determined by bisulfite sequencing and Pacific Biosciences sequencing for MIX02 according to embodiments of the present invention.

FIGS. 120A and 120B show methylation levels in 5-Mb bins for human-only and mouse-only DNA for MIX01 and MIX02 according to embodiments of the present invention.

FIGS. 121A and 121B show methylation levels in 5-Mb bins for the human part and the mouse part of human-mouse hybrid DNA fragments for MIX01 and MIX02 according to embodiments of the present invention.

FIGS. 122A and 122B are representative graphs showing methylation states in a single human-mouse hybrid molecule according to embodiments of the present invention.

FIG. 123 shows a method of detecting chimeric molecules in a biological sample according to embodiments of the present invention.

FIG. 124 illustrates a measurement system according to embodiments of the present invention.

FIG. 125 shows a block diagram of an example computer system usable with systems and methods according to embodiments of the present invention.

Figure 126:
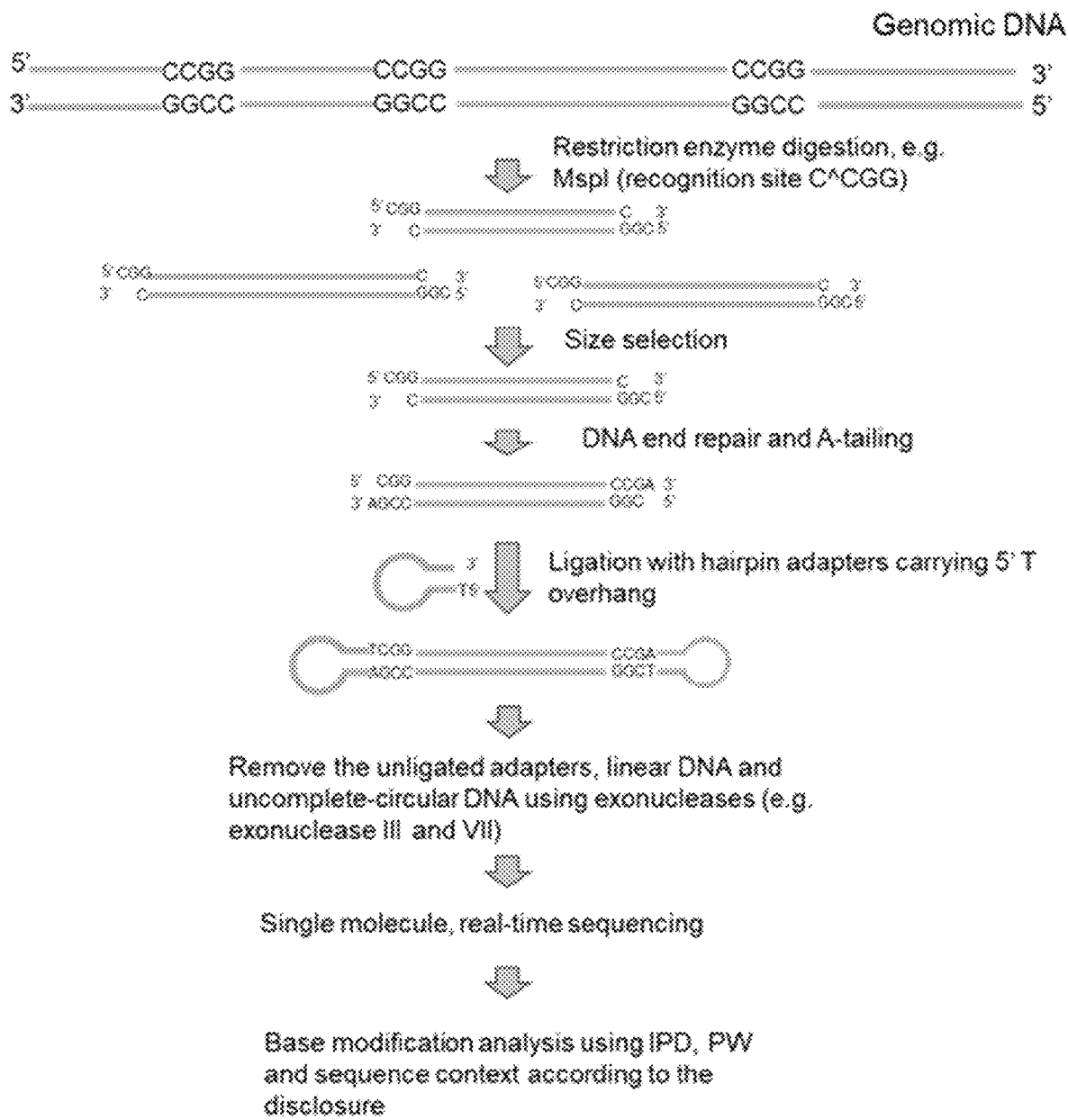

FIG. 126 shows MspI-based targeted single molecule, real-time sequencing with the use of DNA end repair and A-tailing according to embodiments of the present invention.

Figure 127A:
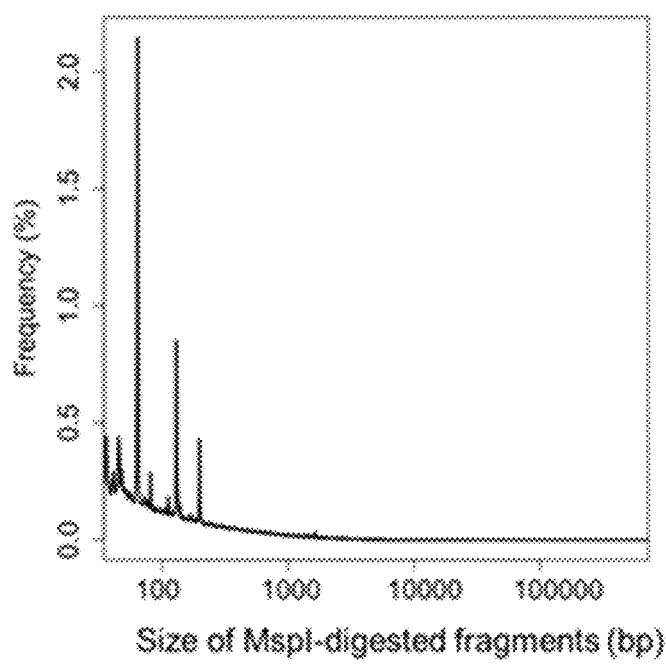
Figure 127B:
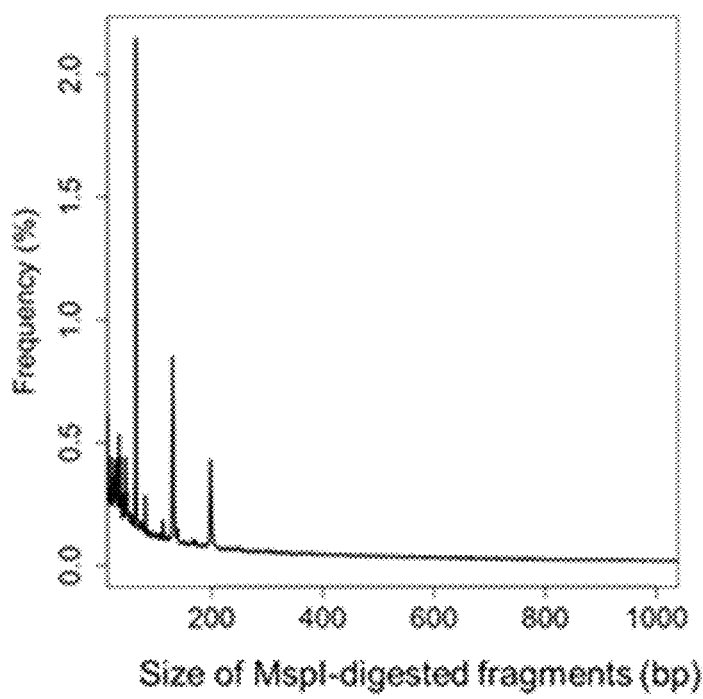

FIGS. 127A and 127B show the size distribution of MspI-digested fragments according to embodiments of the present invention.

FIG. 128 shows a table with the number of DNA molecules for certain selected size ranges according to embodiments of the present invention.

Figure 129:
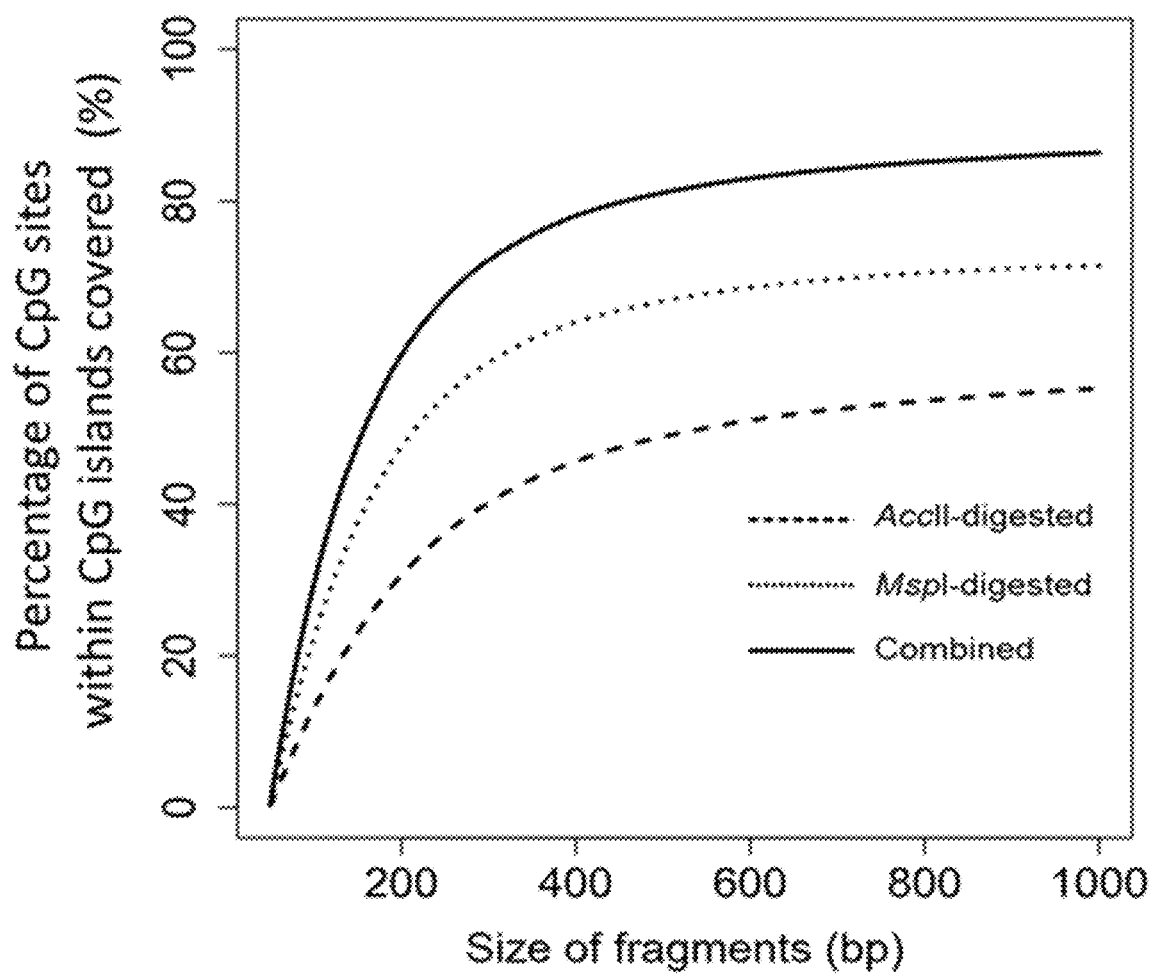

FIG. 129 is a graph of the percentage coverage of CpG sites within CpG islands versus size of DNA fragments after restriction enzyme digestion according to embodiments of the present invention.

Figure 130:
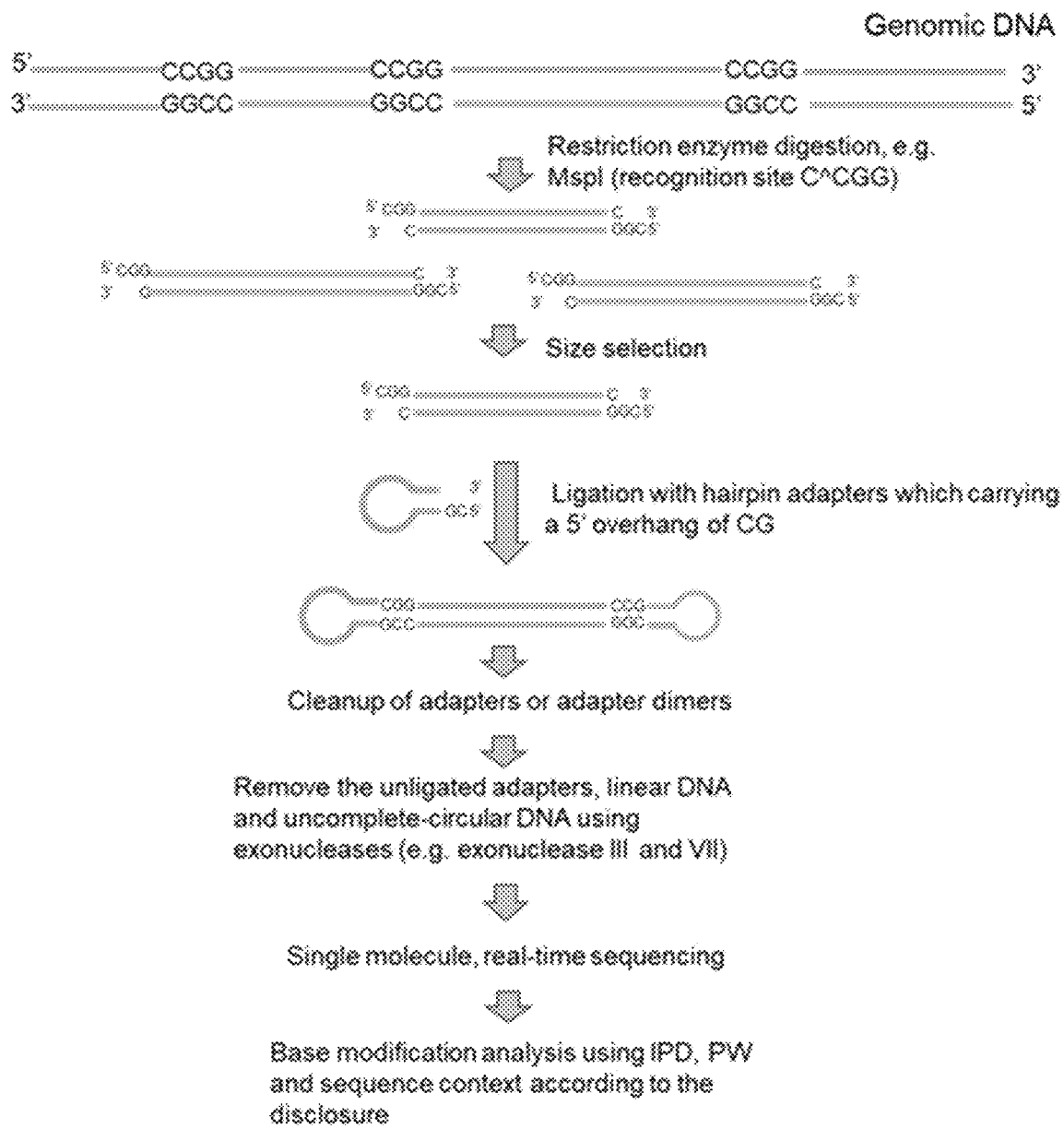

FIG. 130 shows MspI-based targeted single molecule, real time sequencing without the use of DNA end repair and A-tailing according to embodiments of the present invention.

Figure 131:
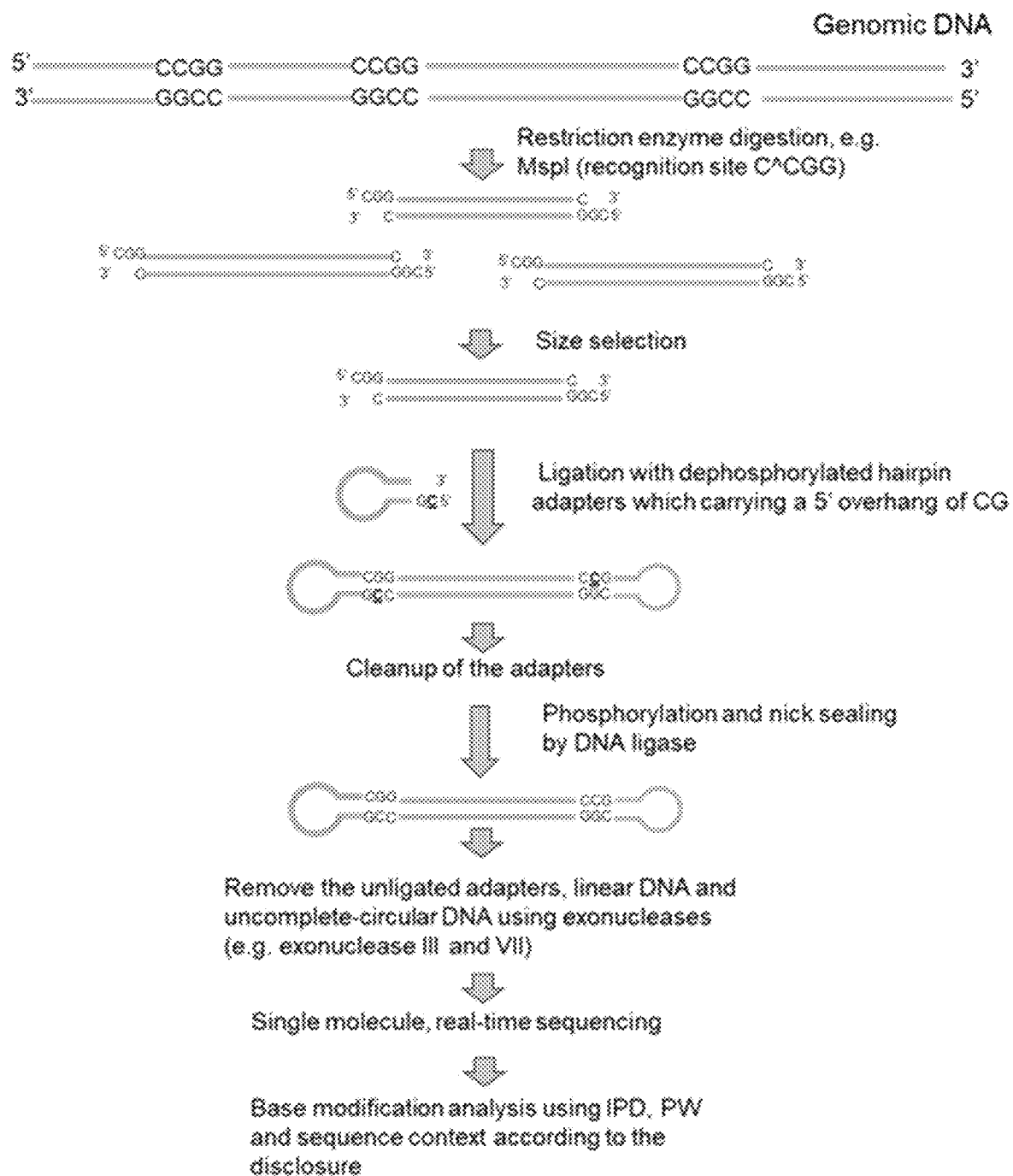

FIG. 131 shows MspI-based targeted single molecule, real time sequencing with a reduced probability of adapter self-ligation according to embodiments of the present invention.

Figure 132:
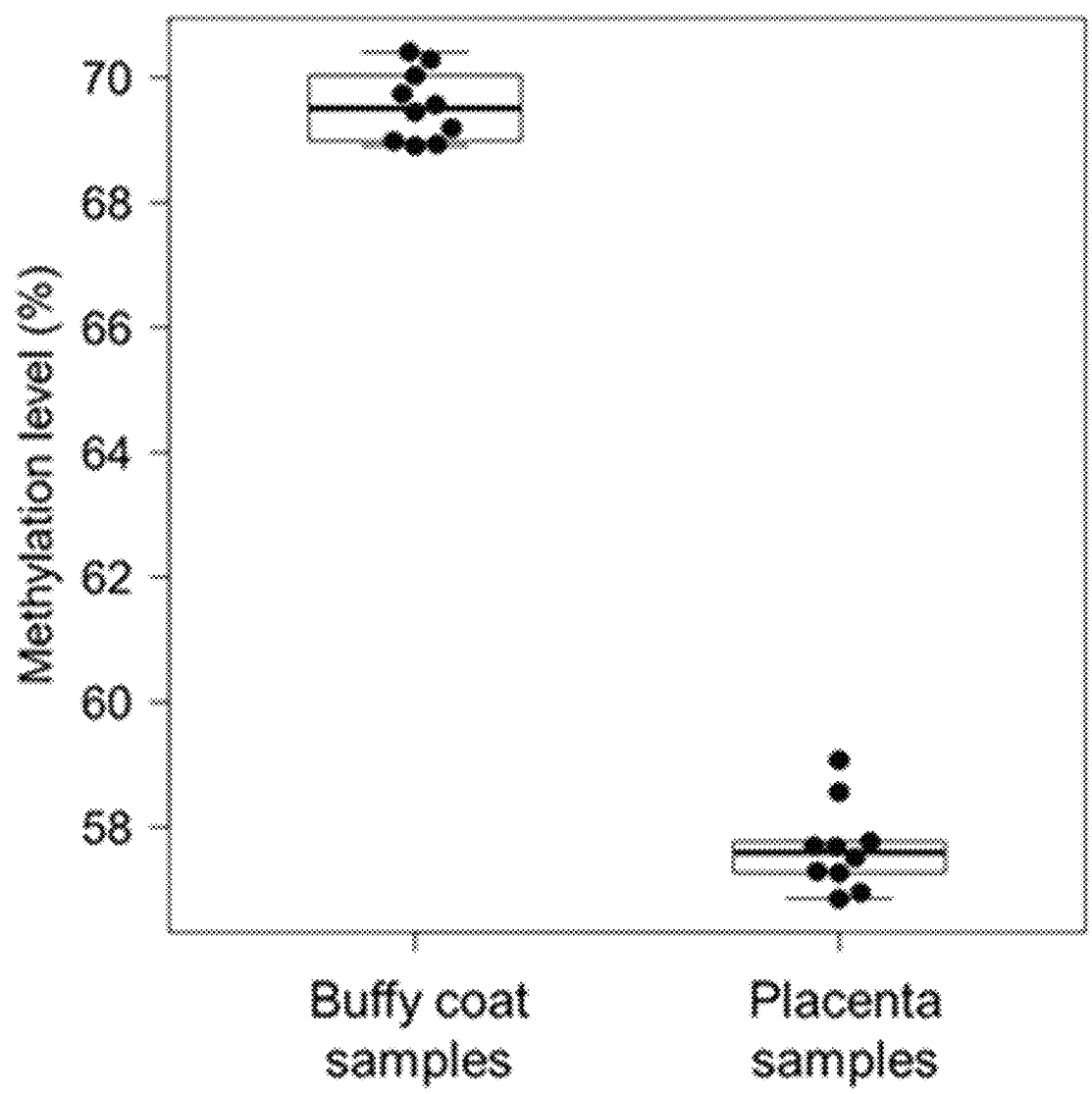

FIG. 132 is a graph of the overall methylation levels between placenta and buffy DNA samples determined by MspI-based targeted single molecule, real-time sequencing according to the embodiments of the present invention.

Figure 133:
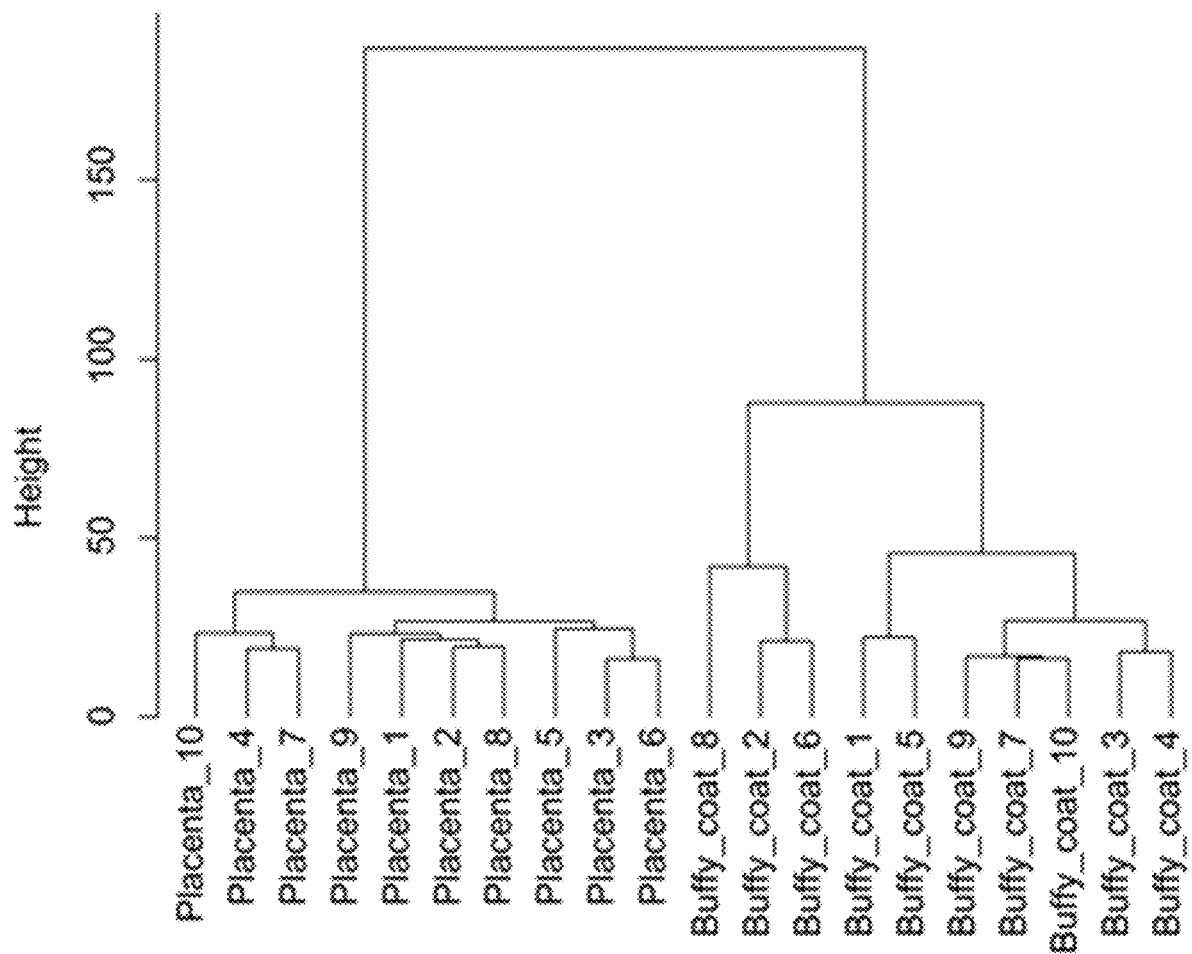

FIG. 133 shows a clustering analysis of placental and buffy coat samples using their DNA methylation profiles determined by MspI-based targeted single molecule, real-time sequencing according to the embodiments of the present invention.

TERMS

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus; tissues in a subject who has received transplantation; tissues of an organism that are infected by a microorganism or a virus) or to healthy cells vs. tumor cells. "Reference tissues" can correspond to tissues used to determine tissue-specific methylation levels. Multiple samples of a same tissue type from different individuals may be used to determine a tissue-specific methylation level for that tissue type.

A "biological sample" refers to any sample that is taken from a human subject. The biological sample can be a tissue biopsy, a fine needle aspirate, or blood cells. The sample can also be for example, plasma or serum or urine from a pregnant woman. Stool samples can also be used. In various embodiments, the majority of DNA in a biological sample from a pregnant woman that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. In certain embodiments, following the 3,000 g centrifugation step, one can follow up with filtration of the fluid part (e.g. using a filter of pore size of 5 μm, or smaller, in diameter).

A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

A "subread" is a sequence generated from all bases in one strand of a circularized DNA template that has been copied in one contiguous strand by a DNA polymerase. For example, a subread can correspond to one strand of circularized DNA template DNA. In such an example, after circularization, one double-stranded DNA molecule would have two subreads: one for each sequencing pass. In some embodiments, the sequence generated may include a subset of all the bases in one strand, e.g., because of the existence of sequencing errors.

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

A "methylation status" refers to the state of methylation at a given site. For example, a site may be either methylated, unmethylated, or in some cases, undetermined.

The "methylation index" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g. primers or probes) that preferentially hybridize to DNA fragments of a particular methylation status at one or more sites. Typically, such reagents are applied after treatment with a process that differentially modifies or differentially recognizes DNA molecules depending on their methylation status, e.g. bisulfite conversion, or methylation-sensitive restriction enzyme, or methylation binding proteins, or anti-methylcytosine antibodies, or single molecule sequencing techniques (e.g. single molecule, real-time sequencing and nanopore sequencing (e.g. from Oxford Nanopore Technologies)) that recognize methylcytosines and hydroxymethyl-cytosines.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer the number of cytosine sites, "C's", that are shown to be methylated (for example unconverted after bisulfite conversion) over the total number of analyzed cytosine residues, i.e. including cytosines outside of the CpG context, in the region. The methylation index, methylation density, count of molecules methylated at one or more sites, and proportion of molecules methylated (e.g., cytosines) at one or more sites are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by single molecule, real-time sequencing (e.g. that from Pacific Biosciences) (Flusberg et al. Nat Methods 2010; 7: 461-465)).

A "methylome" provides a measure of an amount of DNA methylation at a plurality of sites or loci in a genome. The methylome may correspond to all of the genome, a substantial part of the genome, or relatively small portion(s) of the genome.

A "pregnant plasma methylome" is the methylome determined from the plasma or serum of a pregnant animal (e.g., a human). The pregnant plasma methylome is an example of a cell-free methylome since plasma and serum include cell-free DNA. The pregnant plasma methylome is also an example of a mixed methylome since it is a mixture of DNA from different organs or tissues or cells within a body. In one embodiment, such cells are the hematopoietic cells, including, but not limited to cells of the erythroid (i.e. red cell) lineage, the myeloid lineage (e.g., neutrophils and their precursors), and the megakaryocytic lineage. In pregnancy, the plasma methylome may contain methylomic information from the fetus and the mother. The "cellular methylome" corresponds to the methylome determined from cells (e.g., blood cells) of the patient. The methylome of the blood cells is called the blood cell methylome (or blood methylome).

A "methylation profile" includes information related to DNA or RNA methylation for multiple sites or regions. Information related to DNA methylation can include, but not limited to, a methylation index of a CpG site, a methylation density (MD for short) of CpG sites in a region, a distribution of CpG sites over a contiguous region, a pattern or level of methylation for each individual CpG site within a region that contains more than one CpG site, and non-CpG methylation. In one embodiment, the methylation profile can include the pattern of methylation or non-methylation of more than one type of base (e.g. cytosine or adenine). A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as $N^6$-methyladenine, has also been reported.

A "methylation pattern" refers to the order of methylated and non-methylated bases. For example, the methylation pattern can be the order of methylated bases on a single DNA strand, a single double-stranded DNA molecule, or another type of nucleic acid molecule. As an example, three consecutive CpG sites may have any of the following methylation patterns: UUU, MMM, UMM, UMU, UUM, MUM, MUU, or MMU, where "U" indicates an unmethylated site and "M" indicates a methylated site. When one extends this concept to base modifications that include, but not restricted to methylation, one would use the term "modification pattern," which refers to the order of modified and non-modified bases. For example, the modification pattern can be the order of modified bases on a single DNA strand, a single double-stranded DNA molecule, or another type of nucleic acid molecule. As an example, three consecutive potentially modifiable sites may have any of the following modification patterns: UUU, MMM, UMM, UMU, UUM, MUM, MUU, or MMU, where "U" indicates an unmodified site and "M" indicates a modified site. One example of base modification that is not based on methylation is oxidation changes, such as in 8-oxo-guanine.

The terms "hypermethylated" and "hypomethylated" may refer to the methylation density of a single DNA molecule as measured by its single molecule methylation level, e.g., the number of methylated bases or nucleotides within the molecule divided by the total number of methylatable bases or nucleotides within that molecule. A hypermethylated molecule is one in which the single molecule methylation level is at or above a threshold, which may be defined from application to application. The threshold may be 5%, 10%, 20%, 30%, 40%, 50%, 60%, 70%, 80%, 90%, or 95%. A hypomethylated molecule is one in which the single molecule methylation level is at or below a threshold, which may be defined from application to application, and which may change from application to application. The threshold may be 5%, 10%, 20%, 30%, 40%, 50%, 60%, 70%, 80%, 90%, or 95%.

The terms "hypermethylated" and "hypomethylated" may also refer to the methylation level of a population of DNA molecules as measured by the multiple molecule methylation levels of these molecules. A hypermethylated population of molecules is one in which the multiple molecule methylation level is at or above a threshold which may be defined from application to application, and which may change from application to application. The threshold may be 5%, 10%, 20%, 30%, 40%, 50%, 60%, 70%, 80%, 90%, or 95%. A hypomethylated population of molecules is one in which the multiple molecule methylation level is at or below a threshold which may be defined from application to application. The threshold may be 5%, 10%, 20%, 30%, 40%, 50%, 60%, 70%, 80%, 90%, and 95%. In one embodiment, the population of molecules may be aligned to one or more selected genomic regions. In one embodiment, the selected genomic region(s) may be related to a disease such as cancer, a genetic disorder, an imprinting disorder, a metabolic disorder, or a neurological disorder. The selected genomic region(s) can have a length of 50 nucleotides (nt), 100 nt, 200 nt, 300 nt, 500 nt, 1000 nt, 2 knt, 5 knt, 10 knt, 20 knt, 30 knt, 40 knt, 50 knt, 60 knt, 70 knt, 80 knt, 90 knt, 100 knt, 200 knt, 300 knt, 400 knt, 500 knt, or 1 Mnt.

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50×, 100×, etc., where "x" refers to the number of times a locus is covered with a sequence read. Sequencing depth can also be applied to multiple loci, or the whole genome, in which case x can refer to the mean number of times the loci or the haploid genome, or the whole genome, respectively, is sequenced. Ultra-deep sequencing can refer to at least 100× in sequencing depth.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts. A cutoff or threshold may be "a reference value" or derived from a reference value that is representative of a particular classification or discriminates between two or more classifications. Such a reference value can be determined in various ways, as will be appreciated by the skilled person. For example, metrics can be determined for two different cohorts of subjects with different known classifications, and a reference value can be selected as representative of one classification (e.g., a mean) or a value that is between two clusters of the metrics (e.g., chosen to obtain a desired sensitivity and specificity). As another example, a reference value can be determined based on statistical analyses or simulations of samples.

The term "level of cancer" can refer to whether cancer exists (i.e., presence or absence), a stage of a cancer, a size of tumor, whether there is metastasis, the total tumor burden of the body, the cancer's response to treatment, and/or other measure of a severity of a cancer (e.g. recurrence of cancer). The level of cancer may be a number or other indicia, such as symbols, alphabet letters, and colors. The level may be zero. The level of cancer may also include premalignant or precancerous conditions (states). The level of cancer can be used in various ways. For example, screening can check if cancer is present in someone who is not previously known to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance or extent of cancer metastasizing. Detection can mean 'screening' or can mean checking if someone, with suggestive features of cancer (e.g. symptoms or other positive tests), has cancer.

A "level of pathology" (or level of disorder) can refer to the amount, degree, or severity of pathology associated with an organism, where the level can be as described above for cancer. Another example of pathology is a rejection of a transplanted organ. Other example pathologies can include gene imprinting disorders, autoimmune attack (e.g., lupus nephritis damaging the kidney or multiple sclerosis), inflammatory diseases (e.g., hepatitis), fibrotic processes (e.g. cirrhosis), fatty infiltration (e.g. fatty liver diseases), degenerative processes (e.g. Alzheimer's disease), and ischemic tissue damage (e.g., myocardial infarction or stroke). A healthy state of a subject can be considered a classification of no pathology.

A "pregnancy-associated disorder" include any disorder characterized by abnormal relative expression levels of genes in maternal and/or fetal tissue. These disorders include, but are not limited to, preeclampsia, intrauterine growth restriction, invasive placentation, pre-term birth, hemolytic disease of the newborn, placental insufficiency, hydrops fetalis, fetal malformation, HELLP syndrome, systemic lupus erythematosus, and other immunological diseases of the mother.

The abbreviation "bp" refers to base pairs. In some instances, "bp" may be used to denote a length of a DNA fragment, even though the DNA fragment may be single stranded and does not include a base pair. In the context of single-stranded DNA, "bp" may be interpreted as providing the length in nucleotides.

The abbreviation "nt" refers to nucleotides. In some instances, "nt" may be used to denote a length of a single-stranded DNA in a base unit. Also, "nt" may be used to denote the relative positions such as upstream or downstream of the locus being analyzed. In some contexts concerning technological conceptualization, data presentation, processing and analysis, "nt" and "bp" may be used interchangeably.

The term "sequence context" can refer to the base compositions (A, C, G, or T) and the base orders in a stretch of DNA. Such a stretch of DNA could be surrounding a base that is subjected to or the target of base modification analysis. For example, the sequence context can refer to bases upstream and/or downstream of a base that is subjected to base modification analysis.

The term "kinetic features" can refer to features derived from sequencing, including from single molecule, real-time sequencing. Such features can be used for base modification analysis. Example kinetic features include upstream and downstream sequence context, strand information, interpulse duration, pulse widths, and pulse strength. In single molecule, real-time sequencing, one is continuously monitoring the effects of activities of a polymerase on a DNA template. Hence, measurements generated from such a sequencing can be regarded as kinetic features, e.g., nucleotide sequences.

The term "machine learning models" may include models based on using sample data (e.g., training data) to make predictions on test data, and thus may include supervised learning. Machine learning models often are developed using a computer or a processor. Machine learning models may include statistical models.

The term "data analysis framework" may include algorithms and/or models that can take data as an input and then output a predicted result. Examples of "data analysis frameworks" include statistical models, mathematical models, machine learning models, other artificial intelligence models, and combinations thereof.

The term "real-time sequencing" may refer to a technique that involves data collection or monitoring during progress of a reaction involved in sequencing. For example, real-time sequencing may involve optical monitoring or filming the DNA polymerase incorporating incorporate a new base.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to 10%. The term "about" can refer to 5%.

DETAILED DESCRIPTION

Achieving bisulfite-free determination of a base modification, include a methylated base, is the subject of different research efforts but none have been shown to be commercially viable. Recently, a bisulfite-free method for detecting 5mC and 5hmC has been published (Y. Liu et al., 2019) using a mild condition for 5mC and 5hmC base conversion. This method involves multiple steps of enzymatic and chemical reactions including ten-eleven translocation (TET) oxidation, pyridine borane reduction, and PCR. The efficiency for each step of conversion reaction as well as PCR bias would adversely affect the ultimate accuracy in 5mC analysis. For example, the 5mC conversion rate has been reported to be around 96%, with a false-negative rate of around 3%. Such performance would potentially limit one's ability to detect certain subtle changes of methylation in a genome. On the other hand, the enzymatic conversion would not be able to perform equally well across the genome. For example, the conversion rate of 5hmC was 8.2% lower than that for 5mC, and the conversion rate for non-CpG was 11.4% lower than that for CpG contexts (Y. Liu et al., 2019). Thus, the ideal situation is the development of approaches for measuring base modifications of a native DNA molecule without any prior conversion (chemical or enzymatic, or combinations thereof) step and even without an amplification step.

There were a number of proof-of-concept studies (Q. Liu et al., 2019; Ni et al., 2019) in which the electric signals produced by a long-read nanopore sequencing approach (e.g., using the system developed by Oxford Nanopore Technologies) enabled one to detect methylation states with the use of a deep learning method. In addition to Oxford Nanopore, there are other single molecule sequencing approaches that allow long reads. One example is the single molecule, real-time sequencing. One example of a single molecule, real-time sequencing is that commercialized the Pacific Biosciences SMRT system. As the principle of single molecule, real-time sequencing (e.g., the Pacific Biosciences SMRT system) is different from that of a non-optical based nanopore system (e.g. by Oxford Nanopore Technologies), approaches for base modification detection developed for such non-optical based nanopore system cannot be used for single molecule, real-time sequencing. For example, a non-optical nanopore system is not designed for capturing the patterns of fluorescent signals produced by immobilized DNA polymerase based DNA synthesis (employed by single molecule, real-time sequencing such as by the Pacific Biosciences SMRT system). As a further example, in the Oxford Nanopore sequencing platform, each measured electric event is associated with a k-mer (e.g., 5-mer) (Q. Liu et al., 2019). However, in the Pacific Biosciences SMRT sequencing platform, each fluorescent event is generally associated with a single incorporated base. Furthermore, a single DNA molecule would be sequenced multiple times in Pacific Biosciences SMRT sequencing including Watson and Crick strands. Conversely, for the Oxford Nanopore long-read sequencing approach, sequence readout is performed once for each of the Watson and Crick strands.

It has been reported that the polymerase kinetics would be affected by methylation states in the sequences of E. coli (Flusberg et al., 2010). Previous studies showed that when compared with the detection of 6 mA, 4mC, 5hmC, and 8-oxo-guanine, it is much more challenging to use the polymerase kinetics of single molecule, real-time sequencing for deducing the methylation states (5mC versus C) of a particular CpG in a single molecule. The reason is that the methyl group is small and oriented towards the major groove and is not involved in base pairing, leading to very subtle interruption in the kinetics caused by 5mC (Clark et al., 2013). Hence, there is a paucity of approaches for determining the methylation states of cytosines at the single-molecule level.

Suzuki et al developed an algorithm (Suzuki et al., 2016) attempting to combine the interpulse duration (IPD) ratios for neighboring CpG sites to increase the confidence in identifying the methylation states of those sites. However, this algorithm only allowed one to predict a genomic region of being completely methylated or completely unmethylated, but lacked the ability to determine intermediate methylation patterns.

Regarding single molecule, real-time sequencing, current approaches only used one or two parameters independently, achieving a very limited accuracy in detecting 5mC because of the measurement difference between κ-methylcytosine and cytosine. For example, Flusberg et al. demonstrated that IPD was altered in base modifications including N6-methyladenosine, 5-methylcytosine, and 5-hydroxymethylcytosine. However, pulse width (PW) of the sequencing kinetics was not found to have a significant effect. Hence, in the method they used for predicting base modification, using the detection of N6-methyladenosine as an example, only IPD but not PW was used.

In follow-up publications by the same group (Clark et al., 2012; Clark et al. 2013), IPD but not PW was incorporated in the algorithms for the detection of 5-methylcytosine. In Clark et al. 2012, the detection rate of 5-methylcytosine without converting it to 5-methylcytosine only ranged from 1.9% to 4.3%. Furthermore, in Clark et al. 2013, the authors had further reaffirmed the subtlety of the kinetic signature of 5-methylcytosine. To overcome the low sensitivity of detecting 5-methylcytosine, Clark et al. further developed a method which converted 5-methylcytosine to 5-carboxylmethylcytosine using Ten-eleven translocation (Tet) proteins so as to improve the sensitivity of 5-methylcytosine (Clark et al. 2013) because the alteration of IPD caused by 5-carboxylcytosine was much more than by 5-methylcytosine.

In a more recent report by Blow et al., the IPD ratio-based method previously described by Flusberg et al was used to detect the base modifications in 217 bacterial and 13 archaeal species with 130-fold read coverage per organism (Blow et al., 2016). Among all the base modifications they identified, only 5% involved 5-methylcytosine. They attributed this low detection rate of 5-methylcytosine to the low sensitivity of single-molecule real-time sequencing for detecting 5-methylcytosine. In most bacteria, a set of sequence motifs were targeted by DNA methyltransferases (MTases) for methylation (e.g. 5'-GmATC-3' by Dam or 5'-CmCWGG-3' by Dcm in E. coli) at nearly all of these motifs in the genome, with only a small fraction of these motif sites remaining non-methylated (Beaulaurier et al. 2019). Furthermore, the use of the IPD-based method to classify the methylation status of the second C in the 5'-CCWGG-3' motif with, or without treatment, with Tet proteins yielded detection rates of 5-methylcytosine of 95.2% and 1.9%, respectively (Clark et al. 2013). Taken as a whole, the IPD method without prior base conversion (e.g., using Tet proteins) missed the majority of 5-methylcytosine.

In the studies mentioned above (Clark et al., 2012; Clark et al., 2013; Blow et al., 2016), IPD-based algorithms were used without consideration of the sequence context at where the candidate base modification was located. Other groups have attempted to take into account the sequence context of a nucleotide for the detection of base modification. For example, Feng et al. used a hierarchical model to analyze IPDs for the detection of 4-methylcytosine and 6-methyl-adenosine in a respective sequence context (Feng et al. 2013). However, in their method, they only considered the IPD at the base of interest and the sequence context adjacent to that base, but did not use the IPD information of all neighboring bases adjacent to the base of interest. In addition, PW was not considered in the algorithm, and they did not present any data on the detection of 5-methylcytosine.

In another study, Schadt et al. developed a statistical method, called conditional random field, to analyze the IPD information of the base of interest and the neighboring bases to determine if the base of interest was a 5-methylcytosine (Schadt et al., 2012). In this work, they also considered the IPD interaction between these bases by inputting them into an equation. However, they did not input the nucleotide sequence, namely A, T, G, or C, in their equation. When they applied the method to determine the methylation status of the M.Sau3AI plasmid, the area under ROC curve was close to 0.5 even at an 800-fold sequence coverage of the plasmid sequence. Moreover, in their method, they had not taken into account PW in their analysis.

In yet another study by Beckman et al., they compared the IPD of all sequences that shared the same 4-nt or 6-nt motif in the genome between a target bacterial genome and a completely unmethylated genome, e.g., obtained through whole genome amplification (Beckman et al. 2014). The purpose of such analysis was only to identify motifs that would be more frequently affected by base modifications. In the study, they only considered the IPD of a potentially modified base but not the IPD of the neighboring base or PW. Their method was not informative about the methylation status of individual nucleotide.

In summary, these previous attempts of utilizing IPD only or with combination of sequence information in the neighboring nucleotides for grouping data were not able to determine the base modification of 5-methylcytosine with meaningful or practical accuracy. In a recent review by Gouil et al., the authors concluded that because of the low signal-to-noise ratio, the detection of 5-methylcytosine in a single molecule using single-molecule real-time sequencing is inaccurate (Gouil et al., 2019). In these previous studies, it remains unknown as to whether it may be feasible to use the kinetic features for genomewide methylomic analysis, especially for complex genomes such as human genomes, cancer genomes, or fetal genomes.

In contrast to previous studies, some embodiments of methods described in this disclosure are based on measuring and utilizing IPD, PW, and sequence context for every base within the measurement window. We reasoned that if we can use a combination of multiple metrics, for example, concurrently making use of features including upstream and downstream sequence context, strand information, IPD, pulse widths as well as pulse strength, we might be able to achieve the accurate measurement of base modifications (e.g. mC detection) at single-base resolution. Sequence context refers to the base compositions (A, C, G, or T) and the base orders in a stretch of DNA. Such a stretch of DNA could be surrounding a base that is subjected to or the target of base modification analysis. In one embodiment, the stretch of DNA could be proximal to a base that is subjected to base modification analysis. In another embodiment, the stretch of DNA could be far away from abase that is subjected to base modification analysis. The stretch of DNA could be upstream and/or downstream of a base that is subjected to base modification analysis.

In one embodiment, the features of upstream and downstream sequence context, strand information, IPD, pulse widths as well as pulse strength, which are used for base modification analysis, are referred to as kinetic features.

The embodiments present in this disclosure can be used for DNA obtained from, but not limited to, cell lines, samples from an organism (e.g. solid organs, solid tissues, a sample obtained via endoscopy, blood, or plasma or serum or urine from a pregnant woman, chorionic villus biopsy, etc.), samples obtained from the environment (e.g. bacteria, cellular contaminants), food (e.g., meat). In some embodiments, the methods present in this disclosure can also be applied following a step in which a fraction of the genome is first enriched, e.g. using hybridization probes (Albert et al., 2007; Okou et al., 2007; Lee et al., 2011), or approaches based on physical separation (e.g. based on sizes, etc) or following restriction enzyme digestion (e.g. MspI), or Cas9-based enrichment (Watson et al., 2019). While the invention does not require enzymatic or chemical conversion to work, in certain embodiments, such a conversion step can be included to further enhance the performance of the invention.

Embodiments of the present disclosure allow for improved accuracy or practicality or convenience in detecting base modifications or measuring modification levels. The modification may be detected directly. Embodiments may avoid enzymatic or chemical conversion, which may not preserve all modification information for detection. Additionally, certain enzymatic or chemical conversions may not be compatible with certain types of modifications. Embodiments of the present disclosure may also avoid amplification by PCR, which may not transfer base-modification information to the PCR products. Additionally, both strands of DNA may be sequenced together, thereby enabling the pairing of the sequence from one strand with its complementary sequence to the other strand. By contrast, PCR amplification splits the two strands of double-stranded DNA, so such pairing of sequences is difficult.

Methylation profiles, determined with or without enzymatic or chemical conversion, can be used for analyzing biological samples. In one embodiment, the methylation profiles can be used to detect the origin of cellular DNA (e.g., maternal or fetal, tissue, viral, or tumor). Detection of aberrant methylation profiles in tissues aid the identification of developmental disorders in individuals and the identification and prognostication of tumors or malignancies. Imbalances in methylation levels between haplotypes can be used to detect disorders, including cancer. Methylation patterns in a single molecule can identify chimeric (e.g., between a virus and human) and hybrid DNA, (e.g., between two genes normally unfused in a natural genome); or between two species (e.g., through genetic or genomic manipulation).

Methylation analysis may be improved by enhanced training, which may include narrowing the data used in a training set. Specific regions may be targeted for analysis. In embodiments, such targeting can involve an enzyme that either alone, or in combination with other reagent(s), may cleave a DNA sequence or a genome based on its sequence. In some embodiments the enzyme is a restriction enzyme that recognizes and cleaves a specific DNA sequence(s). In other embodiments, more than one restriction enzymes with different recognition sequences can be used in combination. In some embodiments, the restriction enzyme may cleave or not cleave based on the methylation status of the recognition sequences. In some embodiments, the enzyme is one within the CRISPR/Cas family. For example, genomic regions of interest can be targeted using a CRISPR/Cas9 system or other system based on guide RNA (i.e., short RNA sequences which bind to a complementary target DNA sequences and in the process guides an enzyme to act at a target genomic location). In some instances, methylation analysis may be possible without alignment to a reference genome.

I. Methylation Detection with Single Molecule, Real-Time Sequencing

Embodiments of the present disclosure allow for directly detecting base modifications, without enzymatic or chemical conversion. Kinetic features (e.g., sequence context, IPD, and PW) obtained through single molecule, real-time sequencing can be analyzed with machine learning to develop a model to detect modification or the absence of a modification. Modification levels may be used to determine the origin of DNA molecules or the presence or level of the disorder.

Using Pacific Biosciences SMRT sequencing as an example of single molecule, real-time sequencing for illustration purposes, a DNA polymerase molecule is positioned at the bottom of wells that serve as zero-mode waveguides (ZMW). The ZMW is a nanophotonic device for confining light to a small observation volume, which can be a hole whose diameter is very small and does not allow the propagation of light in the wavelength range used for detection such that only emission of optical signals from dye-labeled nucleotide incorporated by the immobilized polymerase are detectable against a low and constant background signal (Eid et al., 2009). The DNA polymerase catalyzes the incorporation of fluorescently labeled nucleotides into complementary nucleic acid strands.

Figure 1:
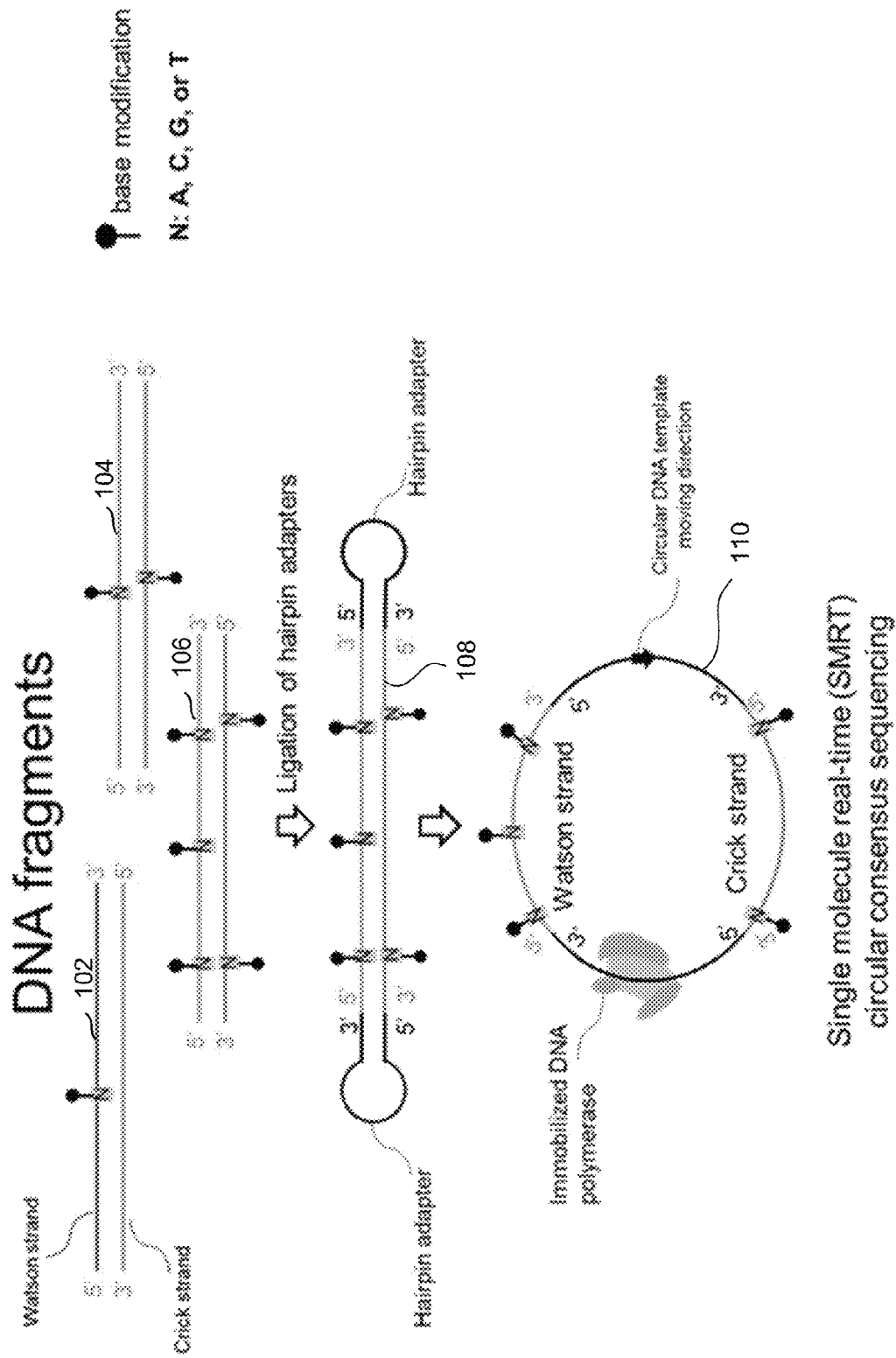
FIG. 1 illustrates SMRT sequencing of molecules carrying base modifications according to embodiments of the present invention.

FIG. 1 shows an example of molecules carrying base modifications that were sequenced by single-molecule circular consensus sequencing. Molecules 102, 104, and 106 carry base modifications. DNA molecules (e.g., molecule 106) may be ligated with hairpin adapters to form ligated molecule 108. Ligated molecule 108 can then form circularized molecule 110. The circularized molecules can bind to immobilized DNA polymerase and can initiate the DNA synthesis. Molecules not carrying base modifications can also be sequenced.

Figure 2:
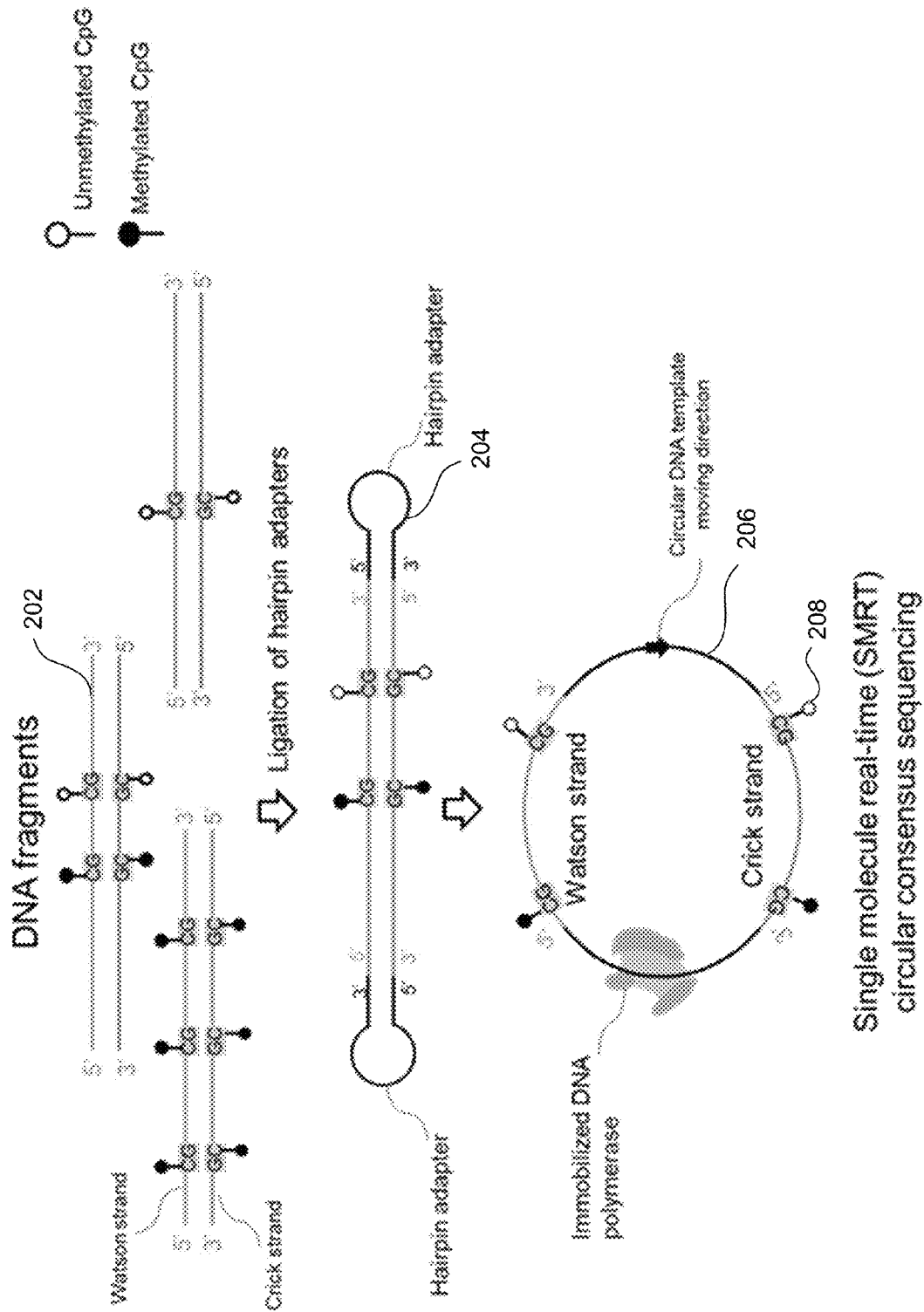
FIG. 2 illustrates SMRT sequencing of molecules carrying methylated and unmethylated CpG sites according to embodiments of the present invention.

FIG. 2 shows an example of molecules carrying methylated and/or unmethylated CpG sites that were sequenced by single molecule, real-time sequencing. DNA molecules were first ligated with hairpin adapters to form circularized molecules which would bind to immobilized DNA polymerase and to initiate the DNA synthesis. In FIG. 2, DNA molecule 202 is ligated with hairpin adapters to form ligated molecule 204. Ligated molecule 204 then forms circularized molecule 206. The molecules without CpG sites can also be sequenced. Circularized molecule 206 includes an unmethylated CpG site 208, which may still be sequenced.

Once the DNA synthesis was initialized, fluorescently dye-labeled nucleotides would be incorporated into the newly synthesized strand by the immobilized polymerase on the basis of a circular DNA template, leading to the emission of optical signals. Because the DNA templates were circularized, the entire circular DNA template would go through the polymerase multiple times (i.e. one nucleotide in a DNA template would be sequenced multiple times). A sequence generated from the process, in which all bases in the circularized DNA template entirely passed through the DNA polymerase, is called a subread. One molecule in a ZMW would generate multiple subreads because the polymerase can continue around the entire circular DNA template multiple times. In one embodiment, a subread may only contain a subset of the sequence, base modifications or other molecular information of the circular DNA template because, in one embodiment, of the existence of sequencing errors.

Figure 3:
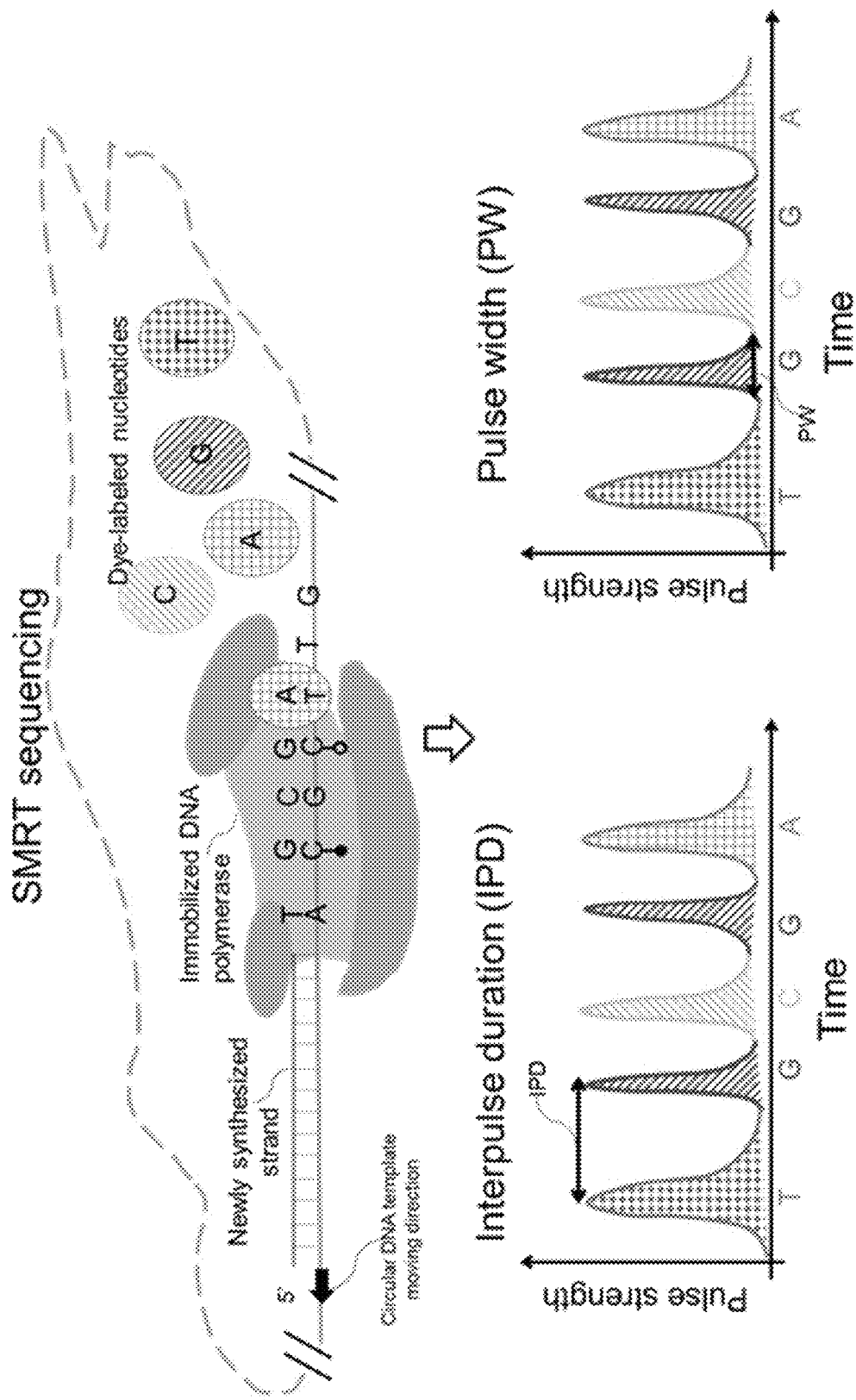
FIG. 3 illustrates interpulse durations and pulse width according to embodiments of the present invention.

As illustrated in FIG. 3, the arrival times and durations of the resultant fluorescence pulses would allow one to measure the polymerase kinetics. The interpulse duration (IPD) is a metric for the length of a time period between two emission pulses each of which would be suggestive of an incorporated fluorescently labeled nucleotide in a nascent strand (FIG. 3). As shown in FIG. 3, the pulse width (PW) is another metric, reflecting polymerase kinetics, in association with the duration of the pulses related to a base call. PW could be the duration of the pulse at 0% of the height of signal peak (i.e., fluorescent intensity of dye-labeled nucleotide as incorporated). In one embodiment, PW could be defined by, for example, but not limited to, the duration of the pulse at 5%, 10%, 20%, 30%, 40%, 50%, 60%, 70%, 80%, or 90% of the height of signal peak. In some embodiments, the PW may be the area under the peak divided by the height of the signal peak.

Such polymerase kinetics such as IPDs have been shown to be affected by base modifications such as N6-methyladenine (6 mA), 5-methylcytosine (5mC) and 5-hydroxymethylcytosine (5hmC) in synthetic and microbial sequences (e.g. E. coli) (Flusberg et al., 2010). Flusberg et al. 2010 did not use sequence context and IPD as independent inputs to detect a modification, which resulted in a model that lacked practically meaningful accuracy for detection. Flusberg et al. only used sequence context to confirm 6 mA occurred in GATC. Flusberg et al. is silent as to using sequence context in combination with IPD as inputs to detect methylation status.

The weak interruptions conferred on the new base incorporation to the 5-methylcytosine in complementary strands make methylation calling extremely challenging even for relatively simple microbial genomes when using IPD signals only, as it was reported that the detection of methylation motif C$^m$CWGG was only ranged from 1.9% to 4.3% (Clark et al., 2013). For example, the analytic software package (SMRT Link v6.0.0) provided by Pacific Biosciences is not able to perform 5mC analysis. Furthermore, a previous version of the SMRT Link v5.1.0 required one to use the Tet1 enzyme to convert 5mC to 5-carboxylcytosine (5caC) prior to methylation analysis, since the IPD signals associated with 5caC would be enhanced (Clark et al., 2013). Thus, it is not surprising that there are no studies showing the feasibility of using single molecule, real-time sequencing to analyze native DNA in a genomewide manner for the human genome.

II. Measurement Window Patterns and Machine Learning Models

Techniques to detect modifications in bases without enzymatic or chemically converting the modification and/or the base are desired. As described herein, modifications in a target base may be detected using kinetic feature data obtained from single molecule, real-time sequencing for bases surrounding the target base. Kinetic features may include interpulse duration, pulse width, and sequence context. These kinetic features may be obtained for a measurement window of a certain number of nucleotides upstream and downstream of the target base. These features (e.g., at particular locations in the measurement window) can be used to train a machine learning model. As an example of the sample preparation, the two strands of a DNA molecule may be connected by hairpin adapters, thereby forming a circular DNA molecule. The circular DNA molecule allows for kinetic features to be obtained for either or both of the Watson and Crick strands. A data analysis framework can be developed based on the kinetic features in the measurement windows. This data analysis framework may then be used to detect modifications, including methylation. The section describes various techniques for detecting modifications.

A. Using Single Strand

Figure 4:
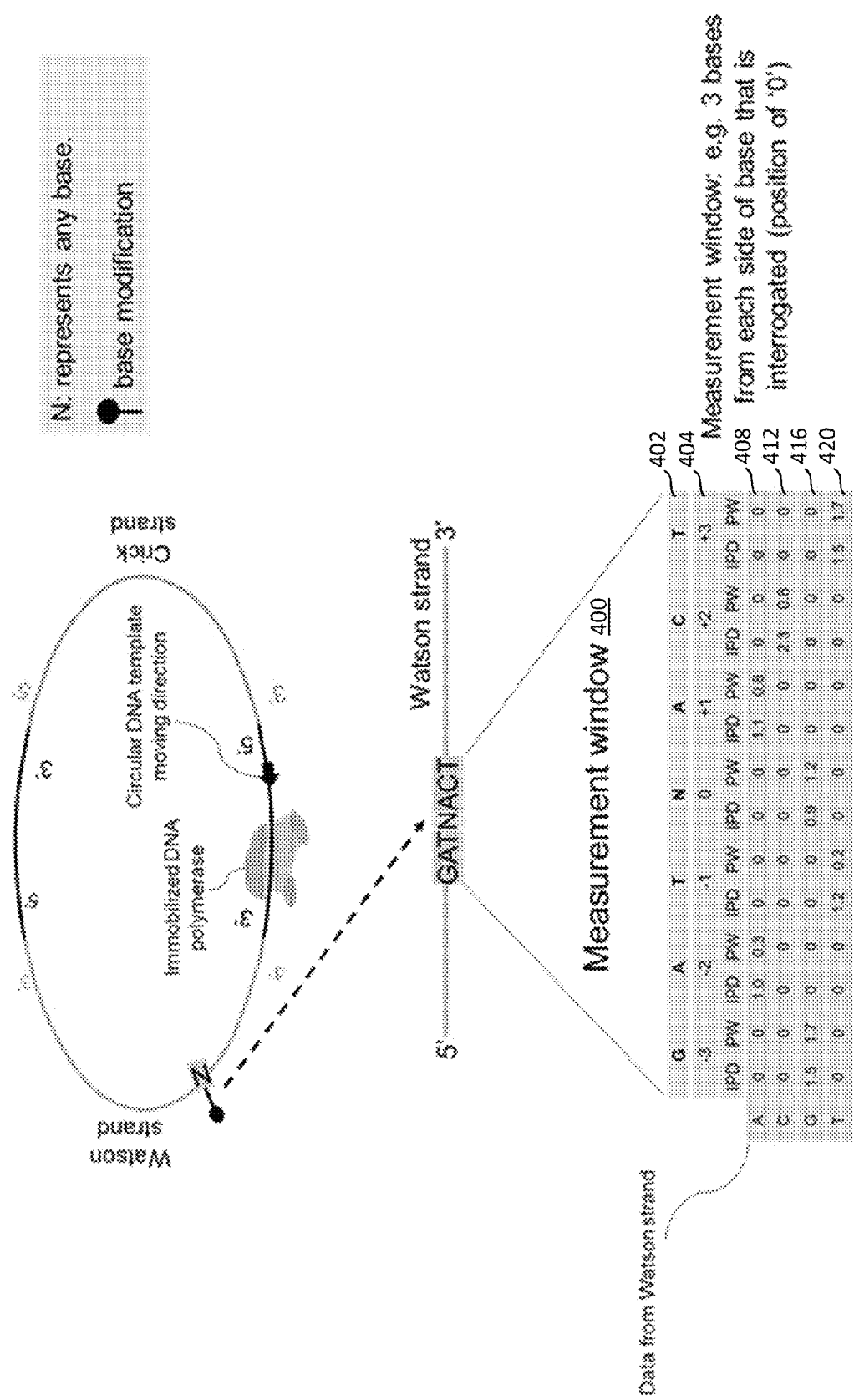
FIG. 4 shows an example of a measurement window of the Watson strand of DNA for detecting a base modification according to embodiments of the present invention.

As shown in FIG. 4, as an example, we obtained the subreads of the Watson strand from Pacific Biosciences SMRT sequencing to analyze one particular base regarding the states of base modifications. In FIG. 4, the 3 bases from each side of a base that was subjected to base modification analysis would be defined as a measurement window 400. In one embodiment, sequence context, IPDs, and PWs for these 7 bases (i.e. 3-nucleotide (nt) upstream and downstream sequence and one nucleotide for base modification analysis) were compiled into a 2-dimensional (i.e. 2-D) matrix as a measurement window. In the example shown, the measurement window 400 is for one subread of the Watson strand. Other variations are described herein.

The first row 402 of the matrix indicated the sequence that was studied. In the second row 404 of the matrix, the position of 0 represented the base for base modification analysis. The relative positions of −1, −2, and −3 indicated the position 1-nt, 2-nt, and 3-nt, respectively, upstream of the base that was subjected to base modification analysis. The relative positions of +1, +2, and +3 indicated the position 1-nt, 2-nt and 3-nt, respectively, downstream of the base that was subjected to base modification analysis. Each position includes 2 columns, which contain the corresponding IPD and PW values. The following 4 rows (rows 408, 412, 416, and 420) corresponded to 4 types of nucleotides (A, C, G, and T) in the strand (e.g. Watson strand), respectively. The presence of IPD and PW values in the matrix depended on which corresponding nucleotide type was sequenced at a particular position. As shown in FIG. 4, at the relative position of 0, the IPD and PW values were shown in the row indicating 'G' in the Watson strand, suggesting that a guanine was called in the sequence result at that position. The other grids in a column that did not correspond to a sequenced base would be coded as '0'. As an example, the sequence information corresponding to the 2-D digital matrix (FIG. 4) would be 5'-GATGACT-3' for the Watson strand.

Figure 5:
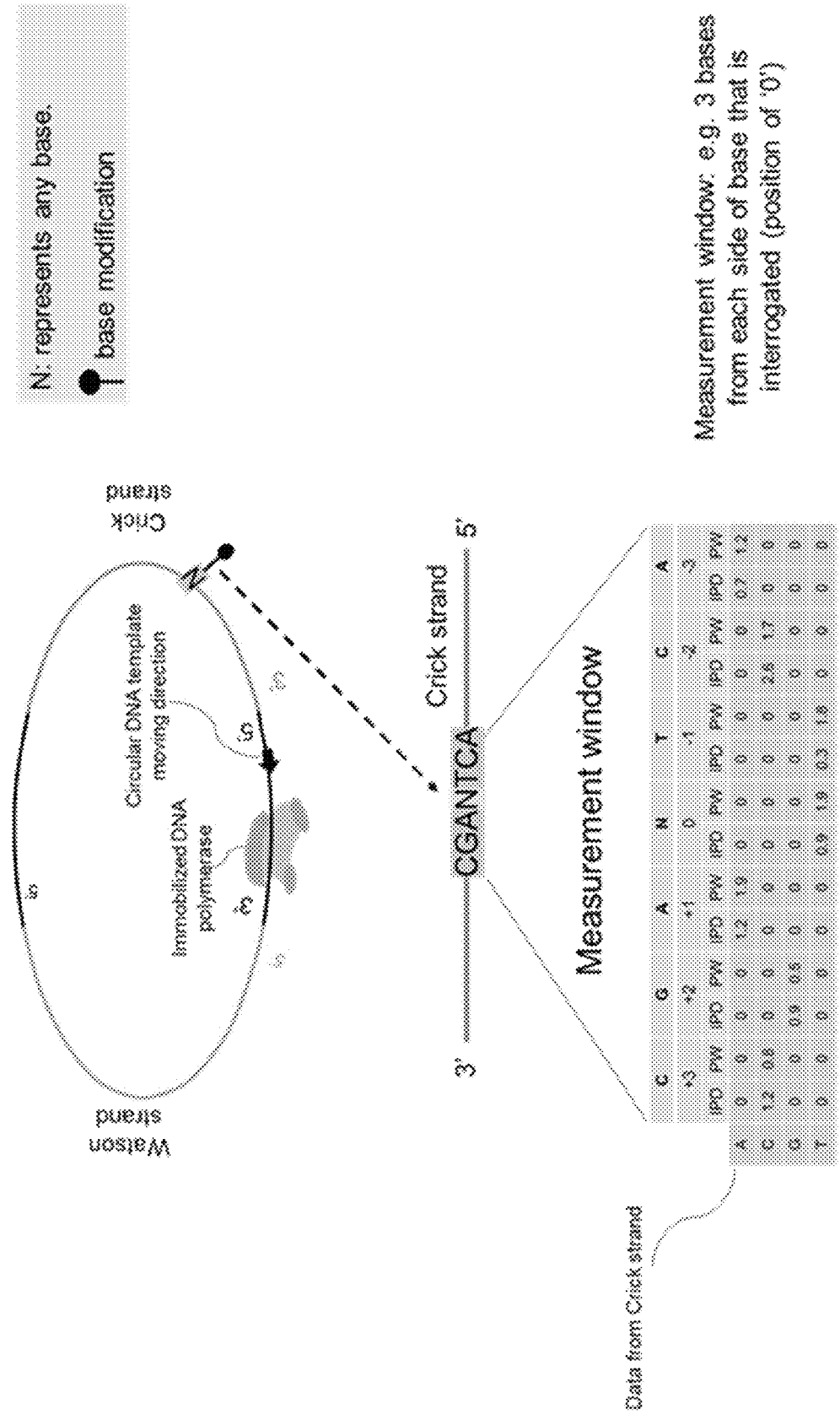
FIG. 5 shows an example of a measurement window of the Crick strand of DNA for detecting a base modification according to embodiments of the present invention.

As shown in one embodiment depicted in FIG. 5, the measurement window could be applied to data from the Crick strand. We obtained the subreads of the Crick strand from single molecule, real-time sequencing to analyze one particular base regarding the states of base modifications. In FIG. 5, the 3 bases from each side of a base that was subjected to base modification analysis and the base subjected to base modification analysis would be defined as a measurement window. In one embodiment, sequence context, IPDs, PWs for these 7 bases (i.e. 3-nucleotide (nt) upstream and downstream sequence and one nucleotide for base modification analysis) were compiled into a 2-dimensional (i.e. 2-D) matrix as a measurement window. The first row of the matrix indicated the sequence that was studied. In the second row of the matrix, the position of 0 represented the base for base modification analysis. The relative positions of −1, −2, and −3 indicated the position 1-nt, 2-nt and 3-nt, respectively, upstream of the base that was subjected to base modification analysis. The relative positions of +1, +2, and +3 indicated the position 1-nt, 2-nt and 3-nt, respectively, downstream of the base that was subjected to base modification analysis. Each position includes 2 columns, which contained the corresponding IPD and PW values. The following 4 rows corresponded to 4 types of nucleotides (A, C, G, and T) in this strand (e.g. the Crick strand). The presence of IPD and PW values in the matrix depended on which corresponding nucleotide type was sequenced at a particular position. As shown in FIG. 5, at the relative position of 0, the IPD and PW values were shown in the row indicating 'T' in the Crick strand, suggesting that a thymine was called in the sequence result at that position. The other grids in a column that did not correspond to a sequenced base would be coded as '0'. As an example, the sequence information corresponding to the 2-D digital matrix (FIG. 5) would be 5'-ACTTAGC-3' for the Crick strand.

B. Using Both Watson and Crick Strands

Figure 6:
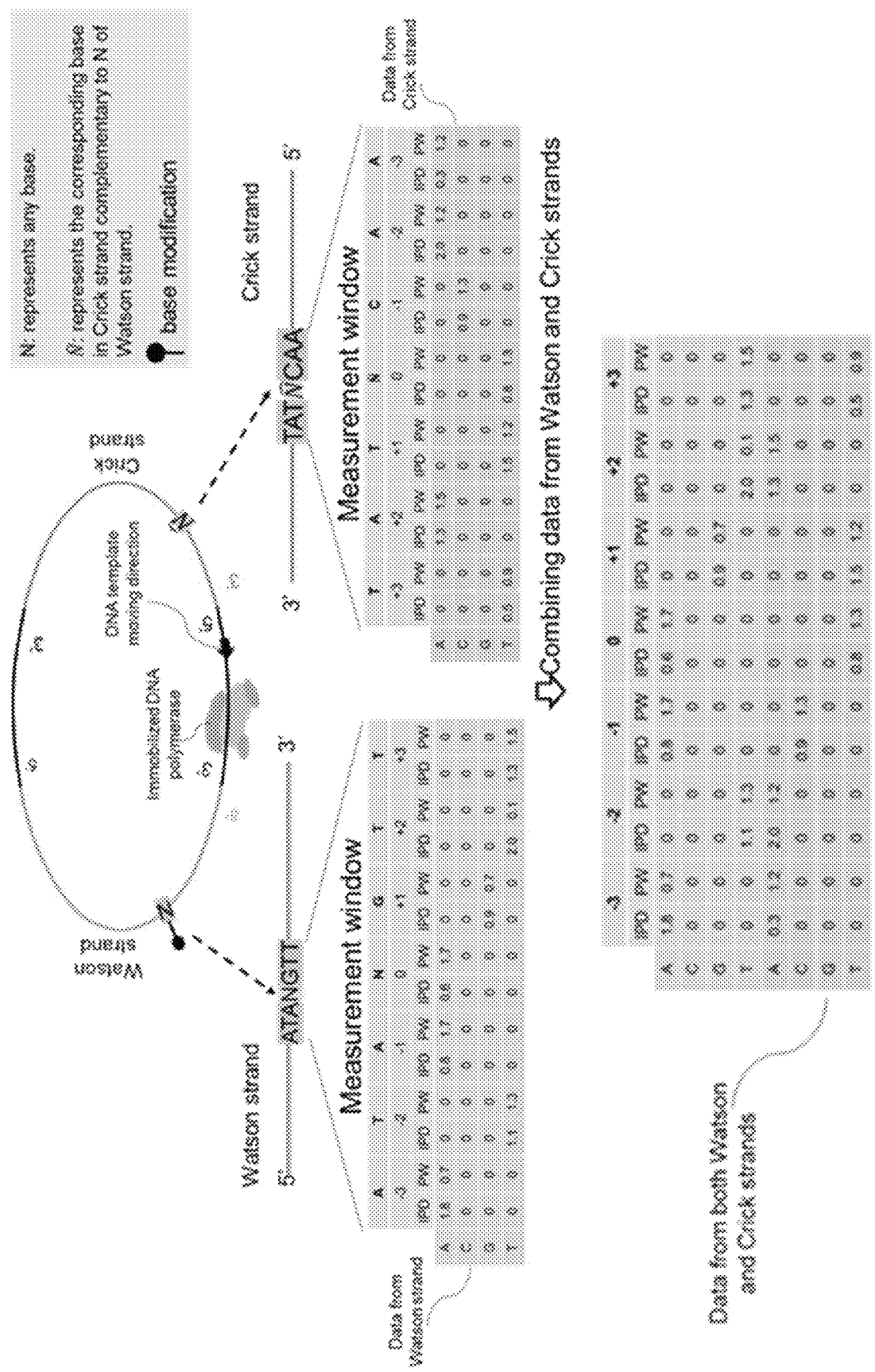
FIG. 6 shows an example of a measurement window by combining data from the Watson strand of DNA and its complementary Crick strand for detecting any base modification according to embodiments of the present invention.

FIG. 6 shows an embodiment where the measurement window could be implemented in a way that data from the Watson strand and its complementary Crick strand could be combined. As shown in FIG. 6, we obtained the subreads of the Watson and Crick strands from single molecule, real-time sequencing to analyze one particular base for modifications. In one embodiment, the measurement window from the Crick strand of the circular DNA template was complementary to the measurement window from the Watson strand, which was subjected to base modification analysis. In FIG. 6, the 3 bases from each side of the first base in the Watson strand that was subject to base modification analysis and the first base would be defined as the first measurement window. The 3 bases from each side of the second base in the Crick strand and the second base would be defined as the second measurement window. The second base was complementary to the first base. In one embodiment, the sequence context, IPDs, PWs for these 7 bases (i.e. 3-nucleotide (nt) upstream and downstream sequence and one nucleotide for base modification analysis) from the Watson and Crick strands were compiled into a 2-dimensional (i.e. 2-D) matrices. These measurement windows from the Watson and Crick strands were considered as the first and second measurement windows, respectively.

The first row of the matrix of the Watson and Crick strands indicated the sequence that was studied. In the second row of the matrix of the Watson strand, the position of 0 represented the first base for base modification analysis. The position of 0 shown in the second row of the matrix of the Crick strand represented the second base complementary to the first base. The relative positions of −1, −2, and −3 indicated the position 1-nt, 2-nt, and 3-nt, respectively, upstream of the first and second bases. The relative positions of +1, +2, and +3 indicated the position 1-nt, 2-nt, and 3-nt, respectively, downstream of the first and second bases. Each position derived from the Watson and Crick strands would correspond to 2 columns which contained the corresponding IPD and PW values. The following 4 rows in the matrices of the Watson and Crick strands corresponded to 4 types of nucleotides (A, C, G, and T) in the specific strand (e.g., the Crick strand), respectively. The presence of IPD and PW values in the matrix depended on which corresponding nucleotide type was sequenced at a particular position.

As shown in FIG. 6, at the relative position of 0, the IPD and PW values were shown in the row indicating 'A' in the Watson strand and 'T' in the Crick strand, suggesting that an adenine and thymine were called in the sequence result at that position of the Watson and Crick strands, respectively. The other grids in a column that did not correspond to sequenced base would be coded as '0'. As an example, the sequence information corresponding to the 2-D digital matrix of the Watson strand (FIG. 6) would be 5'-ATAAGTT-3'. The sequence information corresponding to the 2-D digital matrix of the Crick strand (FIG. 6) would be 5'-AACTTAT-3'.

As shown in this example, data from the Watson and Crick strands can be combined to form a new matrix, which may also be considered as a measurement window. This new matrix can be used as a single sample that is used to train a machine learning model. Thus, all of the values in the new matrix can be treated as separate features, although the particular placement in the 2D matrix can have an impact, e.g., when a convolutional neural network (CNN) is used. The sequence context at the various positions for the different strands can be conveyed via the non-zero entries in the matrix.

Figure 7:
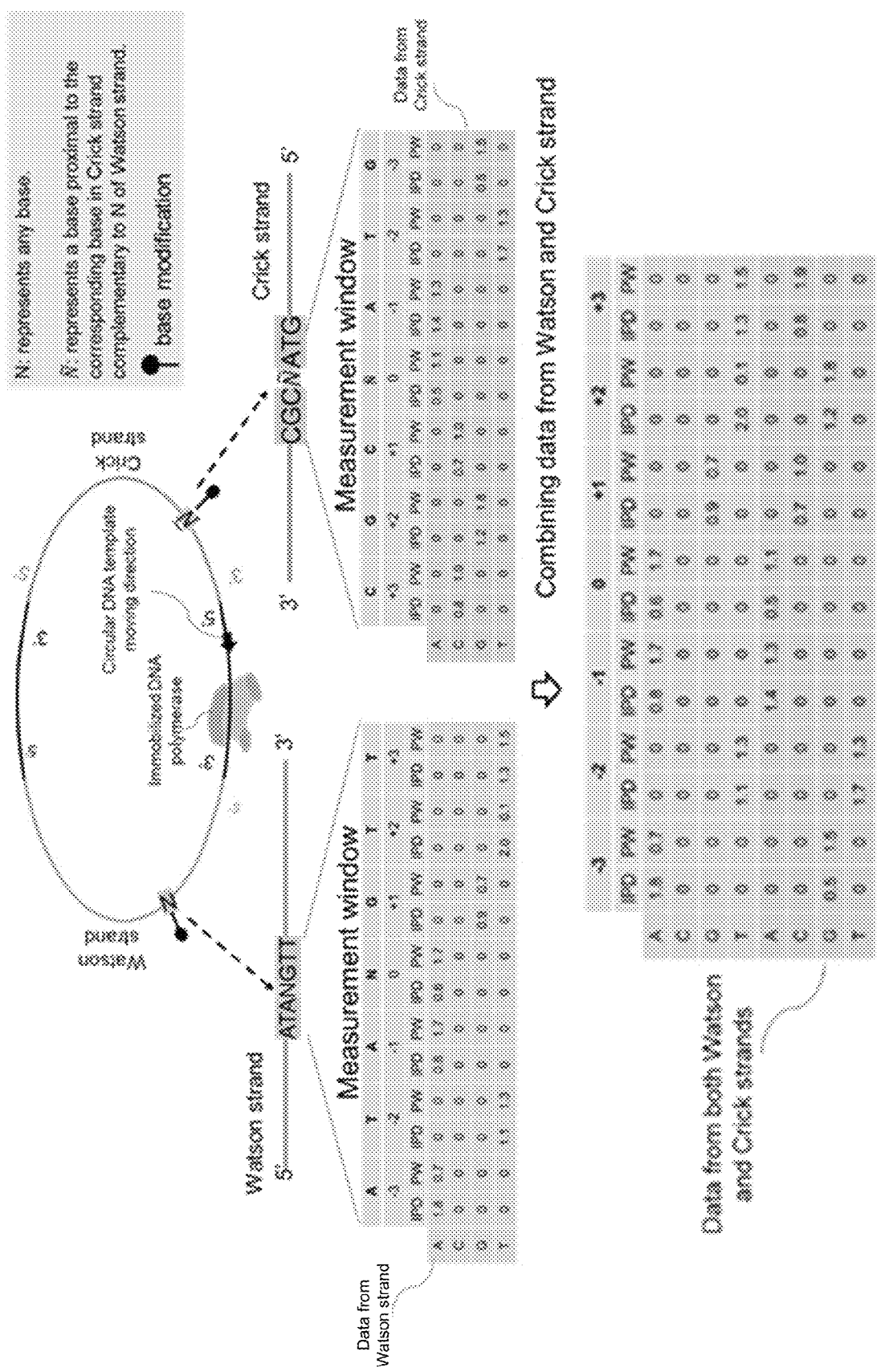
FIG. 7 shows an example of a measurement window by combining data from the Watson strand of DNA and its nearby region's Crick strand for detecting any base modification according to embodiments of the present invention.

FIG. 7 shows that the measurement window could be implemented in a way that data from the Watson and Crick strands are not the positions exactly complementary to each other. As shown in FIG. 7, the first measurement window was 5'-ATAAGTT-3'; and the second measurement window was 5'-GTAACGC-3'. In some embodiments, the Watson and Crick strands may be shifted from each other so that the positions are not complementary.

Figure 8:
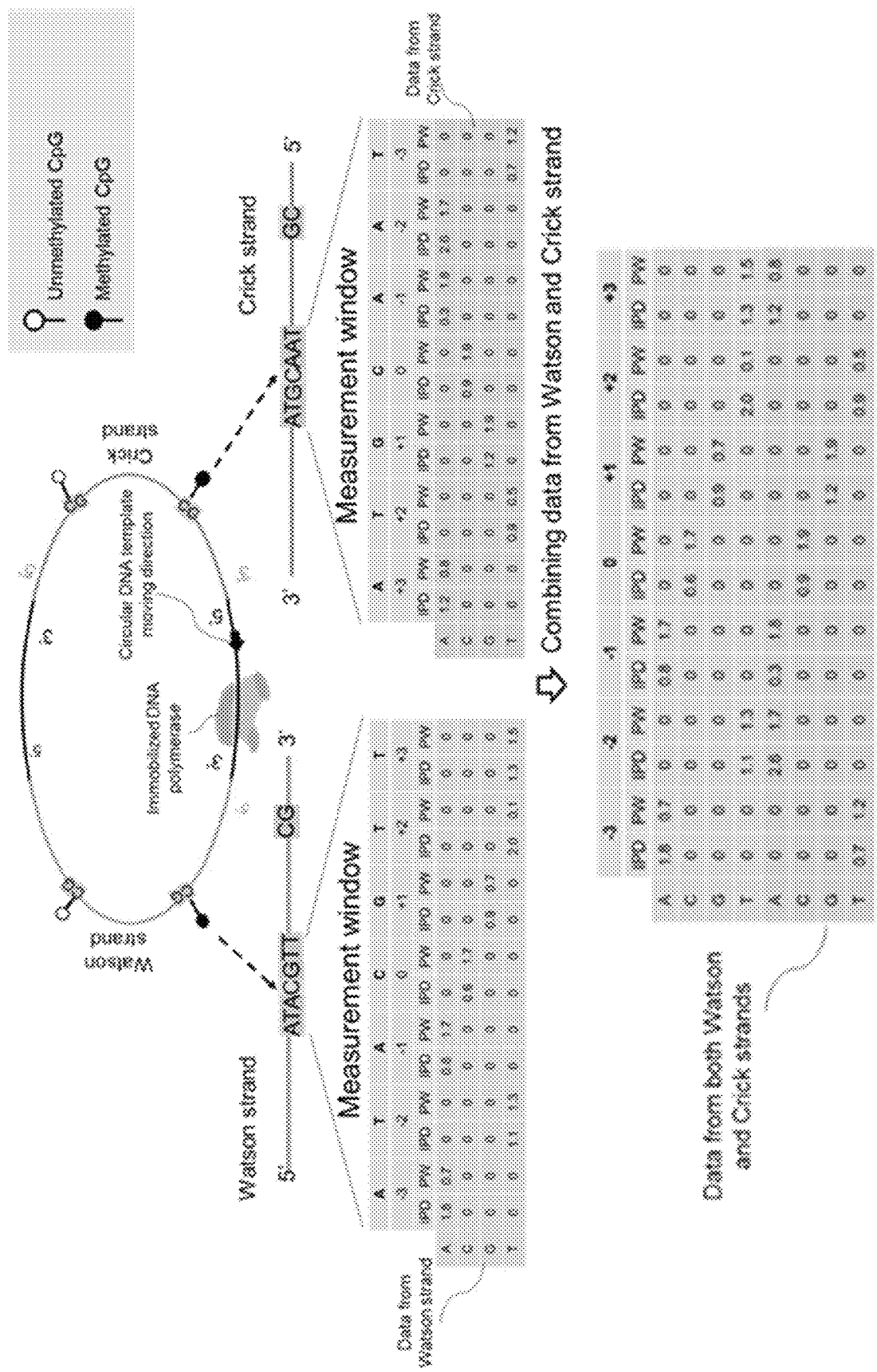
FIG. 8 shows examples of measurement windows of the Watson strand, the Crick strand, and both strands for determining methylation states at CpG sites according to embodiments of the present invention.

FIG. 8 shows that a measurement window could be used to analyze the methylation states at CpG sites. The position of 0 corresponds to the cytosine of the CpG site, and thus there is a shift by one position between the two strands, so that the C is at the 0 position for both strands. Accordingly, only a portion of the sequences included in the measurement window from the Watson and Crick strands are complementary to each other. In other embodiments, all of the sequences in the measurement window from the Watson and Crick strands can be complementary to each other. In yet other embodiments, none of the sequences in the measurement window from the Watson and Crick strands are complementary to each other.

In one embodiment, for a measurement window, the length of DNA stretch surrounding a base that was subjected to base modification analysis could be asymmetrical. For example, X-nt upstream and Y-nt downstream of that base could be used for base modification analysis. X could include, but is not limited to, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 300, 400, 500, 1000, 2000, 4000, 5000, and 10000; Y could include, but was not limited to, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 300, 400, 500, 1000, 2000, 4000, 5000, and 10000.

C. Training Models and Detecting Modifications

Figure 9:
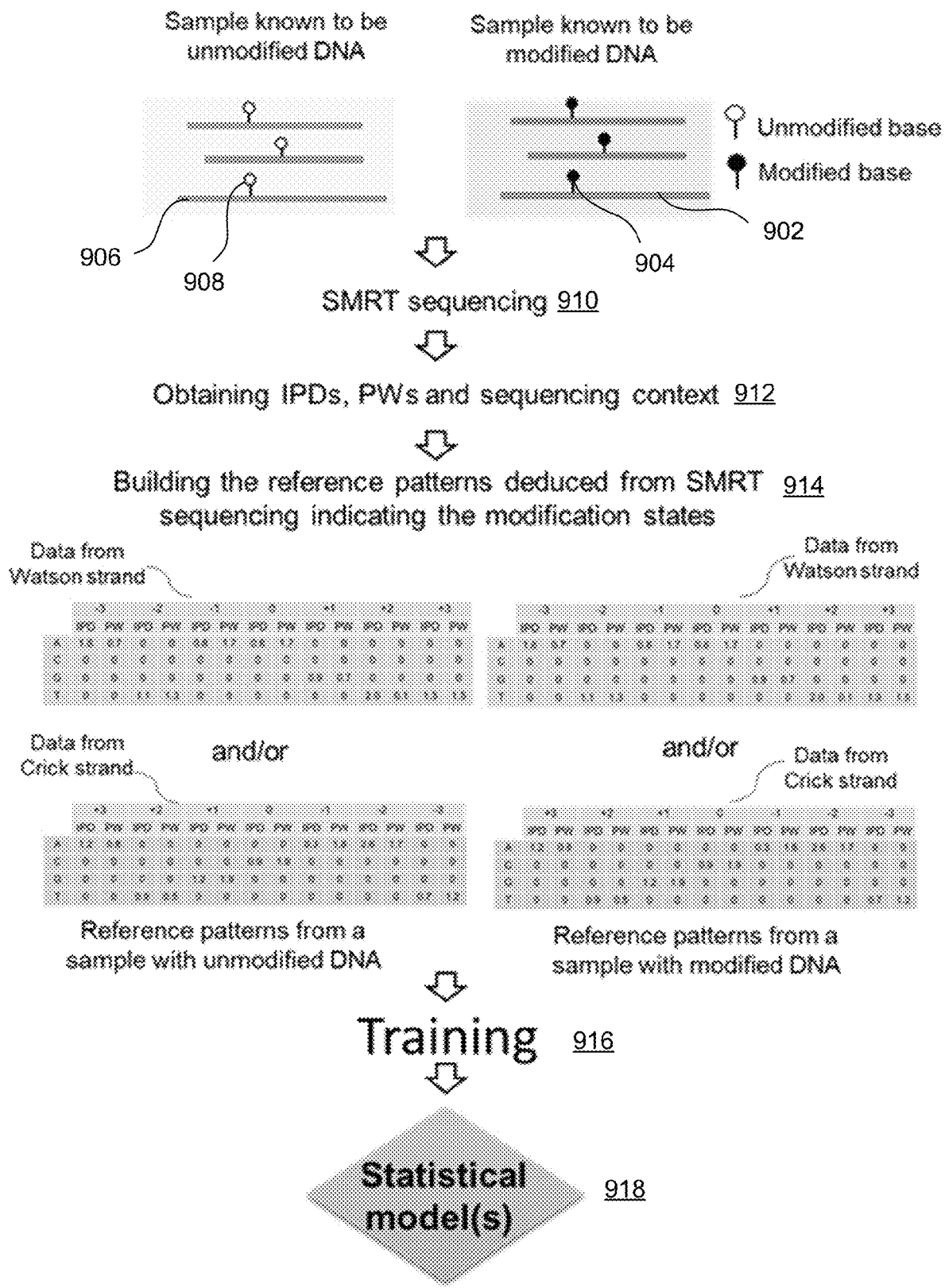
FIG. 9 shows a general procedure of constructing analytical, computational, mathematical, or statistical models for classifying base modifications according to embodiments of the present invention.

FIG. 9 shows a general procedure as to how to use the measurement window to determine any base modifications. DNA samples known to be unmodified and modified were subjected to single molecule, real-time sequencing. The modified DNA (e.g., modified molecule 902) means that the base (e.g., base 904) has the modification (e.g., methylation) at the site. The unmodified DNA (e.g., unmodified molecule 906) means that the base (e.g., base 908) does not have the modification at the site. Both sets of DNA can be artificially created or processed to form the modified/unmodified DNA.

At stage 910, the samples can then undergo single molecule, real-time sequencing. As part of SMRT sequencing, circular molecules could be sequenced multiple times by passing through the immobilized DNA polymerase repeatedly. The sequence information obtained from each time would be deemed as a subread. Thereby, one circular DNA template would generate multiple subreads. The sequencing subreads can be aligned to a reference genome using, for example but not limited to, BLASR (Mark J Chaisson et al, BMC Bioinformatics. 2012; 13: 238). In various other embodiments, BLAST (Altschul S F et al, J Mol Biol. 1990; 215(3):403-410), BLAT (Kent W J, Genome Res. 2002; 12(4):656-664), BWA (Li H et al, Bioinformatics. 2010; 26(5):589-595), NGMLR (Sedlazeck F J et al, Nat Methods. 2018; 15(6):461-468), LAST (Kielbasa S M et al, Genome Res. 2011; 21(3):487-493) and Minimap2 (Li H, Bioinformatics. 2018; 34(18):3094-3100) could be used for aligning subreads to a reference genome. The alignment can allow the data from multiple subreads to be combined (e.g., averaged) as the data in each subread for the same position can be identified.

At stage 912, from the alignment result, IPDs, PWs, and sequence context surrounding a base that was subjected to base modification analysis were obtained. At stage 914, the IPDs, PWs, and sequence context were recorded in a certain structure, for example but not limited to, 2-D matrix as shown in FIG. 9.

At stage 916, a number of 2-D matrices containing the reference kinetic patterns derived molecules with known base modifications were used to train the analytical, computational, mathematical, or statistical model(s). At stage 918, a statistical model is developed resulting from the training. For simplicity, FIG. 9 shows only a statistical model developed by training, but any model or data analysis framework can be developed. Example data analysis frameworks include machine learning models, statistical models, and mathematical models. The statistical models could include, but was not limited to, linear regression, logistic regression, deep recurrent neural network (e.g., long short-term memory, LSTM), Bayes classifier, hidden Markov model (HMM), linear discriminant analysis (LDA), k-means clustering, density-based spatial clustering of applications with noise (DBSCAN), random forest algorithm, and support vector machine (SVM). A DNA stretch surrounding a base that was subjected to base modification analysis could be X-nt upstream and Y-nt downstream of that base, namely "measurement window."

The data structures can be used in a training process, as the correct outputs (i.e., modification state) are known. For example, the IPDs, PWs, and sequence context corresponding to 3-nt upstream and downstream of a base from the Watson and/or Crick strand(s) can be used for constructing the 2-D matrix to be used to train the statistical model(s) for classifying base modifications. In this manner, the training can provide a model that can classify a base modification at a position of a nucleic acid with a previously known status.

Figure 10:
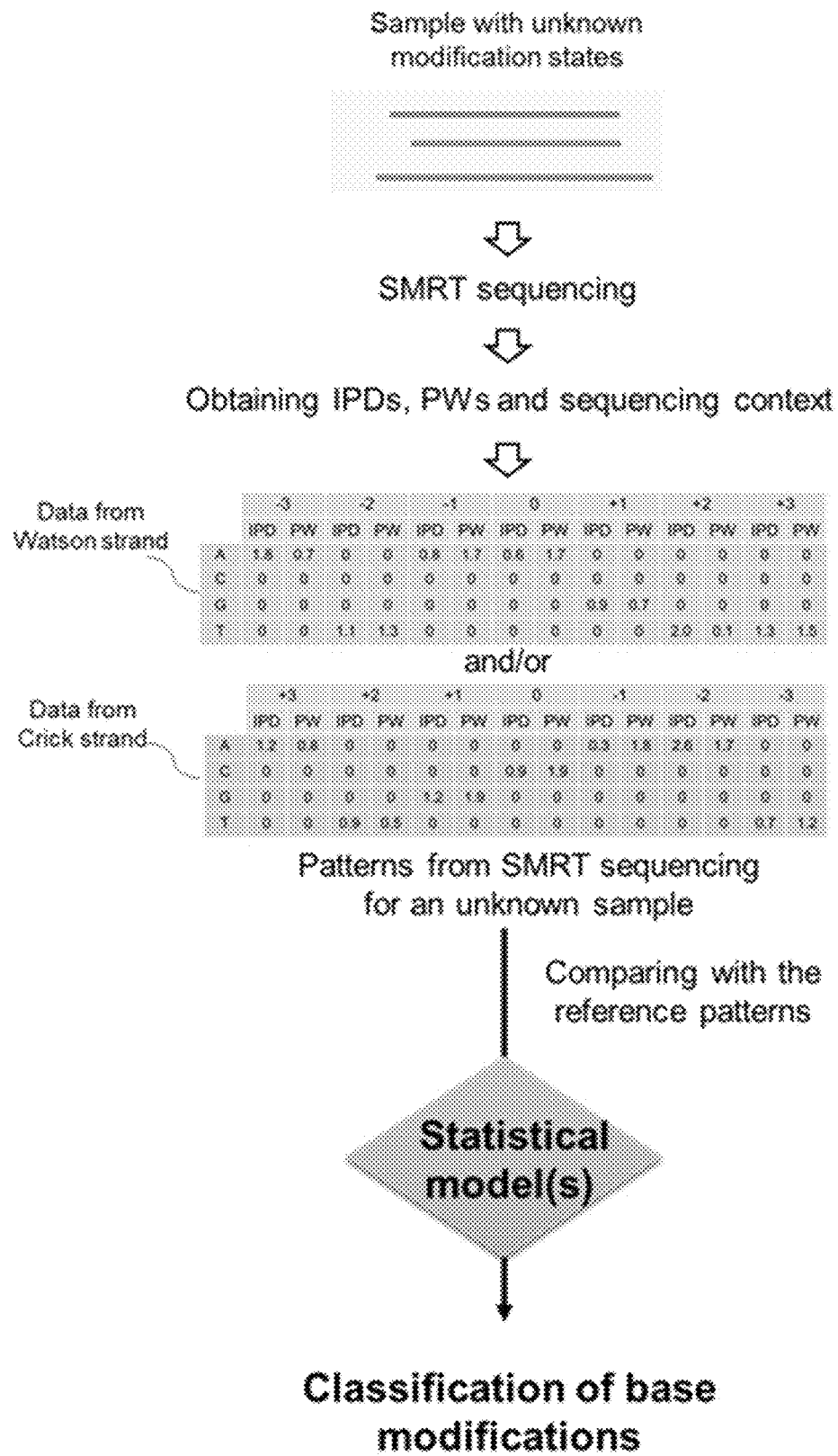
FIG. 10 shows a general procedure of classifying base modifications according to embodiments of the present invention.

FIG. 10 shows a general procedure as to how the statistical model(s) learned from DNA samples that carried known states of base modifications can detect base modifications. A sample with unknown states of base modifications was subjected to SMRT sequencing. The sequencing subreads were aligned to a reference genome using, for example, the techniques mentioned above. In addition or instead, the subreads can be aligned to each other. Yet other embodiments can use just one subread or analyze them independently such that alignment is not performed.

For a base that was subjected to base modification analysis, one would obtain IPDs, PWs, and sequence context from the Watson and/or Crick strand(s) in the alignment results using a comparable measurement window as used in the training step (FIG. 9), and was associated with that base. In another embodiment, the measurement windows between training and testing procedures would be different. For example, the size of the measurement windows between training and testing procedures might be different. Those IPDs, PWs, and sequence context would be transformed into a 2-D matrix. Such 2-D matrix of a testing sample would be compared with the reference kinetic features to determine base modifications. For example, the 2-D matrix of a testing sample can be compared with reference kinetic features through the statistical model(s) that were learned from the training samples, so that the base modifications at sites in nucleic acid molecules in a testing sample could be determined. The statistical models could include, but was not limited to, linear regression, logistic regression, deep recurrent neural network (e.g., long short-term memory, LSTM), Bayes classifier, hidden Markov model (HMM), linear discriminant analysis (LDA), k-means clustering, density-based spatial clustering of applications with noise (DB-SCAN), random forest algorithm, and support vector machine (SVM).

Figure 11:
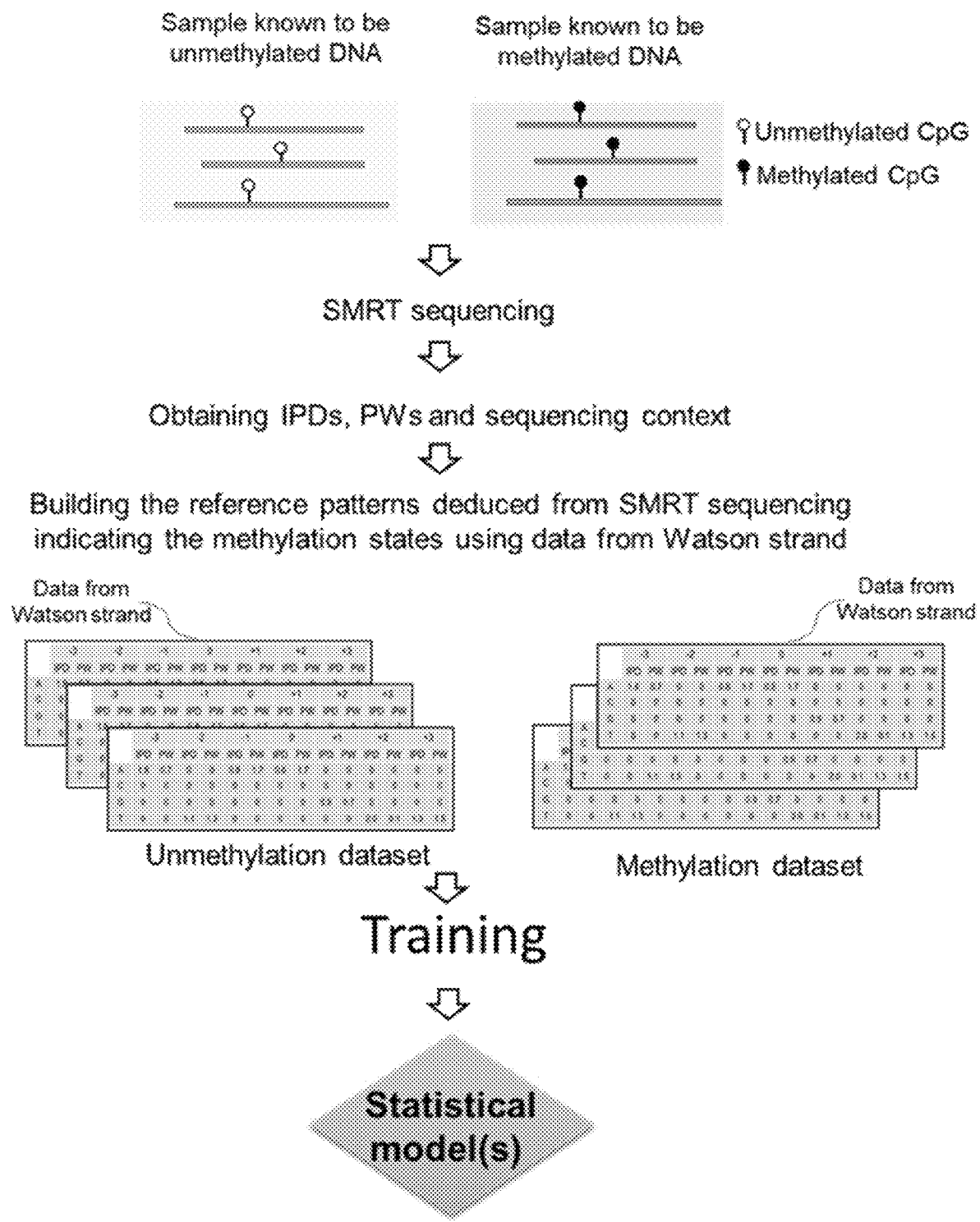
FIG. 11 shows a general procedure of constructing the analytical, computational, mathematical, or statistical models for classifying methylation states at CpG sites using samples with known methylation states of the Watson strand according to embodiments of the present invention.

FIG. 11 shows a general procedure as to how the method could be made for classifying methylation states at CpG sites. DNA samples known to be unmethylated and methylated at CpG sites were subjected to single molecule, real-time sequencing. The sequencing subreads were aligned to a reference genome. Watson strand data were used.

From the alignment result, IPDs, PWs, and sequence context surrounding a cytosine at a CpG site that was subjected to methylation analysis were obtained and recorded in a certain structure, for example but not limited to, 2-D matrix as shown in FIG. 11. A number of 2-D matrices containing the reference kinetic patterns derived molecules with known methylation states were used to train the statistical model(s). A stretch of DNA surrounding a base under interrogation could be X-nt upstream and Y-nt downstream of that base, namely the "measurement window." X could include, but is not limited to, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 300, 400, 500, 1000, 2000, 4000, 5000, and 10000; Y could include, but is not limited to, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 300, 400, 500, 1000, 2000, 4000, 5000, and 10000. In one embodiment, IPDs, PWs, and sequence context corresponding to 3-nt upstream and downstream of a base from the Watson strand could be used for constructing the 2-D matrix that was used to train the statistical model(s) to classify base modifications.

Figure 12:
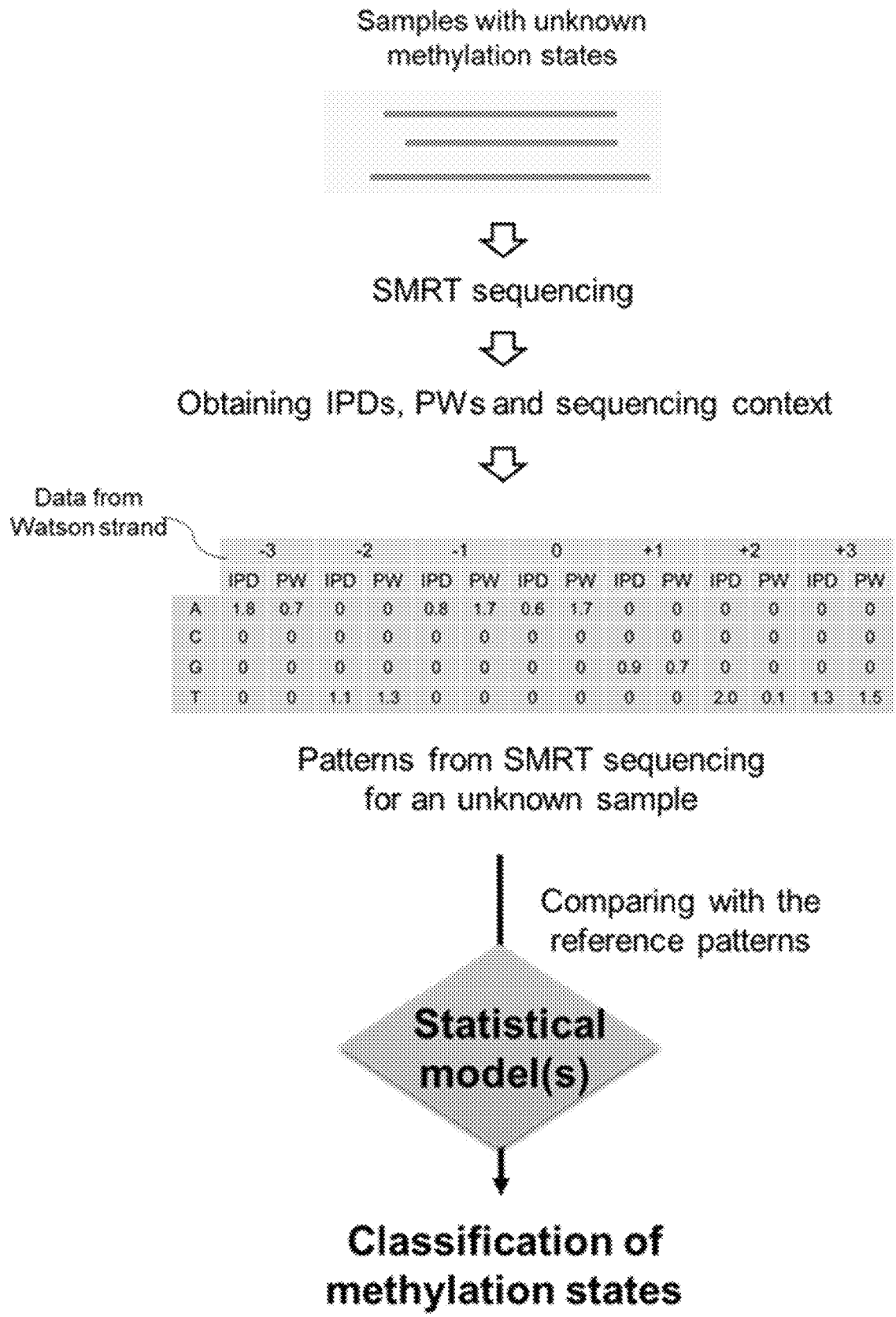
FIG. 12 shows a general procedure of classifying methylation states of the Watson strand for an unknown sample according to embodiments of the present invention.

FIG. 12 shows a general procedure of classifying methylation states of an unknown sample. A sample with unknown methylation states was subject to single molecule, real-time sequencing. The sequencing subreads were aligned to a reference genome.

For a cytosine of a CG site in the alignment result, one would obtain IPDs, PWs, and sequence context from the Watson strand using a comparable measurement window which was applied in the training step (FIG. 11), associated with that base whose modification was under interrogation. Those IPDs, PWs, and sequence context can be transformed into a 2-D matrix. Such 2-D matrix of a testing sample would be compared with the reference kinetic patterns illustrated in FIG. 11 to determine methylation states. X11

Figure 13:
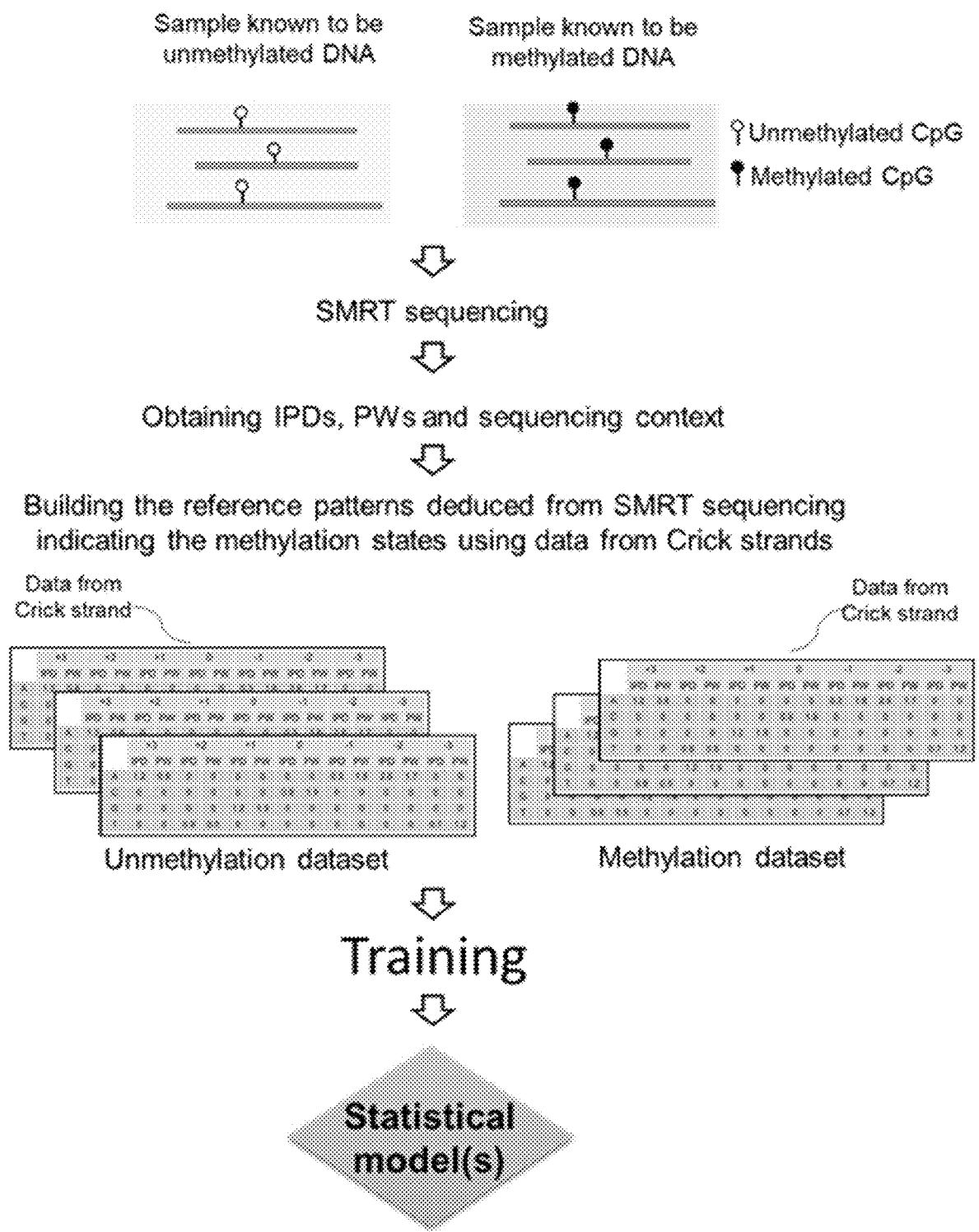
FIG. 13 shows a general procedure of constructing the analytical, computational, mathematical, or statistical models for classifying methylation states at CpG sites using samples with known methylation states of the Crick strand according to embodiments of the present invention.
Figure 14:
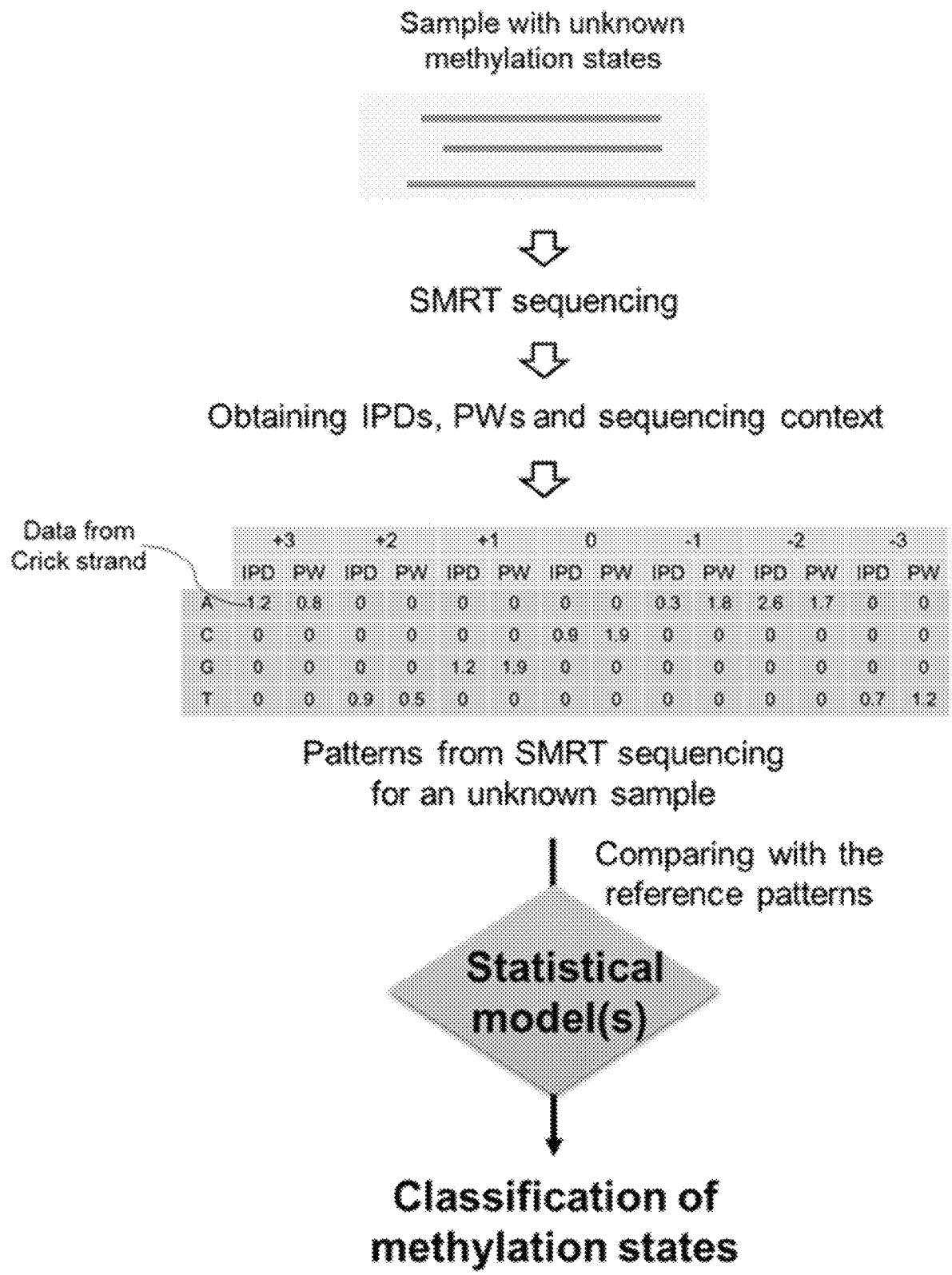
FIG. 14 shows a general procedure of classifying methylation states of the Crick strand for an unknown sample according to embodiments of the present invention.

FIG. 13 and FIG. 14 show that kinetic features from the Crick strand could be used for training and testing procedures as elaborated above, similar to procedures with the Watson strand. The statistical model(s) could be the same or different models. When different models, they could be used to obtain independent classifications, which can be compared, e.g., if they are in agreement then a modification status is identified. If they are not in agreement, then an unclassified status could be identified. When they are the same model, the data can be combined into a single data structure, e.g., the matrix in FIG. 6.

Figure 15:
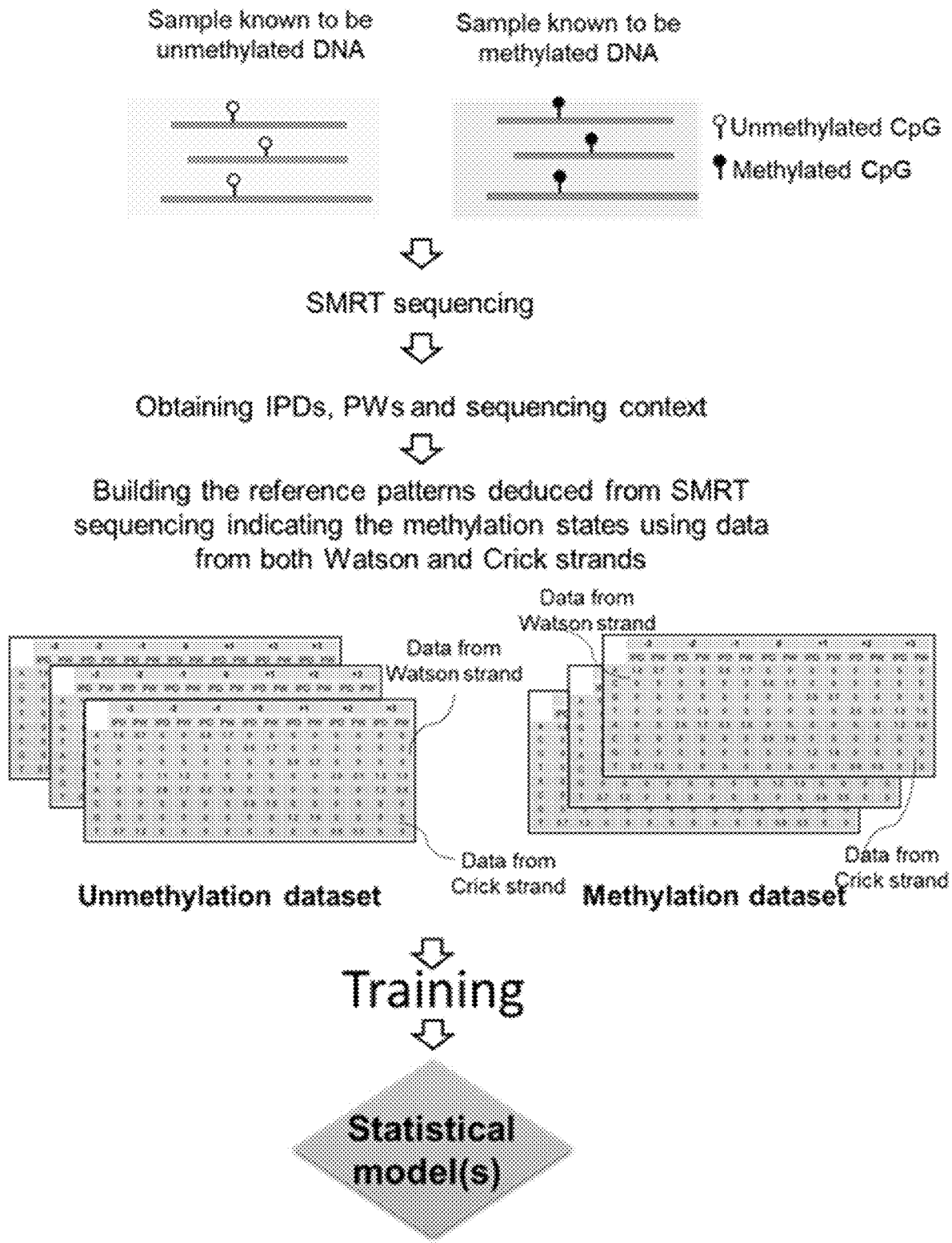
FIG. 15 shows a general procedure of constructing the statistical models for classifying methylation states at CpG sites using samples with known methylation states from both the Watson and Crick strands according to embodiments of the present invention.
Figure 16:
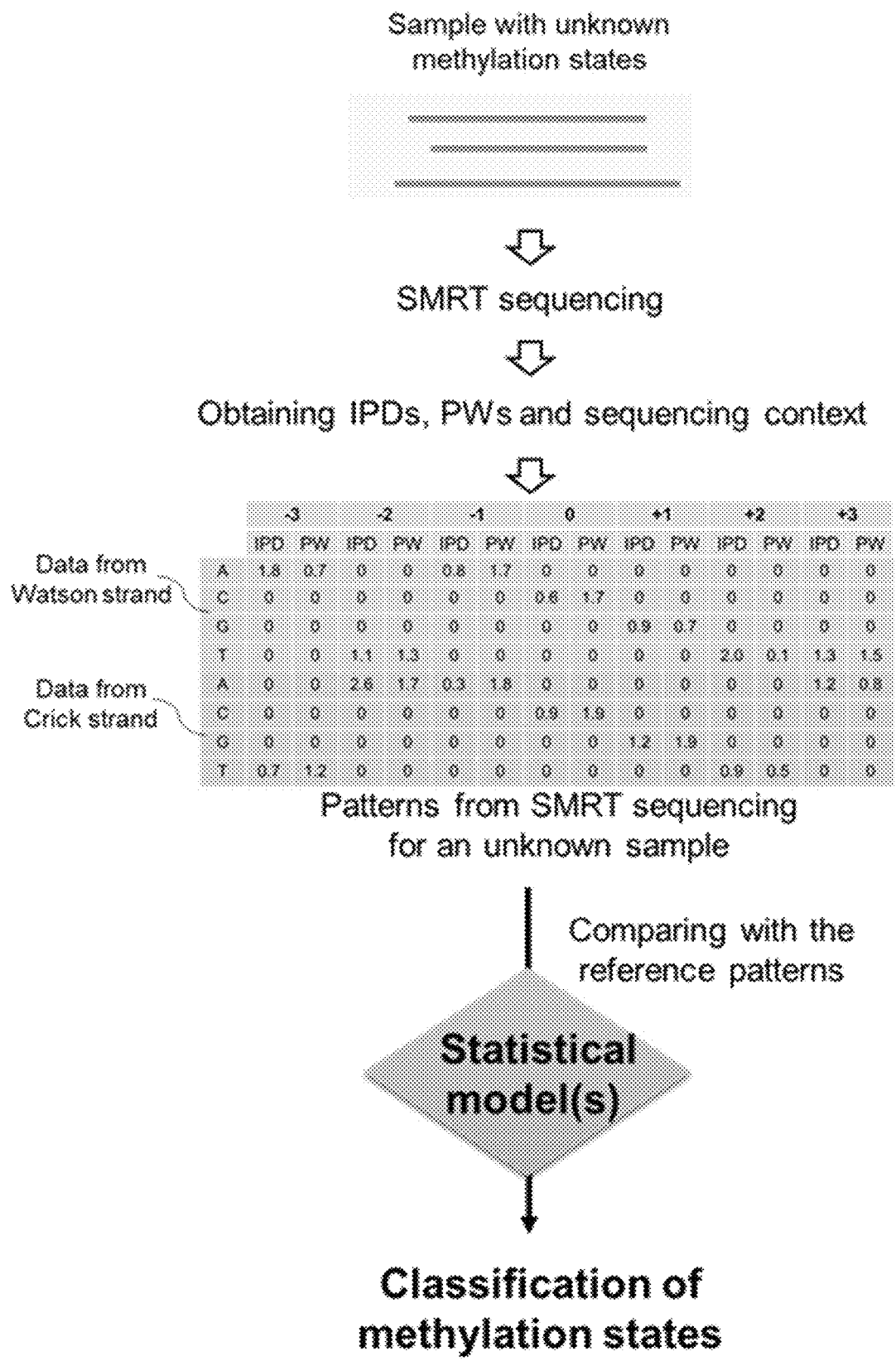
FIG. 16 shows a general procedure of classifying methylation states of an unknown sample from the Watson and Crick strands according to embodiments of the present invention.

FIG. 15 and FIG. 16 show that kinetic features from both the Watson and Crick strands could be used for training and testing procedures as elaborated above. DNA samples known to be unmethylated and methylated at CpG sites were subjected to single molecule, real-time sequencing. The sequencing subreads were aligned to a reference genome, although alignment of the subreads to each other is possible, as can be done for other methods described herein.

For a subread in the alignment result, IPDs, PWs, and sequence context surrounding a cytosine of a CpG site which was subject to methylation analysis were obtained. Because DNA molecules were circularized through the use of two hairpin adaptors (e.g., following a SMRTBell template preparation protocol), the circular molecules could be sequenced more than once, thereby generating multiple subreads of a molecule. The subreads can be used for generating circular consensus sequencing (CCS) reads. In general for all methods described herein, one ZMW could generate multiple subreads but only correspond to one CCS read.

In some embodiments, the fully unmethylated dataset could be created by PCR on human DNA fragments. For example, the fully methylated dataset could be produced through human DNA fragments treated by CpG methyltransferase M.SssI, in which all CpG sites were assumed to be methylated. In other examples, another CpG methyltransferase could be used, such as M.MpeI. In other embodiments, synthetic sequences with known methylation states or pre-existing DNA samples with different methylation levels, or hybrid methylated states creating by restriction enzyme cutting of methylated and unmethylated DNA molecules followed by ligation (which would create a proportion of chimeric methylated/unmethylated DNA molecules) could be used for training the methylation prediction models or classifiers.

The transformation of kinetic patterns, including sequence context, IPD and pulse width (PW), can be a 2-D matrix comprising features from Watson and Crick strands for analyzing methylation sates at CG sites, as illustrated in FIG. 15. This approach allowed us to accurately capture the subtle kinetic changes caused by methylated cytosines as well as its nearby sequence context. As with any of the various methods described herein, for each CpG present in a subread, the measurement window of (e.g., 3-bases upstream and downstream of a cytosine of a CpG site) can be used for subsequent analyses, thus leading to a total of 7 nucleotides (including cytosine of a CpG site) being analyzed together. The IPD and PW for each base among those 7 nucleotides can be calculated. To capture the sequence context attributing to kinetic changes, the IPD and PW signals can be compiled into a particular base call, relative sequencing positions, and the strand information as shown in FIG. 15. Such a data structure is named 2-D digital matrix of kinetics for simplicity.

Such a 2-D digital matrix is analogous to a "2-D digital image". For instance, the first row of the 2-D digital matrix contained the relative positions surrounding a cytosine of a CpG locus that was subjected to methylation analysis, with 3-nt upstream and downstream of that cytosine site. The position of 0 represented the cytosine site whose methylation was to be determined. The relative positions of −1 and −2 indicated the 1-nt and 2-nt upstream of the cytosine that was in question. The relative positions of +1 and +2 indicated the 1-nt and 2-nt downstream of the cytosine that would be used. Each position would correspond to 2 columns which contained the corresponding IPD and PW values. Each row corresponded to the 4 types of nucleotides (A, C, G, and T) in the Watson and Crick strands. The filling of IPD and PW values in the matrix depended on which corresponding nucleotide type was preset in the sequenced result (i.e. subread) at a particular position.

As shown in FIG. 15, at the relative position of 0, the IPD and PW values were shown in the row of 'C' in the Watson strand, suggesting that cytosine was called at that position. The other grids in a column that did not correspond to a sequenced base would be coded as '0'. As an example, the sequence information corresponded the 2-D digital matrix (FIG. 15) would be 5'-ATACGTT-3' and 5'-TAACGTA-3' for the Watson and Crick strands, respectively. In this context, upstream and downstream sequences flanking a cytosine of a CpG site in the Watson and Crick strands would be different. Since the methylation at CpG sites would be symmetrical between the Watson and Crick strands (Lister et al., 2009), the kinetics in both strands were used for training the methylation prediction model in one preferred embodiment. In another embodiment, the Watson and Crick strands might be used for training the methylation prediction model separately.

Considering the high data throughput of single molecule, real-time sequencing, in one embodiment, a deep learning algorithm (e.g. convolutional neural networks (CNN)) (LeCun et al., 1989) may be suited for distinguishing the methylated CpGs from unmethylated CpGs. Other algorithms could also be used in addition or instead, for example, but not limited to, linear regression, logistic regression, deep recurrent neural network (e.g., long short-term memory, LSTM), Bayes classifier, hidden Markov model (HMM), linear discriminant analysis (LDA), k-means clustering, density-based spatial clustering of applications with noise (DBSCAN), random forest algorithm, and support vector machine (SVM), etc. The training can used the Watson and Crick strands separately or in a combined new matrix, as described in FIGS. 6-8.

Another transformation of kinetic patterns could be a N-dimensional matrix. N could, for example, be 1, 3, 4, 5, 6, and 7. For example, the 3-D matrix would be a stack of 2-D matrices stratified according to the number of tandem CG sites for a DNA stretch being analyzed, in which the $3^{rd}$ dimension would be the number of tandem CG sites in that DNA stretch. The pulse strength or pulse magnitude (e.g. measured by the peak height of a pulse, or by the area under the pulse signal) might be also incorporated into a matrix in some embodiments. The pulse strength (a metric for the amplitude of the pulse peak, FIG. 3) could be either added to an extra column adjacent to columns in association with PW and IPD values on top of the original 2-D matrix, or added to a $3^{rd}$ dimension to form a 3-D matrix.

As further examples, a 2D matrix of 8(row)×21(column) can be transformed into a 1-D matrix (i.e. vector) comprising 168 elements. And we can scan this 1-D matrix, e.g., to perform CNN or other modeling. As another example, methods can split an 8×21 2-D matrix to multiple smaller matrices, e.g., two 4×21 2-D matrices. Putting these two smaller matrices together in a vertical direction provides a 3-D matrix (i.e. x=21, y=4, z=2). Methods can scan the 1st 2-D matrix and then the 2nd 2-D matrix, to form the data presentation for machine learning. The data can be split further to form a higher dimensional matrix. Additionally, secondary structure information can be added to the data structure, e.g., an extra matrix (1-D matrix) on top of 2-D matrix. Such an extra matrix can code whether each base within the measurement window is involved in a secondary structure (e.g. stem-loop structure), for example, the base involving the "stem" is coded as 0 and base involving the "loop" is coded as 1.

In one embodiment, the methylation status of a CpG site within a single DNA molecule can be expressed as a probability of being methylated based on a statistical model, rather than giving a qualitative result of "methylated" or "unmethylated." A probability of 1 indicates that, based on the statistical model, a CpG site may be deemed as methylated. A probability of 0 indicates that, based on the statistical model, a CpG site may be deemed as unmethylated. In subsequent downstream analysis, a cutoff value can be used to classify if a particular CpG site is classified as "methylated" or "unmethylated" based on the probability. The possible values of the cutoff include 5%, 10%, 15%, 20%, 25%, 30%, 35%, 40%, 45%, 50%, 55%, 60%, 65%, 70%, 75%, 80%, 85%, 90%, or 95%. The predicted probability of being methylated for a CpG site greater than a predefined cutoff may be classified as "methylated," while the probability of being methylated for a CpG site not greater than a predefined cutoff may be classified as "unmethylated." A desired cutoff would be obtained from training dataset using, for example, receiver operating characteristics (ROC) curve analysis.

FIG. 16 shows a general procedure of classifying methylation states of an unknown sample from the Watson and Crick strands. sample with unknown methylation states was subjected to single molecule, real-time sequencing. The sequencing subreads can be aligned to a reference genome or to each other, as with other methods, to determine consensus values (e.g., average, median, mode, or other statistical value) for a given position. As shown, the measured values for the two strands can be combined into a single 2D matrix.

For a cytosine of a CG site in the alignment result, one would obtain IPDs, PWs, and sequence context from the Watson strand using a comparable measurement window (3-nt upstream and downstream of a cytosine of a CpG site) as applied in the training step (FIG. 16), associated with that base whose modification was under interrogation, although different sized windows can be used. Such a 2-D matrix of a testing sample can be compared with the reference kinetic patterns illustrated in FIG. 16 to determine the methylation states.

III. Example Model Training for Detection of Methylation

To test the feasibility and validity of proposed approaches, we prepared a placenta DNA library with M.SssI treatment (methylated library) and PCR amplification (unmethylated library) prior to single molecule, real-time sequencing. We obtained 44,799,736 and 43,580,452 subreads for methylated and unmethylated libraries, respectively, corresponding to 421,614 and 446,285 circular consensus sequences (CCSs). As a result, each molecule was sequenced with a median of 34 and 32 times in methylated and unmethylated libraries. The data set was generated from DNA prepared by the Pacific Biosciences Sequel Sequencing Kit 3.0. This kit was developed to be used for use of the original Pacific Biosciences Sequel sequencer. To differentiate the Sequel from its successor, the Sequel II, we herein refer to the original Sequel as Sequel I. Hence, the Sequel Sequencing Kit 3.0 would be referred herein as the Sequel I Sequencing Kit 3.0. Sequencing kits designed for the Sequel II sequencer include the Sequel II Sequencing Kit 1.0 and Sequel II Sequencing Kit 2.0 that are also described in this disclosure.

We used 50% of the sequenced molecules generated from methylated and unmethylated libraries to train a statistical model (and used the remaining 50% for validation), which in this case is a convolutional neural network (CNN) model. As an example, the CNN model can have one or more convolutional layers (e.g., 1D or 2D layers). A convolutional layer can use one or more different filters, with each filter using a kernel that operates on matrix values local (e.g., in neighboring or surrounding) to a particular matrix element, thereby providing a new value to the particular matrix element. One implementation used two 1D-convolution layers (each with 100 filters with a kernel size of 4). The filters can be applied separately and then combined (e.g., in a weighted average). A resulting matrix can be smaller than the input matrix.

The convolutional layers can be followed by a ReLU (rectified linear unit) layer, which can be followed by a dropout layer with a dropout rate of 0.5. The ReLU is an example of an activation function that can operate on the individual values resulting in the new matrix (image) from the convolutional layer(s). Other activation functions (e.g., sigmoid, softmax, etc.) can also be used. One or more of such layers can be used. The dropout layer can be used on the ReLU layer or on a maximum pooling layer and act as a regularization to prevent overfitting. The dropout layer can be used during the training process to ignore different (e.g., random) values during different iterations of an optimization process (e.g., to reduce a cost/loss function) that is performed as part of training.

A maximum pooling layer (e.g., a pool size of 2) may be used after the ReLU layer. The maximum pooling layer can act similar to the convolution layer but instead of taking a dot product between the input and the kernel, the maximum of the region from the input overlapped by the kernel can be taken. Further convolutional layer(s) can be used. For example, the data from a pooling layer can be input to another two 1D-convolution layers (e.g., each with 128 filters with a kernel size of 2 followed by a ReLU layer), further using a dropout layer with a dropout rate of 0.5. A maximum pooling layer with a pool size of 2 was used. Finally, a fully connected layer (e.g., with 10 neurons followed by a ReLU layer) can be used. An output layer with one neuron can be followed by a sigmoid layer, thereby yielding the probability of methylation. Various settings of layers, filters, and kernel sizes can be adapted. In this training dataset, we used 468,596 and 432,761 CpG sites from methylated and unmethylated libraries.

A. Results of Training and Testing Datasets

Figure 17B:
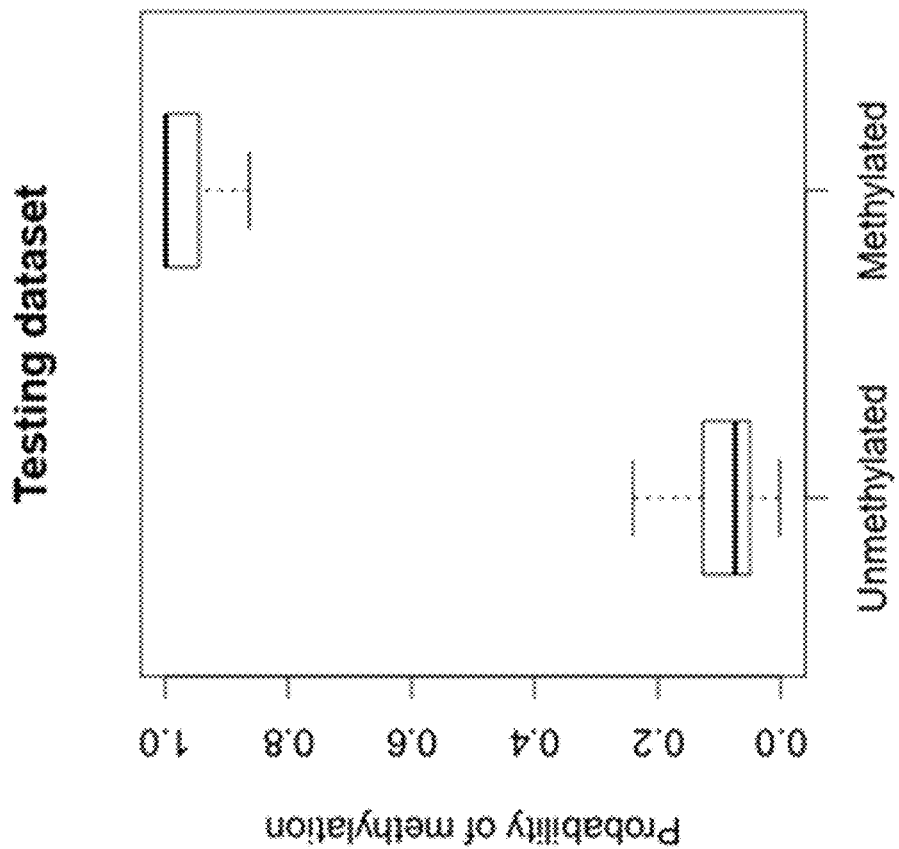
FIGS. 17A and 17B show the performance of a training dataset and a testing dataset for determining methylation according to embodiments of the present invention.
Figure 17A:
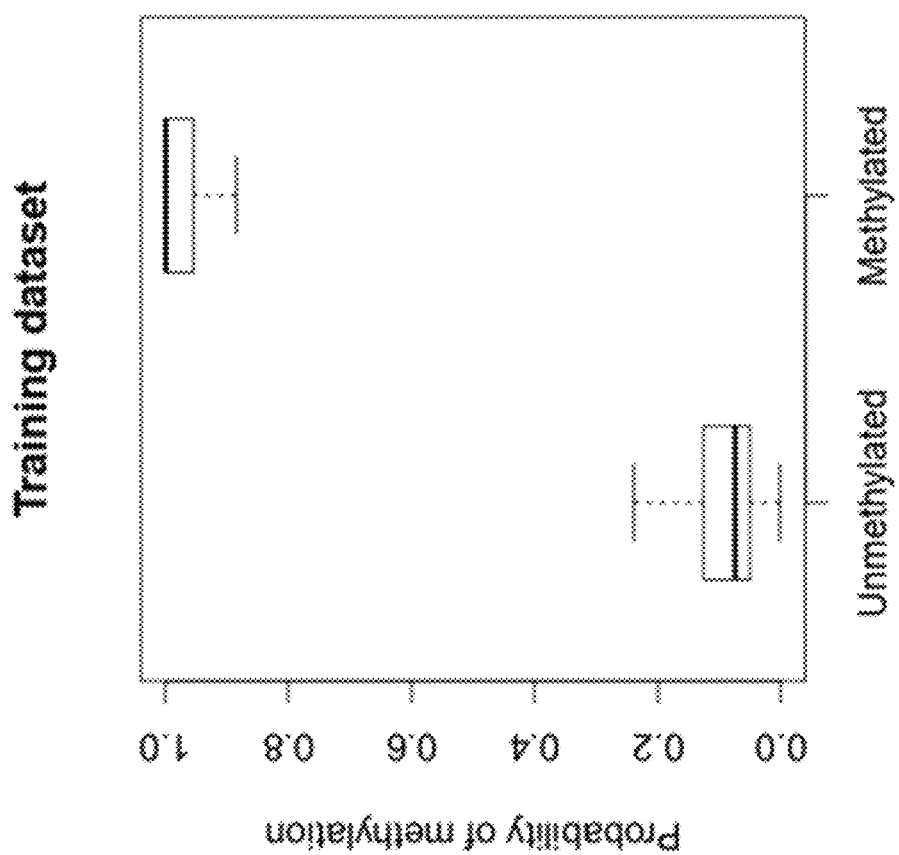

FIG. 17A shows the probability of being methylated for each CpG site in each single DNA molecule in the training dataset. The probability of methylation was much higher in the methylated library than the unmethylated library. For a cutoff of 0.5 for the probability of being methylated, 94.7% of unmethylated CpG sites were correctly predicted to be unmethylated, and 84.7% of methylated CpG were correctly predicted to be methylated.

FIG. 17B shows the performance of the testing dataset. We used a model trained by the training dataset to predict the methylation states of 469,729 and 432,024 CpG sites in an independent testing dataset from methylated and unmethylated libraries. For a cutoff of 0.5 for probability of being methylated, 94.0% of unmethylated CpG sites were correctly predicted to be unmethylated, and 84.1% of methylated CpG were correctly predicted to be methylated. These results suggested that the use of a novel transformation of kinetics coupled with sequence context could enable the determination of methylation states in DNA (e.g. from human subjects).

Figure 18B:
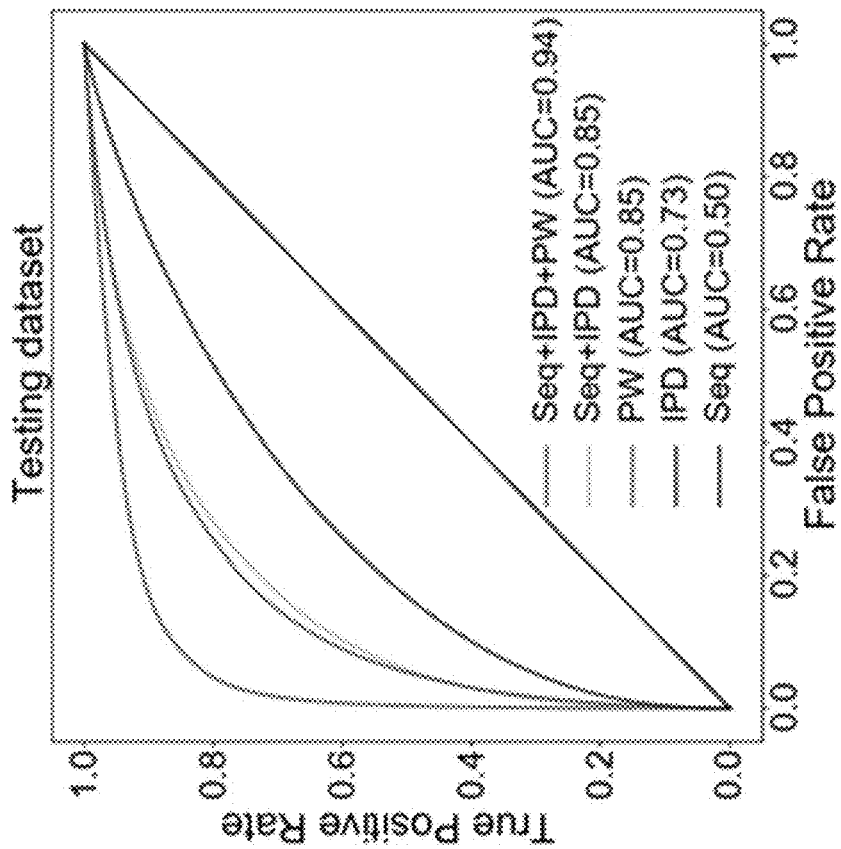
FIGS. 18A and 18B show the performance of a training dataset and a testing dataset for determining methylation according to embodiments of the present invention.
Figure 18A:
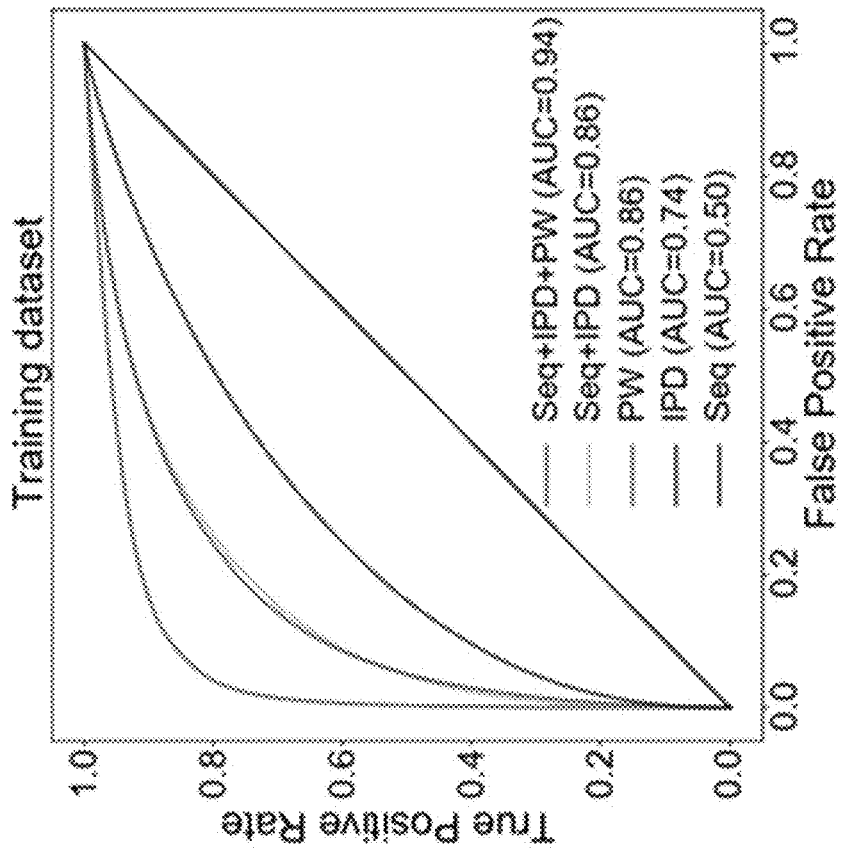

We evaluated the power of each feature (sequence context, IPD, and PW) in predicting the methylation state of CpG by including a subset of the features in the model. In the training dataset, models with (i) sequence context only, (ii) IPD only, and (iii) PW only gave area-under-the-curve (AUC) values of 0.5, 0.74 and 0.86, respectively. While combining IPD and sequence context improved the performance with an AUC of 0.86. The combined analysis of sequence context ("Seq"), IPD, and PW substantially improved the performance with an AUC of 0.94 (FIG. 18A). The performance of an independent testing dataset was comparable to the training dataset (FIG. 18B).

Figure 19A:
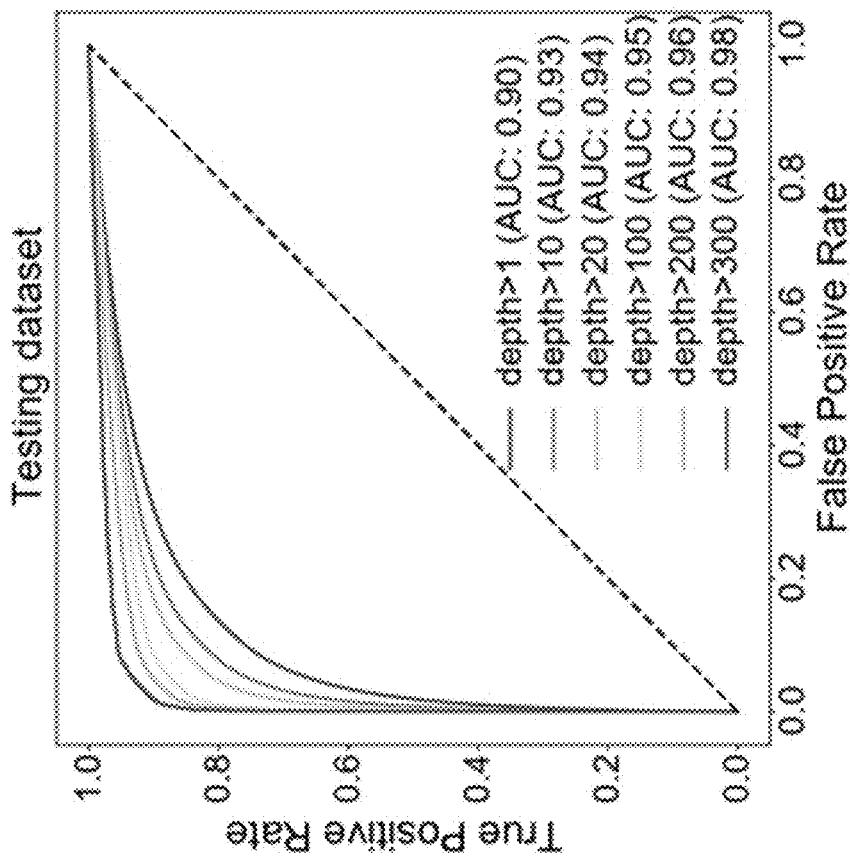
FIGS. 19A and 19B show the performance of a training dataset and a testing dataset at different sequencing depths for determining methylation according to embodiments of the present invention.
Figure 19B:
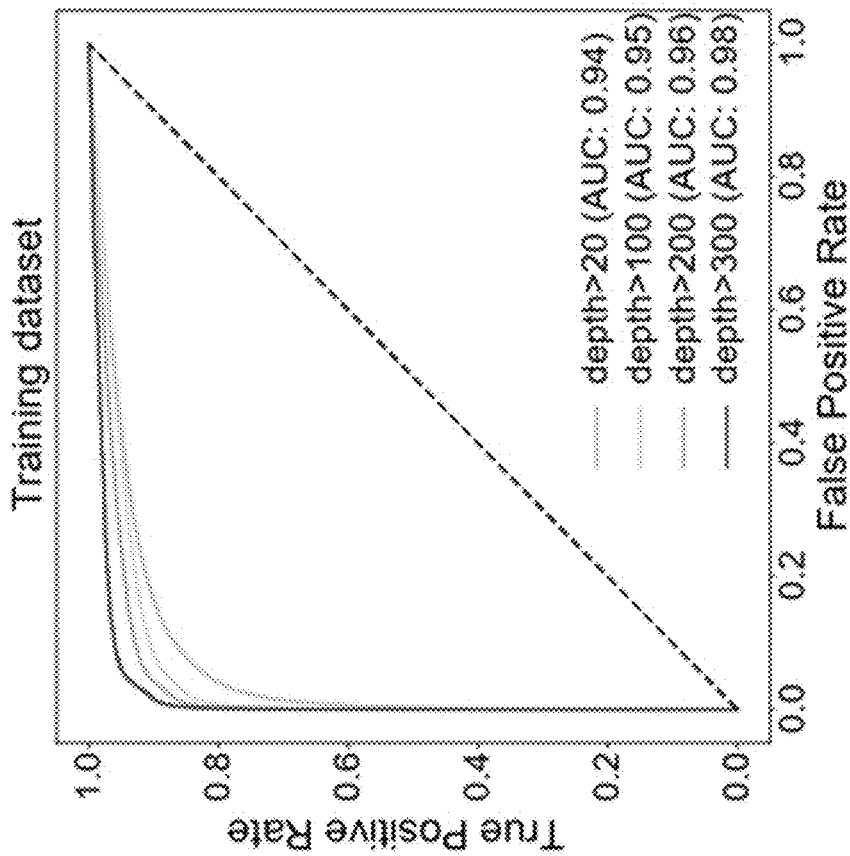

We defined the subread depth of a CpG site as the average number of subreads covering it and its surrounding 10 bp. As shown in FIG. 19A and FIG. 19B, the higher the subread depth of a CpG site, the higher the accuracy of detection of methylation we would achieve. For example, as shown in the testing dataset (FIG. 19B), if the depth of each CpG site was at least 10, the AUC of predicting methylation states would be 0.93. However, if the subread depth of each CpG site is at least 300, the AUC of predicting methylation states would be 0.98. On the other hand, even for the depth of 1, we could achieve an AUC of 0.9, suggesting that our approach could achieve methylation prediction with the use of low sequencing depth.

Figure 20B:
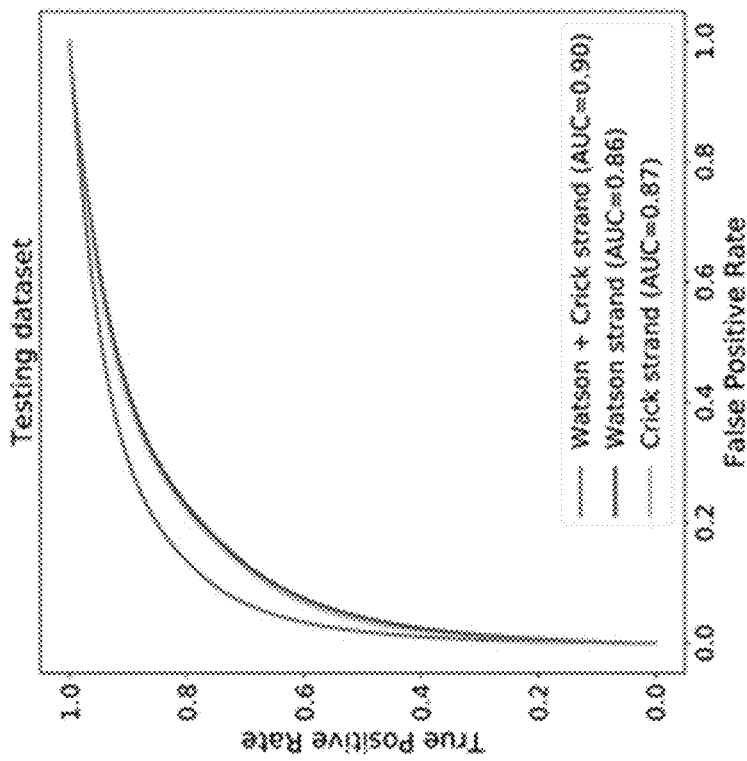
FIGS. 20A and 20B show the performance of a training dataset and a testing dataset for different strands for determining methylation according to embodiments of the present invention.
Figure 20A:
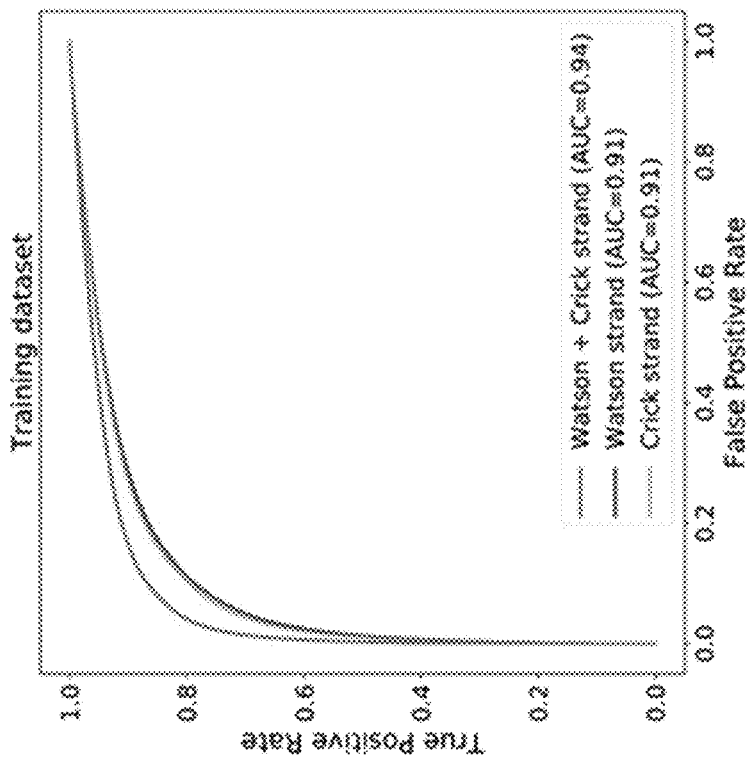

To test the effect of strand information on the performance of methylation analysis, the sequence context, IPD and PW originating from the Watson and Crick strands were used to train according to the embodiments present in this disclosure, respectively. FIG. 20A and FIG. 20B showed that it is feasible to use a single strand, namely either the Watson or Crick strand, for training and testing as the AUC could be achieved up to 0.91 and 0.87 in training and testing datasets. The use of both strands (e.g., as described in FIGS. 6-8) including the Watson and Crick strands would give rise to the best performance (AUC: 0.94 and 0.90 in training and testing datasets, respectively), suggesting the strand information would be important to achieve the optimal performance.

Figures 21A, 21B:
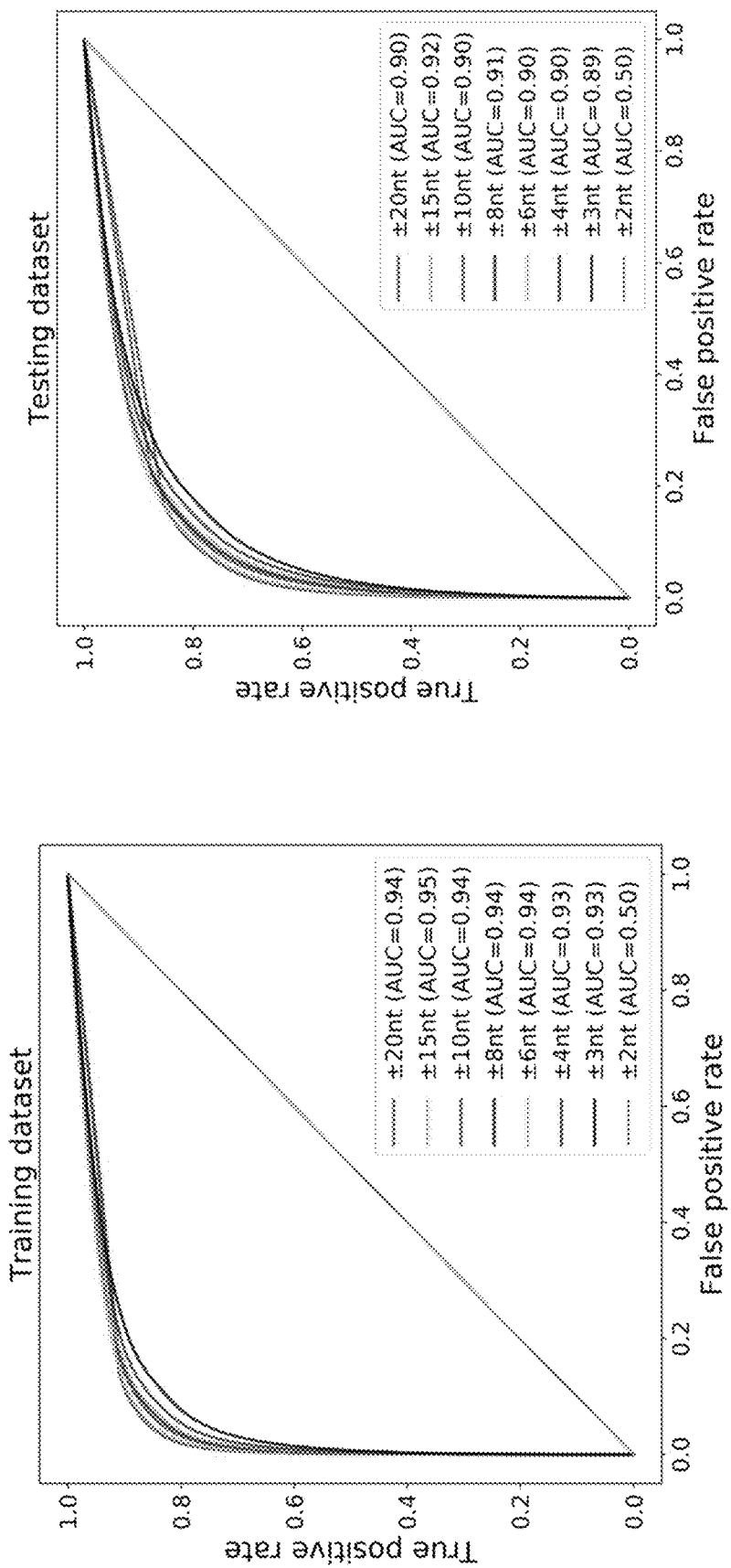
FIGS. 21A and 21B show the performance of a training dataset and a testing dataset for different measurement windows for determining methylation according to embodiments of the present invention.

We further tested the different number of nucleotides upstream and downstream of a CpG site, to study how this parameter affected the performance of according to the embodiments present in this disclosure developed in this disclosure. FIG. 21A and FIG. 21B show that the number of nucleotides upstream and downstream of a cytosine in the context of CpG would affect the accuracy of methylation prediction. For example, as an illustration purpose, considering but not limited to 2 nucleotides (nt), 3 nt, 4 nt, 6 nt, 8 nt, 10 nt, 15 nt, and 20 nt upstream and downstream of a cytosine being analyzed, the AUC of a method using 2 nt upstream and downstream of cytosine being interrogated would be only 0.50 in both training and testing datasets, whereas the AUC of a method using 15 nt upstream and downstream of a cytosine being interrogated would increase to 0.95 and 0.92 in the training and testing datasets. These results suggested that varying the length of upstream and downstream regions flanking cytosines being analyzed would allow to figure out the optimal performance. In one embodiment, as shown in FIG. 21B, one would use 3 nt upstream and downstream of a cytosine to determine the methylation states, which could achieve an AUC of 0.89.

In one embodiment, one could use asymmetrical sequences flanking a cytosine being interrogated to perform the analysis according to the embodiments present in this disclosure. For example, 2 nt upstream combined with 1 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, and 40 nt downstream of a cytosine could be used; 3 nt upstream combined with 1 nt, 2 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, and 40 nt downstream of a cytosine could be used; 4 nt upstream combined with 1 nt, 2 nt, 3 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, and 40 nt downstream of a cytosine could be used. As another example, 2 nt downstream combined with 1 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, and 40 nt upstream of a cytosine could be used; 3 nt downstream combined with 1 nt, 2 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, and 40 nt upstream of a cytosine could be used; 4 nt downstream combined with 1 nt, 2 nt, 3 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, and 40 nt upstream of a cytosine could be used. By taking advantage of IPDs, PWs, strand information, and sequence context in association with n-nt upstream and m-nt downstream of a cytosine could provide an improved accuracy in determining the methylation states in certain embodiments. Such varying measurement windows could be applied to other types of base modification analysis, such 5hmC, 6 mA, 4mC, and oxoG, or any modification disclosed herein. Such varying measurement windows could include DNA secondary structure analysis, such as G-quadruplex and stem-loop structure. Such an example is explained above. Such secondary structure information could also be added as another column in a matrix.

Figure 22B:
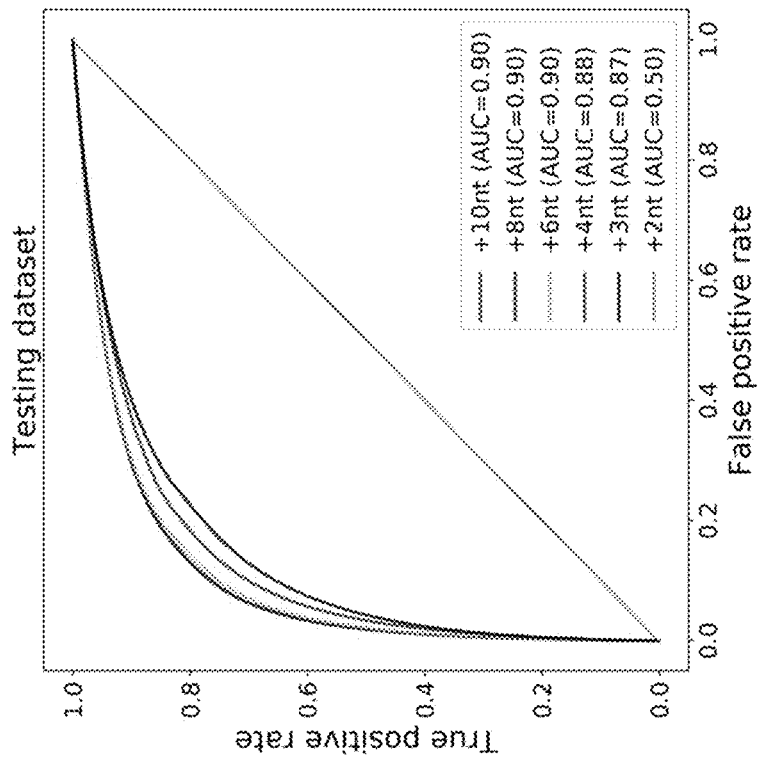
FIGS. 22A and 22B show the performance of a training dataset and a testing dataset for different measurement windows using downstream bases only for determining methylation according to embodiments of the present invention.
Figure 22A:
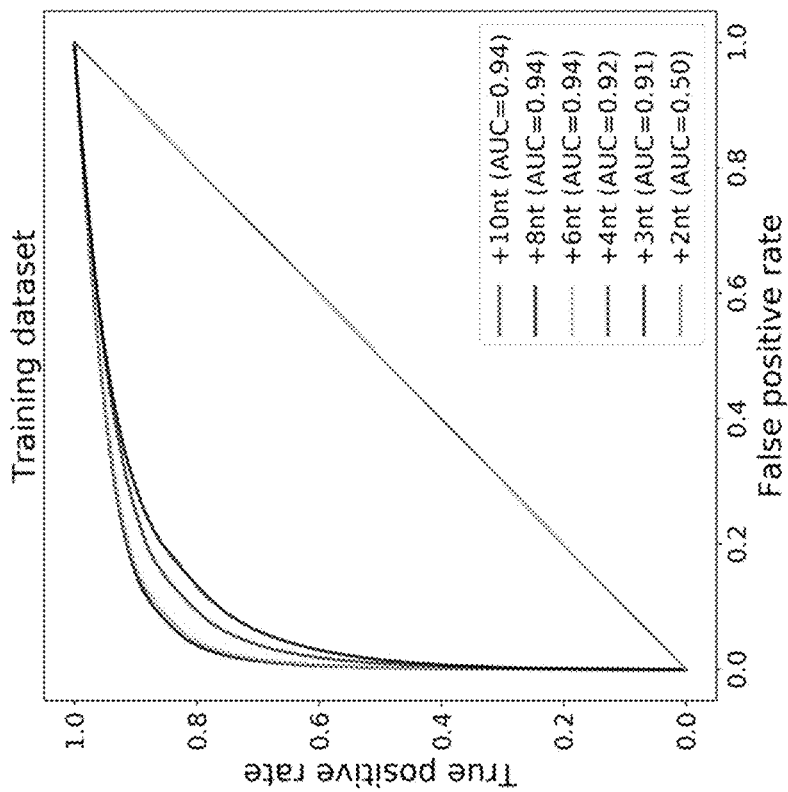

FIG. 22A and FIG. 22B show that it is feasible to determine the methylation states using kinetic patterns associated with only downstream bases of at least 3 bases. According to the embodiments present in this disclosure, with the use of features associated with cytosine and its downstream 3, 4, 6, 8, and 10 bases, the AUCs of the determination of methylation states in training dataset were 0.91, 0.92, 0.94, 0.94, and 0.94, respectively, in the training dataset; the AUCs were 0.87, 0.88, 0.90, 0.90, and 0.90, respectively, in the testing dataset.

Figure 23B:
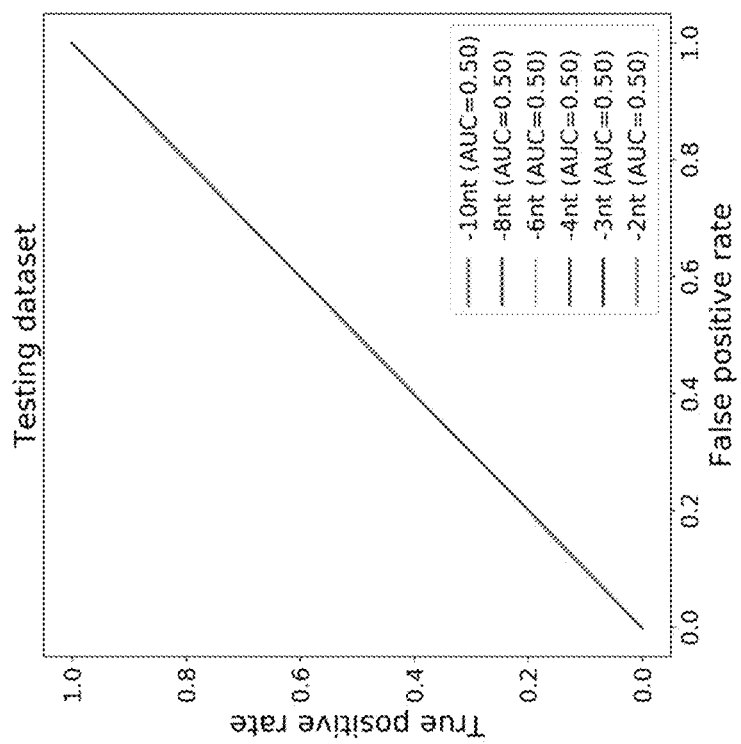
FIGS. 23A and 23B show the performance of a training dataset and a testing dataset for different measurement windows using upstream bases only for determining methylation according to embodiments of the present invention.
Figure 23A:
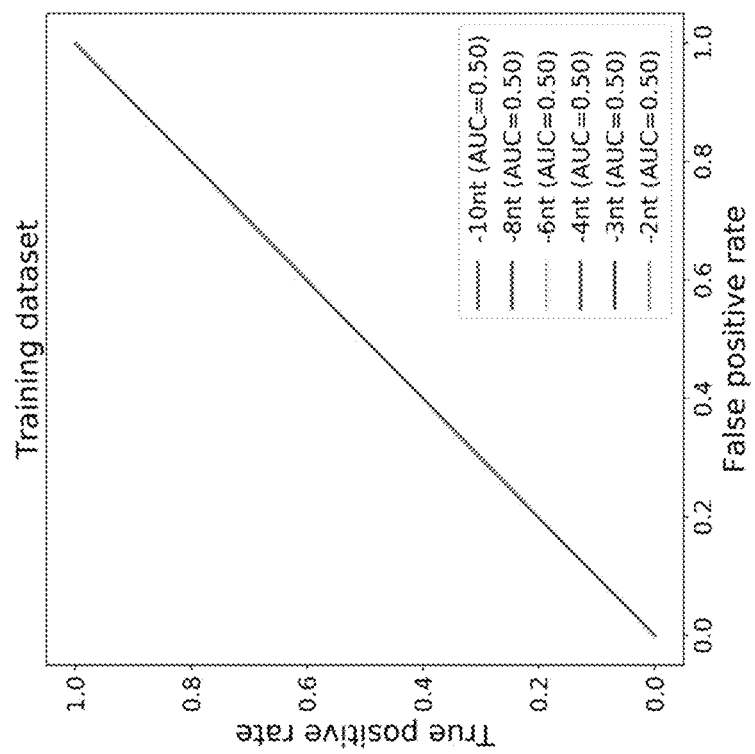

FIG. 23A and FIG. 23B show, however, if one only uses the features associated with the upstream bases, the classification power appears to diminish in one's ability in distinguishing the methylation states. The AUCs in the training dataset and the testing dataset were all 0.50 for 2 to 10 upstream bases.

Figure 24:
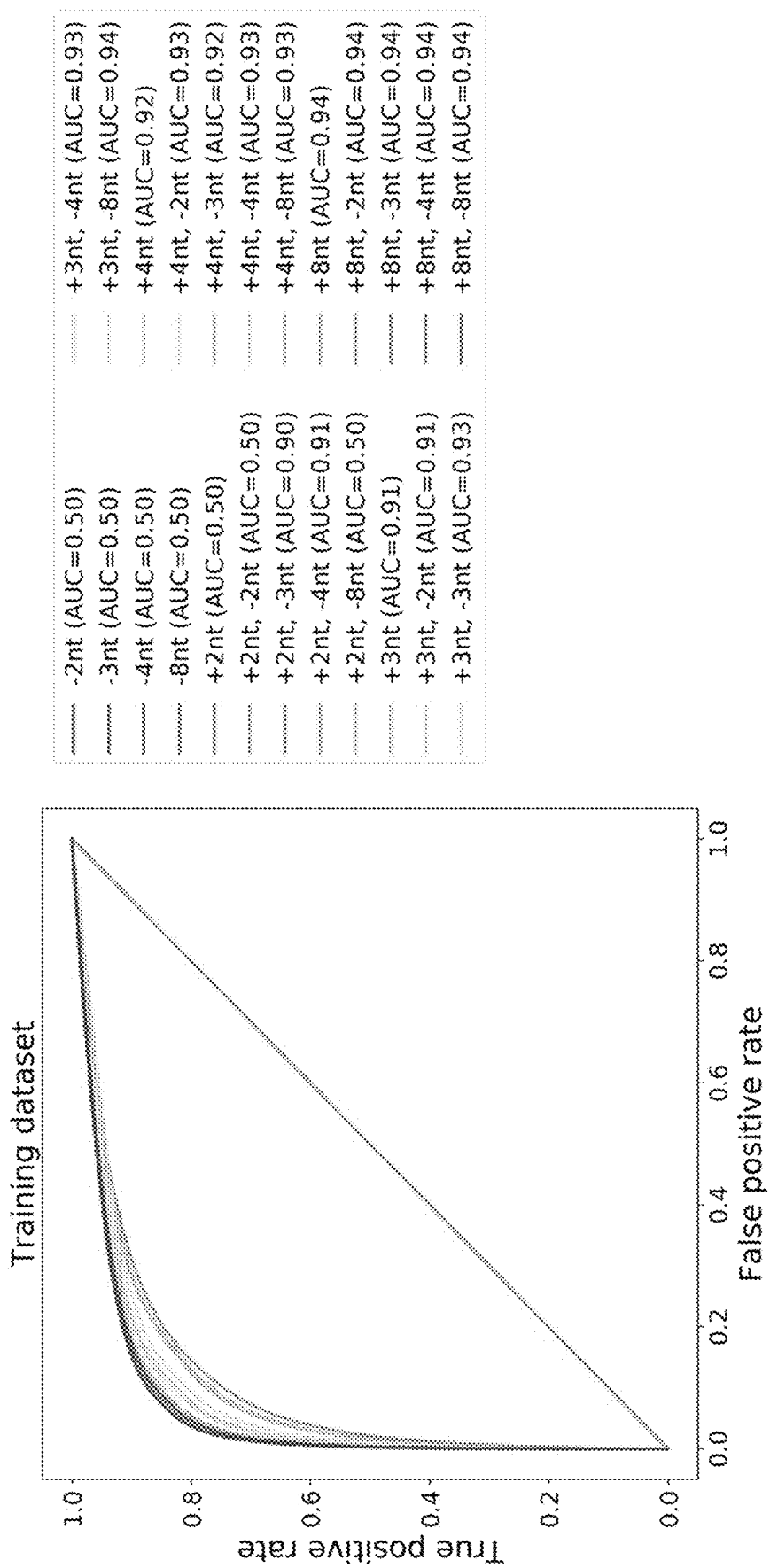
FIG. 24 shows the performance of methylation analysis using kinetic patterns associated with downstream and upstream bases using asymmetric flanking sizes in the training dataset according to embodiments of the present invention.
Figure 25:
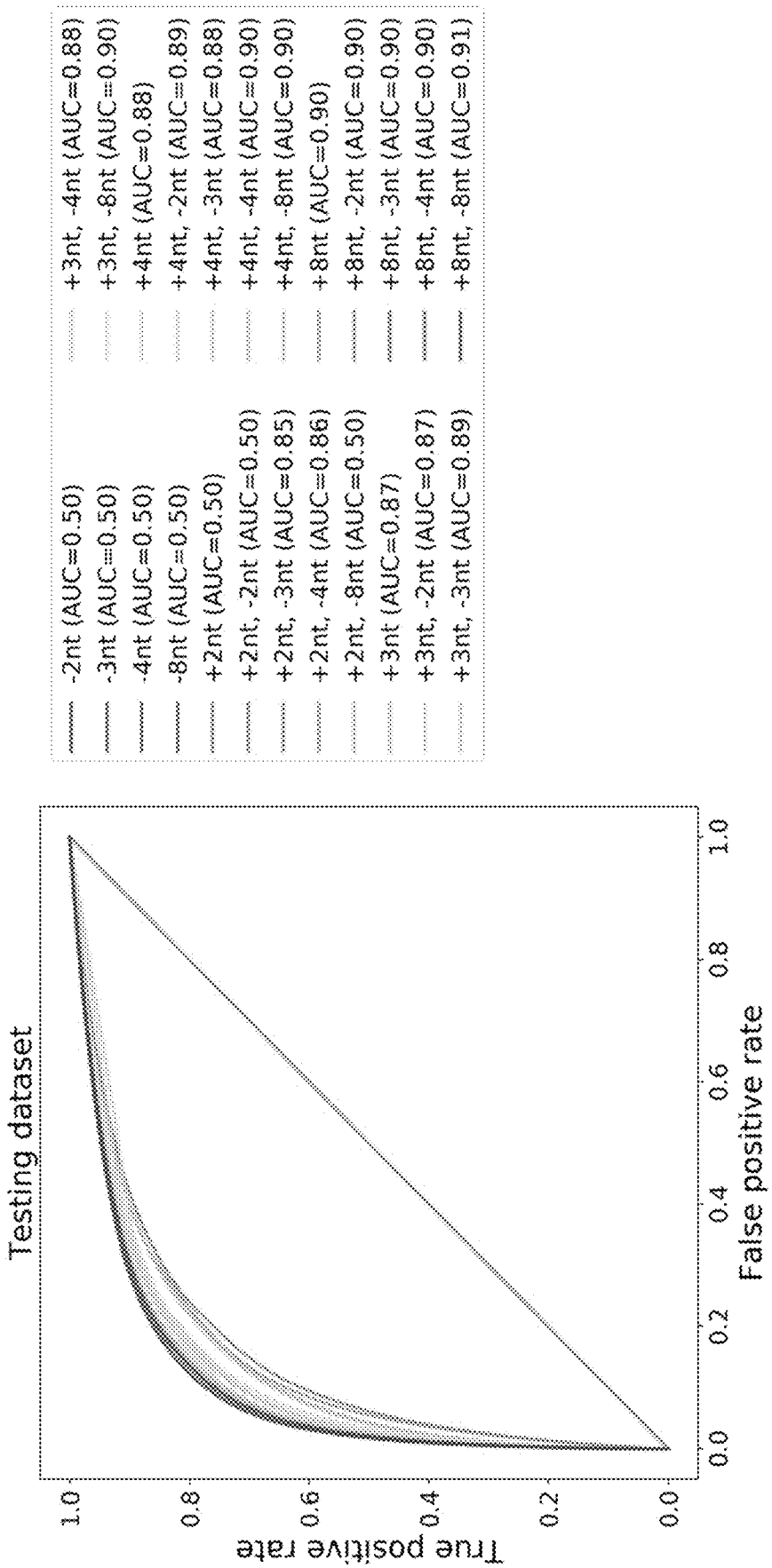
FIG. 25 shows the performance of methylation analysis using kinetic patterns associated with downstream and upstream bases using asymmetric flanking sizes in the testing dataset according to embodiments of the present invention.

FIG. 24 and FIG. 25 show that different combinations of upstream and downstream bases would allow one to achieve an optimal classification power in determining methylation states. For example, the features associated with 8-base upstream and 8-base downstream of a cytosine would achieve a best performance in this dataset, with an AUC of 0.94 and 0.91 in the training and testing datasets, respectively.

Figure 26:
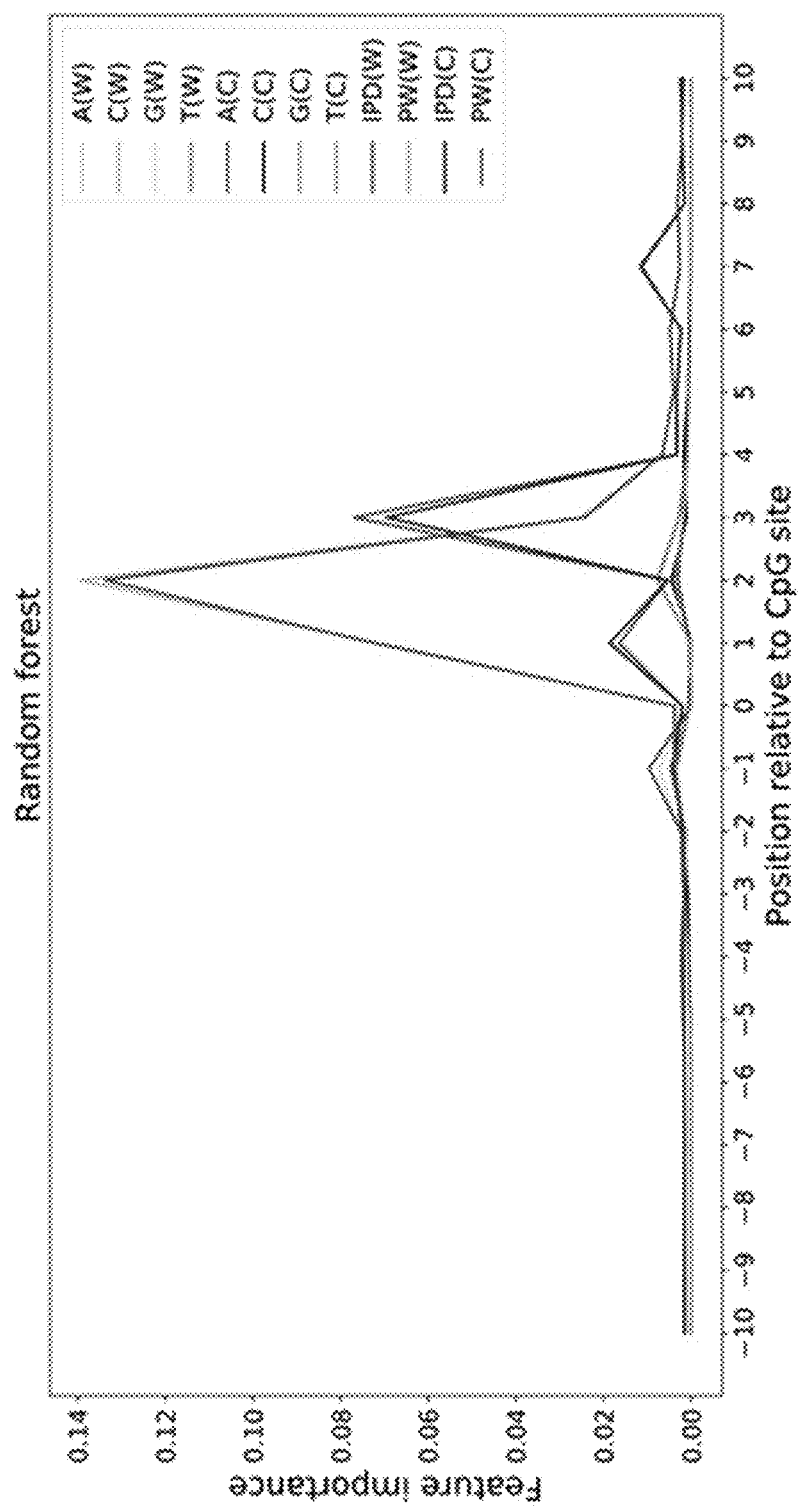
FIG. 26 shows the relative importance of features in regard to classification of methylation states at CpG sites according to embodiments of the present invention.

FIG. 26 shows the relative importance of features in regard to classification of methylation states at CpG sites. 'W' and 'C' in the brackets indicate the strand information, 'W' for the Watson strand and 'C' for the Crick strand. The importance of each feature, including sequence context, IPD and PW, was determined using random forest. The random forest tree analysis showed that the feature importance of IPDs and PWs peaked in the downstream of a cytosine that was under interrogation, revealing that the major contributions to classification power were the IPDs and PWs downstream to a cytosine that was under interrogation.

The random forest was composed of multiple decision trees. During the construction of the decision tree, Gini impurity was used to determine which decision logic for decision nodes should be taken. Important features that have more influence on the final classification outcome were likely in nodes closer to the root of the decision tree, while unimportant features that have less influence on the final classification outcome are likely in nodes further away from the root. So, the feature importance could be estimated by computing the average distance relative to the roots of all decision trees in the random forest.

In some embodiments, the consensus of methylation calls at CpG sites between the Watson and Crick strands could be further used for improving the specificity. For example, it could be required that both strands showing methylated would be called as a methylated state, and both strands showing unmethylated would be called as unmethylated state. Since the methylation at CpG sites was known to be typically symmetrical, the confirmation from each strand can improve the specificity.

In various embodiments, the overall kinetic features from a whole molecule might be used for the determination of methylation states. For example, the methylation in a whole molecule would affect kinetics of the whole molecule during single molecule, real-time sequencing. By modelling sequencing kinetics of the entire template DNA molecule including IPDs, PWs, fragment sizes, strand information, and sequence context, it may improve the accuracy of the classification as to whether a molecule is methylated or not. As an example, the measurement windows may be the entire template molecule. Statistical values (e.g., mean, median, mode, percentile, etc) of IPD, PW, or other kinetic features may be used for determining methylation of a whole molecule.

B. Limitations of Other Analysis Techniques

Figure 27:
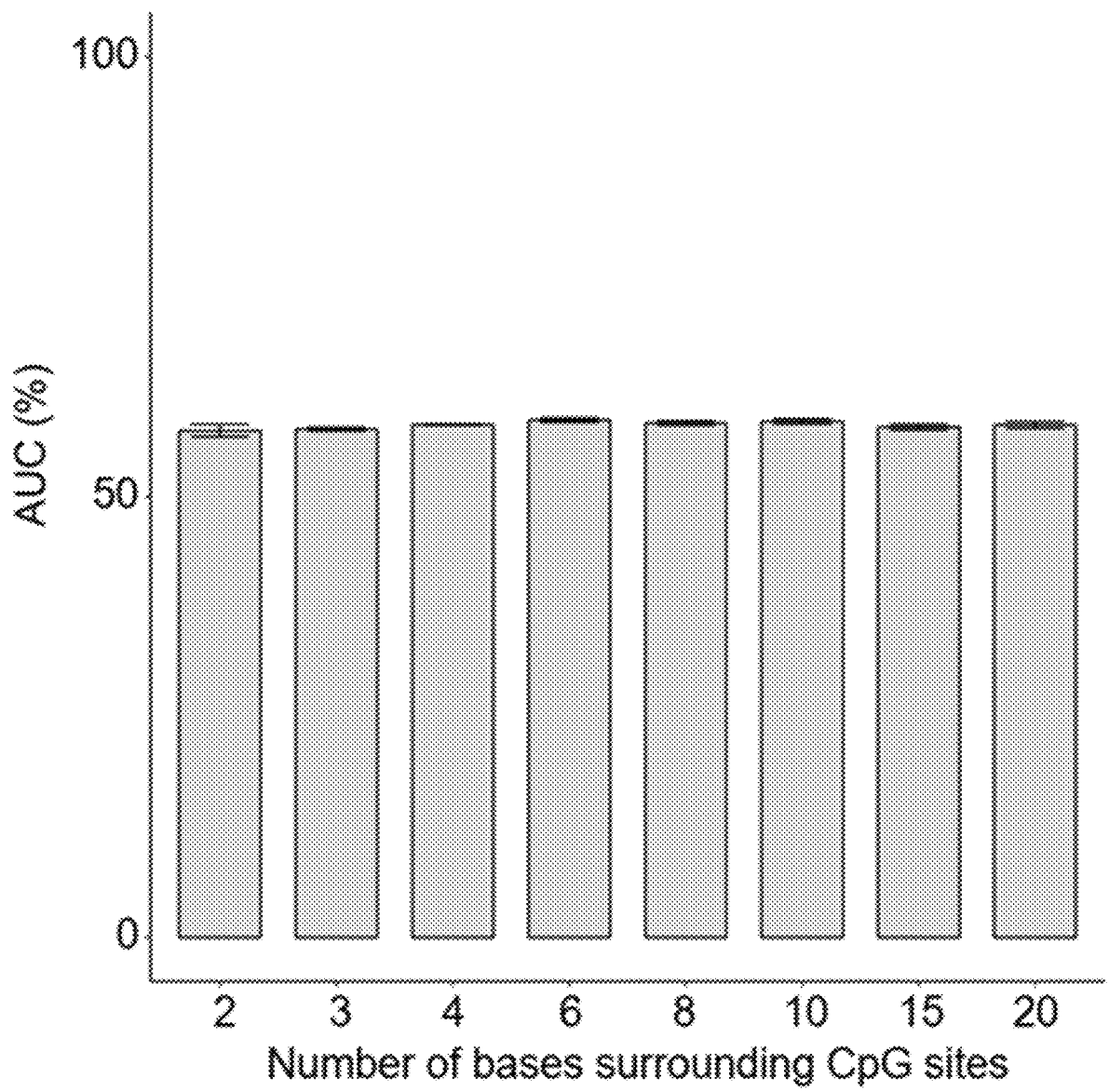
FIG. 27 shows the performance of the motif-based PD analysis for methylation detection without using the pulse width signal according to embodiments of the present invention.

It was reported that the detection of methylation based on IPD for a particular C in a particular sequence motif was very low, for example, a sensitivity of only 1.9% (Clark et al., 2013). We also attempted to reproduce such analysis by combining different sequence motifs with IPDs without using the PW metric, and just using a cutoff for the IPD and not the data structures as described herein. For example, 3-nt upstream and downstream flanking a CpG being interrogated were extracted. IPDs of that CpG were stratified into different groups (4096 groups for the 6 positions) depending on the context of 6-nt flanking sequences (i.e. upstream and downstream 3 nt, respectively) that was centered on that CpG. The IPDs between methylated and unmethylated CpGs within the same sequence motif were studied using ROC. For example, IPDs of CpG in the unmethylated "AATCGGAC" motif and methylated "AAT$^m$CGGAC"

motif were compared, showing an AUC of 0.48. Thus, the use of cutoffs in a particular sequence group performed poorly relatively to embodiment that use various FIG. 27 shows the performance of the above motif-based IPD analysis (Beckmann et al. BMC Bioinformatics. 2014) for methylation detection without using the pulse width signal. The vertical bar plots represent the averaged AUCs across different k-mer motifs flanking CpG sites being studied (i.e. the number of bases surrounding CpG sites being interrogated). FIG. 27 showed that the averaged AUCs for IPD based discriminative powers between methylated and unmethylated cytosines across different k-mer motifs (e.g. 2-mer, 3-mer, 4-mer, 6-mer, 8-mer, 10-mer, 15-mer, 20-mer surrounding CpG sites in question) was found to be less than 60%. These results suggested that the consideration of the IPD of the candidate nucleotide in a given motif context without taking into account the IPDs of the neighboring nucleotides (Flusberg et al., 2010) would be inferior to the methods disclosed herein for the determination of CpG methylation.

Figure 28:
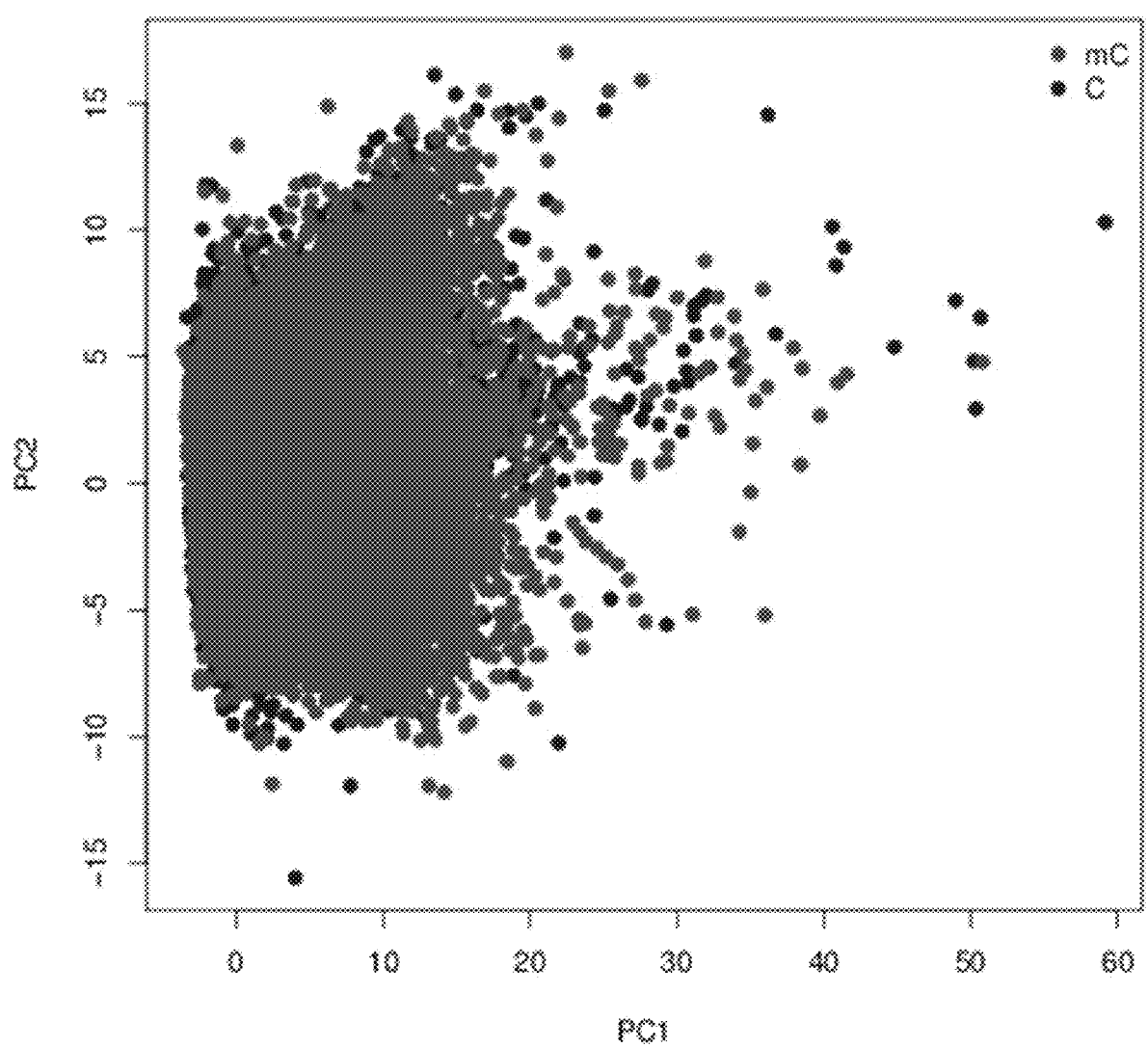
FIG. 28 is a graph of a principal component analysis technique using 2-nt upstream and 6-nt downstream of a cytosine that is subjected to methylation analysis according to embodiments of the present invention.

We also tested the method present in Flusberg et al. study (Flusberg et al., 2010). We analyzed a total of 5,948,348 DNA segments which were 2-nt upstream and 6-nt downstream of a cytosine that was subjected to methylation analysis. There were 2,828,848 segments that were methylated and 3,119,500 segments that were unmethylated. As shown in FIG. 28, the signals deduced from the principal component analysis with the use of IPDs and PWs were found to be largely overlapping between fragments with methylated cytosines (mC) and unmethylated cytosines (C), suggesting that the method as described by Flusberg et al lacks practically meaningful accuracy. These results suggested that the principal component analysis, which linearly combined PW and IPD values at the bases and neighboring bases, as used in Flusberg et al's study (Flusberg et al., 2010) could not reliably or meaningfully differentiate 5-methylcytosine and unmethylated cytosines.

Figure 29:
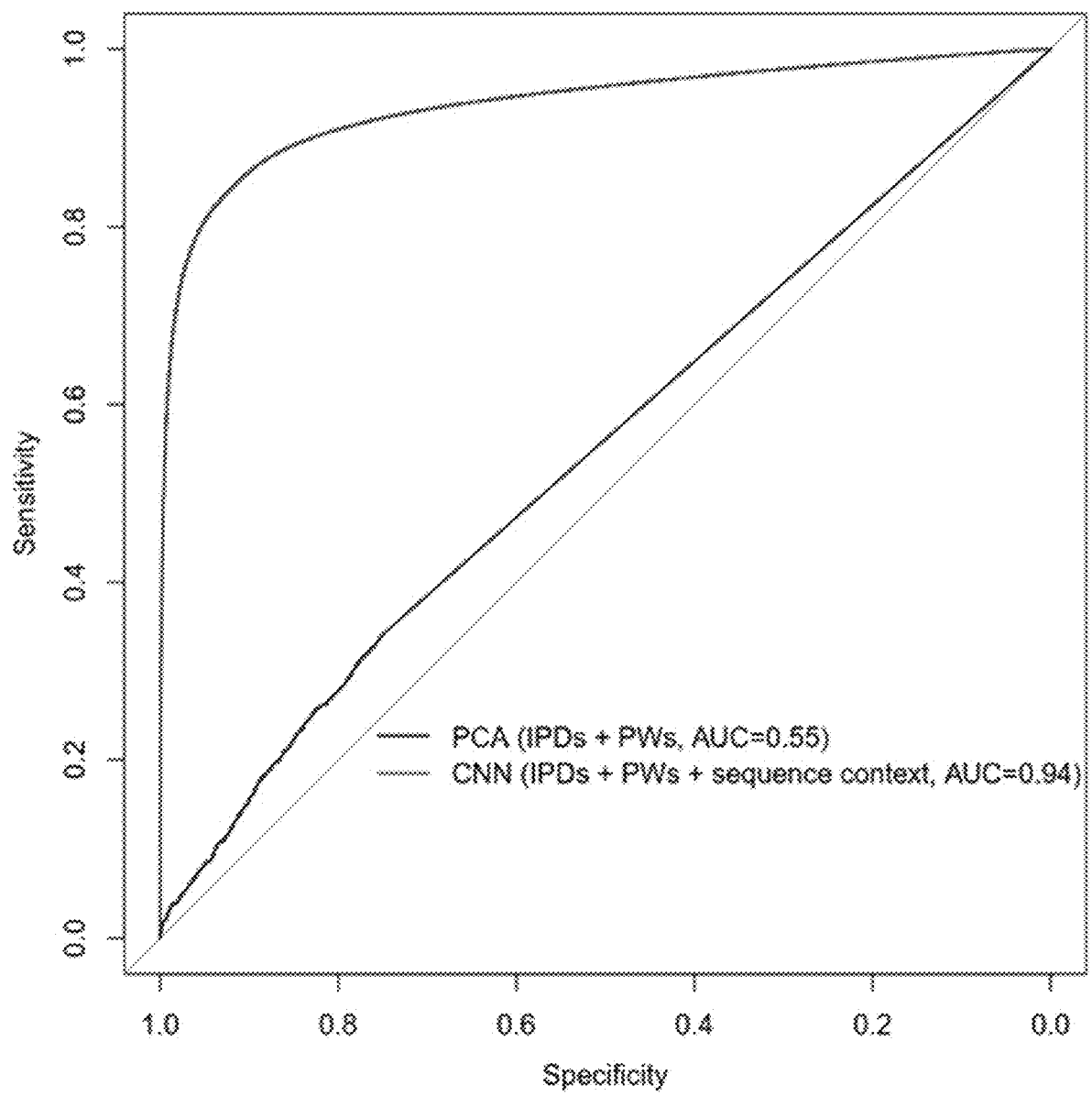
FIG. 29 is a graph of a performance comparison between a method using principal component analysis and a method using a convolutional neural network according to embodiments of the present invention.

FIG. 29 shows that the AUC of the method based on the principal component analysis for which two principal components were used in Flusberg et al's study (Flusberg et al., 2010) involving IPDs and PWs were much less accurate (AUC: 0.55) than the approach based on a convolutional neural network involving IPD and PW as well as sequence context as shown in our disclosure (AUC: 0.94).

C. Other Mathematical/Statistical Models

In another embodiment, other mathematical/statistical models, for example including but not limited to a random forest and logistic regression, could be trained by adapting features developed above. As for the CNN model, the training and testing datasets were constructed from the DNA with M.SssI treatment (methylated) and PCR amplification (unmethylated), which were used to train a random forest (Breiman, 2001). In this random forest analysis, we described each nucleotide with 6 features: IPD, PW, and a 4-component binary vector encoding the base identity. In such a binary vector, A, C, G, and T was coded with [1,0,0,0], [0,1,0,0], [0,0,1,0] and [0,0,0,1], respectively. For each CpG site being analyzed, we incorporated the information of its 10 nt upstream and downstream in both strands, forming a 252-dimension (252-D) vector, with each feature representing one dimension. The training dataset described above with the 252-D vectors was used to train a random forest model, as well as the logistic regression model. The trained model was used to predict the methylation states in an independent testing dataset. The random forest was comprised of 100 decision trees. During tree construction, bootstrap samples were used. While splitting the node of each decision tree, Gini impurity was employed to determine the best split, and a maximum of 15 features would be considered in each split. Also, each leaf of the decision tree was required to contain at least 60 samples.

Figure 30B:
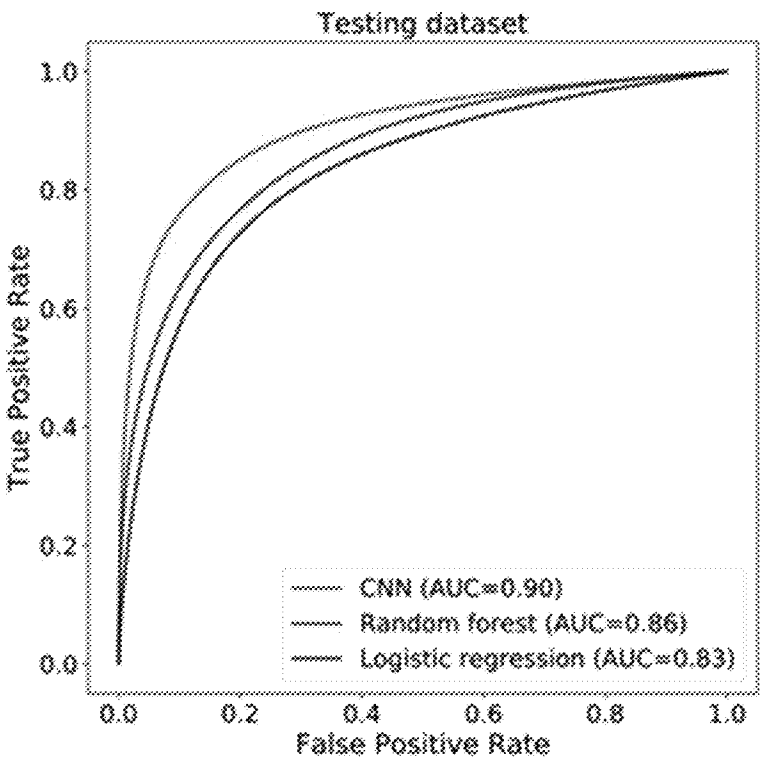
FIGS. 30A and 30B show the performance of a training dataset and a testing dataset for different analytical, computational, mathematical, or statistical models using upstream bases only for determining methylation according to embodiments of the present invention.
Figure 30A:
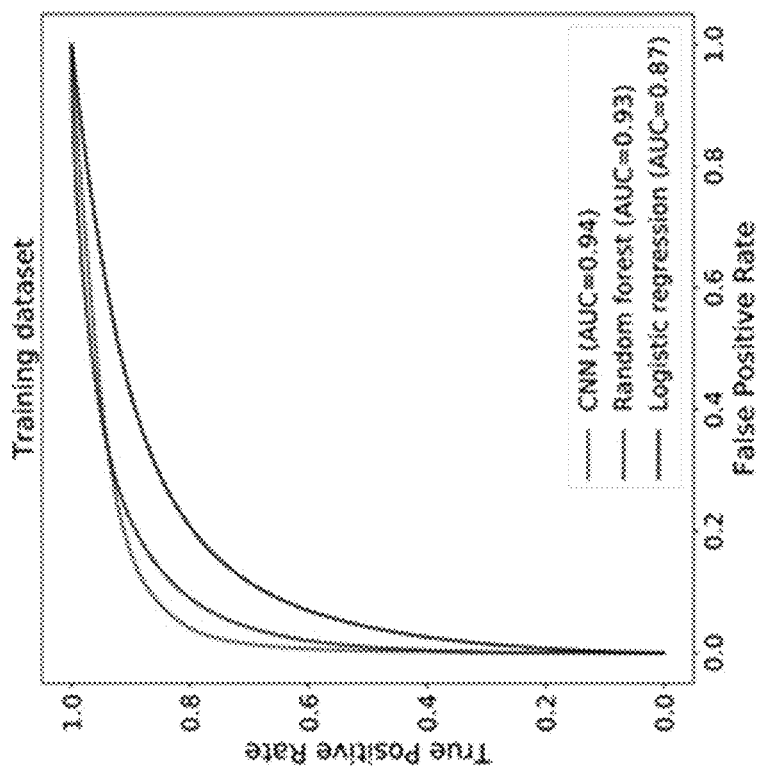

FIG. 30A and FIG. 30B show performance of a method using a random forest and logistic regression for methylation prediction. FIG. 30A shows AUC values in training dataset for CNN, random forest, and logistic regression. FIG. 30B shows AUC values in testing dataset for CNN, random forest and logistic regression. The AUC of a method using random forest achieved 0.93 and 0.86 in the training and testing dataset, respectively.

The training dataset described with the same 252-D vectors was used to train a logistic regression model. The trained model was used to predict the methylation states in an independent testing dataset. A logistic regression model with L2 regularization (Ng and Y., 2004) was fitted with the training dataset. As shown in FIG. 30A and FIG. 30B, the AUC of a method using logistic regression would achieve 0.87 and 0.83 in the training and testing dataset, respectively.

Therefore, these results suggested that certain models (for example, but not limited to the random forest and logistic regression) other than CNN could be used for methylation analysis using the features and analytical protocols we developed in this disclosure. These results also suggested that CNN implemented according to the embodiments in this disclosure with an AUC of 0.90 in the testing dataset (FIG. 30B) was superior to both the random forest (AUC: 0.86) and the logistic regression (AUC: 0.83).

D. Determination of 6 mA Modifications of Nucleic Acids

In addition to methylated CpG, the methods described herein can also detect other DNA base modifications. For example, methylated adenine, including in the form of 6 mA, can be detected.

1. 6 mA Detection Using Kinetic Features and Sequencing Context

To evaluate the performance and utility of the embodiments disclosed for the determination of base modifications of nucleic acids, we further analyzed N6-adenine methylation (6 mA). In one embodiment, approximately 1 ng of human DNA (e.g. extracted from placental tissues) was amplified to obtain 100 ng DNA product through whole genome amplification with unmethylated adenine (uA), unmethylated cytosine (C), unmethylated guanine (G), and unmethylated thymine (T).

Figure 31A:
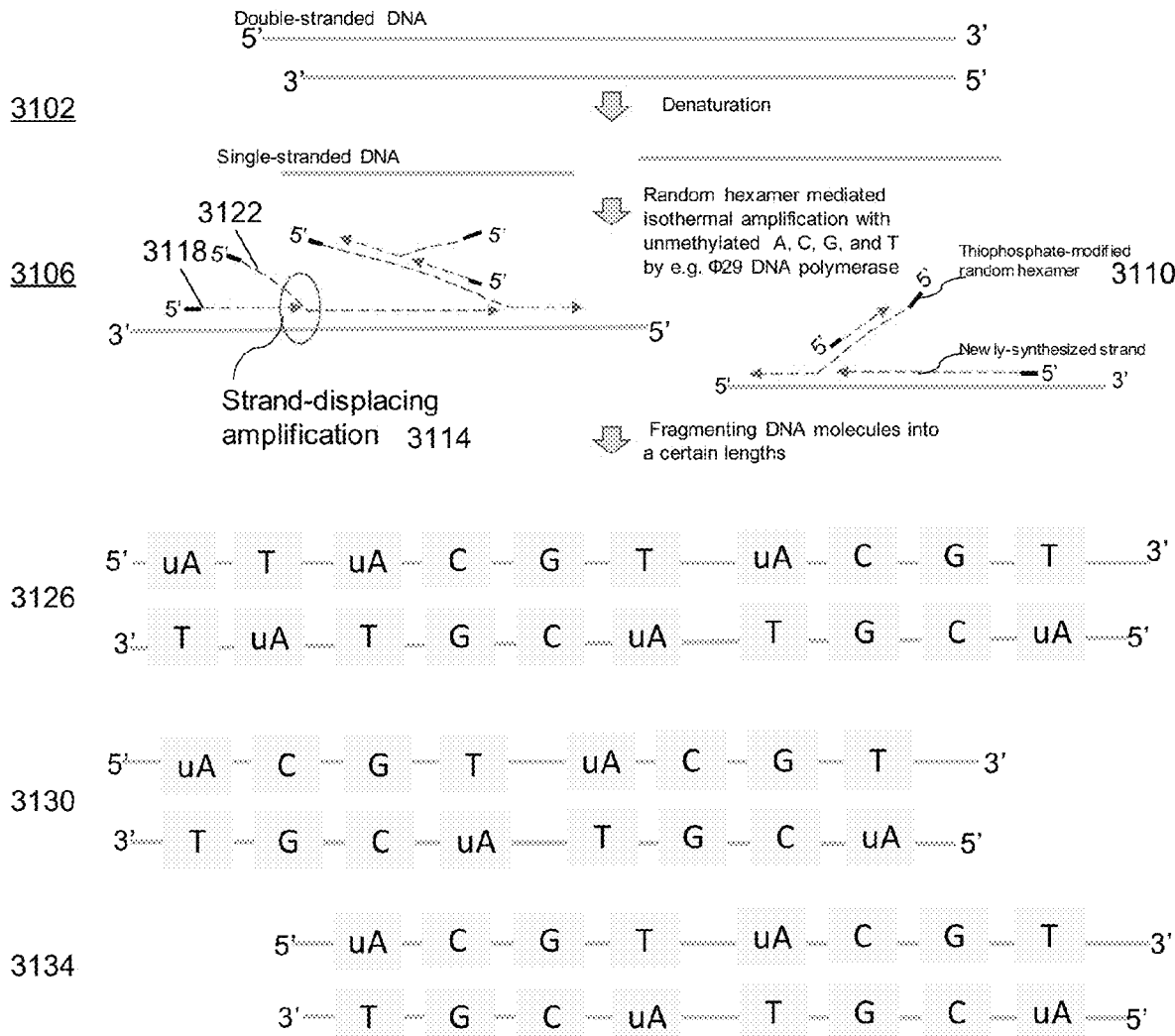
FIG. 31A shows an example of one approach for generating molecules with unmethylated adenines by whole genome amplification according to embodiments of the present invention. FIG. discloses SEQ ID NO: 4.

FIG. 31A shows an example of one approach for generating molecules with unmethylated adenines by whole genome amplification. In the figure, "uA" denotes an unmethylated adenine and "mA" denotes a methylated adenine. Whole genome amplification was performed using exonuclease-resistant thiophosphate-modified random hexamers as primers, which bind randomly over a genome, allowing the polymerase (e.g. Phi29 DNA polymerase) to amplify the DNA (e.g., by isothermal linear amplification). At stage 3102, a double-stranded DNA is denatured. At stage 3106, the amplification reaction is initiated when a number of random hexamers (e.g., 3110) were annealed to the denatured template DNA (i.e. single-stranded DNA). As shown in 3114, when the hexamer-mediated DNA synthesis of strand 3118 proceeded in the 5' to 3' direction and arrived at the next hexamer-mediated DNA synthesis site, the polymerase displaced the newly-synthesized DNA strand (3122) and continued the strand extension. The displaced strands became single-stranded DNA templates for binding of random hexamers again and might initiate new DNA synthesis. Repeated hexamer annealing and strand displacement in an isothermal process would result in a high yield of amplified DNA products. This amplification described here may fall under the technique of multiple displacement amplification (MDA).

The amplified DNA products were further fragmented into, for example, but not limited to, fragments with sizes of 100 bp, 200 bp, 300 bp, 400 bp, 500 bp, 600 bp, 700 bp, 800 bp, 900 bp, 1 kb, 5 kb, 10 kb, 20 kb, 30 kb, 40 kb, 50 kb, 60 kb, 70 kb, 80 kb, 90 kb, 100 kb, or other desired size ranges. The fragmentation process may include enzymatic digestion, nebulization, hydrodynamic shearing, and sonication, etc. As a result, the original base modifications such as 6 mA may be nearly eliminated by whole genome amplification with unmethylated A (uA). FIG. 31A shows possible fragments (3126, 3130, and 3134) of the DNA products, with both strands having unmethylated A. Such whole-genome amplified DNA products without mA were subjected to single-molecule, real-time sequencing to generate uA dataset.

Figure 31B:
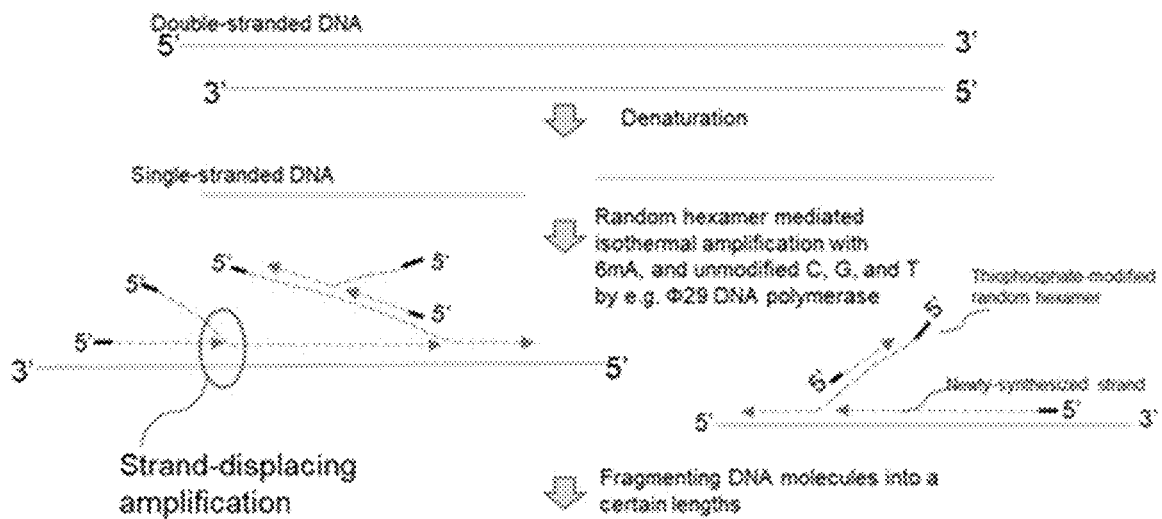
FIG. 31B shows an example of one approach for generating molecules with methylated adenines by whole genome amplification according to embodiments of the present invention. FIG. discloses SEQ ID NO: 5.

FIG. 31B shows an example of one approach for generating molecules with methylated adenines by whole genome amplification. In the figure, "uA" denotes an unmethylated adenine and "mA" denotes a methylated adenine. Approximately 1 ng human DNA was amplified to obtain 10 ng DNA product through whole genome amplification with 6 mA and unmethylated C, G, and T. The methylated adenines can be produced through a series of chemical reactions (J D Engel et al. J Biol Chem. 1978; 253:927-34). As illustrated in FIG. 31B, the whole genome amplification was performed using exonuclease-resistant thiophosphate-modified random hexamers as primers which bind randomly over a genome, allowing the polymerase (e.g. Phi29 DNA polymerase) to amplify the DNA (e.g. by isothermal linear amplification), similar to FIG. 31A. Exonuclease-resistant thiophosphate-modified random hexamers are resistant to the 3'-5' exonuclease activity of proofreading DNA polymerases. Thus, during amplification, the random hexamers will be protected from degradation.

The amplification reaction initiated when a number of random hexamers were annealed to the denatured template DNA (i.e. single-stranded DNA). When the hexamer-mediated DNA synthesis proceeded in the 5' to 3' direction and arrived at the next hexamer-mediated DNA synthesis site, the polymerase displaced the newly-synthesized DNA strand and continue the strand extension. The displaced strands became single-stranded DNA templates for binding of random hexamers again and initiating new DNA synthesis. Repeated hexamer annealing and strand displacement in an isothermal process would result in a high yield of amplified DNA products.

The amplified DNA products were further fragmented into, for example, but not limited to, fragments with sizes of 100 bp, 200 bp, 300 bp, 400 bp, 500 bp, 600 bp, 700 bp, 800 bp, 900 bp, 1 kb, 5 kb, 10 kb, 20 kb, 30 kb, 40 kb, 50 kb, 60 kb, 70 kb, 80 kb, 90 kb, 100 kb, or other combinations in length. As shown in FIG. 31B, the amplified DNA products would include different forms of methylation patterns across adenine sites in each strand. For example, both strands of a double-stranded molecule may be methylated with respect to adenines (Molecule I), which would be generated when two strands are derived from DNA synthesis during whole genome amplification.

As another example, one strand of a double-stranded molecule may contain interlacing methylation patterns across adenine sites (Molecule II). An interlacing methylation pattern is defined as one that includes a mixture of methylated and unmethylated bases present in a DNA strand. In the following examples, we use an interlacing adenine methylation pattern that includes a mixture of methylated and unmethylated adenines present in a DNA strand. This type of double-stranded molecule (Molecule II) would possibly be generated because an unmethylated hexamer containing unmethylated adenines was bound to a DNA strand and initiated DNA extension. Such an amplified DNA product containing the hexamer with unmethylated adenines would be sequenced. Alternatively, this type of double-stranded molecule (Molecule II) would be initiated by fragmented DNA from original template DNA containing unmethylated adenines, since such fragmented DNA could be bound to a DNA strand as a primer. Such an amplified DNA product containing part of the original DNA with unmethylated adenines in a strand would be sequenced. As the unmethylated hexamer primers are only a small portion of the resulting DNA strands, the majority of fragments will still contain 6 mA.

As another example, one strand of a double-stranded DNA molecule may be methylated across adenine sites but the other stand may be unmethylated (Molecule III). This type of double-stranded molecule may be generated when an original DNA strand without methylated adenines is provided as a template DNA molecule for producing a new strand with methylated adenines.

Both strands may be unmethylated (Molecule IV). This type of double-stranded molecule may be due to the reannealing of two original DNA strands without methylated adenines.

The fragmentation process may include enzymatic digestion, nebulization, hydrodynamic shearing, and sonication, etc. Such whole-genome amplified DNA products may be predominantly methylated in terms of A sites. This DNA with mA was subjected to single-molecule, real-time sequencing to generate mA dataset.

For the uA dataset, we sequenced 262,608 molecules with a median of 964 bp in length using single-molecule, real-time sequencing. The median subread depth was 103×. Of the subreads, 48% could be aligned to a human reference genome using the BWA aligner (Li H et al. Bioinformatics. 2009; 25:1754-60). As an example, one could employ the Sequel II System (Pacific Biosciences) to carry out single-molecule, real-time sequencing. The fragmented DNA molecules were subjected to single-molecule real-time (SMRT) sequencing template construction using a SMRTbell Express Template Prep Kit 2.0 (Pacific Biosciences). Sequencing primer annealing and polymerase binding conditions were calculated with the SMRT Link v8.0 software (Pacific Biosciences). Briefly, sequencing primer v2 was annealed to the sequencing template, and then a polymerase was bound to templates using a Sequel II Binding and Internal Control Kit 2.0 (Pacific Biosciences). Sequencing was performed on a Sequel II SMRT Cell 8M. Sequencing movies were collected on the Sequel II system for 30 hours with a Sequel II Sequencing Kit 2.0 (Pacific Biosciences).

For the mA dataset, we sequenced 804,469 molecules with a median of 826 bp in length using single-molecule, real-time sequencing. The median subread depth was 34×. Of the subreads, 27% could be aligned to a human reference genome using the BWA aligner (Li H et al. Bioinformatics. 2009; 25:1754-60).

In one embodiment, the kinetic characteristics including but not limited to IPD and PW were analyzed in a strand-specific manner. For the sequencing results derived from the Watson strand, 644,318 A sites without methylation randomly selected from the uA dataset and 718,586 A sites with methylation randomly selected from the mA dataset were used to constitute a training dataset. Such a training dataset was used to establish the classification models and/or thresholds for differentiating between methylated and unmethylated adenines. A testing data set was constituted from 639,702 A sites without methylation and 723,320 A sites with methylation. Such a testing dataset was used to validate the performance for a model/threshold deduced from a training dataset.

Figure 32A:
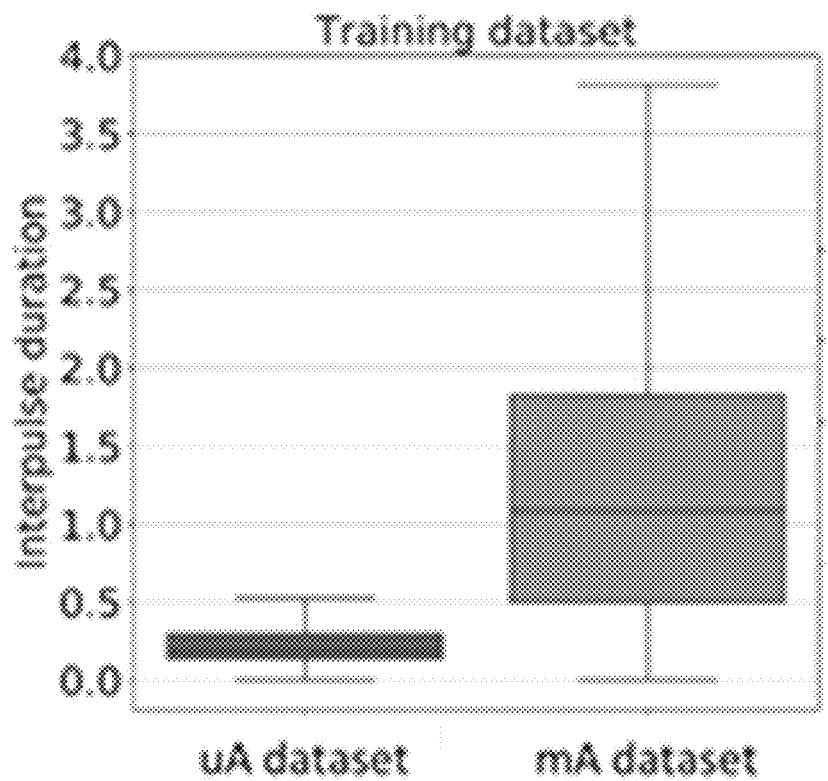
FIGS. 32A and 32B show interpulse duration (IPD) values across sequenced A bases in template DNA of the Watson strand between unmethylated and methylated datasets according to embodiments of the present invention.

We analyzed sequencing results originating from the Watson strands. FIG. 32A shows interpulse duration (IPD) values across the training dataset of the uA and mA datasets. For the training dataset, IPD values across sequenced A sites were observed to be higher in the mA dataset (median: 1.09; range: 0-9.52) than the uA dataset (median: 0.20; range: 0-9.52) (P value <0.0001; Mann Whitney U test).

Figure 32B:
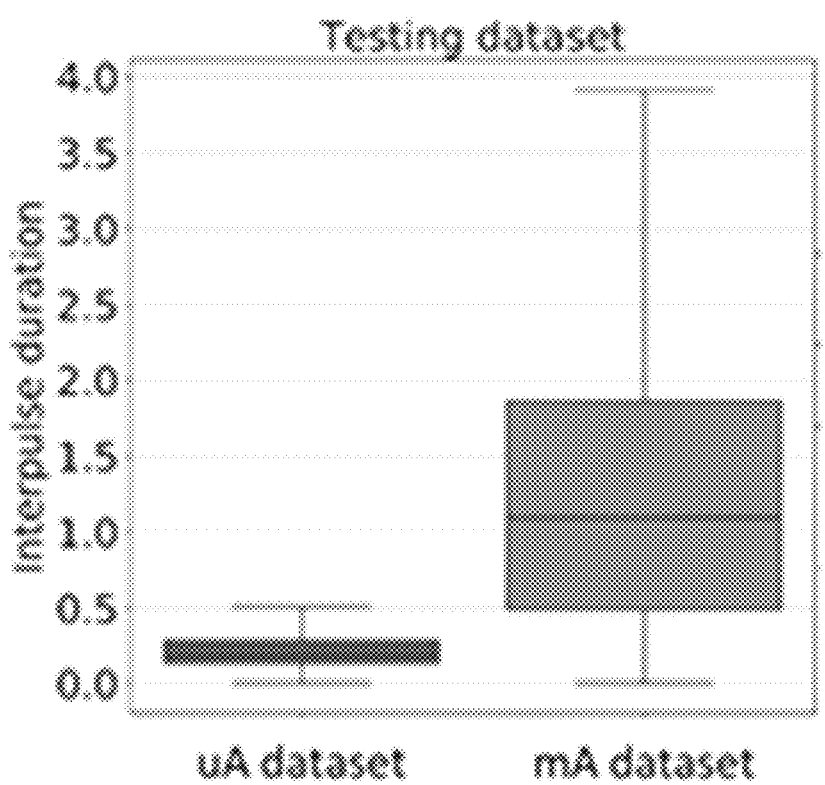

FIG. 32B shows IPD for the testing dataset of the uA and mA datasets. When we studied the IPD values across sequenced A sites in the testing dataset, we observed that IPD values were higher in the mA dataset than the uA dataset (median 1.10 versus 0.19; P value <0.0001; Mann Whitney U test).

Figure 32C:
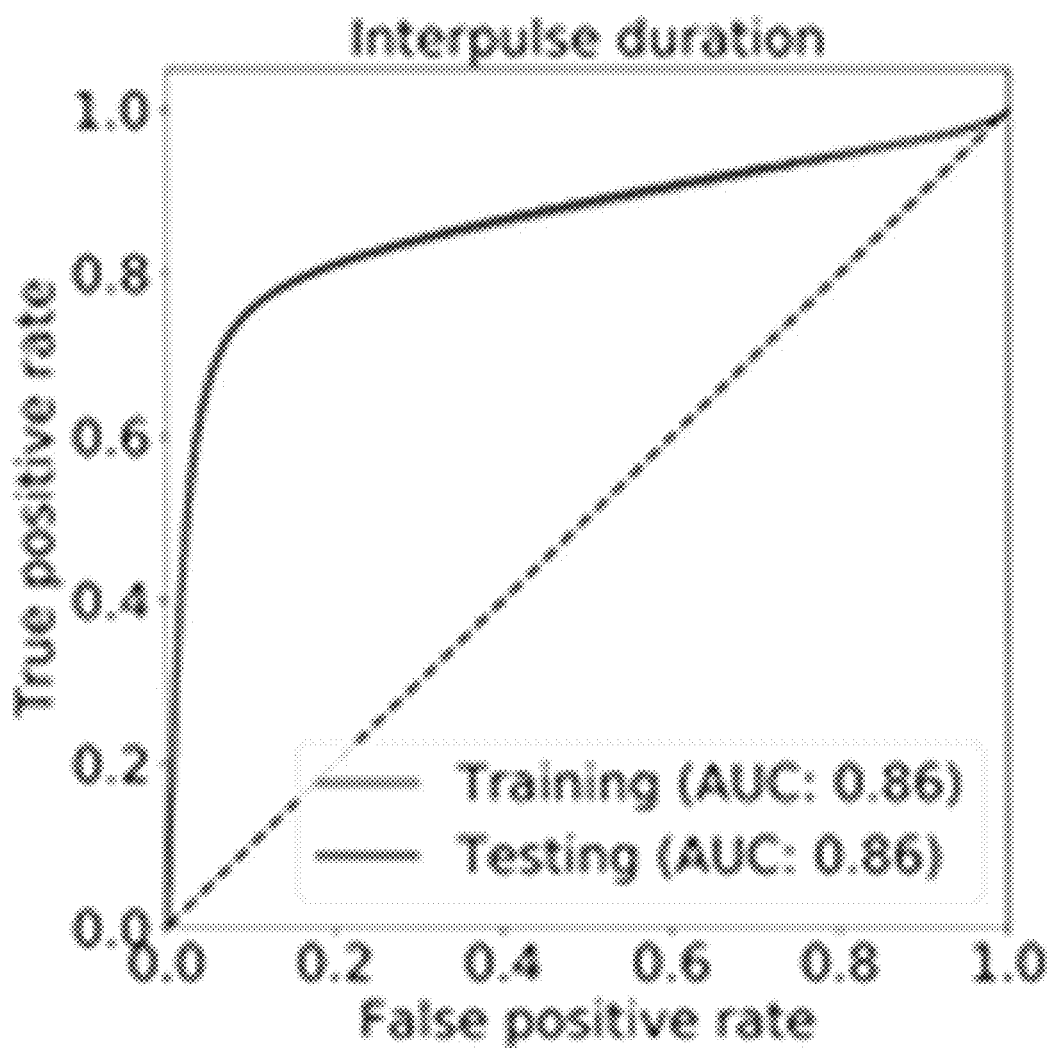
FIG. 32C shows a receiver operating characteristic curve for determining methylation in the Watson strand according to embodiments of the present invention.

FIG. 32C shows the area under the receiver operating characteristic (ROC) curve using the IPD cutoff. The true positive rate is on the y-axis, and the false positive rate is on the x-axis. The area under the receiver operating characteristic curve (AUC) in differentiating sequenced A bases in template DNA molecules with and without methylation using corresponding IPD values was 0.86 for both training and testing datasets.

Figure 33A:
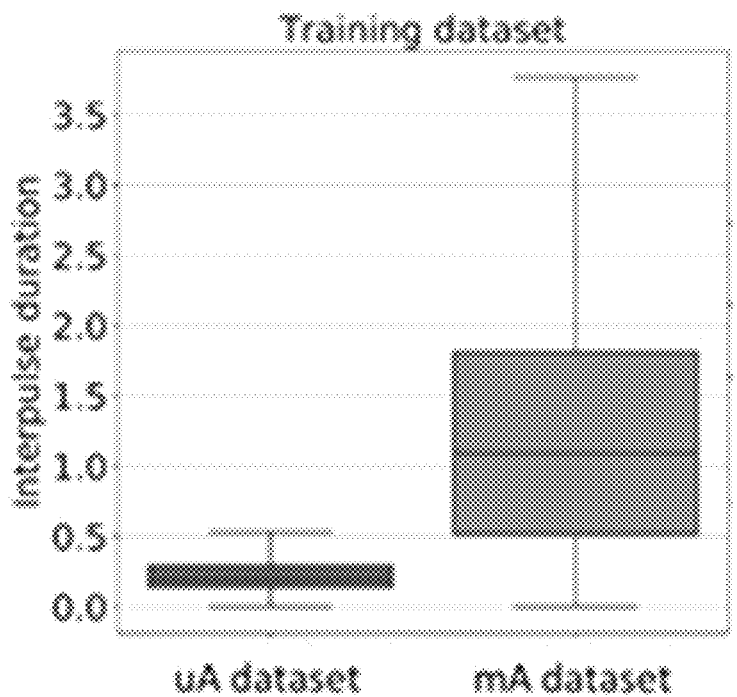
FIGS. 33A and 33B show interpulse duration (IPD) values across sequenced A bases in template DNA of the Crick strand between unmethylated and methylated datasets according to embodiments of the present invention.
Figure 33B:
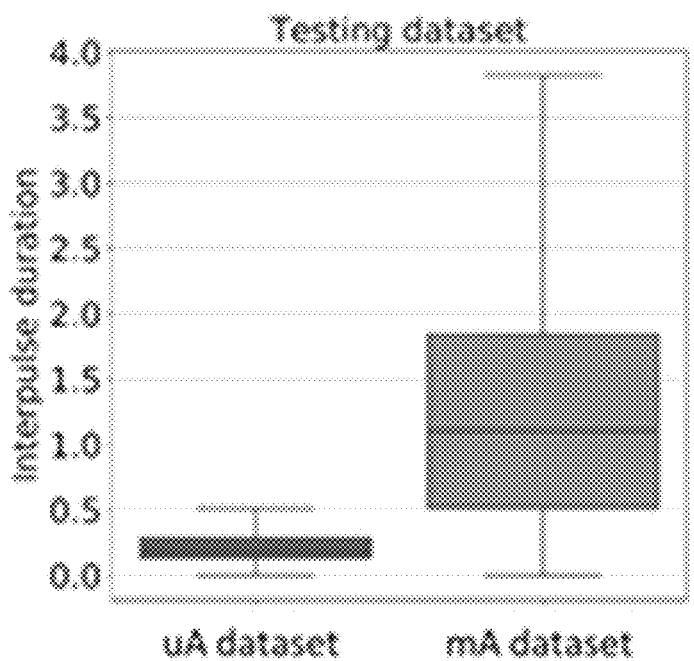

In addition to results from the Watson strand, we analyzed sequencing results originating from the Crick strands. FIG. 33A shows IPD values across the training dataset of uA and mA datasets. For the training dataset, IPD values across sequenced A sites were observed to be higher in the mA dataset (median: 1.10 range: 0-9.52) than in the uA dataset (median: 0.19; range: 0-9.52) (P value <0.0001; Mann Whitney U test).

FIG. 34B shows IPD values for the testing dataset of uA and mA datasets. The higher IPD values across sequenced A sites were also observed in the mA dataset for the testing dataset, compared with the uA dataset (median 1.10 versus 0.19; P value <0.0001; Mann Whitney U test).

Figure 33C:
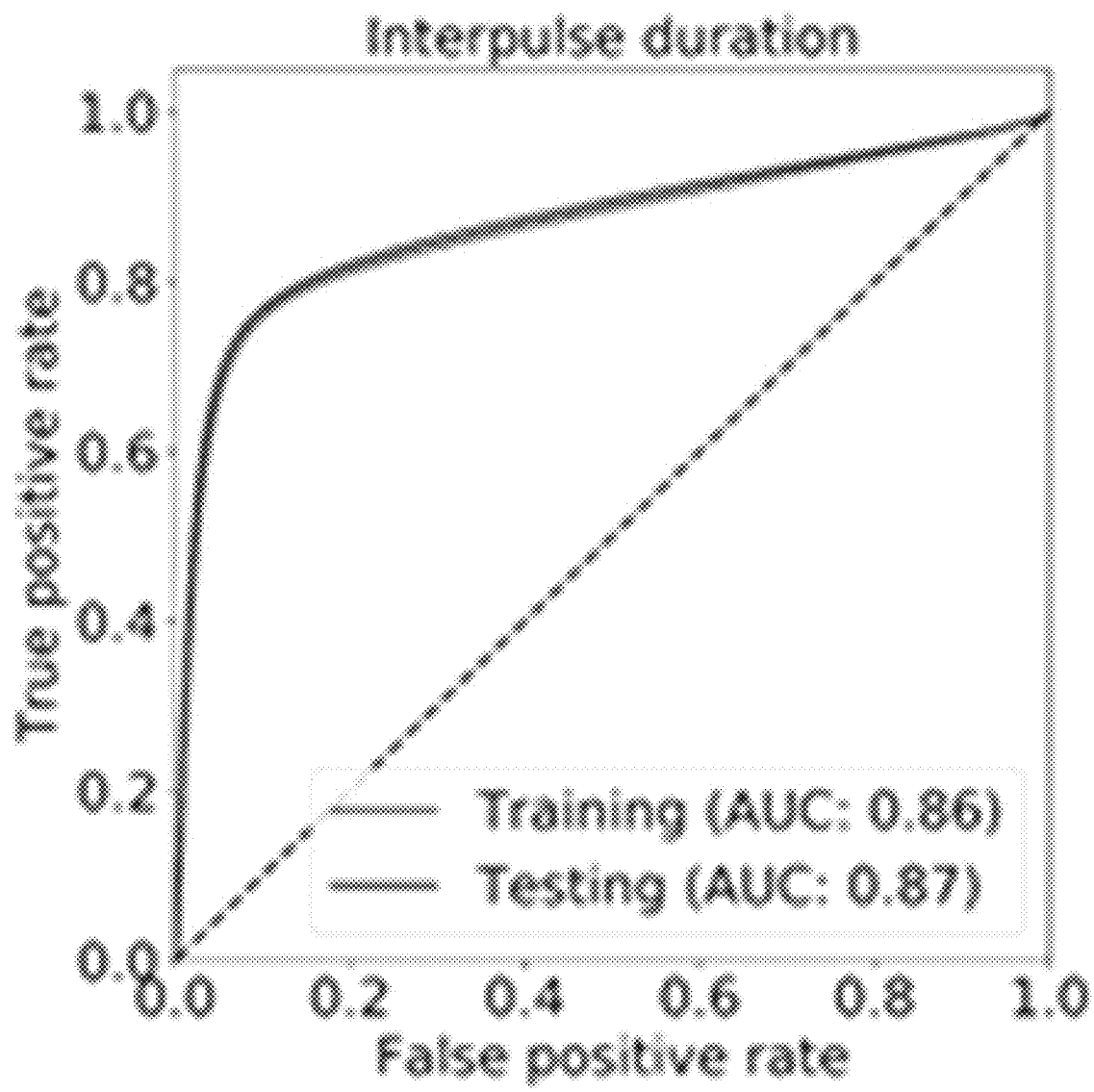
FIG. 33C shows a receiver operating characteristic curve for determining methylation in the Crick strand according to embodiments of the present invention.

FIG. 33C shows the area under ROC curve. The true positive rate is on the y-axis, and the false positive rate is on the x-axis. The area under the ROC curve (AUC) value in differentiating sequenced A bases in template DNA molecules with and without methylation using corresponding IPD values was 0.86 and 0.87 for the training and testing datasets, respectively.

Figure 34:
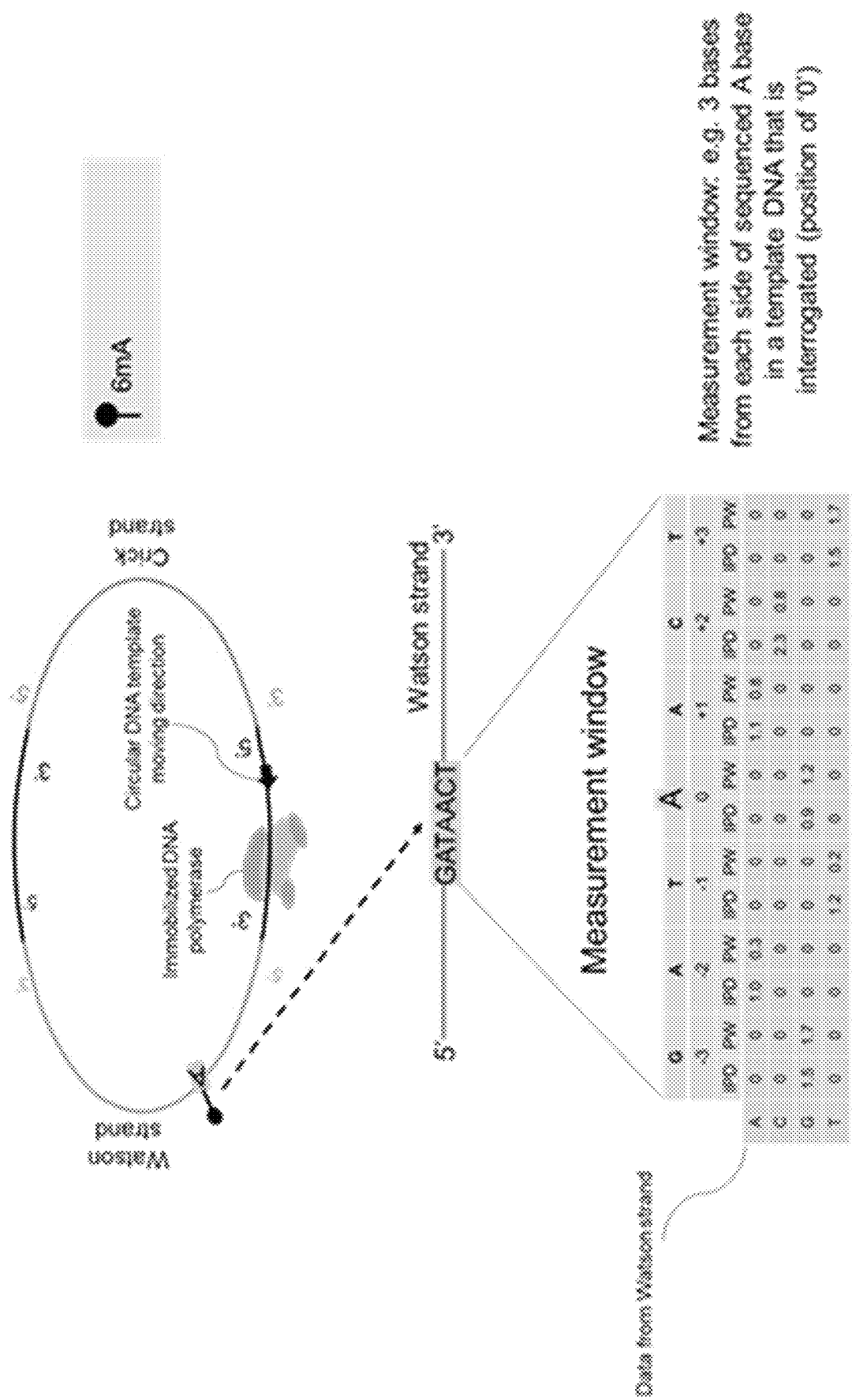
FIG. 34 illustrates 6 mA determination of the Watson strand according to embodiments of the present invention.

FIG. 34 shows an illustration for 6 mA determination of the Watson strand using a measurement window according to embodiments of the present invention. Such a measurement window may include kinetic features such as IPD and PW and nearby sequence context. Determination of 6 mA may be performed similarly as determination of methylated CpG.

Figure 35:
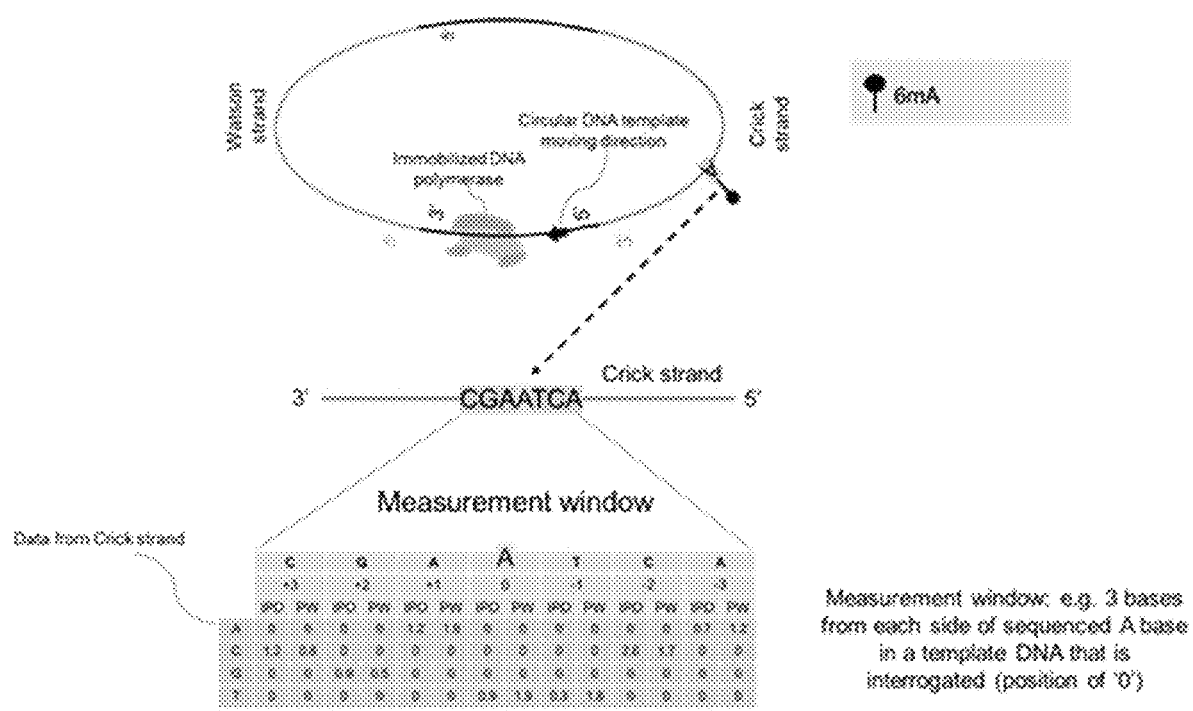
FIG. 35 illustrates 6 mA determination of the Crick strand according to embodiments of the present invention.

FIG. 35 shows an illustration for 6 mA determination of the Crick strand using a measurement window according to embodiments of the present invention. Such a measurement window may include kinetic features such as IPD and PW and nearby sequence context.

As an example, 10 bases from each side of sequenced A base in a template DNA that was being interrogated were used to construct a measurement window. The feature values including IPDs, PWs, and sequence context were used to train a model using a convolutional neural network (CNN) according to the methods disclosed herein. In other embodiments, the statistical models may include, but are not limited to, linear regression, logistic regression, deep recurrent neural network (e.g. long short term memory, LSTM), Bayes classifier, hidden Markov model (HMM), linear discriminant analysis (LDA), k-means clustering, density-based spatial clustering of applications with noise (DBSCAN), random forest algorithm, and support vector machine (SVM), etc.

Figure 36A:
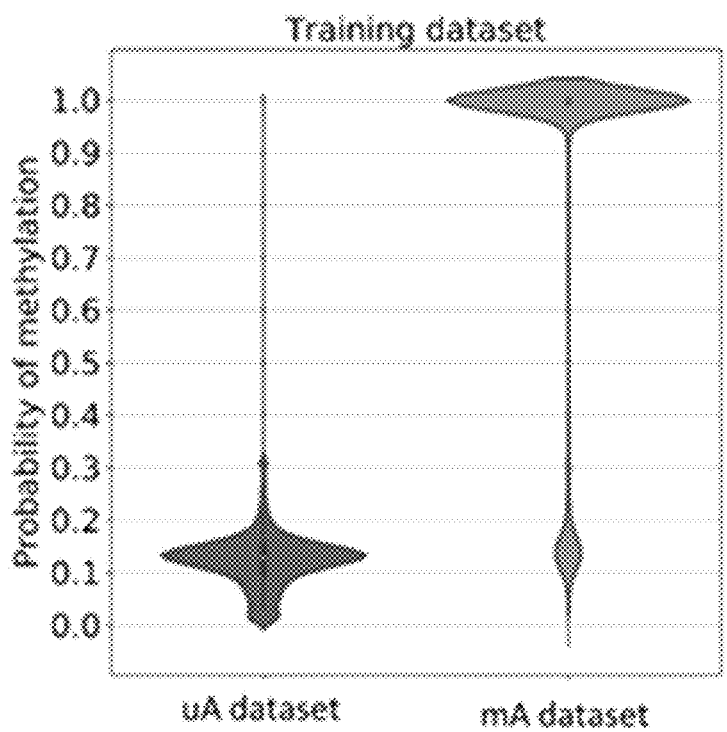
FIGS. 36A and 36B show the determined probability of being methylated for sequenced A bases of the Watson strand between uA and mA datasets using a measurement window based convolutional neural network model according to embodiments of the present invention.
Figure 36B:
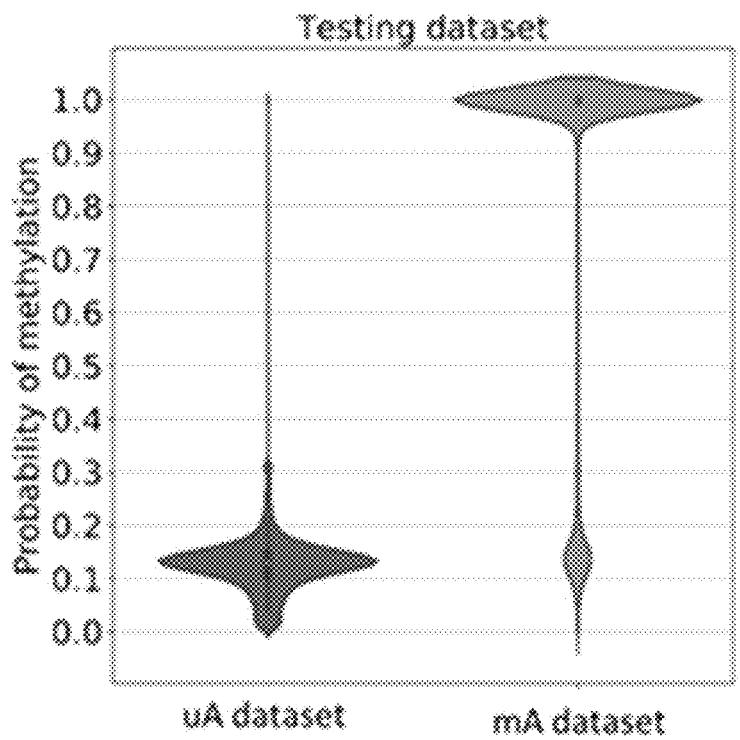

FIG. 36A and FIG. 36B show the determined probability of being methylated for sequenced A bases of the Watson strand between uA and mA datasets using a measurement window based CNN model. FIG. 36A shows that a CNN model was learned from a training dataset. As an example, the CNN model made use of two 1D-convolution layers (each with 64 filters with a kernel size of 4 followed by a ReLU (rectified linear unit) layer), followed by a dropout layer with a dropout rate of 0.5. A maximum pooling layer with a pool size of 2 was used. Then it flowed into two 1D-convolution layers (each with 128 filters with a kernel size of 2 followed by a ReLU layer), further using a dropout layer with a dropout rate of 0.5. A maximum pooling layer with a pool size of 2 was used. Finally, a fully connected layer with 10 neurons followed by a ReLU layer, with an output layer with one neuron followed by a sigmoid layer, thereby yielded the probability of methylation. The other settings of layers, filters, kernel sizes could be adapted, e.g., as described herein for other methylation (e.g., CpG). In this training dataset regarding the sequencing results of the Watson strand, we used 644,318 and 718,586 A bases from unmethylated and methylated libraries.

Based on the CNN model, for the Watson strand related data, sequenced A bases in template DNA molecules from mA database gave rise to a much higher probability of methylation in both the training and testing datasets, in comparison with those A bases present in the uA dataset (P value <0.0001; Mann Whitney U test). For the training dataset, the median probability of methylation on A sites in the uA dataset was 0.13 (interquartile range, IQR: 0.09-0.15), whereas that value in mA dataset was 1.000 (IQR: 0.998-1.000).

FIG. 36A shows the probability of methylation determined for the testing dataset. For the testing dataset, the median probability of methylation on A sites in the uA dataset was 0.13 (IQR: 0.10-0.15), whereas that value in mA dataset was 1.000 (IQR: 0.997-1.000). FIGS. 36A and 36B show that a measurement window based CNN model can be trained to detect methylation in a testing data set.

Figure 37:
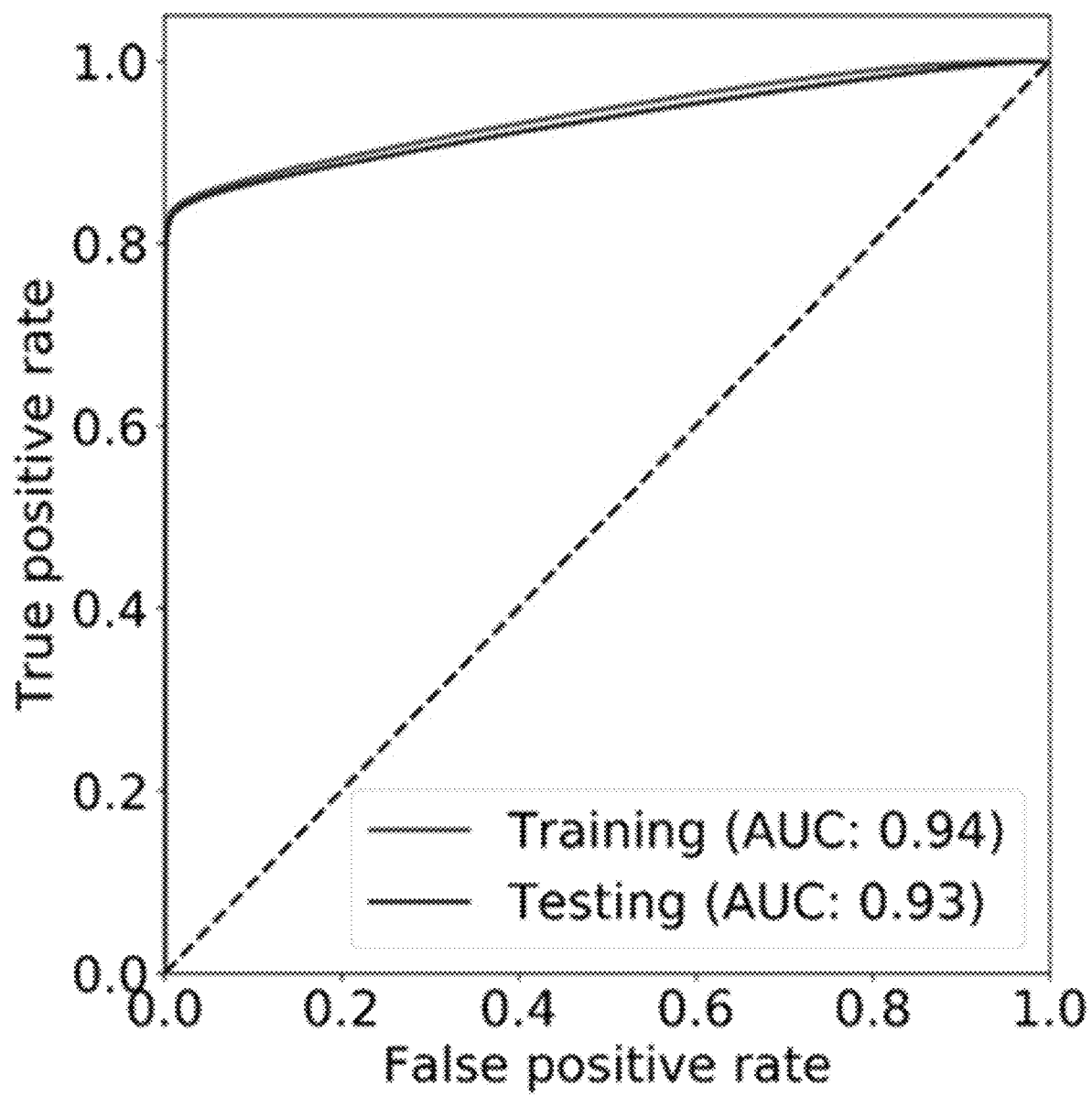
FIG. 37 shows an ROC curve for the detection of 6 mA using a measurement window based CNN model for sequenced A bases of the Watson strand according to embodiments of the present invention.

FIG. 37 is an ROC curve for the detection of 6 mA using a measurement window based CNN model for sequenced A bases of the Watson strand. True positive rate is on the y-axis and false positive rate is on the x-axis. The figure shows that AUC value in differentiating sequenced A sites with and without methylation using a CNN model was 0.94 and 0.93 for training and testing datasets which consisted of the Watson strand sequencing results, respectively. It suggested that it was feasible to use the disclosure herein to determine methylation states on A sites using data of the Watson strand. If we used the determined probability of methylation of 0.5 as cutoff, 99.3% specificity and 82.6% sensitivity could be achieved for 6 mA detection. FIG. 37 shows that a measurement window based CNN model can be used to detect 6 mA with high specificity and sensitivity. The accuracy of the model can be compared to a technique using only an IPD metric.

Figure 38:
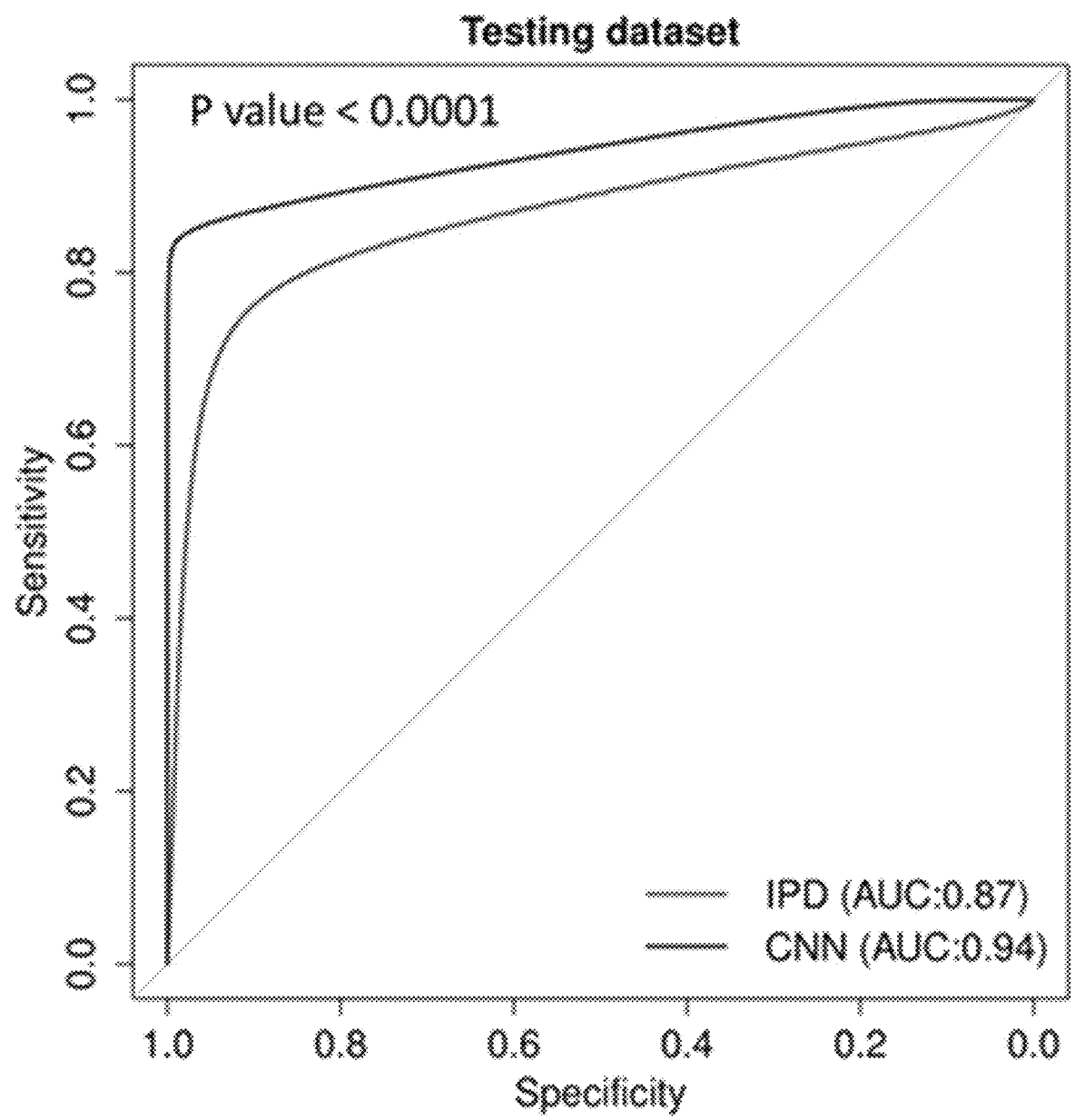
FIG. 38 shows a performance comparison between IPD-metric-based 6 mA detection and a measurement window based 6 mA detection according to embodiments of the present invention.

FIG. 38 shows a performance comparison between IPD-metric-based 6 mA detection and a measurement window based 6 mA detection. Sensitivity is plotted on the y-axis and specificity is plotted on the x-axis. FIG. 38 shows that the performance using measurement window based 6 mA classification according to the disclosure herein (AUC: 0.94) was superior to that conventional method using IPD metric only (AUC: 0.87) (P value <0.0001; DeLong's test). The measurement window based CNN model outperformed the IPD-metric-based detection.

Figure 39A:
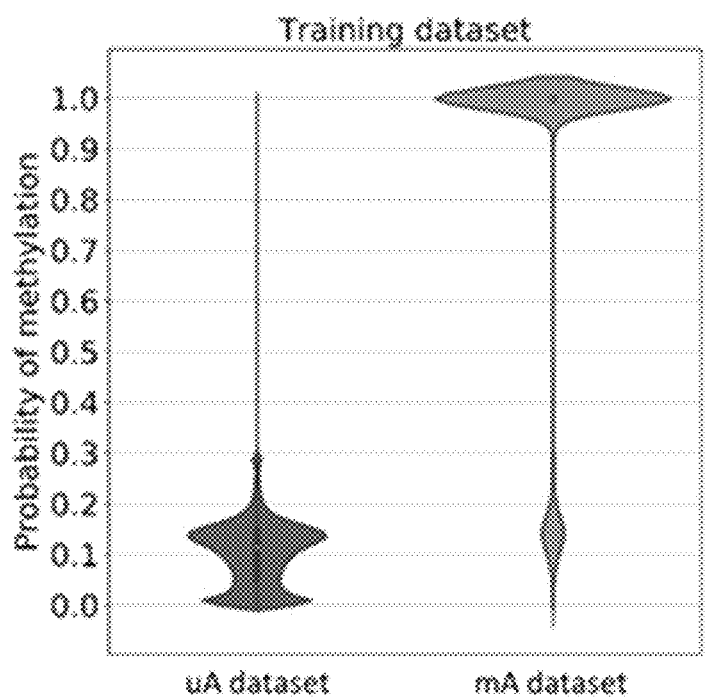
FIGS. 39A and 39B show the determined probability of being methylated for those sequenced A bases of the Crick strand between uA and mA datasets using measurement window based CNN model according to embodiments of the present invention.
Figure 39B:
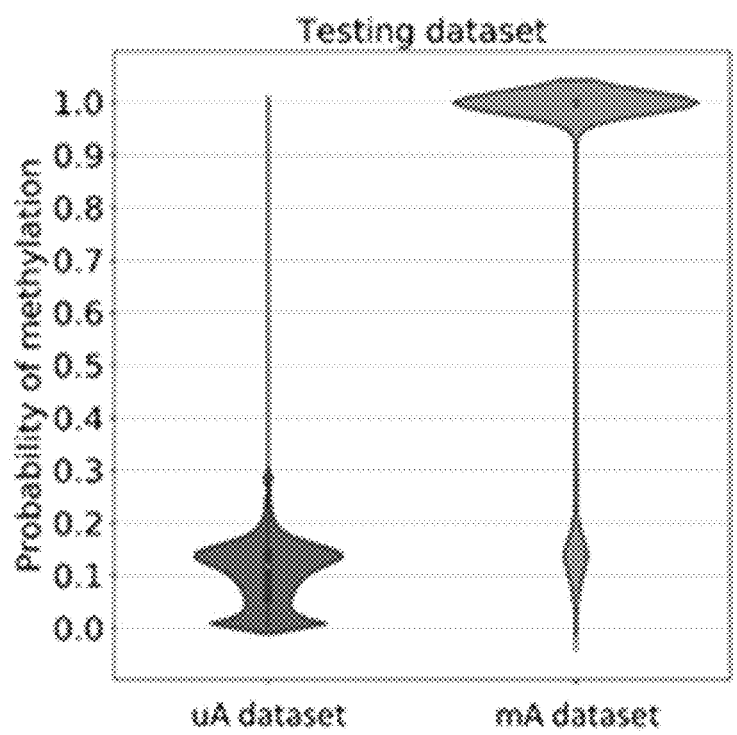

FIGS. 39A and 39B show the determined probability of being methylated for those sequenced A bases of the Crick strand between uA and mA datasets using measurement window based CNN model. FIG. 39A shows the training dataset and FIG. 39B shows the testing dataset. Both figures plot the probability of methylation on the y-axis. FIGS. 39A and 39B show that on the basis of CNN model, for the Crick strand related data, sequenced A bases in template DNA molecules from mA database gave rise to a much higher probability of methylation in both training and testing dataset, in comparison with those A bases present in uA database (P value <0.0001; Mann-Whitney U test).

Figure 40:
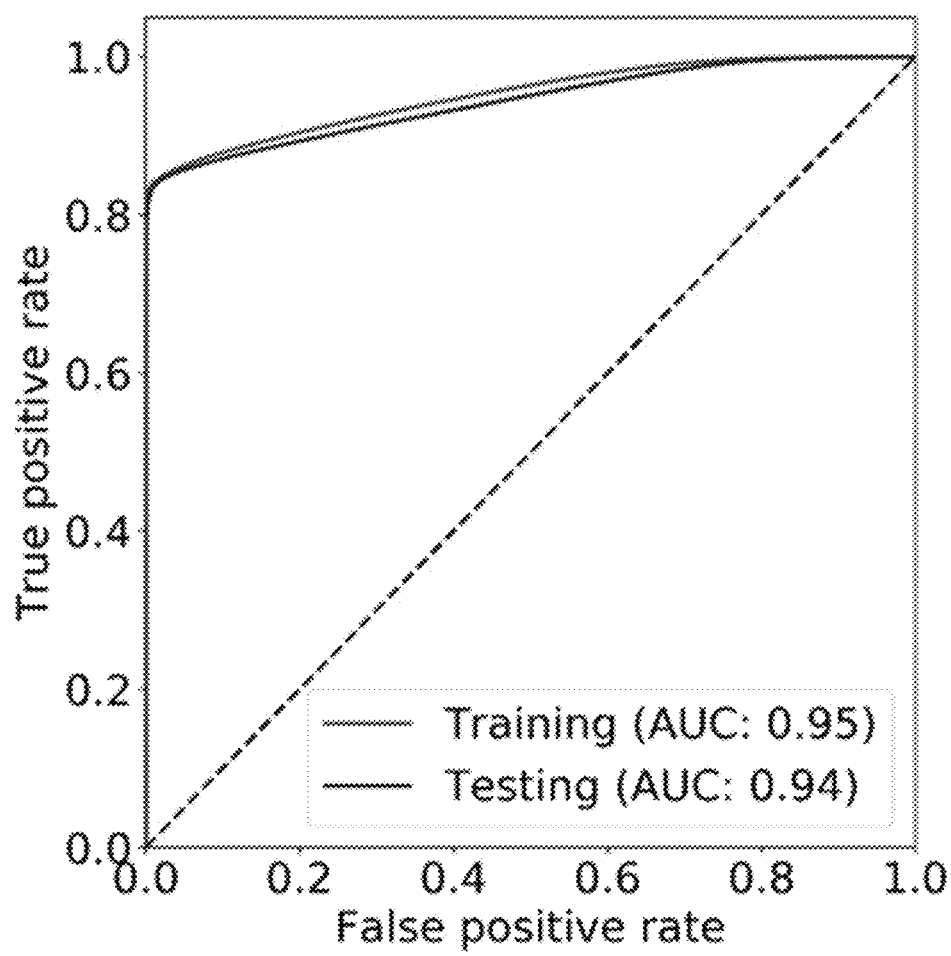
FIG. 40 shows the performance of 6 mA detection using measurement window based CNN model on sequenced A bases of the Crick strand according to embodiments of the present invention.

FIG. 40 shows the performance of 6 mA detection using measurement window based CNN model on sequenced A bases of the Crick strand. The true positive rate is on the y-axis. The false positive rate is on the x-axis. FIG. 40 shows that AUC value in differentiating sequenced A sites with and without methylation using a CNN model was 0.95 and 0.94 for training and testing datasets which consisted of the Crick strand sequencing results, respectively. The performance using the CNN approach disclosed herein (AUC: 0.94) was also shown to be superior to that only using IPD metric (0.87) (P value <0.0001). The results suggested that it was feasible to use the disclosure herein to determine methylation states on A sites using data of the Crick strand. If we used the determined probability of methylation of 0.5 as cutoff, 99.3% specificity and 83.0% sensitivity could be achieved for 6 mA detection. FIG. 40 shows that a measurement window based CNN model can be used to detect 6 mA with high specificity and sensitivity.

Figure 41:
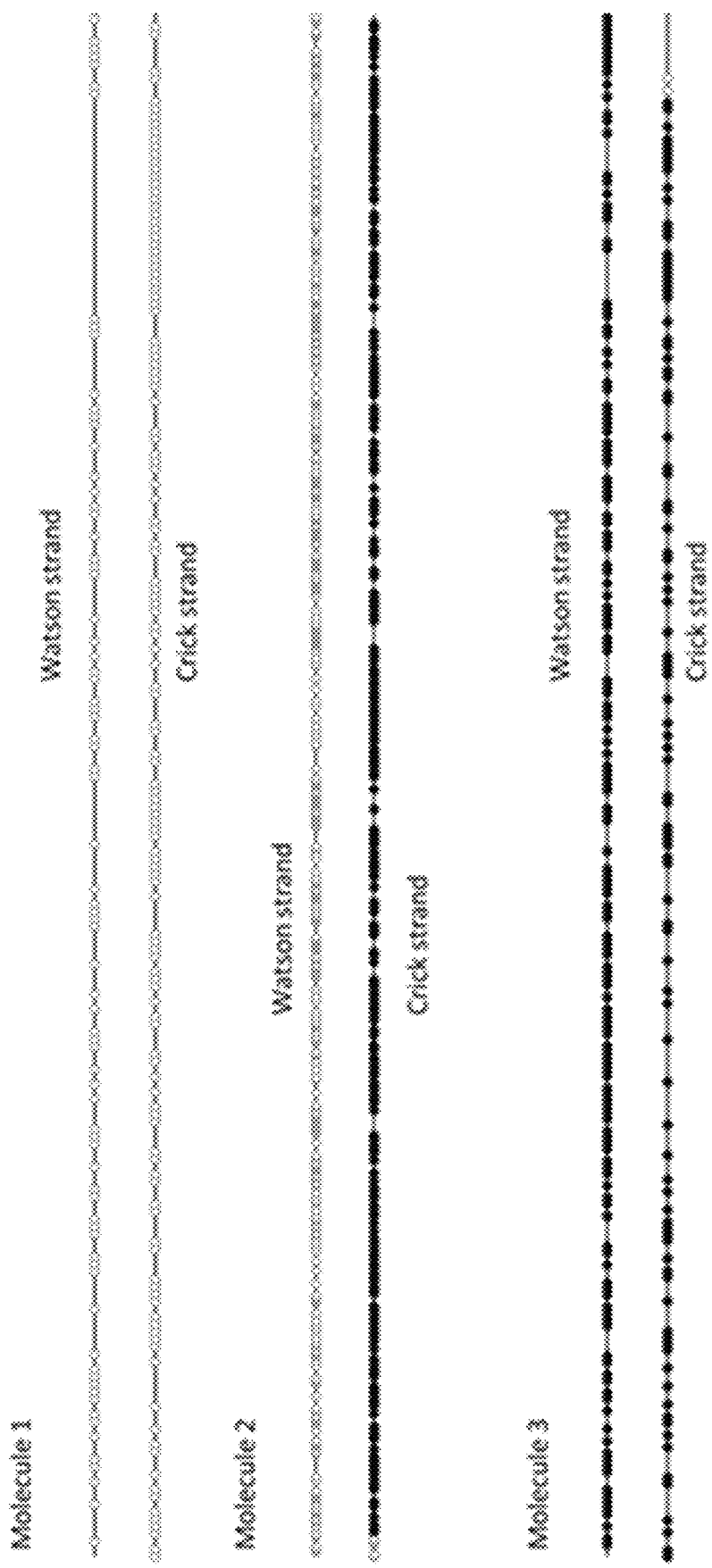
FIG. 41 shows examples of methylation states across A bases in a molecule including the Watson and Crick strands according to embodiments of the present invention.

FIG. 41 shows examples of methylation states across A bases in a molecule including the Watson and Crick strands. The white dots represent unmethylated adenines. The black dots represent methylated adenines. The horizontal lines with dots represent a strand of a double-stranded DNA molecule. Molecule 1 shows that both the Watson and Crick strands are determined to be unmethylated across A bases. Molecule 2 shows that the Watson strand was nearly all unmethylated while the Crick strand was nearly all methylated. Molecule 3 shows that both the Watson and Crick strands were determined to be nearly all methylated across A bases.

2. Enhanced Training Using Selective Dataset

As shown in FIGS. 36A, 36B, 39A, and 39B, there was a bimodal distribution of probability of methylation across sequenced A bases in template DNA molecules in mA dataset. In other words, there existed some molecules with uA signals in the mA dataset. This was further evidenced by the existence of fully-unmethylated molecules and hemi-methylated molecules in mA dataset (FIG. 41). One possible reason may be that molecules with uA in DNA templates would still account for a considerable portion in the mA dataset after whole genome amplification, as molecules with 6 mA would lead to the decreased efficiency of amplifying DNA during the whole-genome amplification step. This explanation was supported by the fact that 1 ng genomic DNA amplified with 6 mA would only lead to 10 ng DNA products, whereas 1 ng genomic DNA amplified with unmethylated A would give rise to 100 ng DNA products under the same amplification conditions. Therefore, for the mA dataset, original template DNA molecules whose adenines are usually unmethylated (e.g. 0.051%) (Xiao C L et al. Mol Cell. 2018; 71:306-318) would account approximately 10% of the total adenines.

In one embodiment, when one attempted to train a CNN model for differentiating between mA and uA, one would selectively use those A bases with relatively higher IPD values in the mA dataset so as to reduce the influence of the uA data on training the model for mA detection. Only A bases with IPD values above a certain cutoff value may be used. The cutoff value may correspond to a percentile. In one embodiment, one would use those A bases in mA dataset with IPD values greater than the value at the $10^{th}$ percentile. In some embodiments, one would use those A with IPD values greater than value at the $1^{st}$, $5^{th}$, $15^{th}$, $20^{th}$, $30^{th}$, $40^{th}$, $50^{th}$, $60^{th}$, $70^{th}$, $80^{th}$, $90^{th}$, or $95^{th}$ percentile. The percentile may be based on data from all nucleic acid molecules in a reference sample or multiple reference samples.

Figure 42:
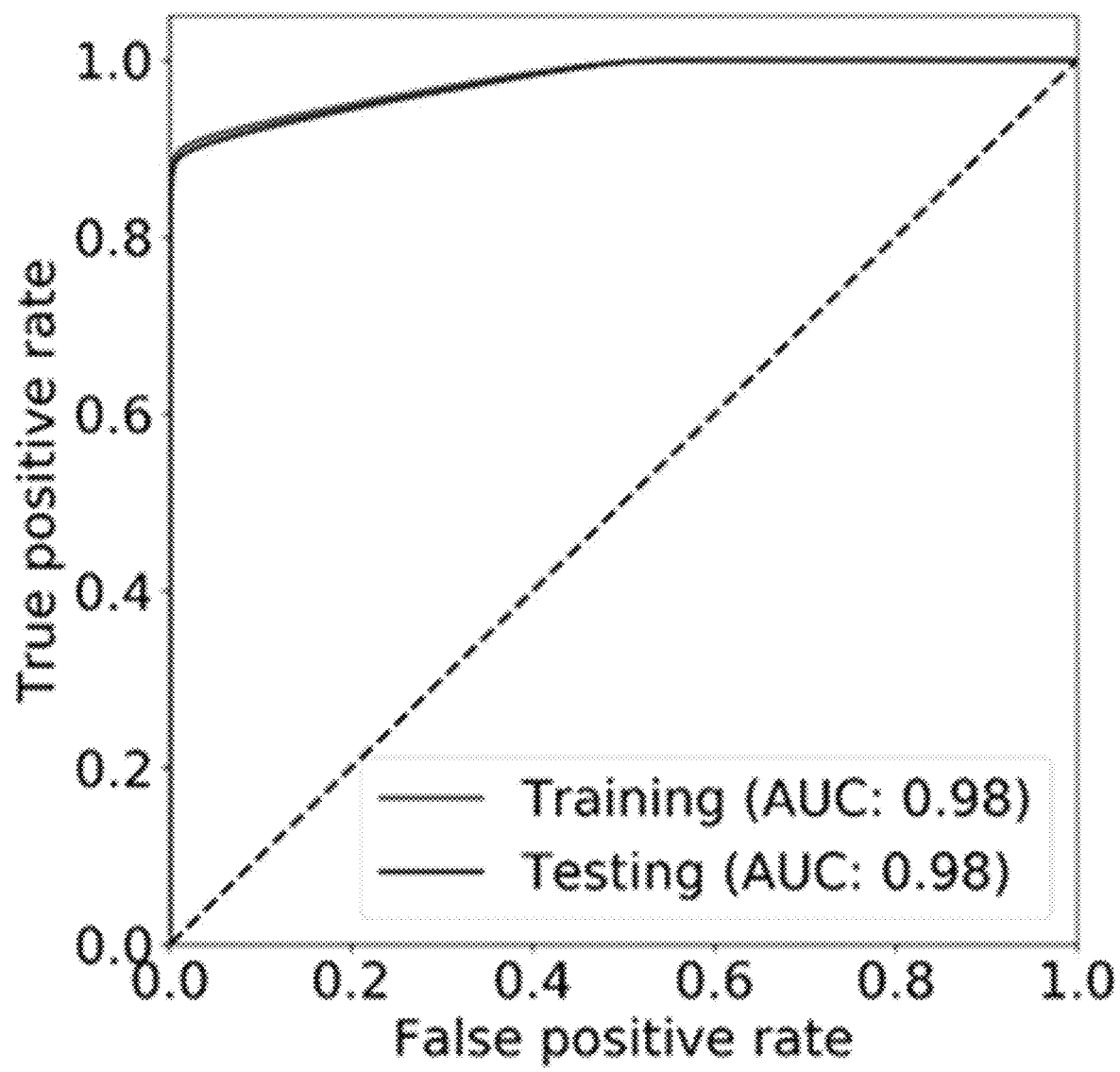
FIG. 42 shows an example of enhanced training by selectively using A bases in mA dataset with IPD values greater than its $10^{th}$ percentile according to embodiments of the present invention.

FIG. 42 shows the performance with enhanced training by selectively using A bases in mA dataset with IPD values greater than its $10^{th}$ percentile. FIG. 42 shows the true positive rate on the y-axis and the false positive rate on the x-axis. The figure shows that with the use of A bases in the mA dataset with IPD values greater than the $10^{th}$ percentile to train a CNN model, the AUC in differentiating between mA and uA bases would increase to 0.98, which was superior to the model (AUC: 0.94) trained by data without the selection according to IPD values prior to training. It suggested that the selection of mA sites using IPD values to create a training dataset would aid in improving the discriminative power.

To further confirm the existence of molecules with uA bases in mA dataset, we hypothesized that the percentage of uA in mA dataset would enrich in those wells with more subreads, as the 6 mA present in a molecule would slow down the polymerase elongation when generating a new strand, in comparison with a molecule without 6 mA.

Figure 43:
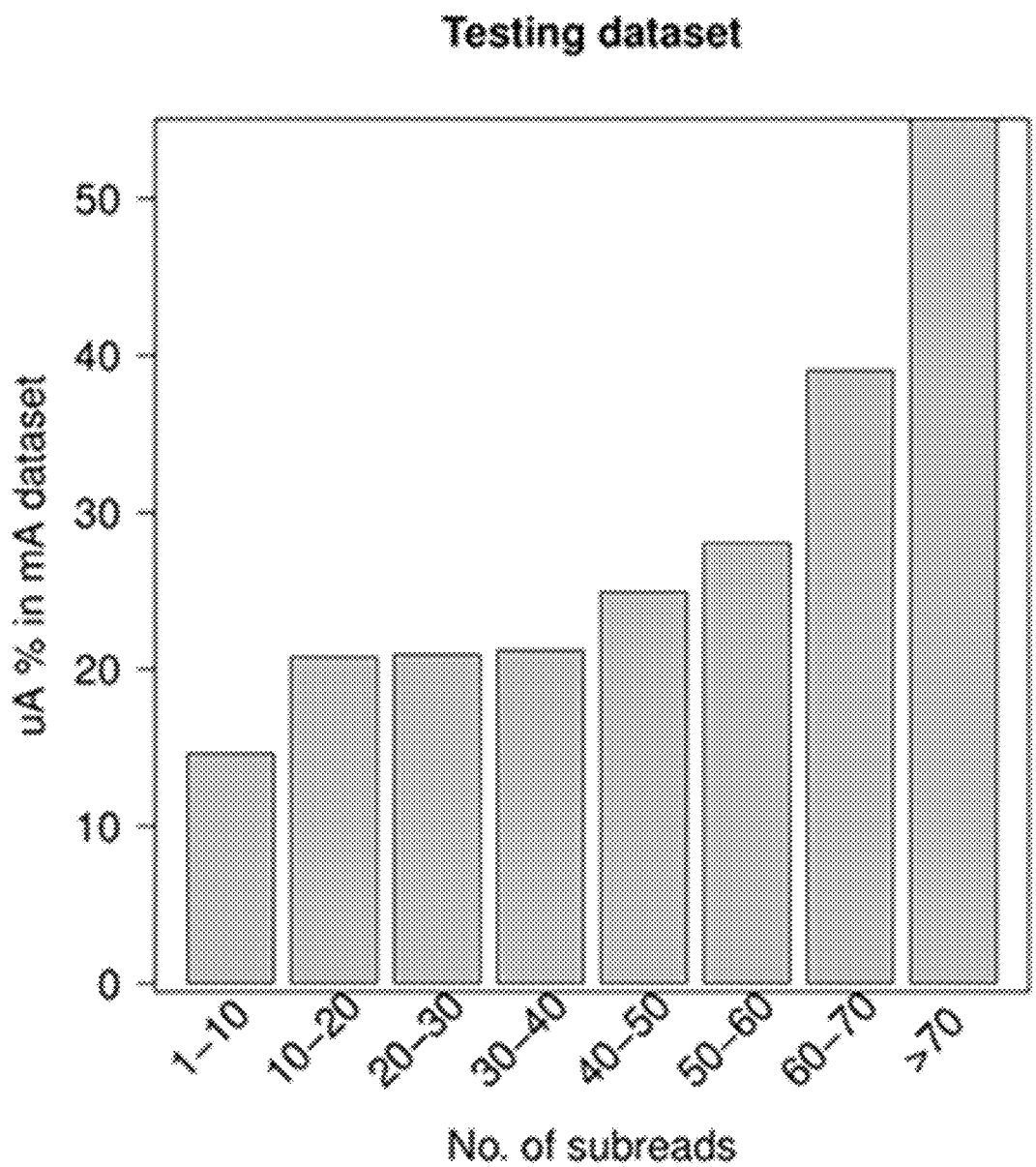
FIG. 43 is a graph of the percentages of unmethylated adenines in the mA dataset versus the number of subreads in each well according to embodiments of the present invention.

FIG. 43 shows a graph of the percentages of unmethylated adenines in the mA dataset versus the number of subreads in each well. The y-axis shows the percentage of uA in the mA dataset. The x-axis shows the number of subreads in each well. The testing dataset was reanalyzed using the enhanced model that was trained by using mA sites after removal of A sites whose IPD values were below the $10^{th}$ percentile. A gradual increase of uA (i.e. rising from 14.6 to 55.05%) was observed as the number of subreads per well increased, including from 1 to 10 subreads per sequencing well, to 10 to 20 subreads per well, to 40 to 50 subreads per well, 60 to 70 subreads per well and above 70. Thus, wells that have a high number of subreads tend to have low mA. The methylation of A may retard the progression of the sequencing reaction. Hence, it is more likely that sequencing wells with a high subread depth will be unmethylated with regard to A. This behavior can be exploited for detection of the unmethylated molecules using a cutoff value for the number of subreads associated with the molecule, e.g., greater than 70 subreads can be identified as majority unmethylated.

Figure 44:
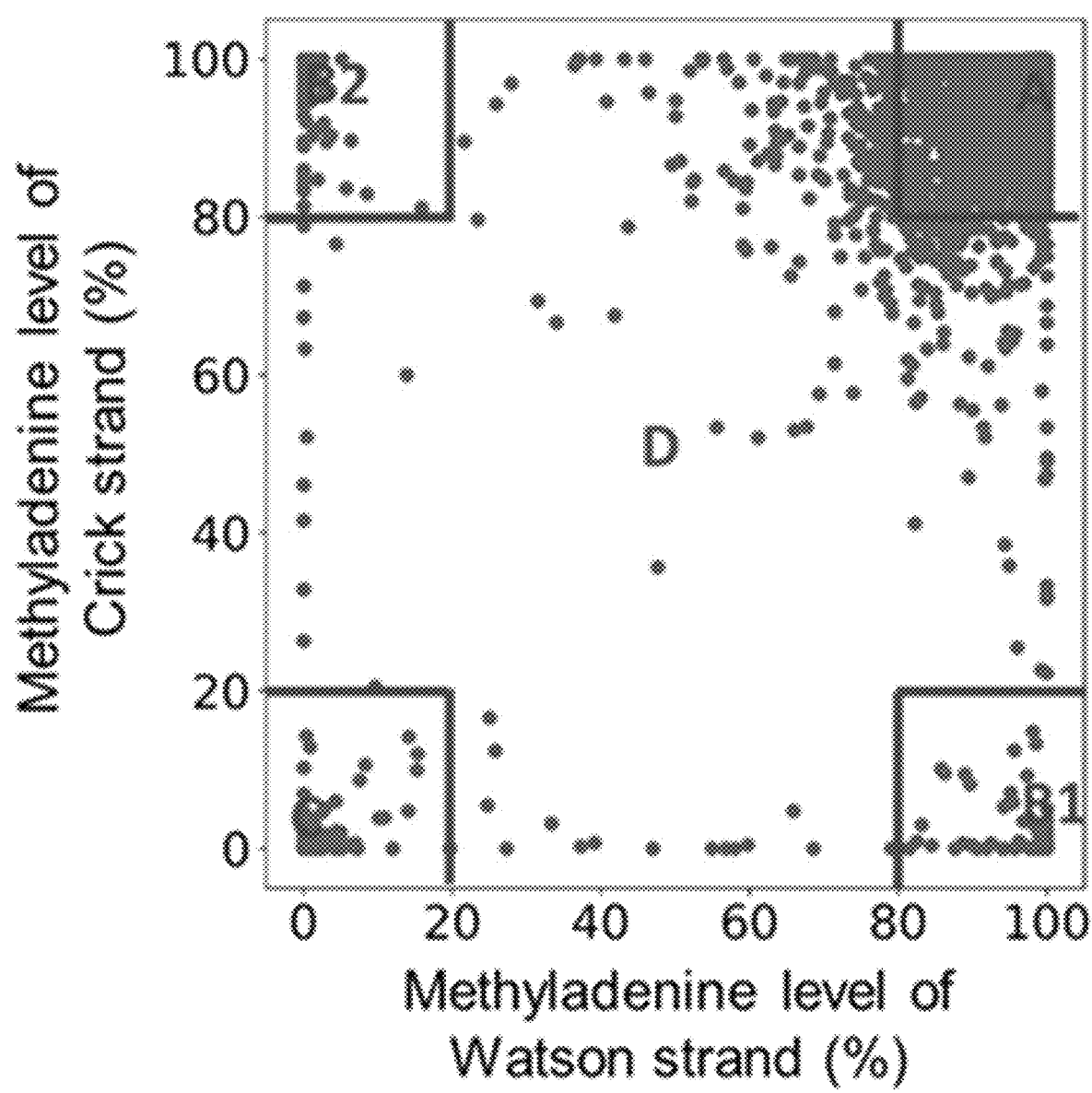
FIG. 44 shows methyladenine patterns between the Watson and Crick strands of a double-stranded DNA molecule in a testing dataset according to embodiments of the present invention.

FIG. 44 shows methyladenine patterns between the Watson and Crick strands of a double-stranded DNA molecule in a testing dataset. The methylation of A is asymmetric, and thus the behavior is different between the two strands. Most of the molecules were methylated due to the incorporation of mA, with some residual unmethylated A. The y-axis shows the methyladenine level of the Crick strand. The x-axis shows the methyladenine level of the Watson strand. Each dot represents a double-stranded molecule. Using the enhanced model that was trained by selected mA sites, the double-stranded molecules may be categorized into different groups according to the methylation level of each strand as follows:

(a) For a double-stranded DNA molecule, the methyladenine levels of the Watson and Crick strands were both greater than 0.8. Such a double-stranded molecule was defined as a fully-methylated molecule regarding adenine sites (FIG. 44, area A). The methyladenine level of a strand was defined as the percentage of A sites that were determined to be methylated among total A sites in that strand.

(b) For a double-stranded DNA molecule, the methyladenine level of one strand was greater than 0.8 whereas the other strand was less than 0.2. Such a molecule was defined as hemi-methylated molecule regarding adenine sites (FIG. 44, areas B1 and B2).

(c) For a double-stranded DNA molecule, the methyladenine levels of the Watson and Crick strands were both less than 0.2. Such a double-stranded molecule was defined as a fully-unmethylated molecule regarding adenine sites (FIG. 44, area C).

(d) For a double-stranded DNA molecule, the methyladenine levels of the Watson and Crick strands did not belong to groups a, b, and c. Such a double-stranded molecule was defined as a molecule with interlacing methylation patterns regarding adenine sites (FIG. 44, area D). The interlacing methylation patterns were defined as a mixture of methylated and unmethylated adenines present in a DNA strand.

In some other embodiments, the cutoffs of methyladenine levels for defining unmethylated strand may be, but are not limited to, less than 0.01, 0.05, 0.1, 0.2, 0.3, 0.4, and 0.5. The cutoffs of methyladenine levels for defining methylated strand would be but not limited to greater than 0.5, 0.6, 0.7, 0.8, 0.9, 0.95, and 0.99.

FIG. 45 is a table showing the percentage of fully-unmethylated molecules, hemi-methylated molecules, fully-methylated molecules, and molecules with interlaced methyladenine patterns in training and testing datasets. The molecules in the testing dataset may be classified into fully-unmethylated molecules (7.0%) with respect to adenine sites, hemi-methylated molecules (9.8%), fully-methylated molecules (79.4%), and molecules with interlacing methyladenine patterns (3.7%). These results were comparable to the results shown in the training dataset, for which there were fully-unmethylated molecules (7.0%) with respect to adenine sites, hemi-methylated molecules (10.0%), fully-methylated molecules (79.4%), and molecules with interlaced methyladenine patterns (3.6%).

Figure 46:
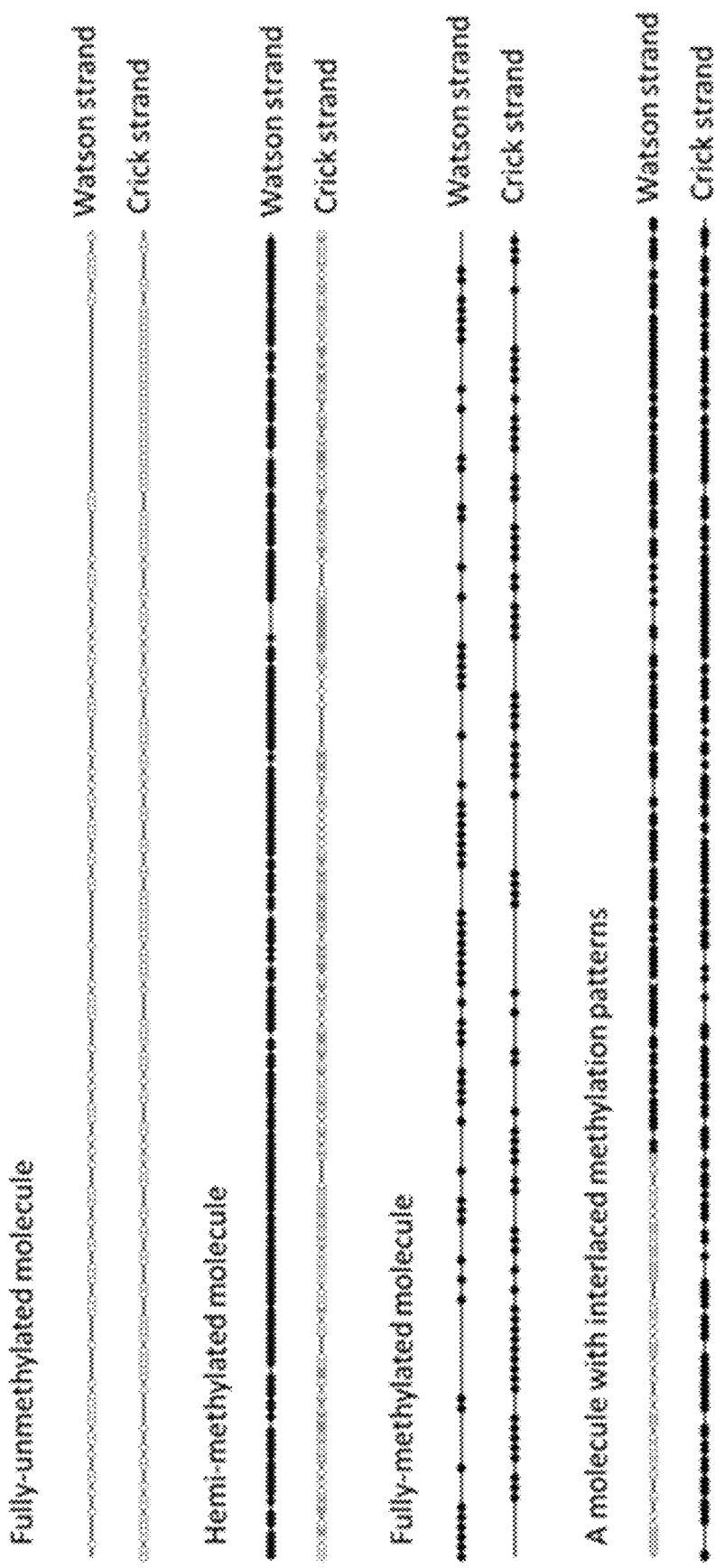
FIG. 46 illustrates representative examples for molecules with fully-unmethylated molecules regarding adenine sites, hemi-methylated molecules, fully-methylated molecules, and molecules with interlaced methyladenine patterns according to embodiments of the present invention.

FIG. 46 illustrates representative examples for molecules with fully-unmethylated molecules regarding adenine sites, hemi-methylated molecules, fully-methylated molecules, and molecules with interlaced methyladenine patterns. The white dots represent unmethylated adenines. The black dots represent methylated adenines. The horizontal lines with dots represent a strand of a double-stranded DNA molecule.

In embodiments, one may improve the performance in differentiating between methylated and unmethylated adenines by increasing the purity of 6 mA bases which were used for training a CNN model. To this end, one may increase the time duration of DNA amplification reaction so that increased newly-produced DNA products can dilute the effect of unmethylated adenines contributed from original DNA templates. In other embodiments, one may incorporate biotinylated bases during DNA amplification with 6 mA. The newly-produced DNA products with 6 mA can be pulled down and enriched using streptavidin coated magnetic beads.

3. Uses of 6 mA Methylation Profiles

DNA 6 mA modification is present in the genomes of bacteria, archaea, protists, and fungi (Didier W et al. Nat Rev Micorbiol. 2009; 4:183-192). It was also reported that 6 mA existed in the human genome, accounting for 0.051% of the total adenines (Xiao C L et al. Mol Cell. 2018; 71:306-318). Considering the low content of 6 mA in a human genome, in one embodiment, one can create a training dataset by adjusting the ratio of 6 mA in dNTP mix (N represents unmodified A, C, G, and T) in the step of whole genome amplification. For example, one could use the ratio of 6 mA to dNTP of 1:10, 1:100, 1:1000, 1:10000, 1:100000, or 1:1000000. In another embodiment, adenine DNA methyltransferase M. EcoGII may be used to create 6 mA training dataset.

The amount of 6 mA was lower in gastric and liver cancer tissues, and this 6 mA downregulation correlated with increased tumorigenesis (Xiao C L et al. Mol Cell. 2018; 71:306-318). On the other hand, it was reported that higher levels of 6 mA were present in glioblastoma (Xie et al. Cell. 2018; 175:1228-1243). Thus, the approach for 6 mA as disclosed herein would be useful for studying cancer genomics (Xiao C L et al. Mol Cell. 2018; 71:306-318; Xie et al. Cell. 2018; 175:1228-1243). In addition, 6 mA was found to be more prevalent and abundant in mammalian mitochondrial DNA, showing in association with hypoxia (Hao Z et al. Mol Cell. 2020; doi:10.1016/j.molcel.2020.02.018). Thus, the approach for 6 mA detection in this disclosure would be useful for studying the mitochondrial stress response under different clinical conditions such as pregnancy, cancer, and autoimmune diseases.

IV. Results and Applications

A. Detecting Methylation

Detecting methylation at CpG sites using methods described above was performed for different biological samples and genomic regions. As an example, methylation determination with cell-free DNA in the plasma of pregnant women using single molecule, real-time sequencing was verified against methylation determination using bisulfite sequencing. The methylation results may be used for different applications, including determining copy number and diagnosing disorders. The methods described below are not limited to CpG sites and may also be applied to any modification described herein.

1. Detection of Methylation for Long DNA Molecules in Placenta Tissue

Single molecule, real-time sequencing could sequence DNA molecules kilobases in length (Nattestad et al., 2018). The deciphering of methylation states for CpG sites using the invention described here would allow one to infer the haplotype information of the methylation states by synergistically making use the long-read information of single molecule, real-time sequencing. To demonstrate the feasibility of inferring the long-read methylation states as well as its haplotype information, we sequenced a placenta tissue DNA with 478,739 molecules which were covered by 28,913,838 subreads. There were 7 molecules greater than 5 kb in size. Each was on average covered by 3 subreads.

Figure 47:
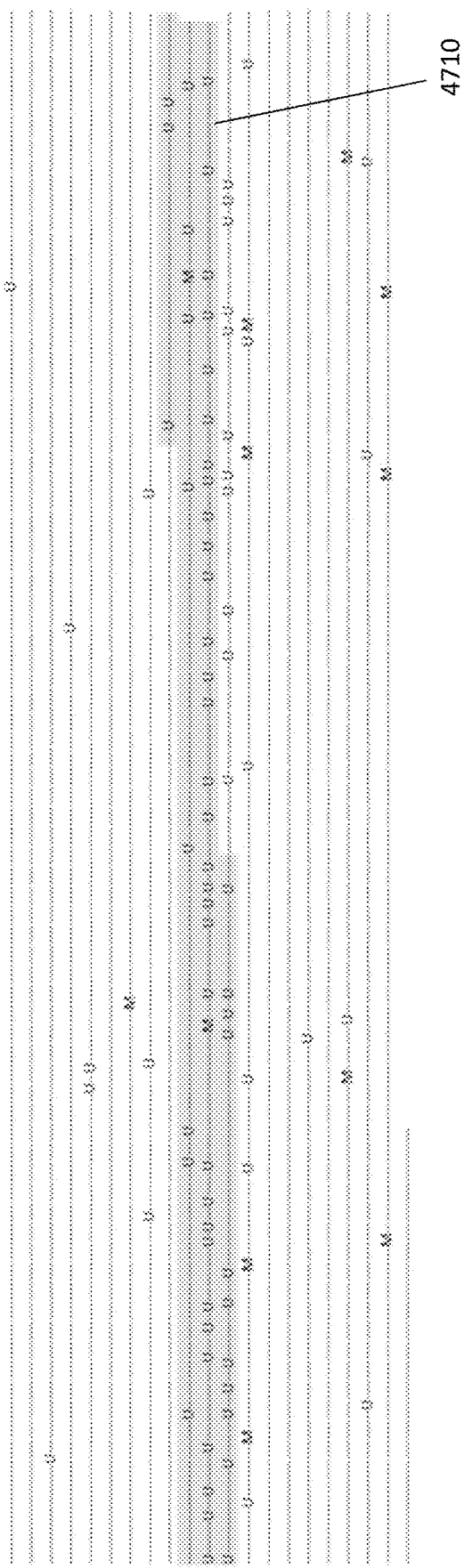
FIG. 47 shows an example of a long read (6,265 bp) harboring a CpG island (as shaded in yellow) according to embodiments of the present invention.

FIG. 47 shows that methylation states along the long DNA molecule with 6,265 bp in size (i.e. a haplotype block), which was sequenced in a ZMW with ZMW hole number m54276_180626_162240/40763503 and mapped to the genomic location of chr:113246546-113252811 in the human genome. '-' represented the non-CpG nucleotide; 'U' represents the unmethylated state at a CpG site; and 'M' represents the methylated state at a CpG site. The region 4710 highlighted in yellow indicated a CpG island region which was known to be unmethylated in general (FIG. 47). The majority of CpG sites in that CpG island were deduced to be unmethylated (96%). In contrast, 75% of CpG sites outside the CpG island were deduced to be unmethylated. These results suggested that the methylation level outside of the CpG island (e.g. CpG island shore/shelf) was higher than that of the CpG island. The mixture of methylated and unmethylated states in a haplotype arrangement in the regions outside that CpG island would indicate the variability of methylation patterns. Such observations were generally in line with current understanding (Zhang et al., 2015; Feinberg and Irizarry, 2010). Thus, this disclosure has enabled one to call different methylation states along a long molecule including methylation and unmethylation states, implying that the haplotype information of methylation states could be phased. Haplotype information refers to the linking of the methylation states of CpG sites on a contiguous stretch of DNA.

In one embodiment, we could use this approach herein for analyzing methylation states along a haplotype to detect and analyze the imprinted regions. Imprinted regions are subjected to epigenetic regulation that causes methylation states in a parent-of-origin fashion. For example, one important imprinted region is located on human chromosome 11p15.5 and contains the imprinted genes IGF2, H19, and CDKN1C (P57$^{kip2}$) which are strong regulators of fetal growth (Brioude et al, Nat Rev Endocrinol. 2018; 14:229-249). The genetic and epigenetic aberrations in imprinted regions would be associated with diseases. Beckwith-Wiedemann syndrome (BWS) is an overgrowth syndrome, with patients often presenting with macroglossia, abdominal wall defects, hemihyperplasia, enlarged abdominal organs and an increased risk of embryonal tumors during early childhood. BWS is considered to be caused by genetic or epigenetic defects within 11p15.5 regions (Brioude et al, Nat Rev Endocrinol. 2018; 14:229-249). A region called ICR1 (imprinting control region 1) which is located between H19 and IGF2 is differentially methylated on the paternal allele. ICR1 directs parent of origin-specific expression of IGF2. Thus, the genetic and epigenetic aberrations in ICR1 would lead to aberrant expression of IGF2 which is one of possible reasons causing BWS. Thus, the detection of methylation states along the imprinted regions would be of clinical significance.

We downloaded data for 92 imprinted genes from a public database which curates currently reported imprinted genes (http://www.geneimprint.org/). The regions 5-kb upstream and downstream of these imprinted genes were used for further analysis. Among these regions, 160 CpG islands are associated with these imprinted genes. We obtained 324,248 circular consensus sequences from a placenta sample. After removing the circular consensus sequences with low quality and short overlapped regions with the CpG islands (e.g. smaller than 50% of the length of that relevant CpG island), we obtained 9 circular consensus sequences overlapping with 9 CpG islands which corresponded to 8 imprinted genes.

FIG. 48 is a table showing that the 9 DNA molecules were sequenced by single molecule, real-time sequencing and overlapping with imprinted regions, including H19, WT1-AS, WT1, DLK1, MEG3, ATP10A, LRRTM1, and MAGI2. The 6$^{th}$ column contained the DNA stretches overlapping with CpG islands involving the imprinted regions. 'U' represents an unmethylated cytosine at the CpG context; 'M' represents a methylated cytosine in the CpG context. '*' represents a CpG site that was not covered in the sequencing result; '-' represents a nucleotide from non-CpG sites; the genotype is indicated in the brackets if a molecule overlaps with a single nucleotide polymorphism (SNP). The 7$^{th}$ column indicates the methylation states for a whole molecule. A molecule can be called as methylated if the majority of CpG sites (e.g. more than 50%) were shown to be methylated according to embodiments present in this disclosure; otherwise it would be called as unmethylated.

Among 9 DNA molecules, 5 DNA molecules (55.6%) were called as methylated, which was not significantly deviated from the expectation in which 50% of DNA molecules would be methylated. As shown in the 6$^{th}$ column of the table of FIG. 48, the majority of the CpG sites were shown to methylated or unmethylated in a concerted manner, i.e., as a methylation haplotype. One embodiment is that a molecule would be called as methylated if the majority of CpG sites (e.g. more than 50%) were shown to be methylated according to embodiments present in this disclosure, it would be called as unmethylated otherwise. Other cutoffs, for determining if a molecule is methylated or not, could be used, for example, but not limited to, at least 10%, 20%, 30%, 40%, 50%, 60%, 70%, 80%, 90%, and 100% of CpG sites in a molecule were analyzed to be deemed methylated.

Figure 49:
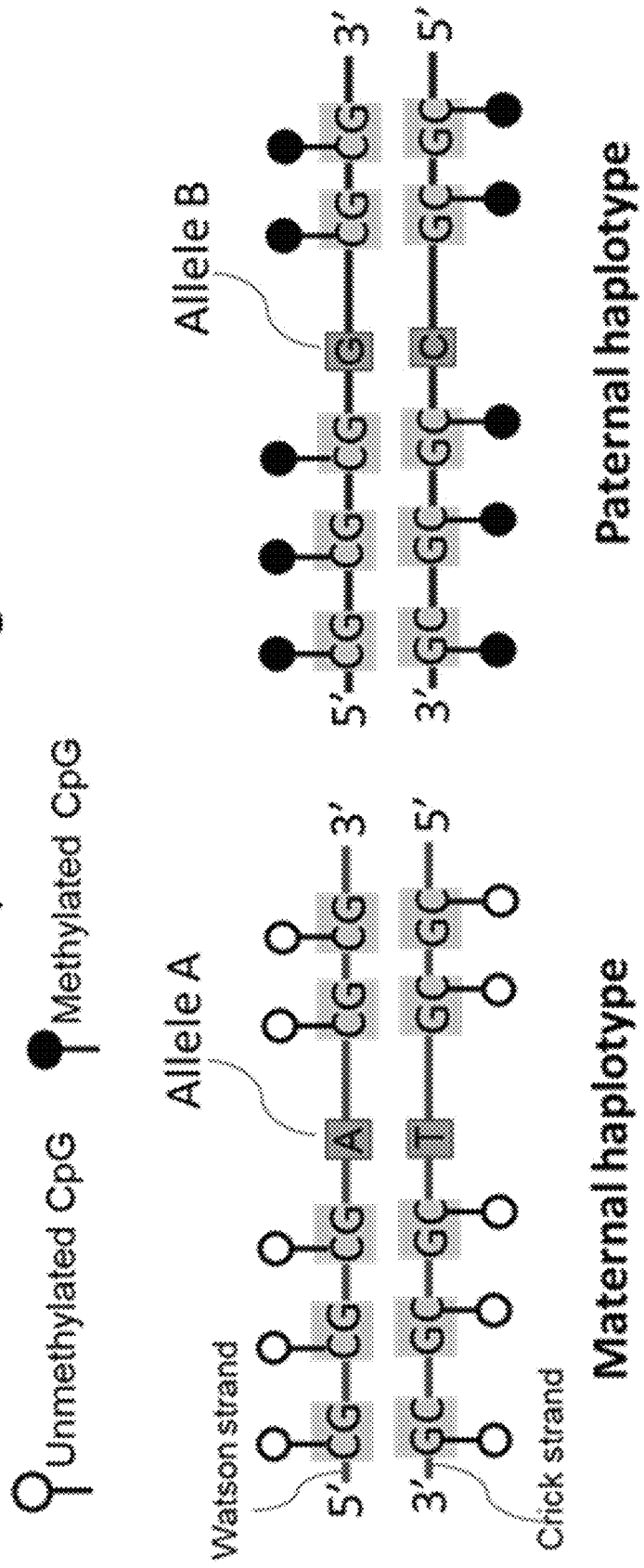
FIG. 49 shows an example of a genomic imprinting according to embodiments of the present invention.

In another embodiment, we could use molecules concurrently comprising at least one SNP and at least one CpG site analysis to determine if a region might be associated with an imprinted region or a known imprinted gene might be aberrant (e.g. loss of imprinting). For illustration purposes, FIG. 49 shows that the first molecule from an imprinting region carried the allele 'A'; and the second molecule from that imprinting region carried the allele 'G'. Assuming that the imprinting region was paternally imprinted, the first molecule from the maternal haplotype was fully unmethylated; and the second molecule from the paternal haplotype was fully methylated. In one embodiment, such an assumption would provide the ground truth of methylation states, allowing for testing the performance of base modification detection according to the embodiments present in this disclosure.

FIG. 49 shows an example for the determination of methylation patterns in an imprinted region. DNA in a biologic sample was extracted and ligated with hairpin adapters to form the circular DNA molecules. Sequence information and base modifications (e.g. methylation states at CpG sites) regarding those circular DNA molecules were not known. Those circular DNA molecules were subjected to single molecule, real-time sequencing. IPDs, PWs, and sequence context for bases in each subread originating from those circular DNA molecules were determined after the subreads were mapped to the reference genome. In addition, genotypes of those molecules were determined. IPDs, PWs, and sequence context in a measurement window associated with CG sites would be compared with the reference kinetic patterns according to the embodiments present in this disclosure to determine the methylation states for each CpG. If two molecules with different alleles showed different methylation patterns in a way that one was fully unmethylated and the other was fully methylated, the genomic region associated with these two molecules would be an imprinted region. In one embodiment, if such genomic region happened to be a known imprinted region, for example, as illustrated in FIG. 49, the methylation patterns for these two molecules were in line with the expected methylation patterns (i.e. ground truth) in a normal situation. It may suggest the accuracy of the methods for the classification of methylation states according to the embodiments present in this disclosure. In one embodiment, the derivation between measured methylation patterns according to embodiments present in this disclosure and expected methylation patterns would indicate the aberrations of imprinting, for example, the loss of imprinting.

Figure 50:
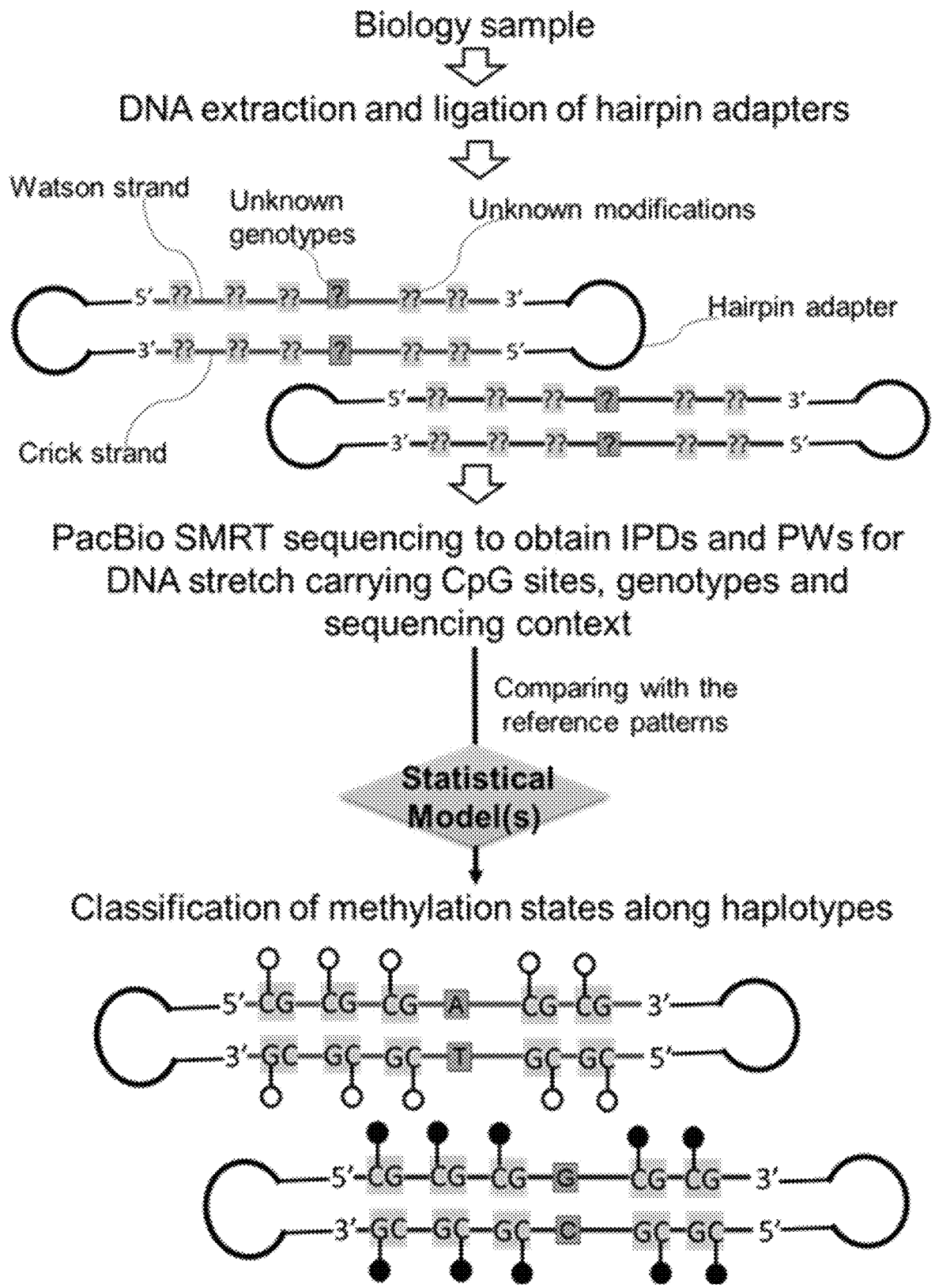
FIG. 50 shows an example for the determination of methylation patterns in an imprinted region according to embodiments of the present invention.

FIG. 50 shows an example for the determination of methylation patterns in an imprinted region. In one embodiment, the imprinting pattern could be further determined through analyzing the methylation patterns of that region across a certain pedigree tree. For example, the analysis of methylation patterns and allelic information across the paternal, maternal genomes and offspring could be performed. Such a pedigree tree could further include the paternal or maternal grandfather's, paternal or maternal grandmother's genomes or other relevant genomes. In another embodiment, such analysis could be extended into family trio (mother, father and child) datasets in a certain population, for example, obtaining methylation and genotype information for each individual according to embodiments present herein.

As shown after the classification, both genotype (allele in box) and the methylation status can be determined. For each of the molecules, a methylation pattern at each site can be provided (e.g., all methylated or all unmethylated) so as to identify which parent the molecule is inherited from. Or, a methylation density can be determined, and one or more cutoffs can classify whether the molecule is hypermethylated (e.g., >80% or other % and from one parent) or hypomethylated (e.g., <20% or other % and from the other parent).

2. Detection of Methylation for cfDNA Molecules

As another example, cell-free DNA (cfDNA) methylation has been also increasingly recognized as important molecular signals for non-invasive prenatal testing. For example, we have shown that cfDNA molecules from regions carrying tissue-specific methylation can be used for determining the proportional contributions from different tissues such as neutrophils, T cells, B cells, liver, placenta in the plasma of pregnant women (Sun et al., 2015). The feasibility of using plasma DNA methylation of pregnant women to detect trisomy 21 has also been demonstrated (Lun et al., 2013). cfDNA molecules in maternal plasma were fragmented with a median size of 166 bp, which is much shorter than artificially-fragmented E. coli DNA with approximately 500 bp in size. It has been reported that cfDNA is non-randomly fragmented, for example, end motifs of plasma DNA in association with the tissue origins such as from the placenta. Such characteristic properties of cell-free DNA give an extremely different sequence context from artificially-fragmented E. coli DNA. Thus, it remains unknown whether such polymerase kinetics would allow for quantitatively deducing the methylation levels, typically for cell-free DNA molecules. The disclosures in this patent application would be applicable to, but not limited to, cell-free DNA methylation analysis in the plasma of pregnant women, for example by using the methylation prediction model trained from above-said tissue DNA molecules.

Using single molecule, real-time sequencing, six plasma DNA samples of pregnant women with a male fetus were sequenced with a median of 30,738,399 subreads (range: 1,431,215-105,835,846), corresponding to a median of 111,834 CCS (range: 61,010-503,582). Each plasma DNA was sequenced with a median of 262 times (range: 173-320). The data set was generated from DNA prepared by Sequel I Sequencing Kit 3.0

To evaluate the detection of methylation for cfDNA molecules, we used bisulfite sequencing (Jiang et al., 2014) to analyze the methylation of the above-said 6 plasma DNA samples of pregnant women. We obtained a median of 66 million paired-end reads (58-82 million paired-end reads). The median overall methylation was found to be 69.6% (67.1%-72.0%).

Figure 51:
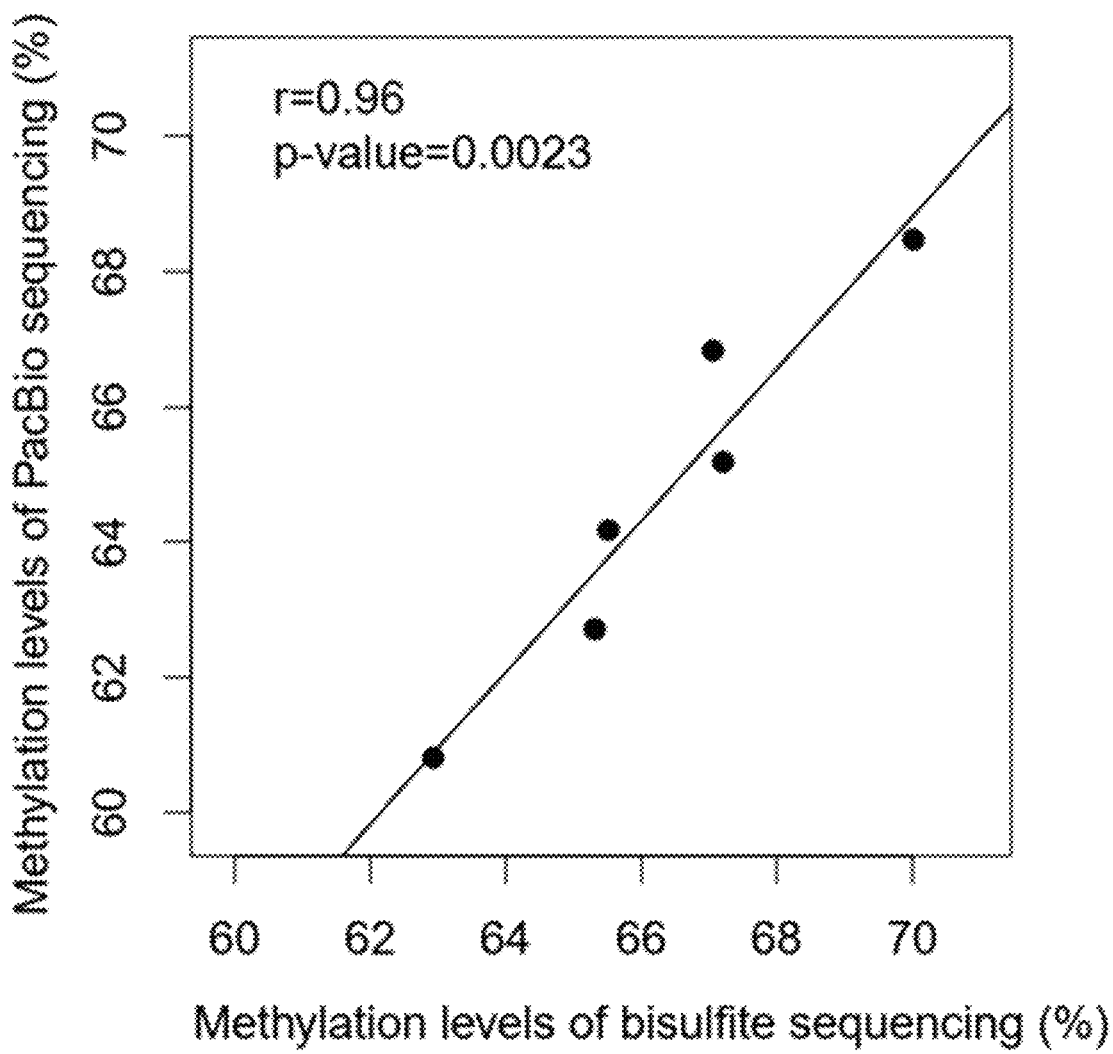
FIG. 51 shows a comparison of methylation levels deduced by between the new approach and conventional bisulfite sequencing according to embodiments of the present invention.

FIG. 51 shows the comparison of methylation levels deduced by the new approach and conventional bisulfite sequencing. The y-axis is the methylation levels predicted according to the embodiments present in this patent application. The x-axis is the methylation levels deduced by bisulfite sequencing. A median of 314,675 CpG sites (range: 144,546-1,382,568) were analyzed for plasma DNA results generated from single molecule, real-time sequencing. The median proportion of CpG sites that were predicted to be methylated was 64.7% (range: 60.8-68.5%), which appeared to be comparable with results deduced from bisulfite sequencing. As shown in FIG. 51, there was a good correlation (r: 0.96, p-value=0.0023) between overall methylation levels deduced by the single molecule, real-time sequencing with the present methylation prediction approach and bisulfite sequencing.

Figure 52B:
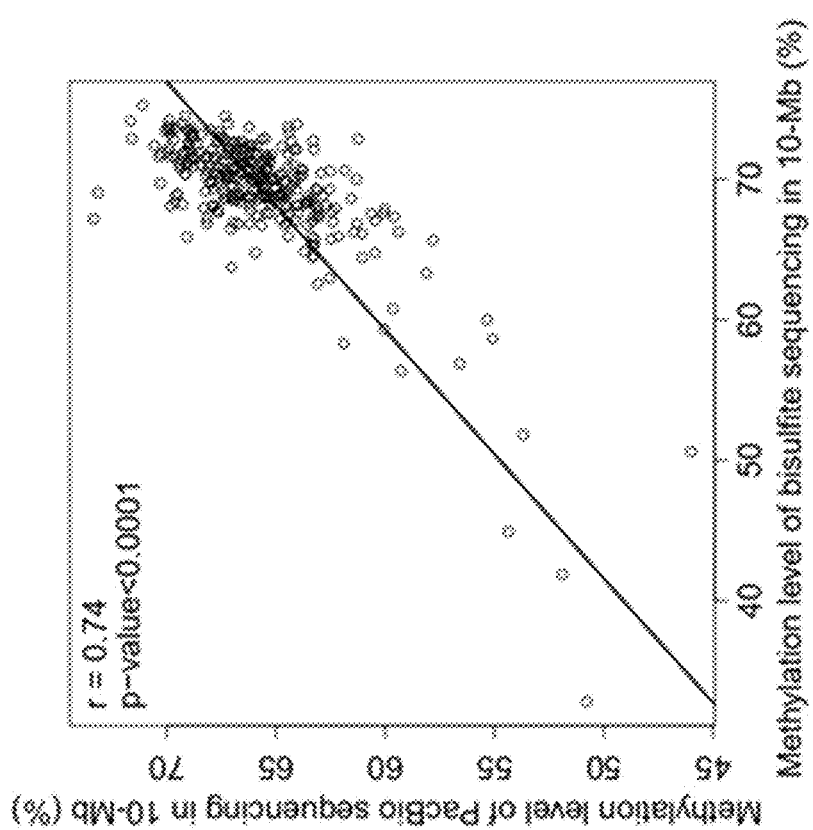
FIGS. 52A and 52B show the performance of detection of methylation of plasma DNA according to embodiments of the present invention. (A) The relationship between the predicted probability of methylation versus the ranges of methylation levels quantified by bisulfite sequencing. (B) The correlation between the methylation levels determined by Pacific Biosciences (PacBio) sequencing according to the embodiments present in this disclosure (y-axis) and methylation levels quantified by bisulfite sequencing (x-axis) in 10-Mb resolution.
Figure 52A:
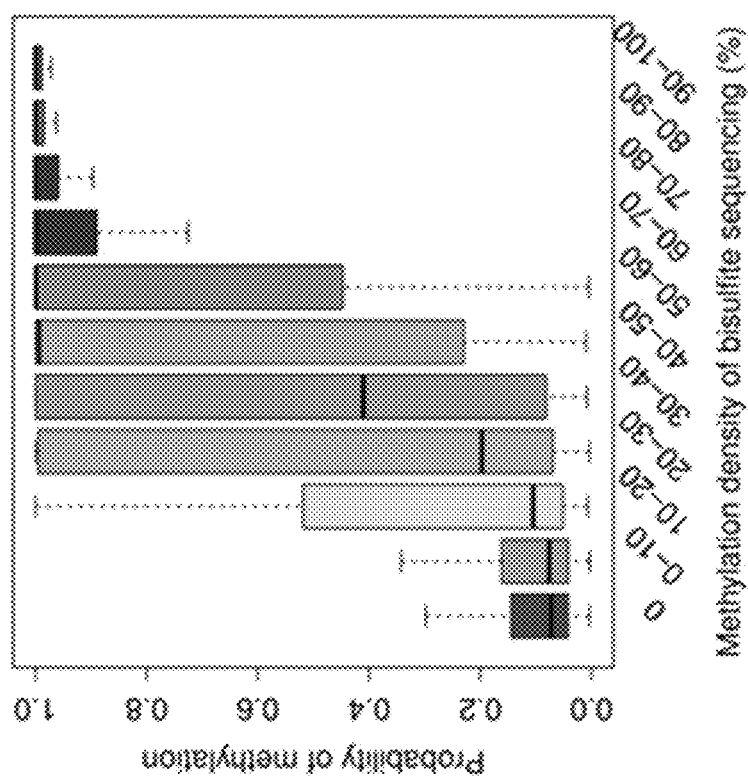

Because of the shallow depth of bisulfite sequencing, it might not be robust for deducing the methylation levels (i.e. the fraction of sequenced CpG being methylated) for each CpG in the human genome. Instead, we calculated the methylation levels in some regions with multiple CpG sites, by aggregating read signals covering CpG sites of a genomic region in which any two consecutive CpG sites were within 50 nt and the number of CpG sites was at least 10. The percentage of sequenced cytosine among the sum of sequenced cytosines and thymines across CpG sites in a region indicated the methylation levels of that region. The regions were divided into different groups according to regional methylation levels. The probability of methylation predicted by the model learned from the previous training datasets (i.e. tissue DNA) was elevated accordingly as the methylation levels increased (FIG. 52A). These results further suggested the feasibility and validity of using single molecule, real-time sequencing to predict methylation states of cfDNA molecules in pregnant women. FIG. 52B showed that the methylation level in a 10-Mb genomic window estimated using single molecule, real-time sequencing according to the embodiments present in this disclosure was well corrected with that by bisulfite sequencing (r=0.74; p-value <0.0001)

Figure 53:
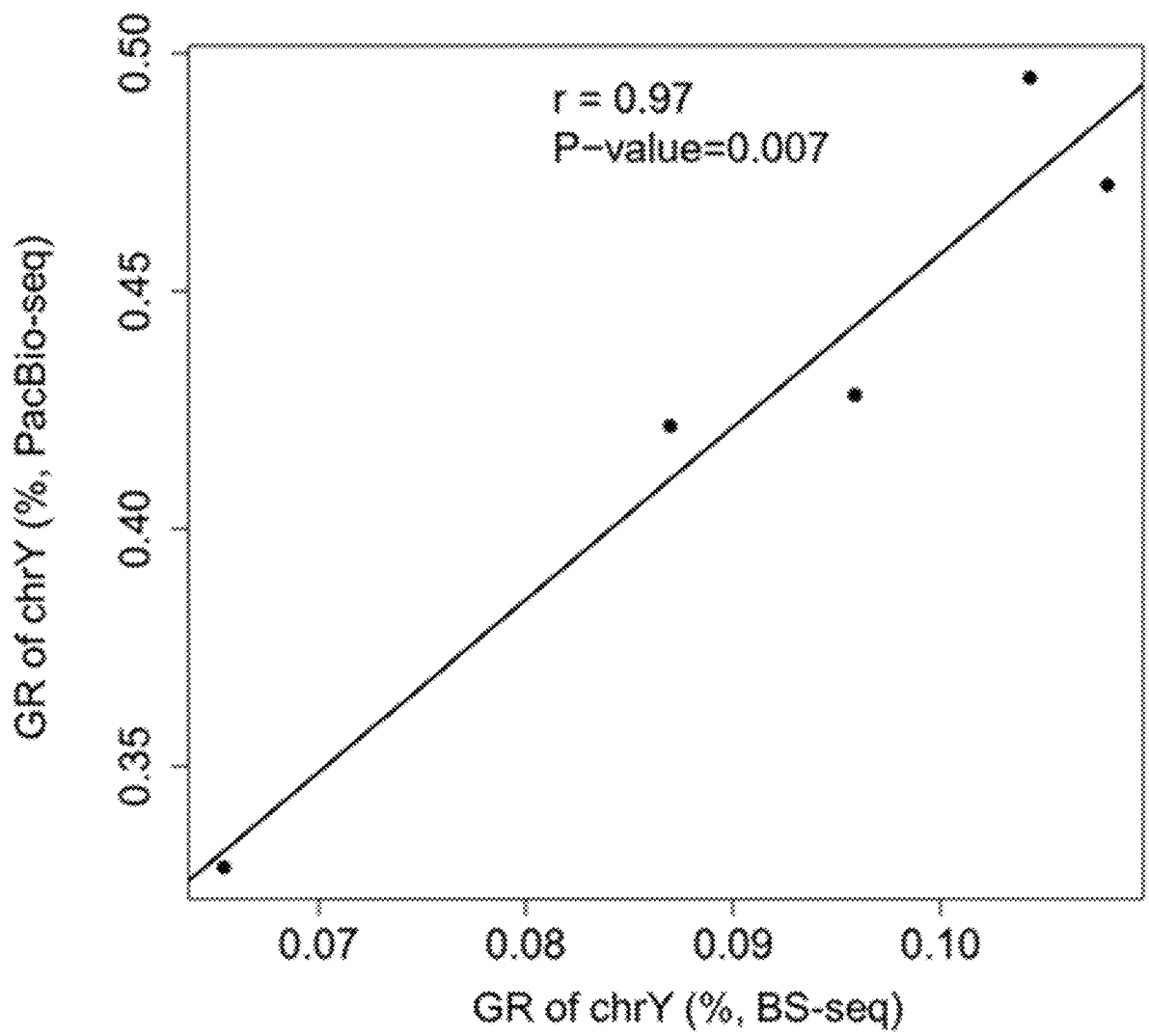
FIG. 53 shows a correlation of the genomic presentation (GR) of the Y chromosome between Pacific Biosciences SMRT sequencing and BS-seq according to embodiments of the present invention.

FIG. 53 showed that the genomic representations (GR) of Y chromosome in maternal plasma of pregnant women that was measured by single molecule, real-time sequencing were well correlated with those measured by BS-seq (r=0.97; P-value=0.007). These results suggested that single molecule, real-time sequencing would also allow the accurate quantification of DNA molecules originating from non-hematopoietic tissues such as placenta, whose contributed DNA generally represented a minority. In other words, this disclosure demonstrated the feasibility for simultaneously analyzing copy number aberrations and methylation states for native molecules without any base conversions and amplifications prior to sequencing.

3. CpG Block-Based Method

Some embodiments can perform a methylation analysis on a number of genomic regions harboring multiple CpG sites, for example but not limited to 2, 3, 4, 5, 10, 20, 30, 40, 50, 100 CpG sites, etc. The size of such a genomic region can be, for example, but not limited to, 50, 100, 200, 300, and 500 nt, etc. The distance between CpG sites in this region could be, for example but not limited to 10, 20, 30, 40, 50, 100, 200, 300 nt, etc. In one embodiment, we could merge any two consecutive CpG sites within 50 nt to form a CpG block such that the number of CpG sites in this block was more than 10. In such a block-based method, multiple regions can be combined into one window represented as a single matrix, effectively treating the regions together.

Figure 54:
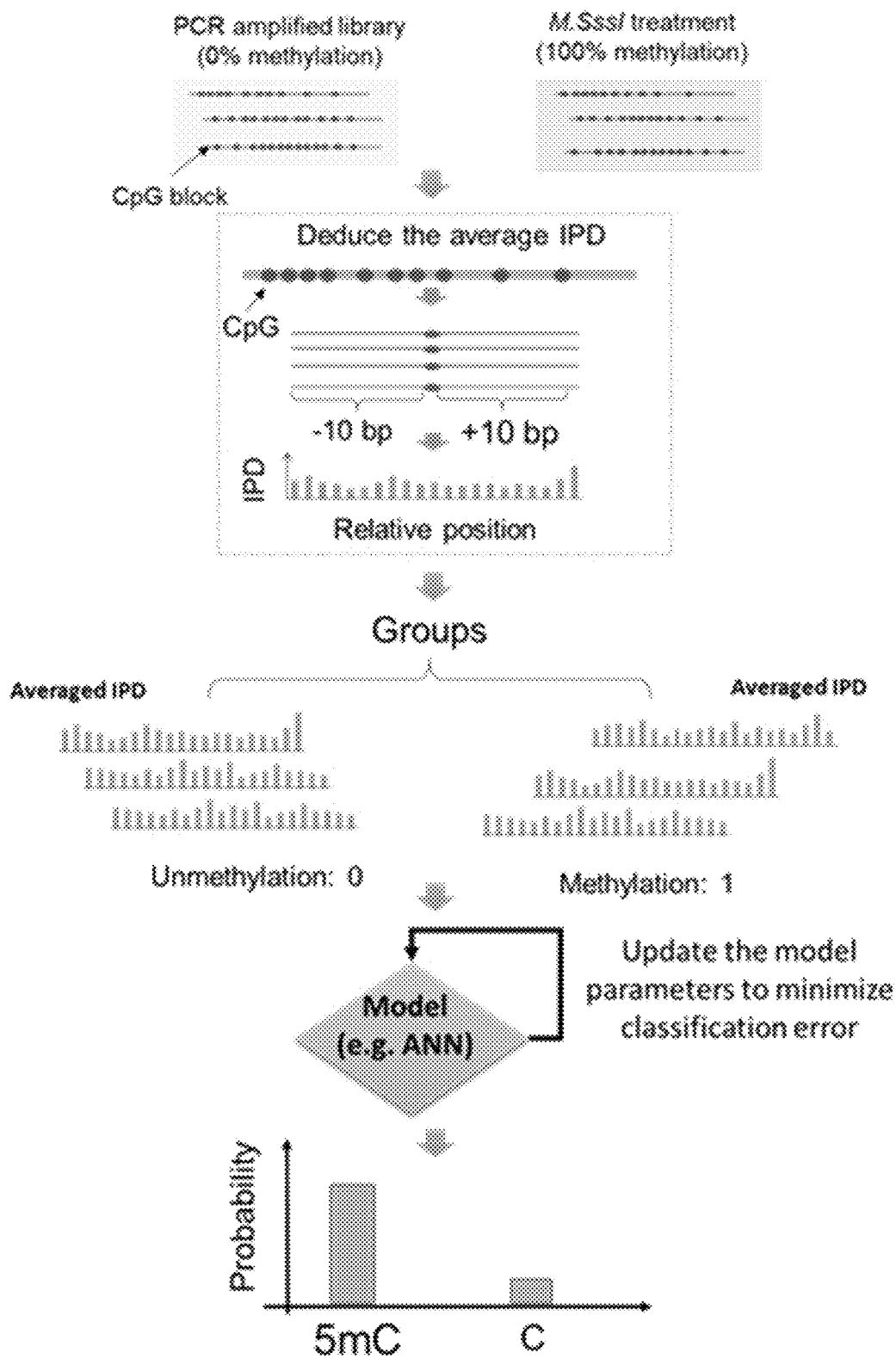
FIG. 54 shows an example of CpG block based detection of methylation using CpG blocks each of which harbor a series of CpG sites according to embodiments of the present invention. 5mC: methylation; C: unmethylation.

As an example, as shown in FIG. 54, the kinetics of all subreads associated with a CpG block were used for methylation analysis. The projected IPD profiles of the upstream and downstream 10 nt flanking at each CpG in that block were artificially aligned relative to CpG sites to calculate the average IPD profile (FIG. 54). The word "projected" means that we had aligned the subread kinetic signals to each corresponding CpG site in question. The average IPD profiles for a CpG block were used for training a model (e.g. using artificial neural network, ANN for short) to identify the methylation states for each block. The ANN analysis included an input layer, two hidden layers, and an output layer. Each CpG block was characterized by a feature vector of 21 IPD values that would be input to the ANN. The first hidden layer included 10 neurons with ReLu as an activation function. The second hidden layer included 5 neurons with ReLu as an activation function. Finally, the output layer included 1 neuron with Sigmoid as an activation function which would output the probability of methylation. A CpG site showing the probability of methylation >0.5 was deemed as methylation, otherwise deemed as unmethylation. The average IPD profile may be used for analyzing the methylation state of a whole molecule. The whole molecule may be considered methylated if a certain number of sites above a threshold (e.g., 0, 1, 2, 3, etc.) are methylated or if the molecule has a certain methylation density.

Figure 55B:
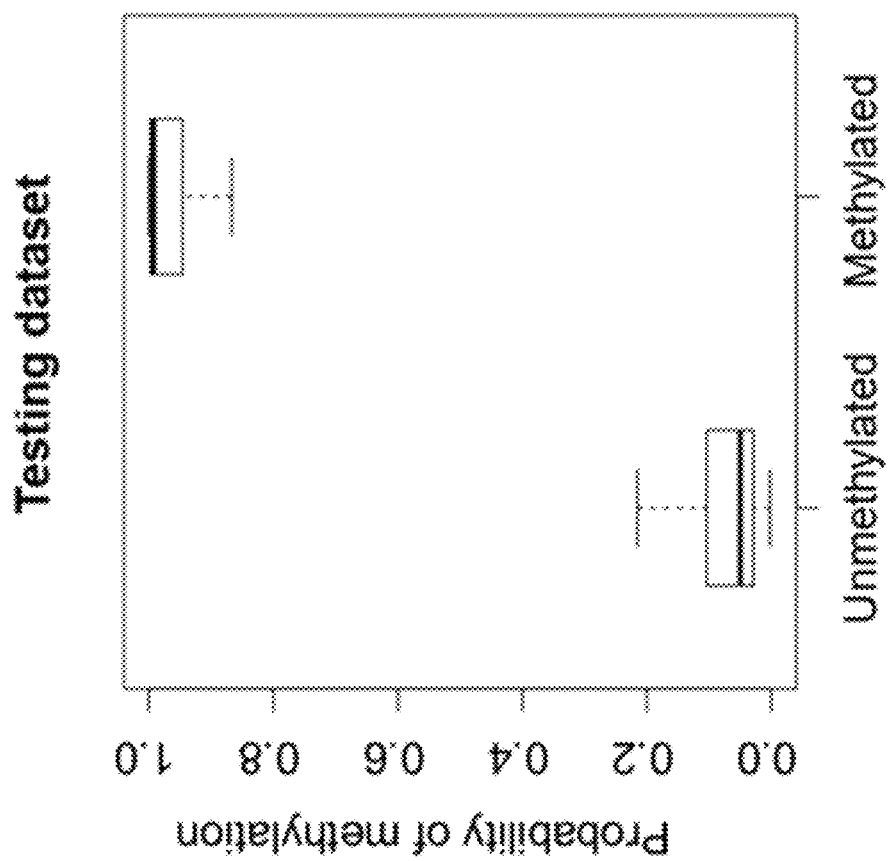
FIGS. 55A and 55B show training and testing of methylation calling for human DNA molecules using the CpG block-based approach according to embodiments of the present invention. (A) Performance in the training dataset. (B) Performance in an independent testing dataset.
Figure 55A:
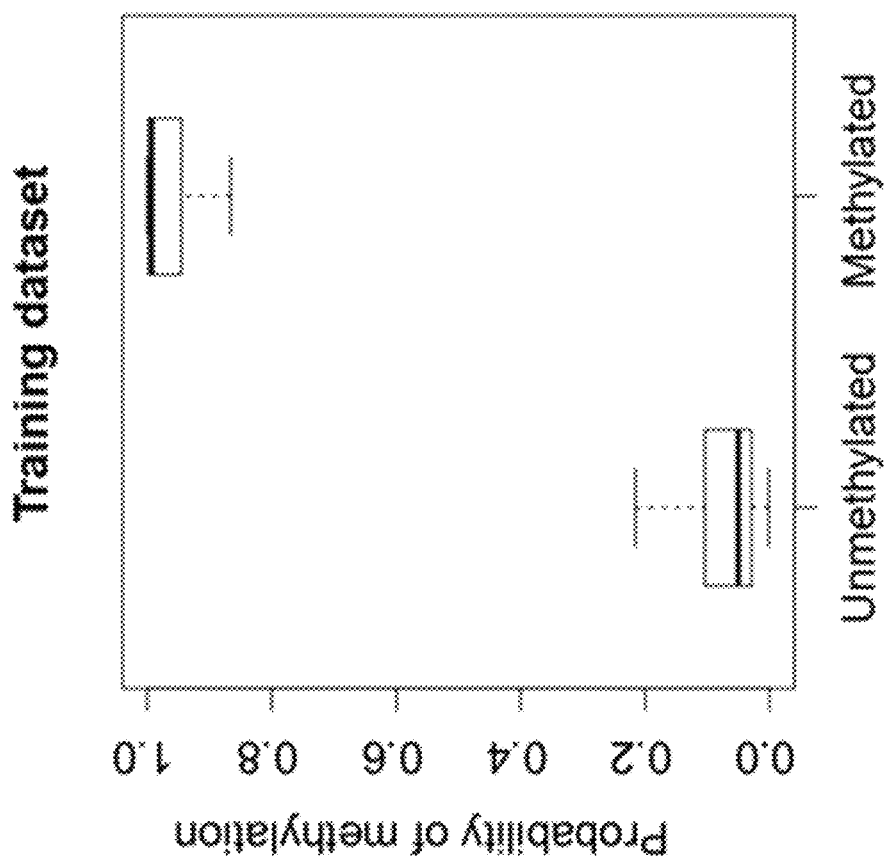

There were 9,678 and 9,020 CpG blocks in unmethylated and methylated libraries, each of which harbored at least 10 CpG sites. Those CpG blocks covered 176,048 and 162,943 CpG sites for unmethylated and methylated libraries. As shown in FIG. 55A and FIG. 55B, we could achieve greater than 90% overall accuracy in predicting methylation states in both training dataset and testing dataset. However, such embodiment relied on CpG blocks would greatly reduce the number of CpGs that were able to be assessed. By definition, the requirement of the least number of CpG sites would restrict the methylation analysis to some particular genomic regions (e.g. preferentially analyzing CpG islands).

B. Determination of Origin or Disorder

Methylation profiles may be used to detect tissue origin or determine the classification of a disorder. Methylation profile analysis may be used in conjunction with other clinical data, including imaging, conventional blood panels, and other medical diagnostic information. Methylation profiles may be determined using any method described herein.

1. Determination of Copy Number Aberration

This section shows that SMRT is accurate for determining copy number, and thus the methylation profile and copy number profile can be analyzed concurrently.

It has been shown that copy number aberrations can be revealed by sequencing of the tumor tissues (Chan (2013)). Here, we show that the cancer-associated copy number aberrations can be identified by the sequencing of tumor tissues using single molecule, real-time sequencing. For example, for case TBR3033, we obtained 589,435 and 1,495,225 consensus sequences (the minimal requirement of subreads used for constructing each consensus sequence was 5) for the tumor DNA and its paired adjacent non-tumoral liver tissue DNA, respectively. The data set was generated from DNA prepared by Sequel II Sequencing Kit 1.0. In one embodiment, the genome was divided, in silico, into 2-Mb windows. The percentage of consensus sequences mapping to each window was calculated, resulting in a genomic representation (GR) at 2-Mb resolution. The GR can be determined by a number of reads at a position as normalized by total sequence reads across the genome.

Figure 56A:
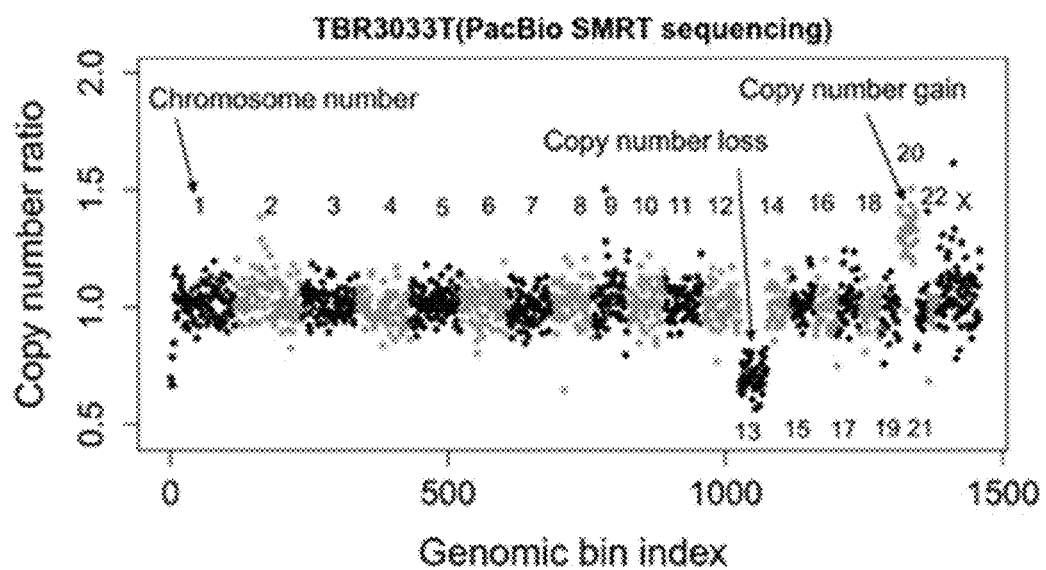
FIGS. 56A and 56B show copy number changes in tumor tissue according to embodiments of the present invention.

FIG. 56A shows the ratio of GR between the tumor and its paired adjacent non-tumoral tissue DNA using single molecule, real-time sequencing. The copy number ratio between the tumor DNA to the paired adjacent normal tissue DNA is shown on the y-axis, and the genomic bin index for each 2-Mb window including chromosomes 1 to 22 is shown on the x-axis. For this figure, a region having the ratio of GR above the $95^{th}$ percentile of all 2-Mb windows was classified as having copy number gain, whereas a region having the ratio of GR below the $5^{th}$ percentile of all 2-Mb windows was classified as having copy number loss. We observed that the chromosome 13 harbored copy number losses, while the chromosome 20 harbored copy number gains. Such gains and losses are the correct result.

Figure 56B:
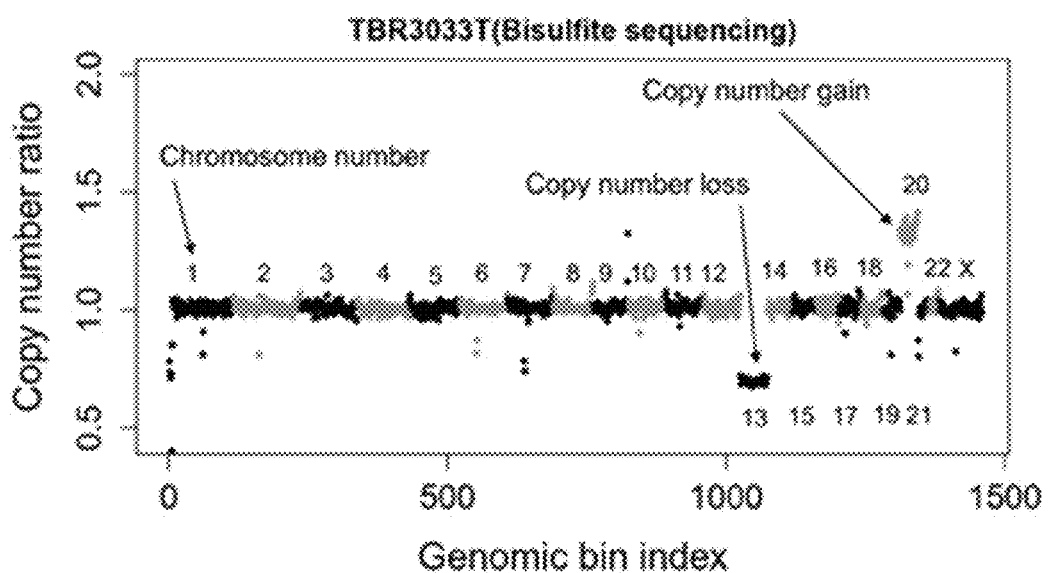

FIG. 56B shows the ratio of GR between tumor and its paired adjacent non-tumoral tissue using bisulfite sequencing. The copy number ratio between the tumor DNA to the paired adjacent normal tissue DNA is shown on the y-axis, and the genomic bin index for each 2-Mb window including chromosomes 1 to 22 is shown on the x-axis. The copy number changes identified by single molecule, real-time sequencing in FIG. 56A were verified in the matched bisulfite sequencing results in FIG. 56B.

For case TBR3032, we obtained 413,982 and 2,396,054 consensus sequences (the minimal requirement of subreads used for constructing each consensus sequence was 5) for the tumor DNA and its paired adjacent non-tumoral tissue DNA, respectively. In one embodiment, the genome was divided, in silico, into 2-Mb windows. The percentage of consensus sequences mapping to each window was calculated, namely 2-Mb genomic representation (GR).

Figure 57A:
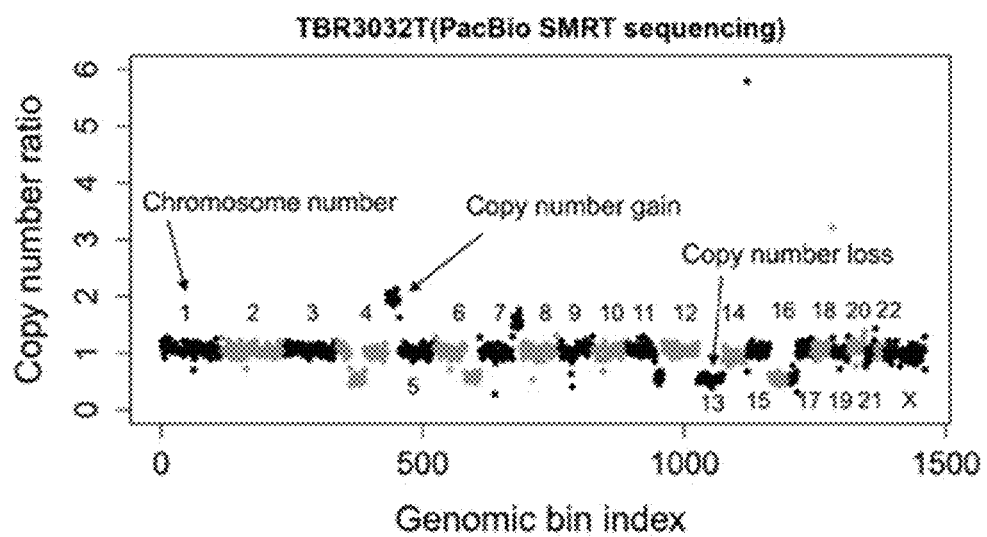
FIGS. 57A and 57B show copy number changes in tumor tissue according to embodiments of the present invention.

FIG. 57A shows the ratio of GR between the tumor and its paired adjacent non-tumoral tissue DNA using single molecule, real-time sequencing. The copy number ratio between the tumor DNA to the paired adjacent normal tissue DNA is shown on the y-axis, and the genomic bin index for each 2-Mb window including chromosomes 1 to 22 is shown on the x-axis. For this figure, a region having the ratio of GR above the $95^{th}$ percentile of all 2-Mb windows was classified as having copy number gain, whereas a region having the ratio of GR below the $5^{th}$ percentile of all 2-Mb windows was classified as having copy number loss. We observed that the chromosomes 4, 6, 11, 13, 16, and 17 harbored copy number losses, while the chromosomes 5 and 7 harbored copy number gains.

Figure 57B:
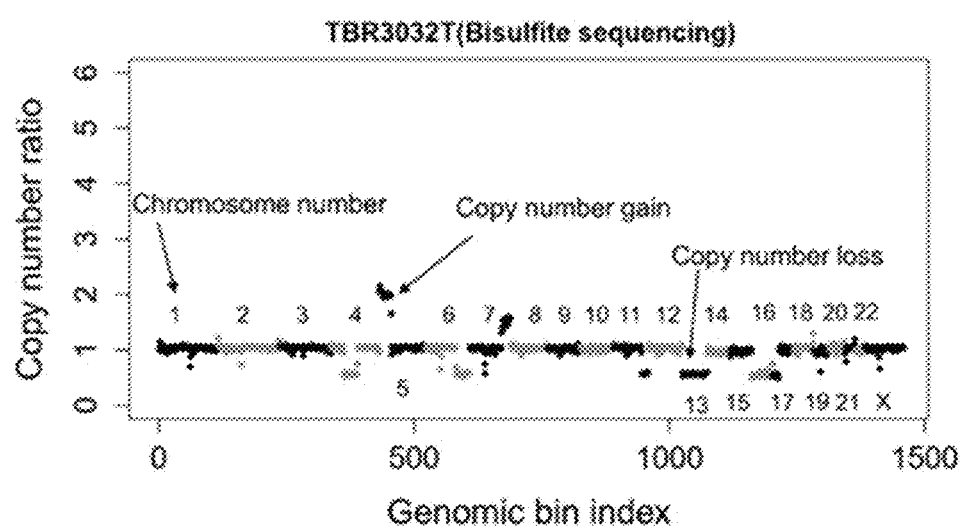

FIG. 57B shows the ratio of GR between tumor and its paired adjacent non-tumoral tissue using bisulfite sequencing. The copy number ratio between the tumor DNA to the paired adjacent normal tissue DNA is shown on the y-axis, and the genomic bin index for each 2-Mb window including chromosomes 1 to 22 is shown on the x-axis. The copy number changes identified by single molecule, real-time sequencing in FIG. 57A were verified in the matched bisulfite sequencing results in FIG. 57B.

Accordingly, the methylation profile and copy number profile can be analyzed concurrently. In this exemplification, since the tumor purity of a tumor tissue is generally not always 100%, the amplified regions would relatively increase the tumor DNA contribution while the deleted regions would relatively decrease the tumor DNA contribution. Because the tumor genome is characterized with global hypomethylation, the amplified regions would further decrease the methylation levels in comparison with the deleted regions. As an illustration, for case TBR3033, the methylation level of chromosome 22 (copy number gains) as measured using the current invention was 48.2%, which was lower than that of chromosome 3 (copy number losses) (methylation level: 54.0%). For case TBR3032, the methylation level of chromosome 5p arm (copy number gains) as measured using the current invention was 46.5%, which was lower than that of chromosome 5q arm (copy number losses) (methylation level: 54.9%).

2. Plasma DNA Tissue Mapping in Pregnant Women

Figure 58:
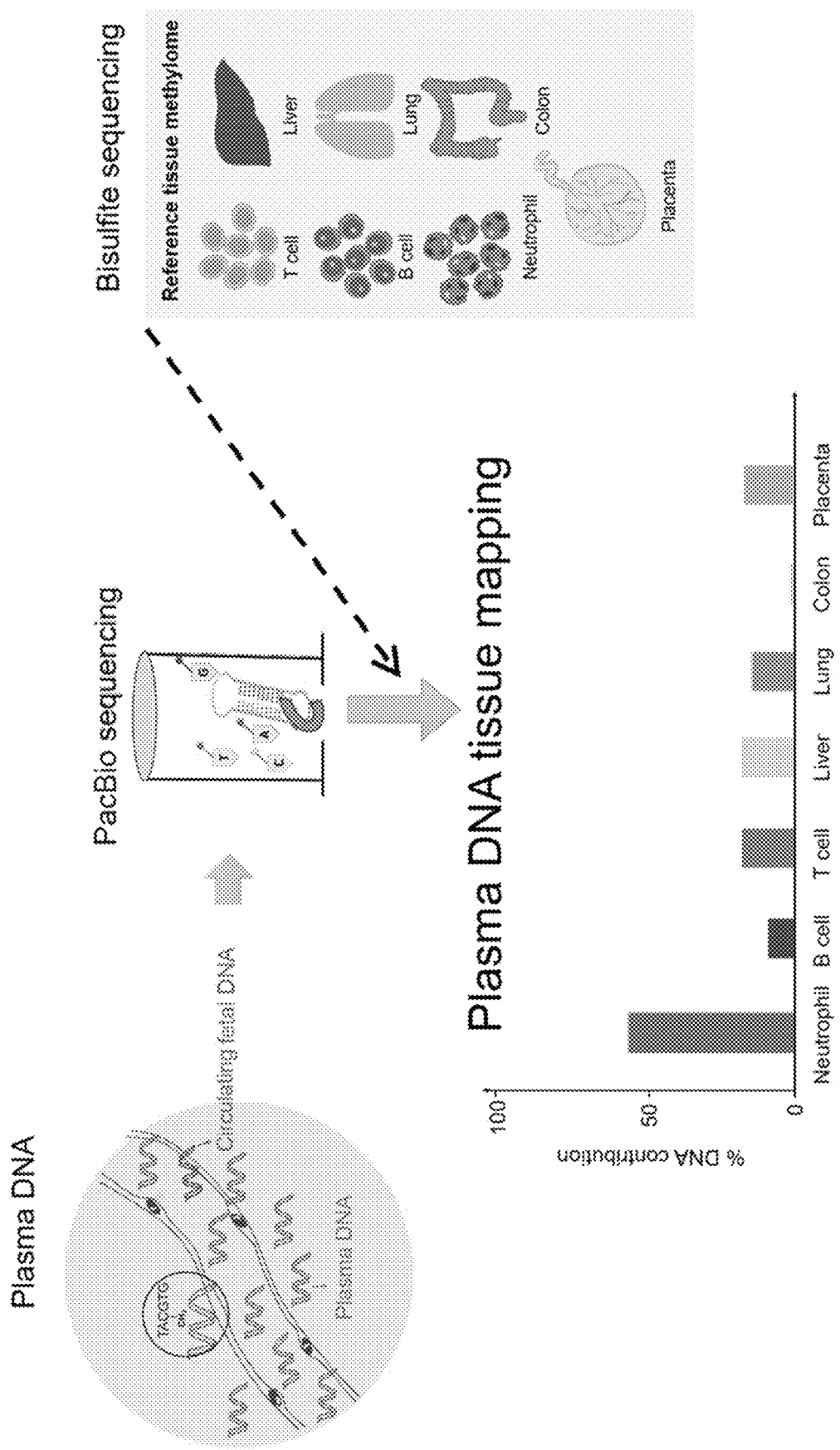
FIG. 58 shows a schematic illustration of plasma DNA tissue mapping from the plasma of a pregnant woman using the methylation levels deduced according to embodiments of the present invention.

As shown in FIG. 58, we reasoned that the accuracy of methylation analysis would allow us to compare the plasma DNA methylation profiles of a pregnant woman with the methylation profiles of different reference tissues (e.g., liver, neutrophils, lymphocytes, placenta, T cells, B cells, heart, brain, etc). Thus, the DNA contributions in the plasma DNA pool in a pregnant woman from different cell types could be deduced using the following procedures. The CpG methylation levels of a DNA mixture (e.g. plasma DNA) determined according to the embodiments present in this disclosure were recorded in a vector (X) and the retrieved reference methylation levels across different tissues were recorded in a matrix (M) which could be quantified by, but not limited to, bisulfite sequencing. The proportional contributions (p) from different tissues to a DNA mixture could be solved by, but not limited to, quadratic programming. Here, we use mathematical equations to illustrate the deduction of the proportional contribution of different organs to a DNA mixture being analyzed. The mathematical relationship between the methylation densities of the different sites in a DNA mixture and the methylation densities of the corresponding sites across different tissues can be expressed as:

$$\overline{X}_i = \Sigma_k (p_k \times M_{ik}),$$

where $\overline{X}_i$ represents the methylation density of a CpG site i in a DNA mixture; $p_k$ represents the proportional contribution of cell type k to a DNA mixture; $M_{ik}$ represents the methylation density of the CpG site i in the cell type k. When the number of sites is the same or larger than the number of organs, the values of individual $p_k$ could be determined. To improve the informativeness, the CpG sites showed small variability of methylation levels across all reference tissue types were discarded. In one embodiment, we used a specific set of CpG sites to perform the analysis. For example, those CpG sites were characterized with the coefficient of variation (CV) of methylation levels across different tissues greater than 30% and a difference between a maximum and a minimum methylation levels among tissues more than 25%. In some other embodiments, CV of 5%, 10%, 20%, 30%, 40%, 50%, 60%, 80%, 90%, 100%, 110%, 200%, 300%, etc. could also be used; and a difference between a maximum and a minimum methylation levels among tissues more than 5%, 10%, 15%, 20%, 25%, 30%, 40%, 50%, 60%, 70%, 80%, 90%, 100%, etc. could be used.

Additional criteria can be included in the algorithm to improve the accuracy. For example, the aggregated contribution of all cell types would be constrained to be 100%, i.e.

$$\Sigma_k p_k = 100\%.$$

Furthermore, all the organs' contributions would be required to be non-negative:

$$p_k \geq 0, \forall k$$

Due to biological variations, the observed overall methylation pattern may not be completely identical to the methylation pattern deduced from the methylation of the tissues. In such a circumstance, the mathematical analysis would be required to determine the most likely proportional contribution of the individual tissues. In this regard, the difference between the observed methylation pattern in the DNA and the deduced methylation pattern from the tissues is denoted by W:

$$W = \overline{X}_i - \sum_k (p_k \times M_{ik})$$

The most likely value of each $p_k$ can be determined by minimizing W, which is the difference between the observed and deduced methylation patterns. This equation can be solved using mathematical algorithms, for example by, but not limited to, using quadratic programming, linear/non-linear regression, expectation-maximization (EM) algorithm, maximum likelihood algorithm, maximum a posteriori estimation, and the least squares method.

Figure 59:
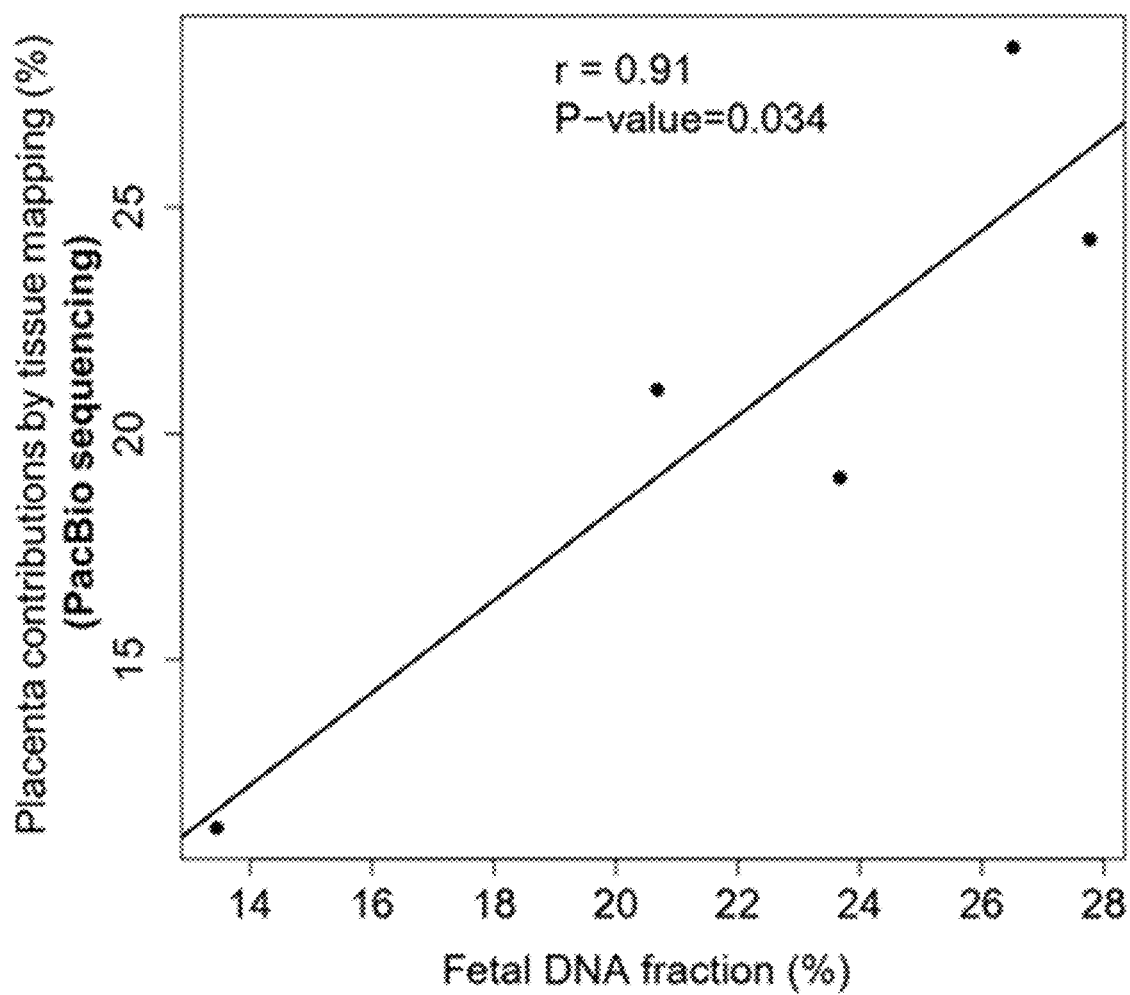
FIG. 59 shows a correlation between the placental contribution to maternal plasma DNA deduced and fetal DNA fraction deduced by Y chromosome reads according to embodiments of the present invention.

As shown in FIG. 59, we observed that the placental DNA contribution to the maternal plasma of pregnant women carrying male fetuses, using the method of plasma DNA tissue mapping present in FIG. 58, was well correlated with the fetal DNA fractions that were estimated by Y chromosome reads. This result suggested the feasibility of using kinetics for tracing the tissues of origin of plasma DNA in pregnant women.

3. Regional Methylation Level Quantification

This section describes techniques for determining a representative level of methylation for selected genomic regions, which can be done using a relatively low level of sequencing. Methylation levels can be determined per strand or per molecule, or a per region basis, using the number of methylated sites and a total number of methylated sites. The methylation levels of various tissues are also analyzed.

We sequenced 11 human tissue DNA samples to a median of 30.7 million subreads (range: 9.1-88.6 million) per sample which could be aligned to a human reference genome (hg19). The subreads from each sample were generated from a median of 3.8 million Pacific Biosciences Single Molecular Real-Time (SMRT) Sequencing wells (range: 1.1-11.5 million), each of which contained at least one subread that could be aligned to a human reference genome. On average, each molecule in a SMRT well was sequenced on average 9.9 times (range: 6.5-13.4 times). The human tissue DNA samples included 1 maternal buffy coat sample of a pregnant subject, 1 placenta sample, 2 hepatocellular carcinoma (HCC) tumor tissues, 2 adjacent non-tumor tissues paired with the 2 previously mentioned HCC tissues, 4 buffy coat samples from healthy control subjects (M1 and M2 were from male subjects; F1 and F2 were from female subjects), 1 HCC cell line (HepG2). The details of the sequencing data summary are shown in FIG. 60.

FIG. 60 shows the different tissue groups in the first column and the sample names in the second column. "Total subreads" indicates the total number of sequences generated from SMRT wells, including those from the Watson and Crick strands. "Mapped subreads" lists the number of subreads that could be aligned to a human reference genome. "Subread mappability" refers to the proportion of subreads that could be aligned to a human reference genome. "Mean subread depth per SMRT well" indicates the mean number of subreads generated from each SMRT well. "No. of SMRT wells" refers to the number of SMRT wells that produced detectable subreads. "Mappable wells" indicates the number of wells containing at least one alignable subread. "Mappable well rate (%)" is the percentage of wells that contained at least one alignable subread.

a) Methylation Level and Pattern Analysis Techniques

In one embodiment, one can measure the methylation density of a single nucleic acid strand (e.g. DNA or RNA), which is defined as the number of methylated bases within the strand divided by the total number of methylatable bases within that strand. This measurement is also referred to as "single strand methylation level". This single strand measurement is particularly feasible in the context of the current disclosure because the single molecule real-time sequencing platform can obtain sequencing information from each of the two strands of a double-stranded DNA molecule. This is facilitated with the use of hairpin adaptors in preparing the sequencing libraries so that the Watson and Crick strands of a double-stranded DNA molecule would be connected in a circular format and be sequenced together. In fact, this structure also enables the partnering Watson and Crick strands of the same double-stranded DNA molecule to be sequenced in the same reaction so that the methylation status of the corresponding complementary sites on the Watson and Crick strands of any double-stranded DNA molecules could be individually determined and directly compared (e.g., FIGS. 20A and 20B).

These strand-based methylation analyses could not be readily achieved with other technologies. Because without the use of the direct methylation analysis method as disclosed in this application, one would need to apply another means to differentiate methylated from unmethylated bases, e.g. by bisulfite conversion. Bisulfite conversion requires the DNA to be treated with sodium bisulfite so that the methylated cytosines and unmethylated cytosines could be distinguished as cytosines and thymines, respectively. Under the denaturing conditions of many bisulfite conversion protocols, the two strands of a double-stranded DNA molecule dissociate from one another. In many sequencing applications, using for example the Illumina platform, the bisulfite converted DNA is then amplified by polymerase chain reaction (PCR), which involves the dissociation of double-stranded DNA into single strands.

With Illumina sequencing, one may prepare PCR-free sequencing libraries using methylated adaptors before bisulfite conversion. Even with the use of this strategy, each DNA strand of a double-stranded DNA molecule would be randomly chosen for bridge amplification in the flow cell. Due to the random nature of the sequencing, it is unlikely that each strand from the same DNA molecule is sequenced in the same reaction. Even if more than one sequence read from the same locus is analyzed in the same run, there is no easy means to determine if the two reads are from each of the partnering Watson and Crick strands of one double-stranded DNA molecule or are from two different double-stranded DNA molecules. Such considerations are important because in certain embodiments of this invention, the two strands of a double-stranded DNA molecule might exhibit different methylation patterns. When the single strand methylation densities of multiple nucleic acid strands (e.g. DNA or RNA) are measured, one can also determine a "multiple strand methylation level" based on the concepts and equation regarding "methylation level of a genomic region of interest" in FIG. 61.

Figure 61:
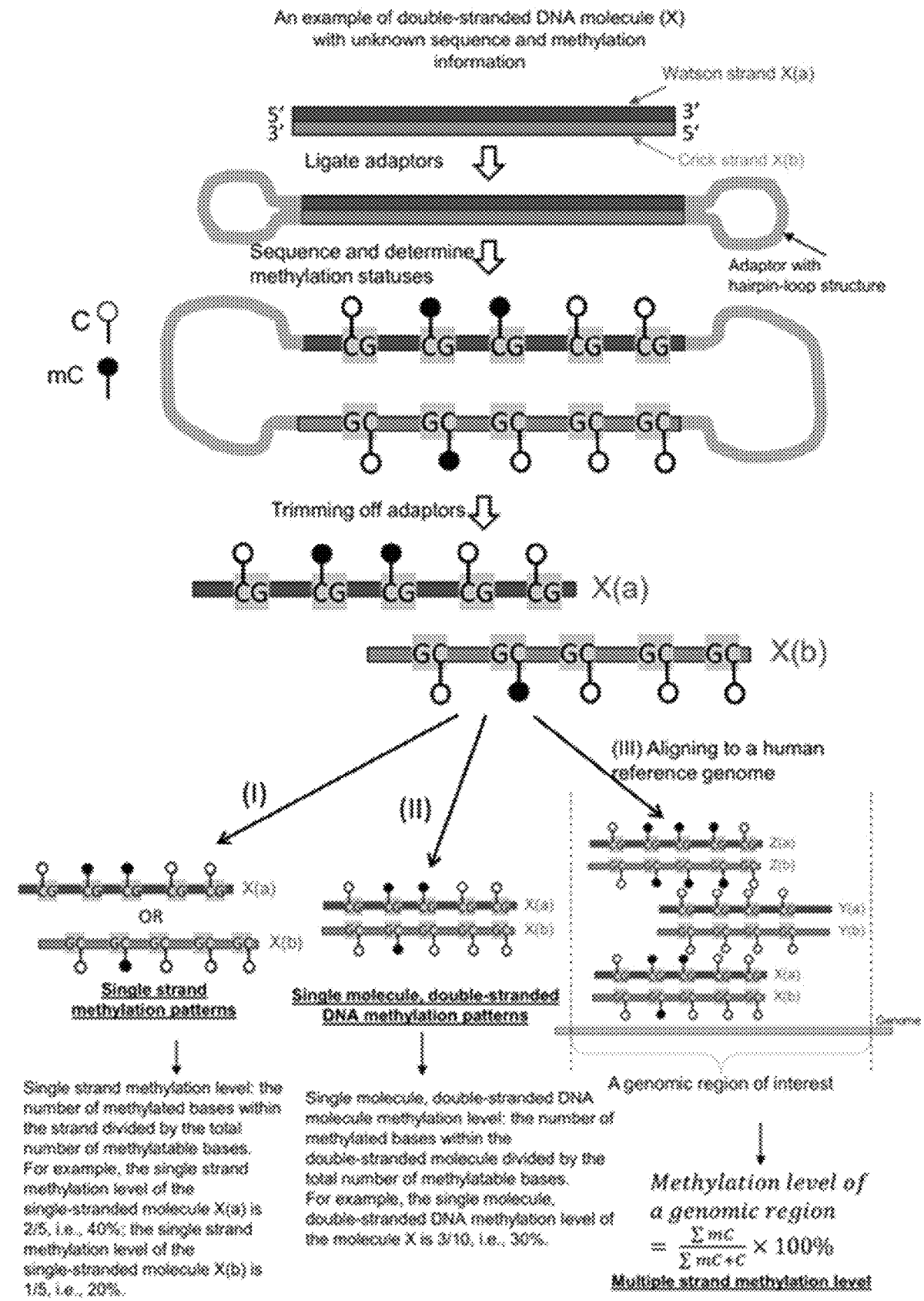
FIG. 61 shows an illustration of various ways of analyzing methylation patterns according to embodiments of the present invention.

FIG. 61 shows various ways of analyzing methylation patterns. A double-stranded DNA molecule (X) with unknown sequence and methylation information is ligated with adaptors, which forms a hairpin-loop structure in one example. As a result, the two single strands of the DNA molecule, including both the Watson X(a) and Crick X(b) strands are physically partnered together in a circular form in this example. The methylation statuses of the sites in both the Watson and Crick strands may be obtained using methods described in this disclosure (e.g., using kinetic, electronic, electromagnetic, optical signals, or other type of physical signals from the sequencer). The Watson and Crick strands in the circularized DNA molecule may be interrogated in the same reaction. After sequencing, the adaptor sequences are trimmed off.

Different methylation levels may be determined from analysis. In (I) of FIG. 61, the methylation pattern of only a single stranded molecule, such as either X(a) or X(b) can be analyzed. This analysis can be referred to be as single strand methylation pattern analysis. The analysis may include but is not limited to determining the methylation status of sites or the methylation pattern. In FIG. 61, the single stranded molecule X(a) shows a methylation pattern 5'-UMMUU-3' wherein "U" indicates an unmethylated site and "M" indicates a methylated site while the complementary single stranded molecule X(b) shows a methylation pattern 3'-UMUUU-5'. Thus, X(b) has a different methylation pattern from X(a). The corresponding single strand methylation levels of X(a) and X(b) are 40% and 20%, respectively.

In contrast, as shown in (II), one can analyze the methylation patterns in a single double-stranded DNA molecule level (i.e. take into account the methylation patterns of both the Watson and Crick strands. This analysis can be referred to be as single molecule, double-stranded DNA methylation pattern analysis. The single molecule, double-stranded DNA methylation level of this exemplar molecule X is 30%. One variant of this analysis, the kinetic signals from both the Watson and Crick strands would be combined to analyze the modification. In particular, as the methylation on CpG sites are generally symmetrical, the kinetic signals from the Watson and Crick strands could be combined for a site prior to determining the methylation statuses of the sites. In some situations, the performance of determining base modifications using kinetic signals combined from the Watson and Crick strands of a molecule would be superior to one that independently using kinetic signals of single strand. For example, as shown in FIG. 20B, the combined use of kinetic signals from both strands including the Watson and Crick strands would give rise to a larger AUC (0.90) in a testing dataset compared to the independent use of single strand (AUC: 0.85).

In (III) of FIG. 61, the methylation level of a genomic region of interest is determined, where different DNA molecules, carrying different molecular sizes and different number of methylatable sites (e.g. CpG sites), can contribute to the genomic region of interest. This analysis may be referred to be as multiple strand methylation level analysis. The term "multiple strand" can refer to multiple single-stranded DNA molecules, or multiple double-stranded DNA molecules, or any combination thereof. In this example, there are three double-stranded DNA molecules covering a genomic region of interest: the molecules "X", "Y", and "Z", each having "a" and "b" strands. The corresponding methylation level of this region is 9/28, i.e., 32%. The size of the genomic region to be analyzed may have a size of 1 nt, 10 nt, 20 nt, 30 nt, 40 nt, 50 nt, 100 nt, 1 knt (kilonucleotides, i.e., one thousand nucleotides), 2 knt, 3 knt, 4 knt, 5 knt, 10 knt, 20 knt, 30 knt, 40 knt, 50 knt, 100 knt, 200 knt, 300 knt, 400 knt, 500 knt, 1 Mnt (meganucleotides, i.e. 1 million nucleotides), 2 Mnt, 3 Mnt, 4 Mnt, 5 Mnt, 10 Mnt, 20 Mnt, 30 Mnt, 40 Mnt, 50 Mnt, 100 Mnt, or 200 Mnt. The genomic region may be a chromosomal arm or the whole genome.

A methylation pattern can also be determined after determining methylation statuses for sites in a molecule. For example, in one scenario where there are three sequential CpG sites on a single double-stranded DNA molecule, the methylation pattern on each of the Watson and Crick strands can be revealed to as methylated (M), non-methylated (N) and methylated (M) for the three sites. This pattern, MNM, e.g. for the Watson strand, can be referred to as the "methylation haplotype" for the Watson strand for this region. Because of the presence of DNA methylation maintenance activity, the methylation pattern of the Watson and Crick strands of a double-stranded DNA molecule may be complementary of one another. For example, if a CpG site is methylated on the Watson strand, the complementary CpG site on the Crick strand may also be methylated. Similarly, a non-methylated CpG site on the Watson strand may be complementary to a non-methylated CpG site on the Crick strand.

In one embodiment, one can measure the methylation level of a single DNA molecule, which is defined as the number of methylated bases or nucleotides within the molecule divided by the total number of methylatable bases or nucleotides within that molecule. This measurement is also referred to as "single molecule methylation level". This single molecule measurement may be particularly useful in the context of the current disclosure because of the long read length possible with the single molecule, real-time sequencing platform. When the single molecule methylation levels of multiple DNA molecules are measured, one can also determine a "multiple molecule methylation level" based on the concepts and equation in FIG. 61. For example, the "multiple molecule methylation level" may be a mean or a median of the single molecule methylation levels.

In some embodiments, one or more genetic polymorphisms (e.g. single nucleotide polymorphisms (SNPs)) can be analyzed on the DNA molecule along with the methylation status of a site on the molecule, thus revealing both genetic and epigenetic information of that molecule. Such analysis would reveal the "phased methylation haplotype" for the analyzed DNA molecule. Phased methylation haplotype analysis is useful, for example, in the study of genomic imprinting and cell-free nucleic acids in maternal plasma (containing a mixture of cell-free DNA molecules carrying maternal and fetal genetic and epigenetic signatures).

b) Comparison of Methylation Results

Figure 62B:
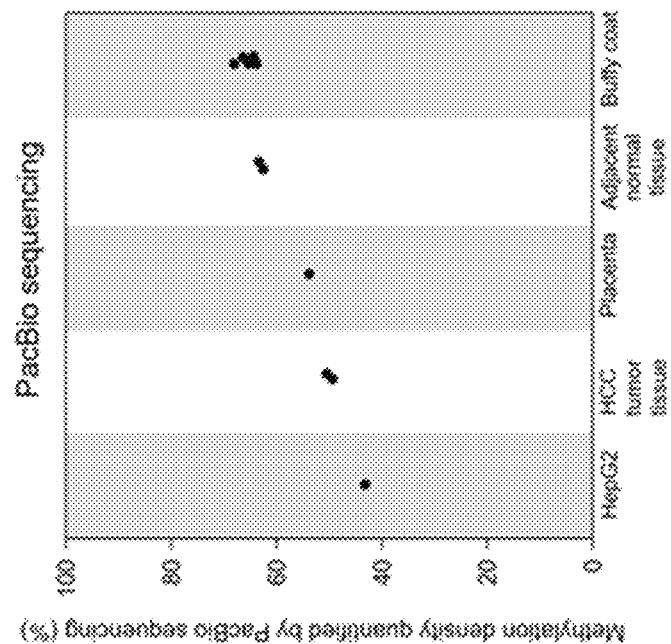
FIGS. 62A and 62B show a comparison of methylation densities at the whole-genome level quantified by bisulfite sequencing and single molecule, real-time sequencing according to embodiments of the present invention.
Figure 62A:
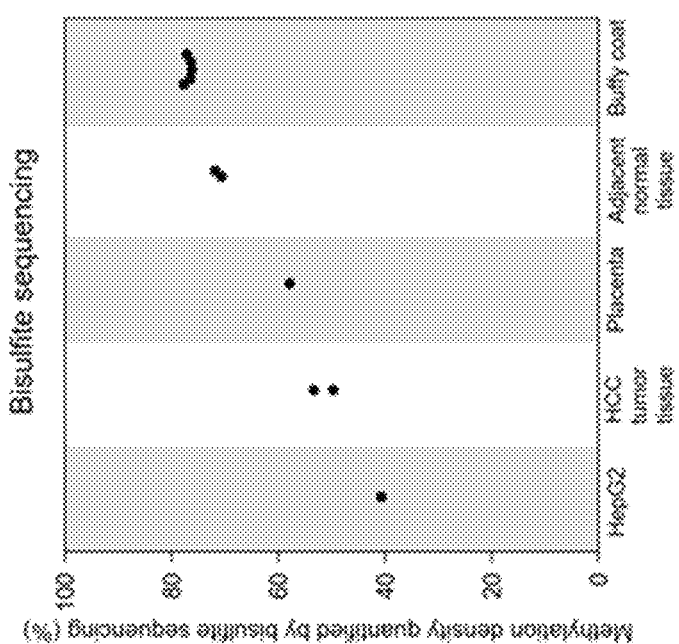

The methylation densities at a whole-genome level of the tissues in the table in FIG. 60 are determined using bisulfite sequencing and using single molecule, real-time sequencing as described in this disclosure. FIG. 62A shows the methylation density as quantified by bisulfite sequencing on the y-axis and the tissue type on the x-axis. FIG. 62B shows methylation density as quantified by single molecule, real-time sequencing as described in this disclosure on the y-axis and the tissue type on the x-axis.

FIG. 62A shows the methylation densities across different tissues using bisulfite sequencing (i.e. samples were bisulfite converted and then subjected to Illumina sequencing) (Lister et al. Nature. 2009; 462:315-322), including HepG2, HCC tumor tissues, matched normal liver tissues adjacent to the HCC tumor (i.e. adjacent normal tissues), placental tissue and buffy coat samples. HepG2 displayed the lowest methylation level, with a methylation level of 40.4%. Buffy coat samples displayed the highest methylation level, with a methylation level of 76.5%. The mean methylation density of HCC tumor tissues (51.2%) was found to be lower than that of matched adjacent normal tissues (71.0%). This is consistent with the expectation that tumors of HCC are hypomethylated at the genomewide level compared with the adjacent normal tissues (Ross et al. Epigenomics. 2010; 2:245-69). The data set was generated from DNA prepared by Sequel II Sequencing Kit 1.0.

Portions of the same tissues were subjected to methylation analysis using single molecule, real-time sequencing and the methods according to this disclosure. The results are shown in FIG. 62B. Methylation analysis using the single molecule, real-time sequencing methods of this disclosure was able to show that the HepG2 cell line was the most hypomethylated, followed by the HCC tumor tissue analyzed, and then followed by the placental tissue. The adjacent non-tumoral liver tissue sample was more methylated than the other tissues including HCC and placental tissues, with the buffy coat being most hypermethylated.

FIGS. 63A, 63B, and 63C show correlation of overall methylation levels quantified by bisulfite sequencing and single molecule, real-time sequencing according to methods described herein. FIG. 63A shows the methylation level quantified by bisulfite sequencing on the x-axis and the methylation level quantified by single molecule, real-time sequencing using methods described herein on the y-axis. The solid black line is a fitted regression line. The dashed line is where the two measurements are equal.

There was a very high correlation of methylation levels between bisulfite sequencing and single molecule, real-time sequencing according to the invention disclosed herein (r=0.99; P value <0.0001). These data indicated that methylation analysis using the single molecule, real-time sequencing methods disclosed hereby were effective means to determine methylation levels between tissues and enabled the comparison of the methylation states and profiles between these tissues. For two measures of methylation levels, we noted that the slope of regression line in FIG. 63A deviated from one. These results suggested that there is a deviation between the two measurements (in some context, this deviation can be referred to as bias) might be present in the determination of methylation levels using single molecule, real-time sequencing according to the disclosure compared with the conventional massively parallel bisulfite sequencing.

In one embodiment, we could quantify the bias using linear or LOESS (locally weighted smoothing) regression. As an example, if we considered massively parallel bisulfite sequencing (Illumina) to be a reference, the results determined by single molecule, real-time sequencing according to the disclosure could be transformed using the regression coefficients, thus reconciling the readouts between different platforms. In FIG. 63A, the linear regression formula was Y=aX+b, where "Y" represented the methylation levels determined by single molecule, real-time sequencing according to the disclosure; "X" represented the methylation levels determined by bisulfite sequencing; "a" represented the slope of the regression line (e.g. a=0.62); "b" represented the intercept in y-axis (e.g. b=17.72). In this situation, the reconciled methylation values determined by single molecule, real-time sequencing would be calculated by (Y−b)/a. In another embodiment, one could use the relationship of the deviation between two measurements (ΔM) and the corresponding average of the two measurements ($\overline{M}$), which were defined by formula (1) and (2) below:

$$\Delta M = S - \text{Bisulfite based methylation} \quad (1)$$

$$\overline{M} = \frac{S + \text{Bisulfite based methylation}}{2}, \quad (2)$$

where "S" represents the methylation level determined by single molecule, real-time sequencing according to the present invention and "Bisulfite based methylation" represents the methylation level determined by bisulfite sequencing.

FIG. 63B shows the relationship between $\Delta M$ and $\overline{M}$. The average of the two measurements ($\overline{M}$) is plotted on the x-axis, and the deviation between the two measurements ($\Delta M$) is plotted on the y-axis. The dashed line represents a line horizontally across zero on which a data point suggests that there is no difference between two measurements. These results suggested that the deviation varied depending on the averaged values. The higher the average of the two measurements, the larger in magnitude the deviation would be. The median of $\Delta M$ values was −8.5% (range: −12.6% to +2.5%), suggesting that the discrepancy between methods existed.

FIG. 63C shows the average of the two measurements ($\overline{M}$) on the x-axis and the relative deviation (RD) on the y-axis. The relative deviation is defined by the formula below:

$$RD = \frac{\Delta M}{\overline{M}} \times 100\%. \quad (3)$$

The dashed line represents a line horizontally across zero on which a data point suggests that there is no difference between two measurements. These results suggested that the relative deviation varied depending on the averaged values. The larger the average of the two measures, the larger in magnitude the relative derivation would be. The median of RD values was −12.5% (range: −18.1% to +6.0%).

It was reported that the conventional whole-genome bisulfite sequencing (Illumina) introduced a significant biased sequence output and overestimated global methylation, with substantial variations in quantifying methylation levels between methods at specific genomic regions (Olova et al. Genome Biol. 2018; 19:33). The methods disclosed herein can be performed without bisulfite conversion that would degrade DNA drastically and can be performed without PCR amplification that may complicate the process or may introduce additional error into determining methylation levels.

Figure 64B:
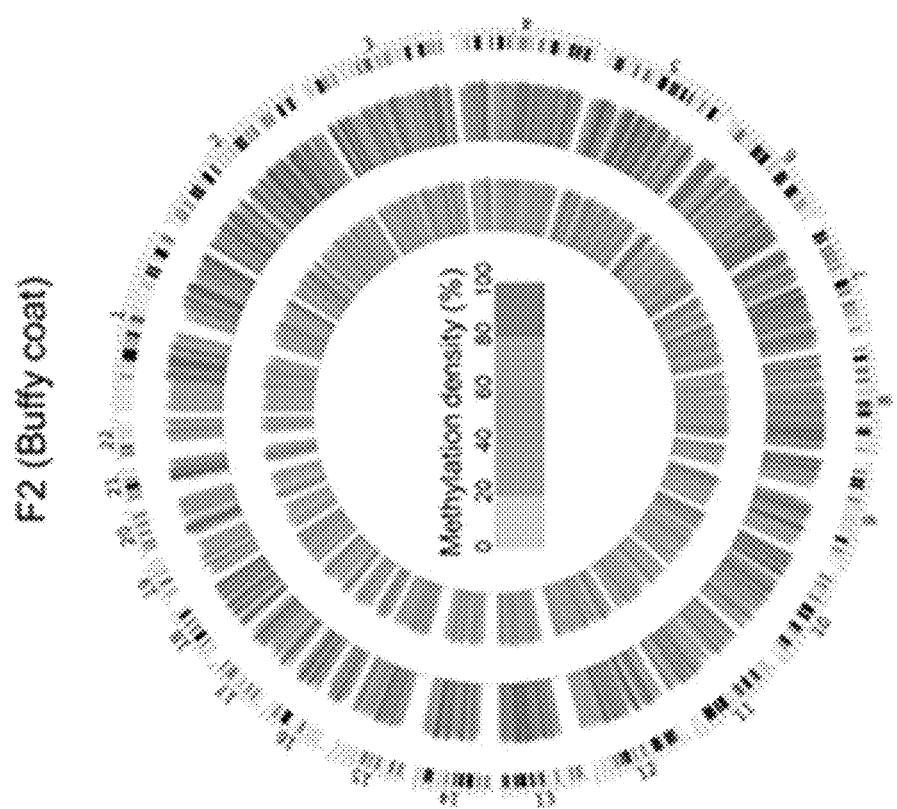
FIGS. 64A and 64B show methylation patterns at 1-Mnt resolution for a hepatocellular carcinoma (HCC) cell line and a buffy coat sample from a health control subject with methylation levels determined by bisulfite sequencing and by single molecule, real-time sequencing according to embodiments of the present invention.
Figure 64A:
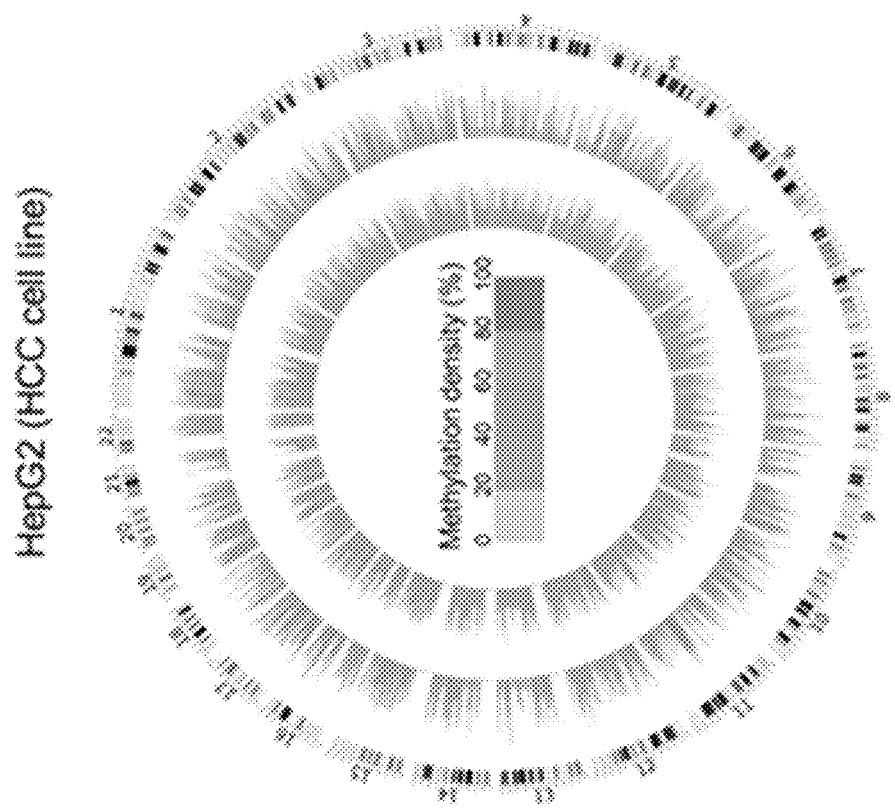

FIGS. 64A and 64B show methylation patterns at 1-Mb resolution. FIG. 64A shows the methylation pattern for an HCC cell line (HepG2). FIG. 64B shows the methylation pattern for a buffy coat sample from a healthy control subject. The chromosome ideograms (outermost ring in each figure) are organized from pter to qter in a clockwise direction. The second ring from the outside (also described as a middle ring) shows the methylation levels determined by bisulfite sequencing. The innermost ring shows the methylation levels determined by single molecule, real-time sequencing according to the disclosure. The methylation levels are classified into 5 grades, namely, 0-20% (light green), 20-40% (green), 40-60% (blue), 60-80% (light red), and 80-100% (red). As shown in FIGS. 64A and 64B, the methylation profiles at 1-Mb resolution were consistent between bisulfite sequencing (middle track) and single molecule, real-time sequencing (innermost track) according to the present disclosure. The methylation level of the maternal buffy coat sample was shown to be higher than the HCC cell line (HepG2).

Figure 65A:
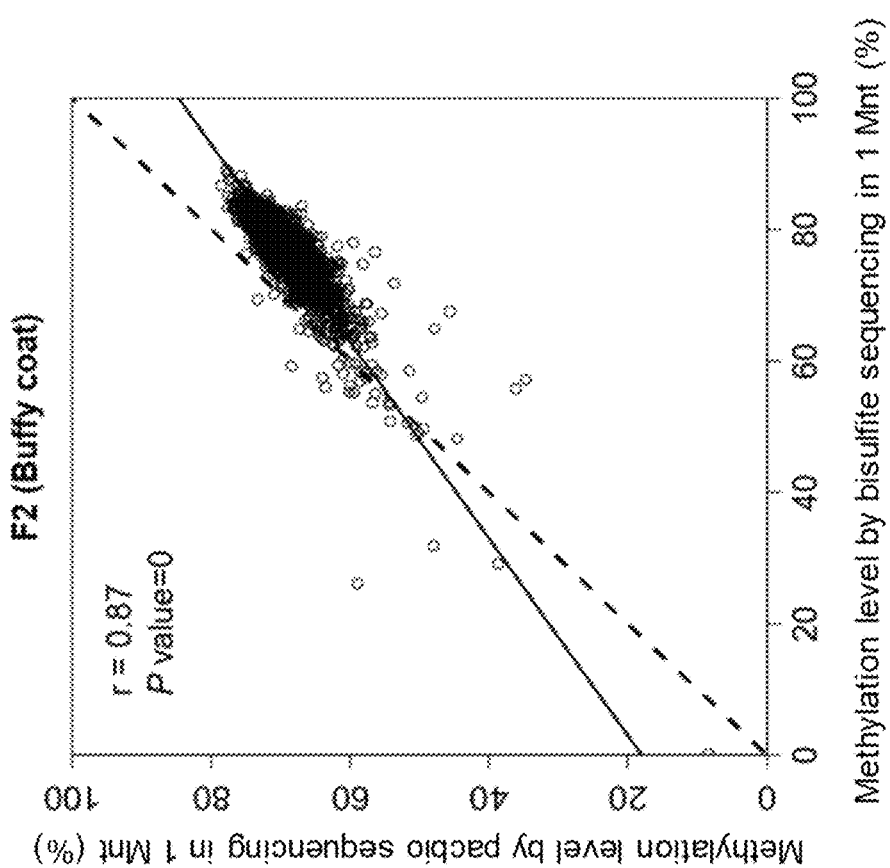
FIGS. 65A and 65B show scatter plots of methylation levels at a 1-Mnt resolution determined by bisulfite sequencing and single molecule, real-time sequencing according to embodiments of the present invention for an HCC cell line (HepG2) and buffy coat sample from a healthy control subject.
Figure 65B:
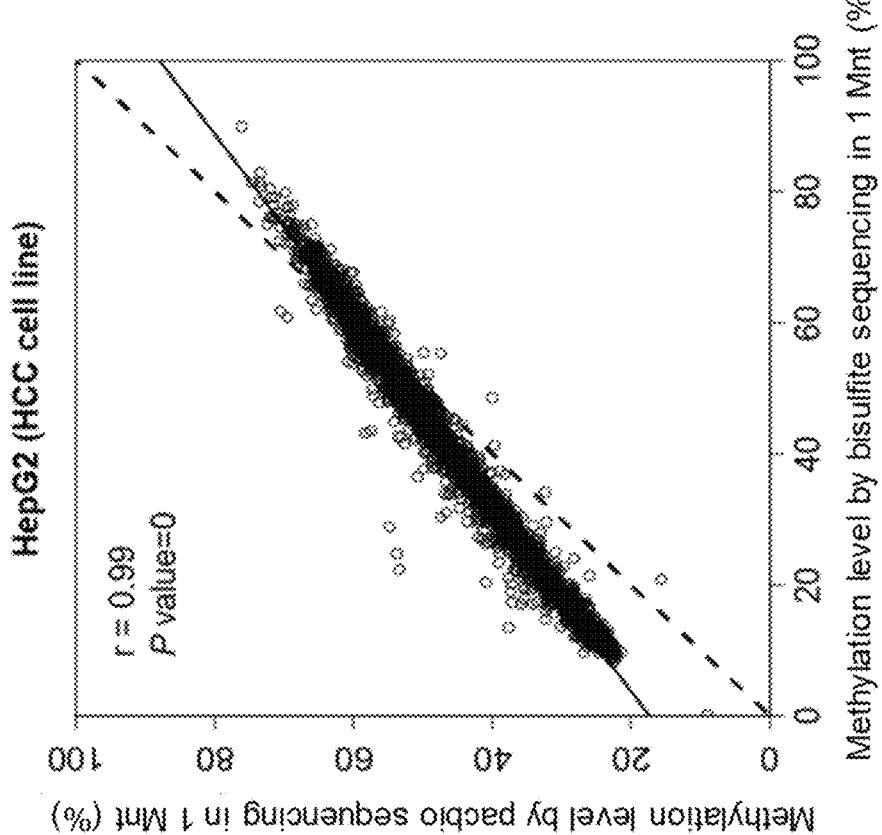

FIGS. 65A and 65B show scatter plots of the methylation levels measured at 1-Mb resolution. FIG. 65A shows the methylation levels for the HCC cell line (HepG2). FIG. 65B shows methylation levels for a buffy coat sample from a healthy control subject. For both FIG. 65A and FIG. 65B, the methylation levels quantified by bisulfite sequencing are on the x-axis, and the methylation levels measured by single molecule, real-time sequencing according to the present disclosure are on the y-axis. The solid line is a fitted regression line. The dashed line is where the two measurement techniques are equal. For the HCC cell line, the methylation level determined by single molecule, real-time sequencing in a 1-Mb resolution was well correlated with that measured by bisulfite sequencing (r=0.99; P<0.0001) (FIG. 65A). Correlation was also observed for the data from the buffy coat sample (r=0.87, P<0.0001) (FIG. 65B).

Figure 66A:
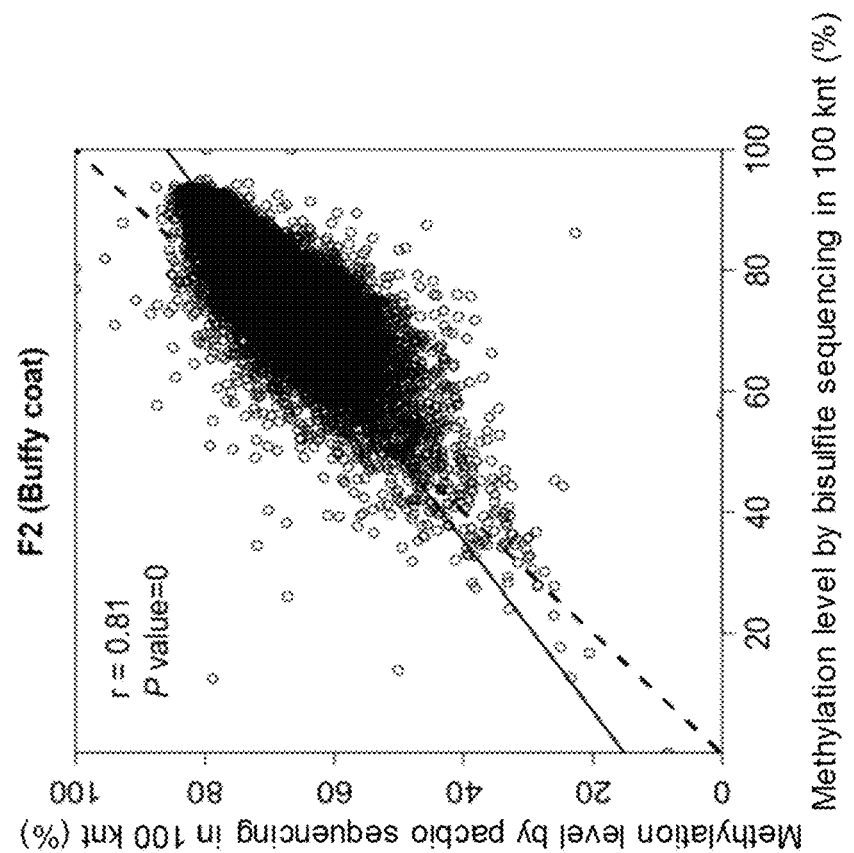
FIGS. 66A and 66B show scatter plots of methylation levels at a 100-knt resolution determined by bisulfite sequencing and single molecule, real-time sequencing according to embodiments of the present invention for HCC cell line (HepG2) and buffy coat sample from a healthy control subject.
Figure 66B:
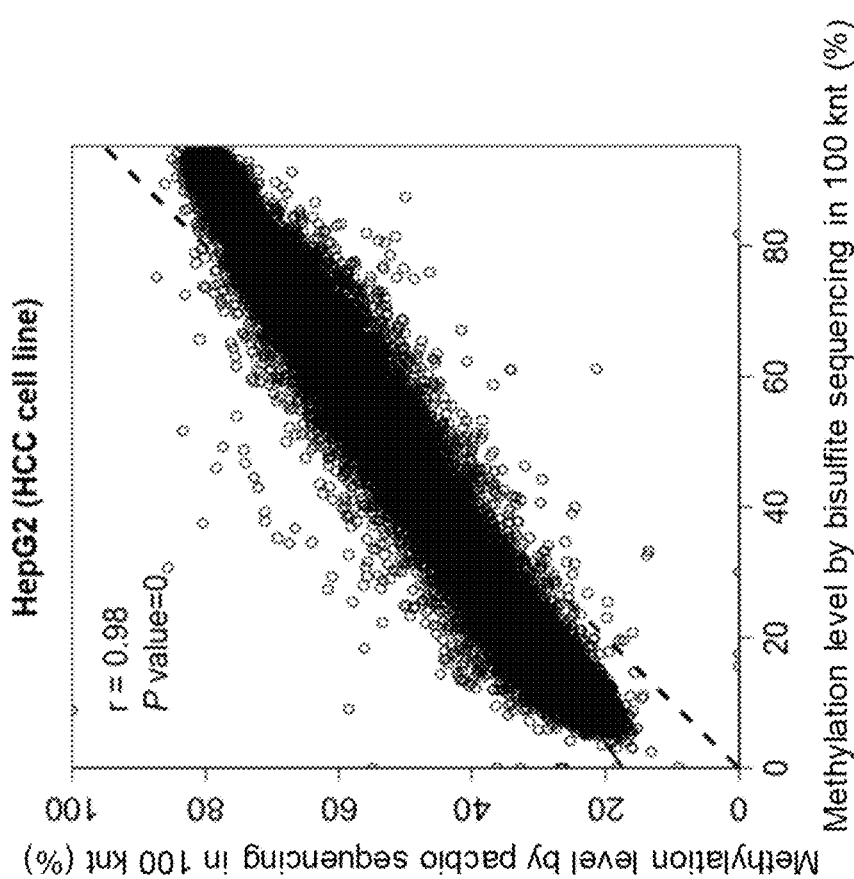

FIGS. 66A and 66B show scatter plots of the methylation levels measured at 100-kb resolution. FIG. 66A shows the methylation levels for the HCC cell line (HepG2). FIG. 66B shows methylation levels for a buffy coat sample from a healthy control subject. For both FIG. 66A and FIG. 66, the methylation levels quantified by bisulfite sequencing are on the x-axis, and the methylation levels measured by single molecule, real-time sequencing according to the present disclosure are on the y-axis. The solid line is a fitted regression line. The dashed line is where the two measurement techniques are equal. The high degree of correlation between the methylation quantitative measurements between the two methods at 1-Mb (or 1-Mnt) resolution was also observed when the resolution of the analysis increased to every 100-kb (or 100-knt) window. All these data indicate that the single molecule, real-time approach of this disclosure is an effective tool for quantifying methylation levels or methylation densities within genomic regions, varying at different degrees of resolution, for example at 1-Mb (or 1-Mnt) or at 100-kb (or 100-knt). The data also indicate that the present invention is an effective tool for assessing the methylation profiles or methylation patterns between regions or between samples.

Figure 67B:
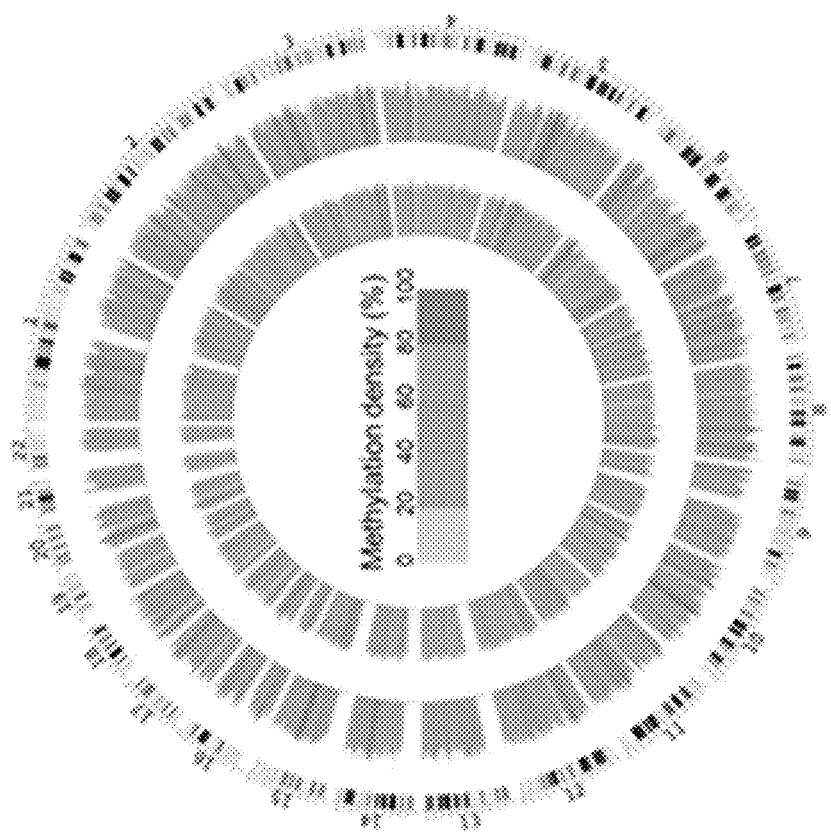
FIGS. 67A and 67B show methylation patterns at 1-Mnt resolution for an HCC tumor tissue and adjacent normal tissue with methylation levels determined by bisulfite sequencing and by single molecule, real-time sequencing according to embodiments of the present invention.
Figure 67A:
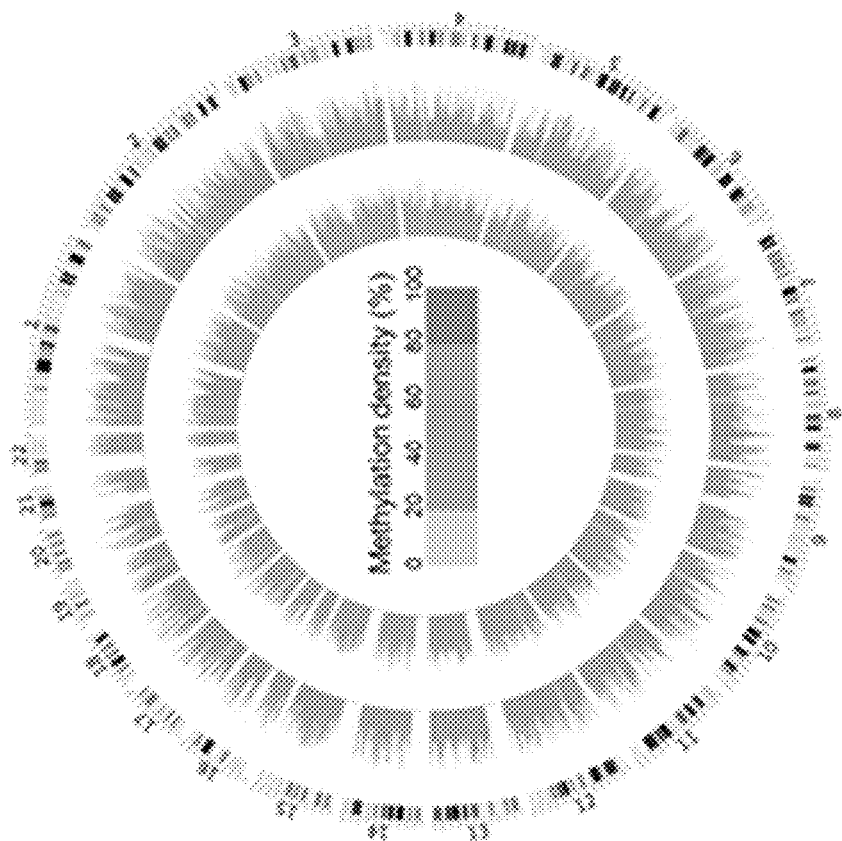

FIGS. 67A and 67B show methylation patterns at 1-Mb resolution. FIG. 67A shows the methylation pattern for an HCC tumor tissue (TBR3033T). FIG. 67B shows the methylation pattern for adjacent normal tissue (TBR3033N). The chromosome ideograms (outermost ring in each figure) are organized from pter to qter in a clockwise direction. The second ring from the outside (also described as a middle ring) shows the methylation levels determined by bisulfite sequencing. The innermost ring shows the methylation levels determined by single molecule, real-time sequencing according to the disclosure. The methylation levels are classified into 5 grades, namely, 0-20% (light green), 20-40% (green), 40-60% (blue), 60-80% (light red), and 80-100% (red). As shown in FIG. 67A, we could detect the hypomethylation in HCC tumor tissue DNA (TBR3033T), which could be differentiated from adjacent normal liver tissue DNA (TBR3033N) in FIG. 67B. The methylation levels and patterns determined by bisulfite sequencing (middle track) and single molecule, real-time sequencing (innermost track) according to the disclosure were consistent. The methylation level of the adjacent normal tissue DNA was shown to be higher than that of HCC tumor tissue DNA.

Figure 68B:
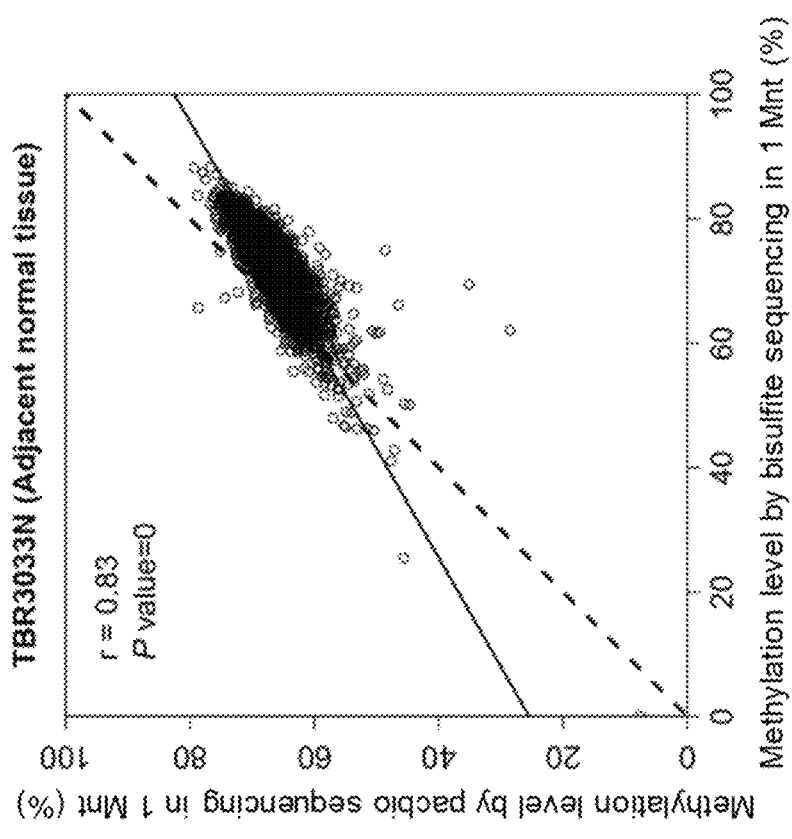
FIGS. 68A and 68B show scatter plots of methylation levels at a 1-Mnt resolution determined by bisulfite sequencing and single molecule, real-time sequencing according to embodiments of the present invention for HCC tumor tissue and adjacent normal tissue.
Figure 68A:
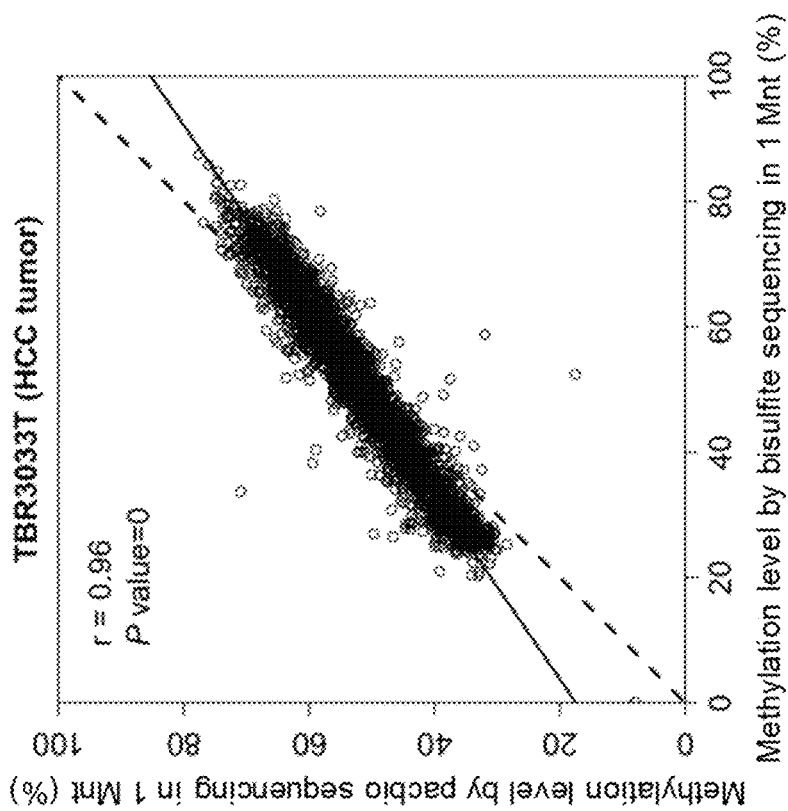

FIGS. 68A and 68B show scatter plots of the methylation levels measured at 1-Mb resolution. FIG. 68A shows the methylation levels for the HCC tumor tissue (TBR3033T). FIG. 68B shows methylation levels for the adjacent normal tissue. For both FIG. 68A and FIG. 68B, the methylation levels quantified by bisulfite sequencing are on the x-axis, and the methylation levels measured by single molecule, real-time sequencing according to the present disclosure are on the y-axis. The solid line is a fitted regression line. The dashed line is where the two measurement techniques are equal. For the HCC tumor tissue DNA, the methylation level measured by single molecule, real-time sequencing in a 1-Mb resolution was well correlated with that determined by bisulfite sequencing (r=0.96; P value <0.0001) (FIG. 68A). The data from the adjacent normal liver tissue sample were also correlated (r=0.83, P value <0.0001) (FIG. 68B).

Figure 69B:
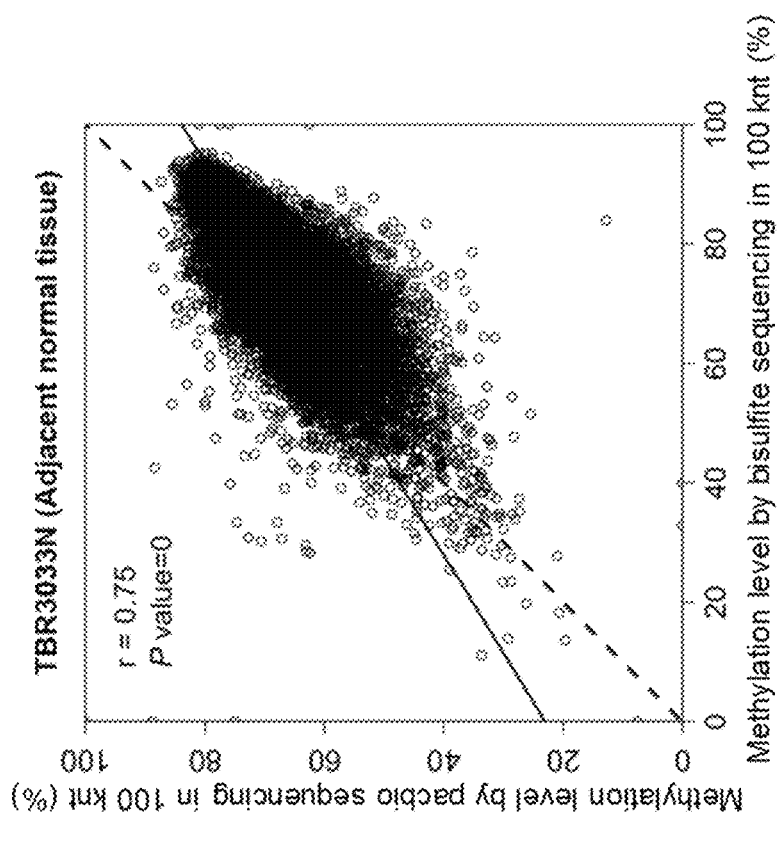
FIGS. 69A and 69B show scatter plots of methylation levels at a 100-knt resolution determined by bisulfite sequencing and single molecule, real-time sequencing according to embodiments of the present invention for HCC tumor tissue and adjacent normal tissue.
Figure 69A:
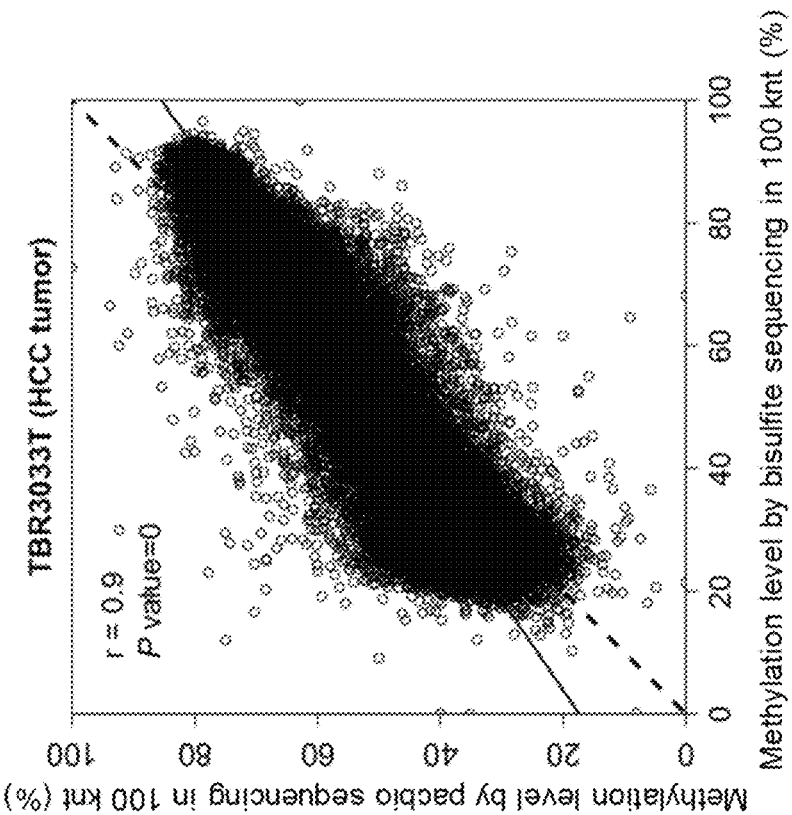

FIGS. 69A and 69B show scatter plots of the methylation levels measured at 100-kb resolution. FIG. 69A shows the methylation levels for the HCC tumor tissue (TBR3033T). FIG. 69B shows methylation levels for adjacent normal tissue (TBR3033N). For both FIG. 69A and FIG. 69B, the methylation levels quantified by bisulfite sequencing are on the x-axis, and the methylation levels measured by single molecule, real-time sequencing according to the present disclosure are on the y-axis. The solid line is a fitted regression line. The dashed line is where the two measurement techniques are equal. Such a high degree of correlation of the methylation quantitative data between the two methods at 1-Mb resolution was also observed when the measurement of the methylation levels was performed at a higher resolution, for example, at 100-kb windows.

Figure 70B:
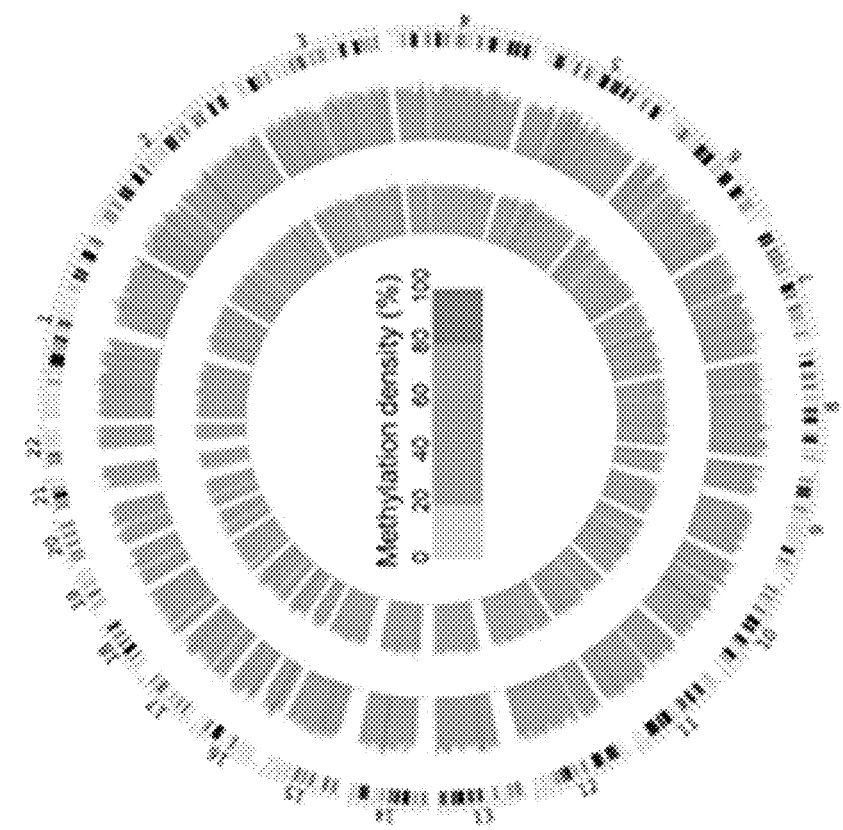
FIGS. 70A and 70B show methylation patterns at 1-Mnt resolution for an HCC tumor tissue and adjacent normal tissue with methylation levels determined by bisulfite sequencing and by single molecule, real-time sequencing according to embodiments of the present invention.
Figure 70A:
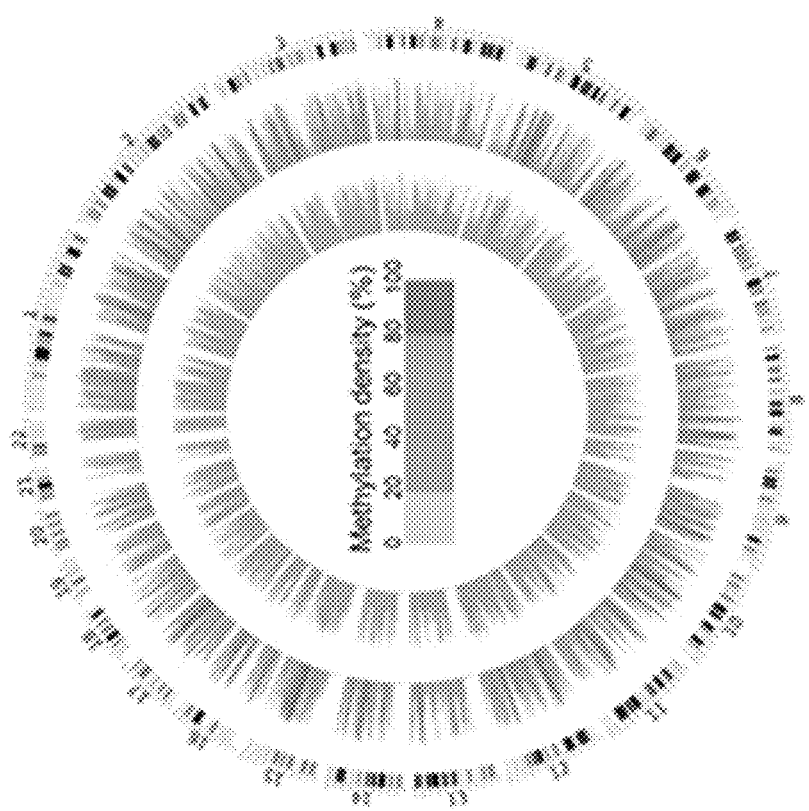

FIGS. 70A and 70B show methylation patterns at 1-Mb resolution for other tumor tissue and normal tissue. FIG. 70A shows the methylation pattern for an HCC tumor tissue (TBR3032T). FIG. 70B shows the methylation pattern for adjacent normal tissue (TBR3032N). The chromosome ideograms (outermost ring in each figure) are organized from pter to qter in a clockwise direction. The second ring from the outside (also described as a middle ring) shows the methylation levels determined by bisulfite sequencing. The innermost ring shows the methylation levels determined by single molecule, real-time sequencing according to the disclosure. The methylation levels are classified into 5 grades, namely, 0-20% (light green), 20-40% (green), 40-60% (blue), 60-80% (light red), and 80-100% (red). As shown in FIG. 70A, we could detect the hypomethylation in HCC tumor tissue DNA (TBR3032T), which could be differentiated from adjacent normal liver tissue DNA (TBR3032N) in FIG. 70B. The methylation levels and patterns determined by bisulfite sequencing (middle track) and single molecule, real-time sequencing using the current invention (innermost track) were consistent. The methylation level of the adjacent normal tissue DNA was shown to be higher than that of HCC tumor tissue DNA.

Figure 71B:
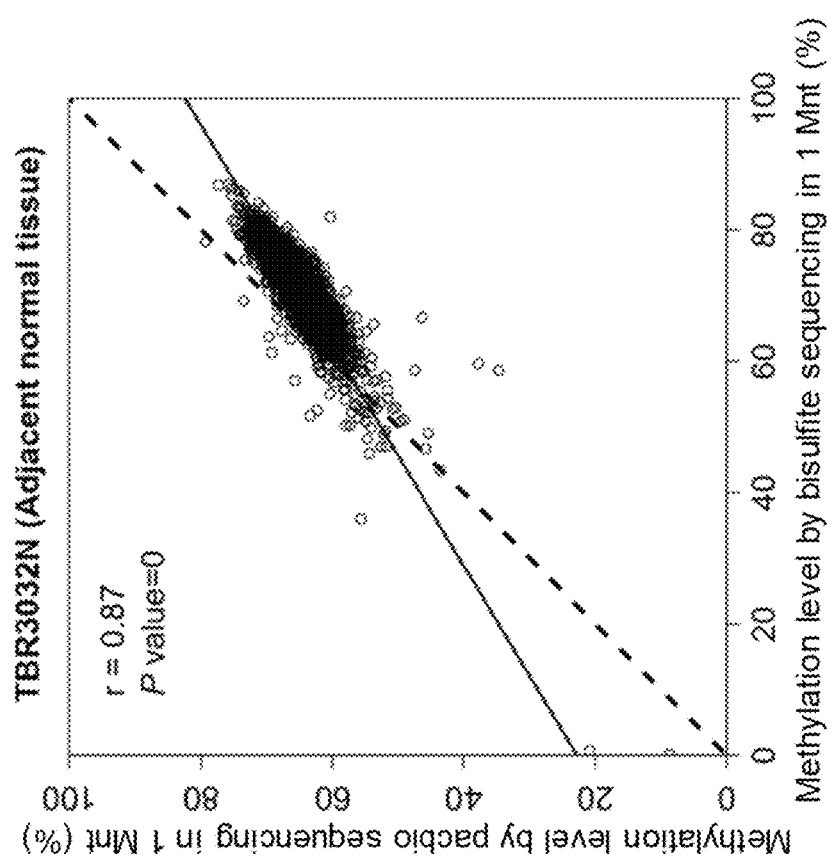
FIGS. 71A and 71B show scatter plots of methylation levels at a 1-Mnt resolution determined by bisulfite sequencing and single molecule, real-time sequencing according to embodiments of the present invention for HCC tumor tissue and adjacent normal tissue.
Figure 71A:
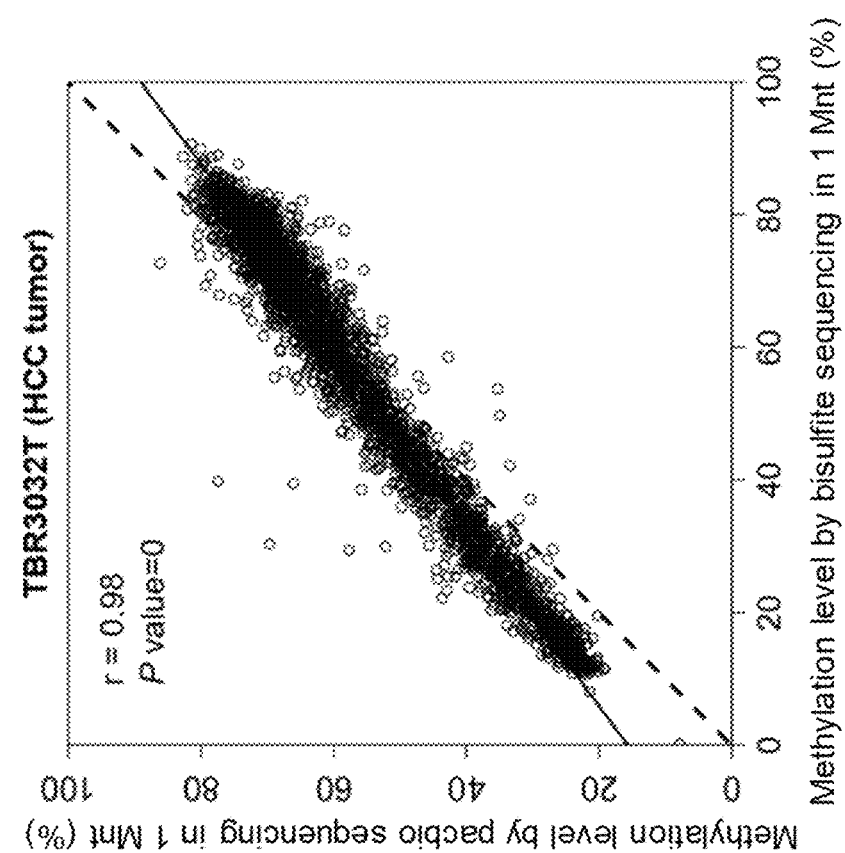

FIGS. 71A and 71B show scatter plots of the methylation levels measured at 1-Mb resolution. FIG. 71A shows the methylation levels for the HCC tumor tissue (TBR3032T). FIG. 71B shows the methylation levels for the adjacent normal tissue. For both FIG. 71A and FIG. 71B, the methylation levels quantified by bisulfite sequencing are on the x-axis, and the methylation levels measured by single molecule, real-time sequencing according to the present disclosure are on the y-axis. The solid line is a fitted regression line. The dashed line is where the two measurement techniques are equal. For the HCC tumor tissue DNA, the methylation level measured by single molecule, real-time sequencing in a 1-Mb resolution was well correlated with that determined by bisulfite sequencing (r=0.98; P<0.0001) (FIG. 71A). The data from the adjacent normal liver tissue sample were also correlated (r=0.87, P<0.0001) (FIG. 71B).

Figure 72B:
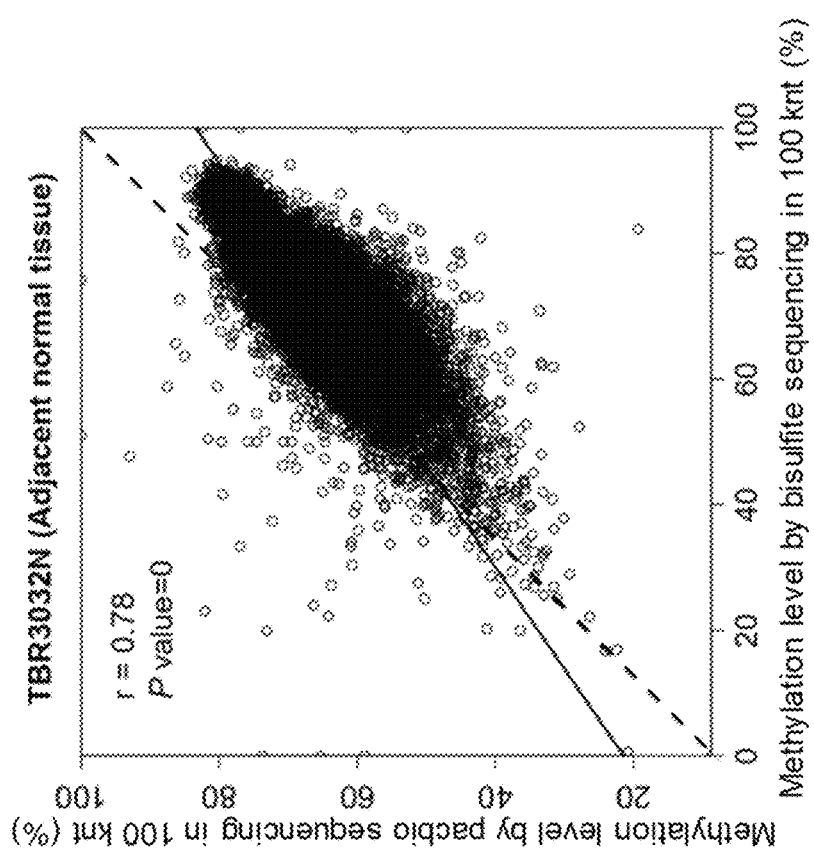
FIGS. 72A and 72B show scatter plots of methylation levels at a 100-knt resolution determined by bisulfite sequencing and single molecule, real-time sequencing according to embodiments of the present invention for HCC tumor tissue and adjacent normal tissue.
Figure 72A:
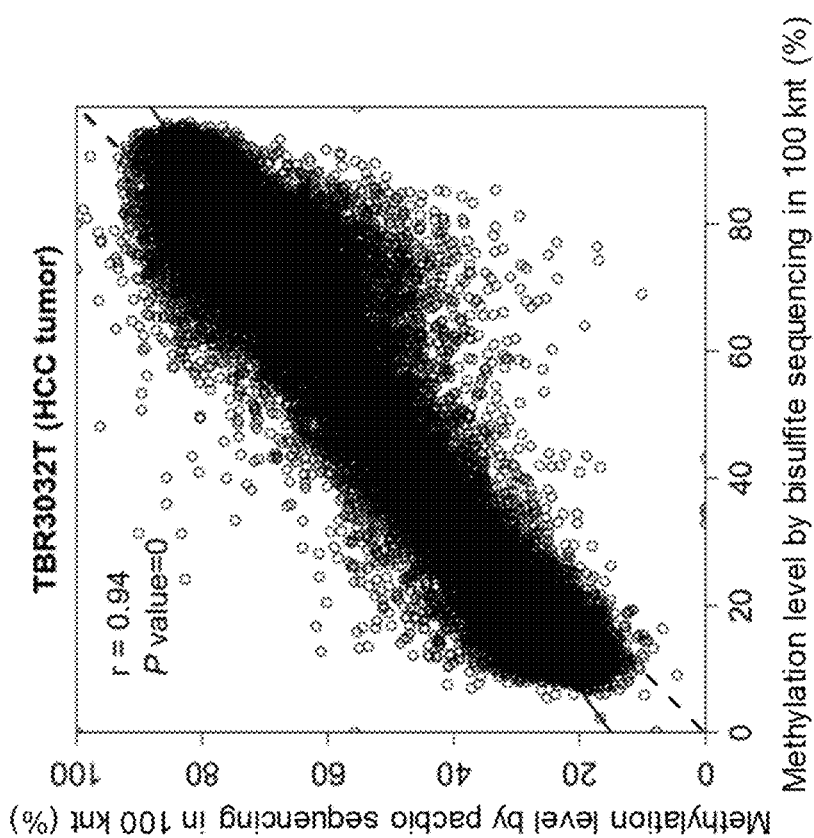

FIGS. 72A and 72B show scatter plots of the methylation levels measured at 100-kb resolution. FIG. 72A shows the methylation levels for the HCC tumor tissue (TBR3032T). FIG. 72B shows methylation levels for adjacent normal tissue (TBR3032N). For both FIG. 72A and FIG. 72B, the methylation levels quantified by bisulfite sequencing are on the x-axis, and the methylation levels measured by single molecule, real-time sequencing according to the present disclosure are on the y-axis. The solid line is a fitted regression line. The dashed line is where the two measurement techniques are equal. Such a high degree of correlation of the methylation quantitative data between the two methods at 1-Mb resolution was also observed when the measurement of the methylation levels was performed at a higher resolution, for example, at 100-kb windows.

4. Differential Methylation Regions Between Tumor and Adjacent Normal Tissues

Methylomic aberrations are often found in regions of cancer genomes. One example of such aberrations is hypomethylation and hypermethylation of selected genomic regions (Cadieux et al. Cancer Res. 2006; 66:8469-76; Graff et al. Cancer Res. 1995; 55:5195-9; Costello et al. Nat Genet. 2000; 24:132-8). Another example is the aberrant pattern of methylated and unmethylated bases in selected genomic regions. This section shows that techniques of determining methylation can be used in performing quantitative analysis and diagnostics in analyzing tumors.

Figure 73:
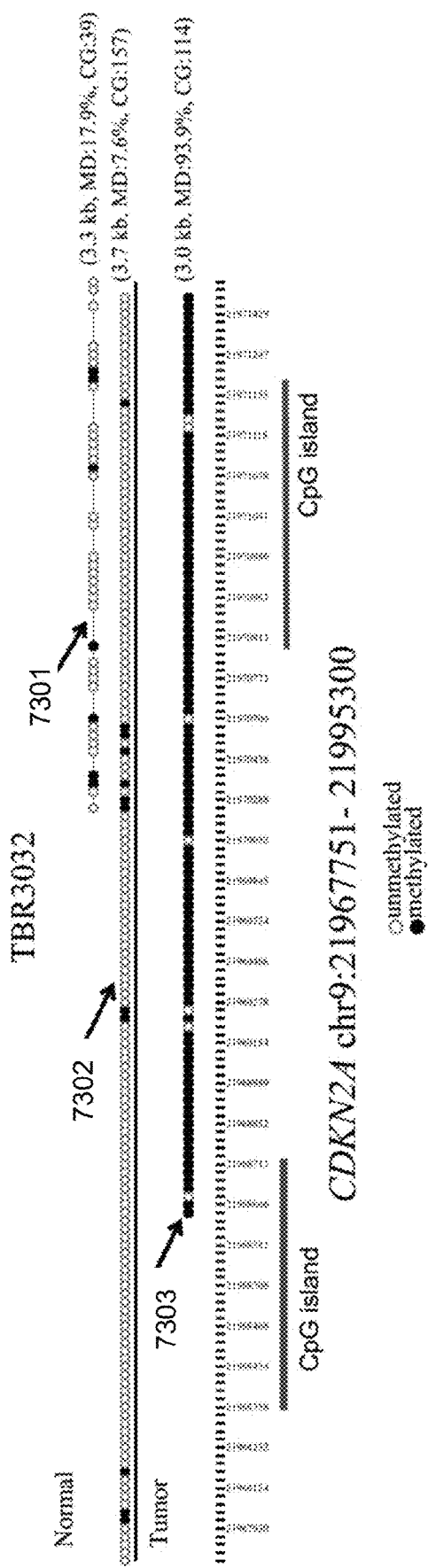
FIG. 73 shows an example of the aberrant pattern of methylation nearby the tumor suppressor gene CDKN2A according to embodiments of the present invention.

FIG. 73 shows an example of the aberrant pattern of methylation nearby the tumor suppressor gene CDKN2A. The coordinates highlighted in blue and underlined indicate CpG islands. Black filled dots indicate methylated sites. Unfilled dots indicate unmethylated sites. The numbers in parentheses on the right of each horizontal line with dots indicate the size of the fragment, single molecular methylation density, and the number of CpG sites. For example, (3.3 kb, MD:17.9%, CG:39) means that the size of this fragment is 3.3 kb, the methylation level of this fragment is 17.9% and the number of CpG sites is 39. MD represents methylation density.

As shown in FIG. 73, the CDKN2A (cyclin dependent kinase inhibitor 2A) gene codes for two proteins including the INK4A (p16) and ARF (p14), acting as tumor suppressors. There were two molecules (molecule 7301 and molecule 7302) covering the region overlapping the CDKN2A gene in the nontumoral tissue adjacent to the tumor tissue. The methylation levels of single double-stranded DNA molecule for molecule 7301 and molecule 7302 were shown to be 17.9% and 7.6%, respectively. In contrast, the methylation level of single double-stranded DNA molecule for molecule 7303 present in the tumoral tissue was found to be 93.9%, which was much higher than that of molecules present in the paired adjacent nontumoral tissues. On the other hand, one could also calculate the multiple strand methylation level using molecule 7301 and 7302 present in the nontumoral tissue adjacent to the tumor tissue. As a result, the multiple strand methylation level was 9.7%, which was lower than that of the tumor tissue (93.9%). The different methylation levels suggest that one could use the single double-stranded molecule methylation level and/or multiple strand methylation level to detect or monitor diseases such as cancer.

Figure 74A:
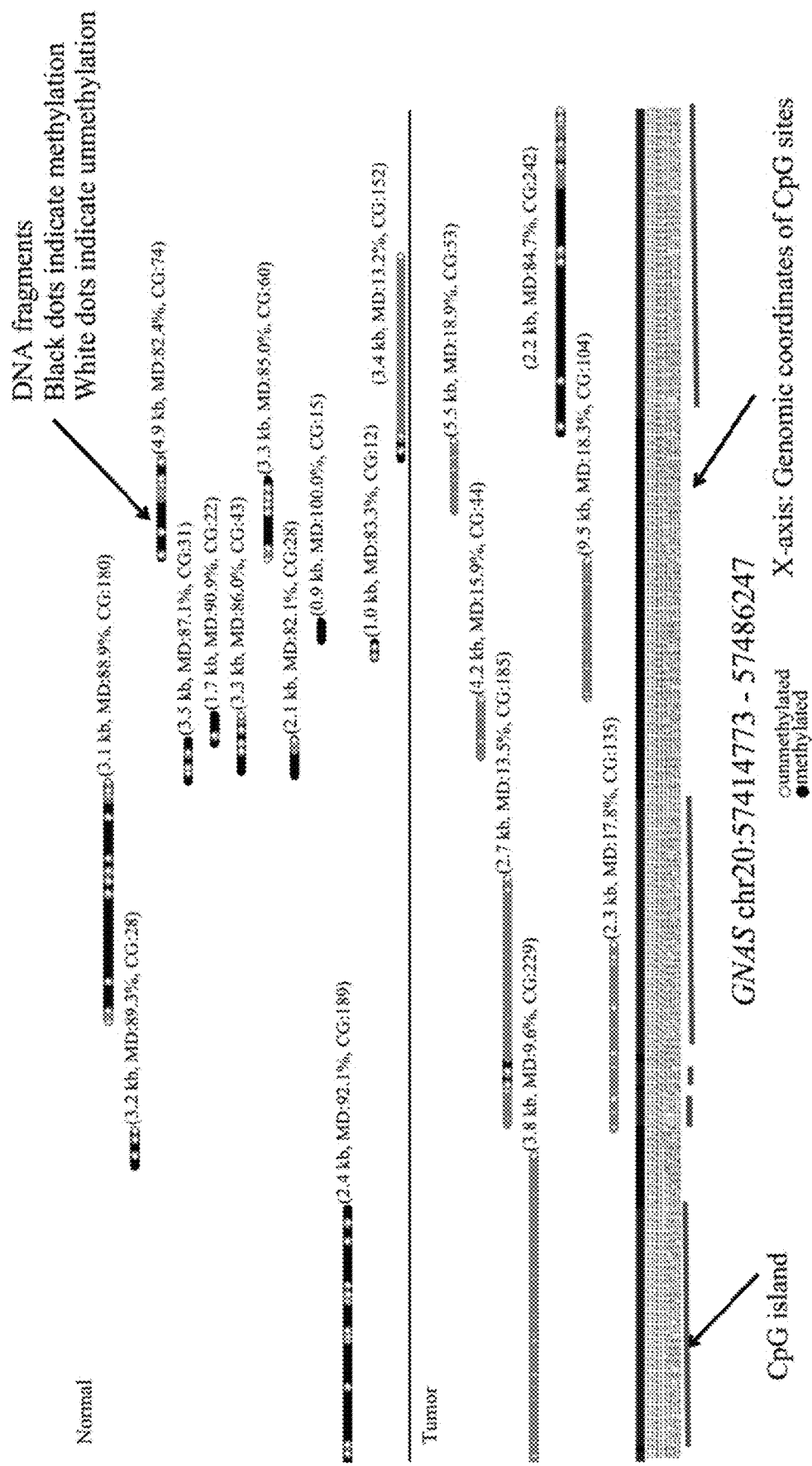
FIGS. 74A and 74B show differential methylation regions detected by single molecule, real-time sequencing according to embodiments of the present invention.
Figure 74B:
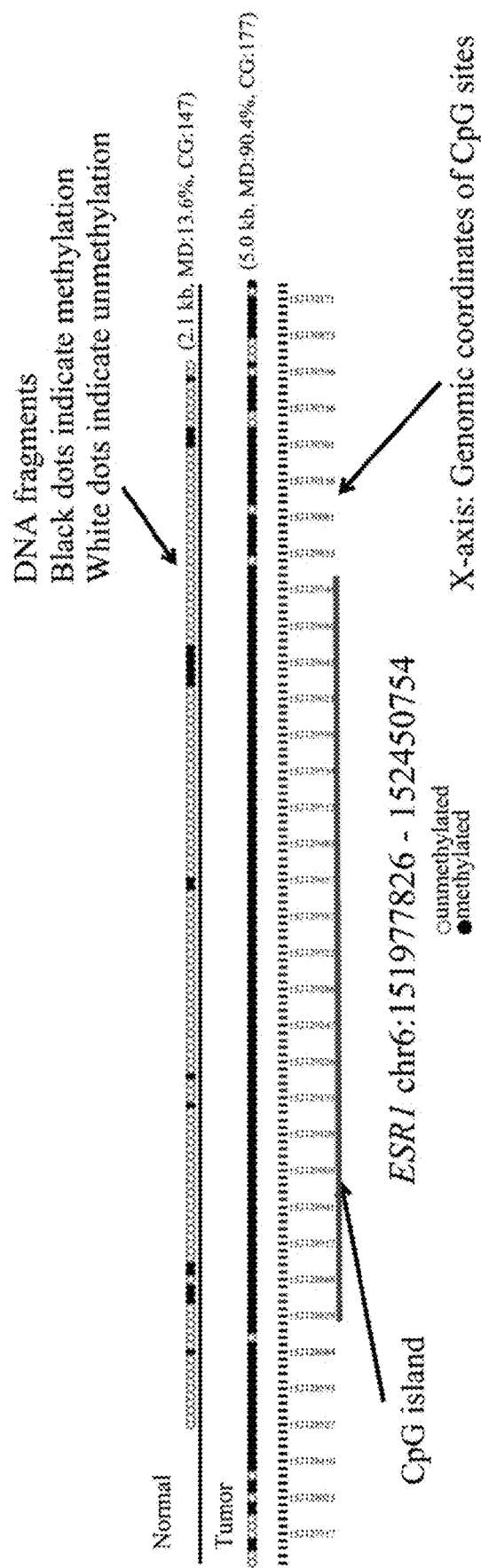

FIG. 74A and FIG. 74B show differential methylation regions detected by single molecule, real-time sequencing according to embodiments of the present invention. FIG. 74A shows hypomethylation in the cancer genome. FIG.

74B shows hypermethylation in the cancer genome. The x-axis indicates the coordinates of CpG sites. The coordinates highlighted in blue and underlined indicate CpG islands. Black filled dots indicate methylated sites. Unfilled dots indicate unmethylated sites. The numbers in parentheses on the right of each horizontal line with dots indicate the size of the fragment, fragment-level methylation density, and the number of CpG sites. For example, (3.1 kb, MD:88.9%, CG:180) means that the size of this fragment is 3.1 kb, the methylation density of this fragment is 88.9% and the number of CpG sites is 180.

FIG. 74A shows a region close to the GNAS gene displaying more hypomethylated fragments in the HCC tumor tissue compared with the adjacent normal liver tissue. FIG. 74B shows a region close to the ESR1 gene displaying a hypermethylated fragment in the HCC tissue but a DNA fragment from the paired adjacent non-tumoral tissue aligning to the corresponding region showed hypomethylation instead. As shown in FIG. 74B, the methylation profiles or methylation haplotypes of individual DNA molecules were adequate to reveal the aberrant methylation status of those genomic regions, namely GNAS and ESR1, when cancer samples are compared with non-cancer samples.

These data indicate that the single molecule, real-time sequencing methylation analysis disclosed hereby could determine the methylation status at each CpG site (whether methylated or unmethylated) on individual DNA fragments. The read length of single molecule, real-time sequencing is much longer (in the order of kilobases long) than that for Illumina sequencing which could typically span 100-300 nt in length per read (De Maio et al. Micob Genom. 2019; 5(9)). Combining the long read length property of single molecule, real-time sequencing with the methylation analysis method we have hereby disclosed, one could readily determine the methylation haplotype of multiple CpG sites that are present along any single DNA molecule. The methylation profile refers to the methylation status of CpG sites from one coordinate of the genome to another coordinate within a contiguous stretch of DNA (e.g., on the same chromosome, or within a bacterial plasmid, or within a single stretch of DNA in a virus genome).

Because single molecule, real-time sequencing analyzes each DNA molecule individually without the need for prior amplification, the methylation profile determined for any individual DNA molecule is in fact a methylation haplotype, meaning the methylation status of CpG sites from one end to another end of the same DNA molecule. If one or more molecules are sequenced from the same genomic region, the % methylation (namely methylation level or methylation density) of each CpG site across all the sequenced CpG sites in the genomic region could be aggregated from the data of the multiple DNA fragments using the same formula as shown in FIG. 61. The % methylation of each CpG site could be reported for all sequenced CpG site providing the methylation profile of the sequenced genomic region. Alternatively, the data could be aggregated from all reads and all sites within the sequenced genomic region to provide one % methylation value of the region, namely in the same manner as how the methylation levels for the 1-Mb or the 1-kb regions were calculated as shown in FIGS. 64 to 72.

5. Viral DNA Methylation Analysis

This section shows that methylation techniques of this disclosure can be used to accurately determine methylation levels in viral DNA.

Figure 75:
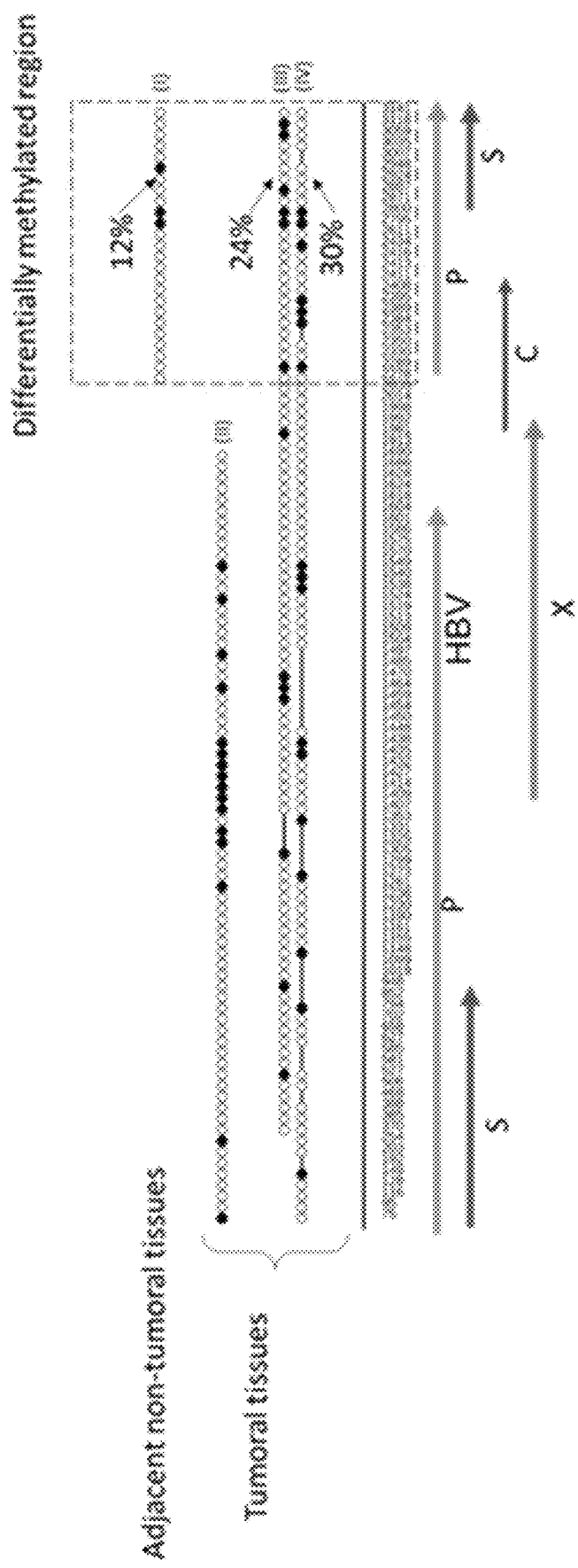
FIG. 75 shows methylation patterns of hepatitis B virus DNA between HCC tissues and adjacent non-tumoral tissues using single molecule, real-time sequencing according to embodiments of the present invention.

FIG. 75 shows methylation patterns of hepatitis B virus DNA between two pairs of HCC tissue samples and adjacent non-tumoral tissue samples using single molecule, real-time sequencing. Each arrow represents a gene annotation in an HBV genome. The arrows with 'P', 'S', 'X', and 'C' indicate the gene annotation about a HBV genome: encoding polymerase, surface antigen, X protein, and core protein, respectively. We identified one fragment (molecule I) with 1,183 bp in size originating from adjacent non-tumoral tissues, spanning a HBV genome from 2,278 to 3,141 highlighted in a dashed rectangle, showing a methylation level of 12%. We also identified three fragments (molecule II, III, and IV) with 3,215 bp, 2,961 bp, and 3,105 bp originating from tumoral tissues. Among them, two fragments (molecule III and IV) in HCC tumors overlapped with the HBV genomic regions spanned by the molecule I in non-tumoral tissues. In contrast to the low methylation level (12%) in the HBV region highlighted in a dashed rectangle (HBV genomic locations: 2,278-3,141), the methylation levels were higher for those fragments (molecule III and IV) in HCC tissues (i.e. 24% and 30%). These results suggested that the approach using single molecule, real-time sequencing was feasible to determine the methylation patterns in the viral genome and able to identify the differentially methylated region (DMR) of HBV between HCC and non-HCC tissues. Therefore, the determination of methylation states across viral genomes using single molecule, real-time sequencing according to the disclosure would provide a new tool to study the clinical relevance using tissue biopsies.

This DMR region happened to overlap with gene P, C, and S. It was reported that this region was also shown to be hypermethylated in HCC tissues compared with that in liver tissues with HBV infection but without cancer (Jain et al. Sci Rep. 2015; 5:10478; Fernandez et al. Genome Res. 2009; 19:438-51).

Figure 76A:
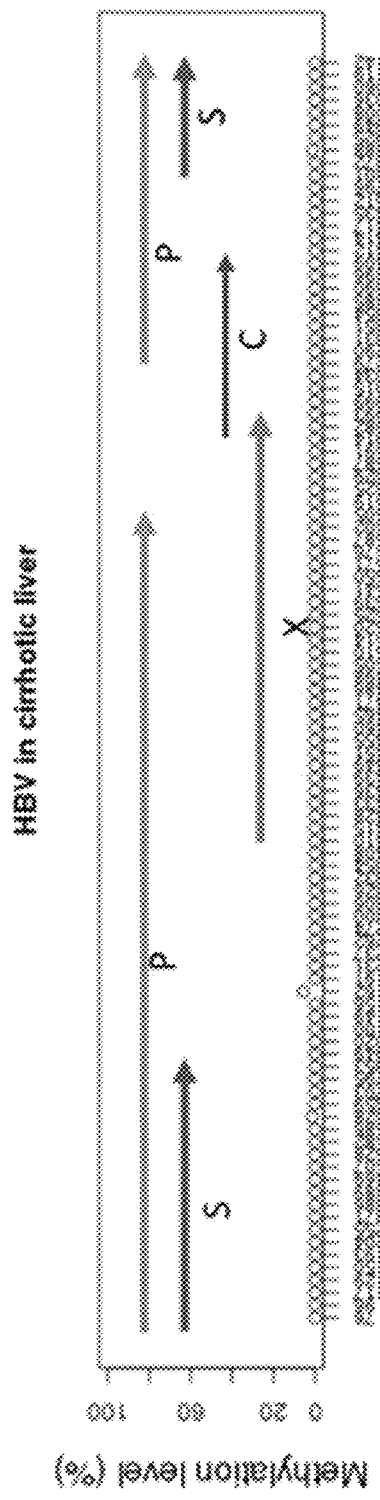
FIG. 76A shows methylation levels of hepatitis B virus DNA in liver tissues from patients with cirrhosis but without HCC using bisulfite sequencing according to embodiments of the present invention.
Figure 76B:
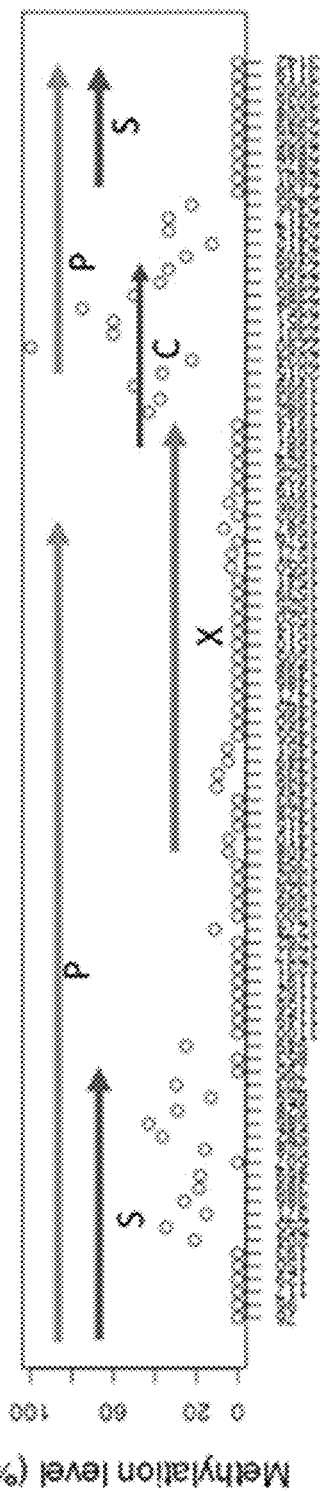
FIG. 76B shows methylation levels of hepatitis B virus DNA in HCC tissues using bisulfite sequencing according to embodiments of the present invention.

We pooled bisulfite sequencing results of liver tissues from four patients with cirrhosis but without HCC, obtaining 1,156 HBV fragments for methylation analysis. FIG. 76A shows methylation levels for hepatitis B virus DNA in liver tissues from patients with cirrhosis but without HCC. In addition, we pooled bisulfite sequencing results of HCC tumor tissues from 15 patients, obtaining 736 HBV fragments for methylation analysis. FIG. 76B shows methylation levels for hepatitis B virus DNA in HCC tumor tissue. As shown in FIG. 76A and FIG. 76B, we also observed a DMR region of HBV (HBV genomic locations: 1,982-2, 435) that had a higher methylation level in HCC tissues than cirrhotic liver tissues by massively parallel bisulfite sequencing. These results suggested that the approach for determining the methylation status of viral genomes would be valid.

6. Variant-Associated Methylation Analysis

Different alleles may be associated with different methylation profiles. For example, imprinted genes may have one allele with a higher methylation level than the other allele. This section shows that methylation profiles can be used to distinguish alleles in certain genomic regions.

One single molecule, real-time sequencing well containing a single DNA template would generate a number of subreads. The subreads include kinetic features [e.g. interpulse duration (IPD) and pulse width (PW)] and nucleotide compositions. In one embodiment, subreads from one single molecule, real-time sequencing well can be used to generate a consensus sequence (also called circular consensus sequence, CCS) which may dramatically reduce the sequencing errors (e.g. mismatches, insertions or deletions). Additional details of CCS are described herein. In one embodiment, the consensus sequence can be constructed using those subreads aligned to a human reference genome. In another embodiment, the consensus sequence could be constructed by mapping the subreads to the longest subread in the same single molecule, real-time sequencing well.

Figure 77:
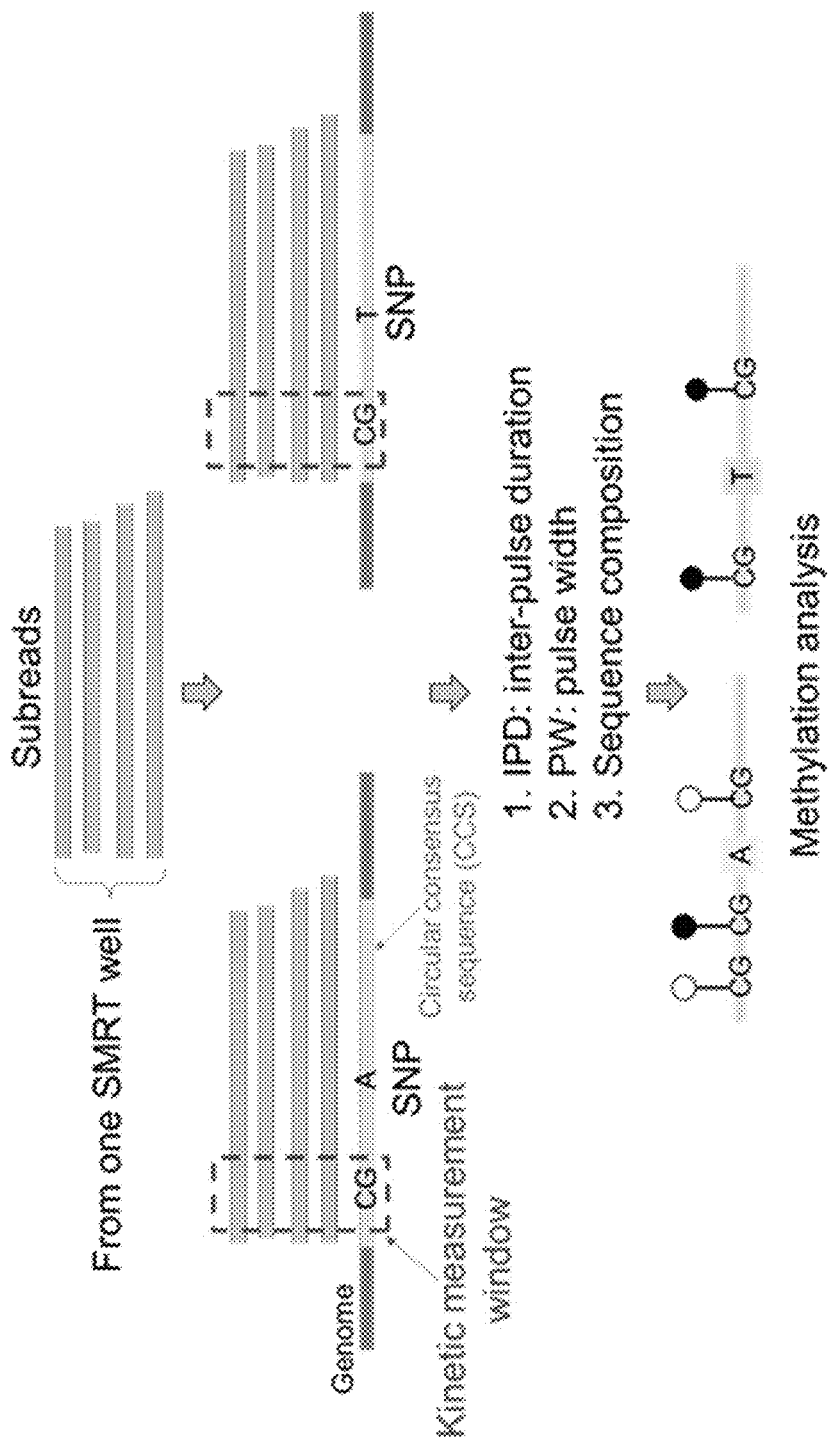
FIG. 77 illustrates methylation haplotype analysis according to embodiments of the present invention.

FIG. 77 illustrates the principle of phased methylation haplotype analysis. The filled lollipops represent the CpG sites that are classified as methylated. The unfilled lollipops represent the CpG sites that are classified as unmethylated.

As shown in one embodiment in FIG. 77, the subreads were aligned to a human reference genome. The aligned subreads from one single molecule, real-time sequencing well were collapsed to form a consensus sequence. The consensus sequence generally could be determined using the most frequent nucleotides present in subreads across each aligned position. Therefore, the nucleotide variants, including but not limited to single nucleotide variants, insertions, and deletions, could be identified from consensus sequences. The averaged IPDs and PWs in the same molecule tagged by a nucleotide variant could be used to determine the methylation patterns according to the disclosure. Thus, we could further determine the variant-associated methylation patterns. The methylation states in the same molecule could be deemed as a methylation haplotype. The methylation haplotype may not be readily and directly constructed from two or more short DNA molecules because there may be no molecular marker allowing for differentiating whether two or more fragmented short DNA molecules are derived from an original single molecule or contributed by two or more different original molecules. Synthetic long read technologies (such as linked-read sequencing developed by 10× Genomics) offer a possibility to distribute a single long DNA molecule into a partition (such as a droplet) and tag short DNA molecules, originating from that long DNA molecule, with the same molecular barcode sequences. However, this barcoding step involves PCR amplification that would not preserve the original methylation states.

Furthermore, if one attempts to use bisulfite to treat the long DNA molecules, the first step prior to bisulfite treatment involves DNA denaturation under destructive conditions, changing double-stranded DNA into single-stranded DNA as the bisulfite could only act on single-stranded DNA molecules in certain chemical conditions. This DNA denaturation step would degrade long DNA molecules into short fragments, resulting in the loss of original methylation haplotype information. The second drawback of bisulfite-based methylation analysis would denature double-stranded DNA into single-stranded DNA in the bisulfite conversion step, namely the Watson and Crick strands. For a molecule, there is 50% chance of sequencing the Watson and a 50% chance of sequence the Crick strand. Among millions of Watson and Crick strands, there is an extremely low chance to simultaneously sequence both Watson and Crick strands of a molecule. Even though both Watson and Crick strands of a molecule are assumed to be sequenced, it is still impossible to definitely determine whether such Watson and Crick strands are derived from an original single fragment or contributed by two or more different original fragments. Liu et al recently introduced a bisulfite-free sequencing method for detecting methylated cytosines and hydroxymethylcytosine (Liu et al. Nat Biotechnol. 2019; 37:424-429) using Ten-eleven translocation (TET) enzyme-based conversion under mild conditions, leading to less degradation of DNA. However, it involves two sequential steps of enzymatic reactions. A low conversion rate of either step of enzymatic reaction would dramatically affect the overall conversion rate. In addition, even for this bisulfite-free sequencing method for detecting methylated cytosines, the difficulty in distinguishing Watson and Crick strands of a molecule in the sequencing results still exists.

In contrast, in embodiments of the present invention, the Watson and Crick strands of a molecule is covalently ligated via bell-shaped adaptors to form circular DNA molecules. As a result, both the Watson and Crick strands of a molecule are sequenced in the same reaction well and the methylation states for each strand can be determined.

One advantage of embodiments of the present invention is the ability to ascertain the methylation and genetic (i.e. sequence) information on a long contiguous DNA molecule (e.g. kilobases or kilonucleotides in length). It is more difficult to generate such information using short read sequencing technologies. For short read sequencing technologies, one has to combine sequencing information on multiple short reads using scaffolds of genetic or epigenetic signatures, so that a long stretch of methylation and genetic information can be deduced. However, this could prove challenging in many scenarios due to the distances between such genetic or epigenetic anchors. For example, on average there is one SNP per 1 kb while current short read sequencing technologies could typically sequence up to 300 nt per read, resulting in 600 nt even in a paired-end format.

In one embodiment, the variant-associated methylation haplotype analysis could be used to study the methylation patterns in imprinted genes. Imprinted regions are subjected to epigenetic regulations (e.g. CpG methylation) in a parent-of-origin fashion. For example, one buffy coat DNA sample (M2) in the table in FIG. 60 was sequenced to obtain around 152 million subreads. For this sample, 53% of single molecule, real-time sequencing wells generated at least one subread that could be aligned to a human reference genome. The mean subread depth for each SMRT well was 7.7×. In total, we obtained around 3 million consensus sequences. About 91% of the reference genome was covered by consensus sequences at least once. For covered regions, the sequencing depth was 7.9×. The data set was generated from DNA prepared by Sequel II Sequencing Kit 1.0.

Figure 78:
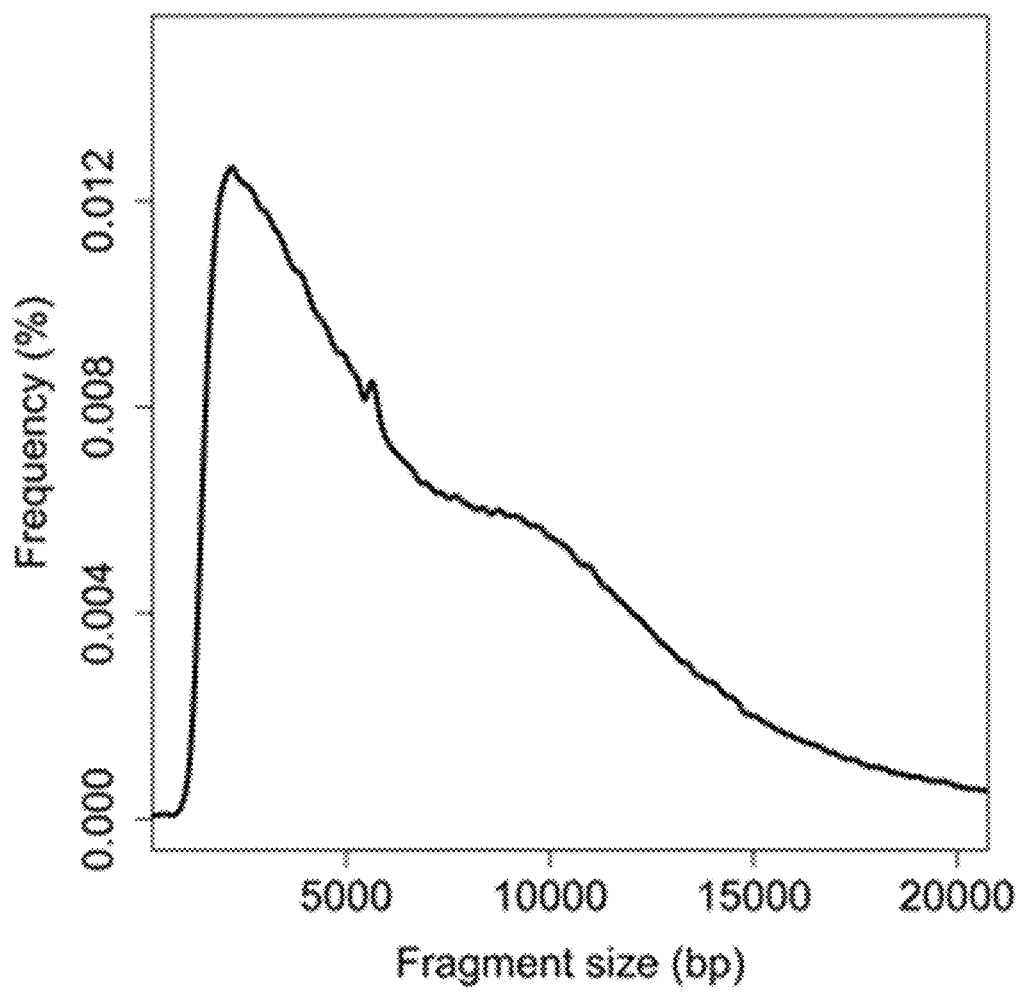
FIG. 78 shows the size distribution of the sequenced molecules determined from consensus sequences according to embodiments of the present invention.

FIG. 78 shows the size distribution of the sequenced molecules determined from consensus sequences, with a median size of 6,289 bp (range: 66-198,109 bp). The fragment size (bp) is shown on the x-axis, and the frequency (%) associated with the fragment size is shown on the y-axis.

FIGS. 79A, 79B, 79C, and 79D show examples of allelic methylation patterns in the imprinted regions. The x-axis indicates the coordinates of CpG sites. The coordinates highlighted in blue and underlined indicate CpG islands. Black filled dots indicate methylated CpG sites. Unfilled dots indicate unmethylated CpG sites. The alphabet embedded among each horizontal series of filled and unfilled dots (i.e. CpG sites) indicates the allele at the SNP site. The numbers in parentheses on the right of each horizontal series of dots indicate the size of the fragment, fragment-level methylation density, and the number of CpG sites. For example, (10.0 kb, MD:79.1%, CG:139) suggested the size of the corresponding fragment was 10.0 kb, the methylation density of the fragment was 79.1% and the number of CpG sites was 139. The dashed rectangles outline the most differentially methylated regions within each gene.

Figure 79A:
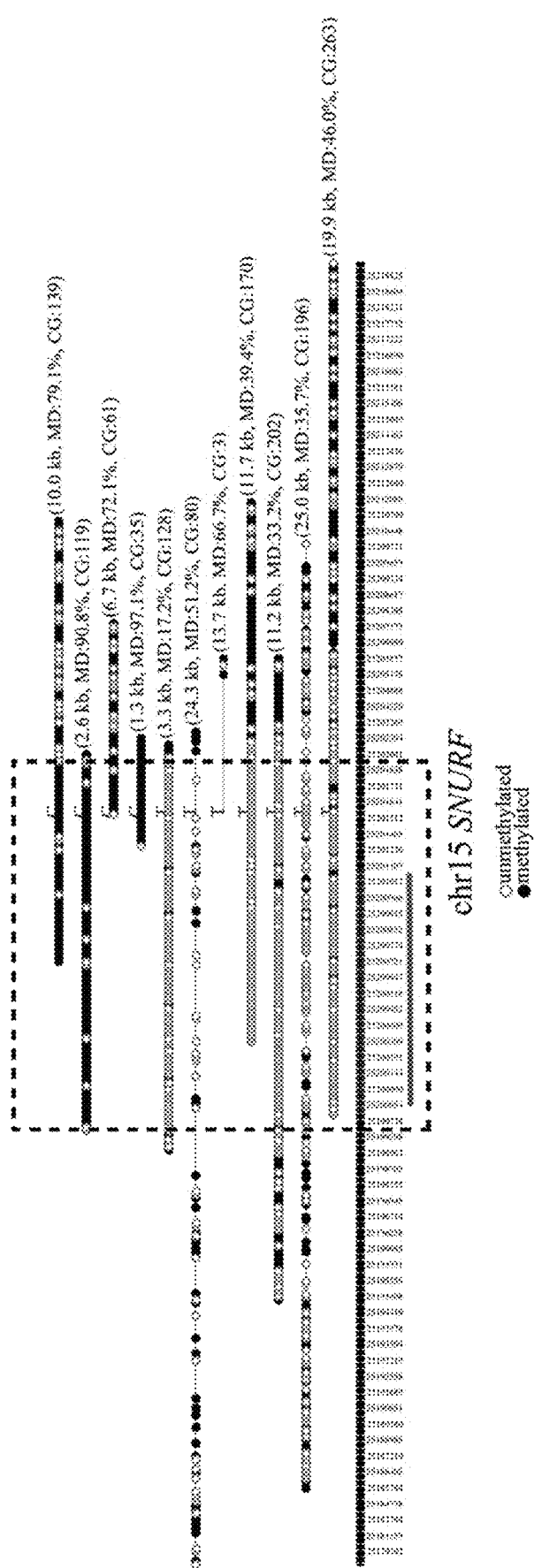
FIGS. 79A, 79B, 79C, and 79D show examples of allelic methylation patterns in the imprinted regions according to embodiments of the present invention.

FIG. 79A shows 11 sequenced fragments with a median size of 11.2 kb (range: 1.3-25 kb), originating from the SNURF gene. The SNURF gene was maternally imprinted, meaning that the copy of the gene that an individual has inherited from the mother is methylated and transcriptionally silent. As shown in FIG. 79A, in the dashed rectangle, the C allele associated fragments were highly methylated, whereas the T allele associated fragments were highly unmethylated. Highly methylated may indicate that over 70%, 80%, 90%, 95%, or 99% of the sites are methylated.

Figure 79B:
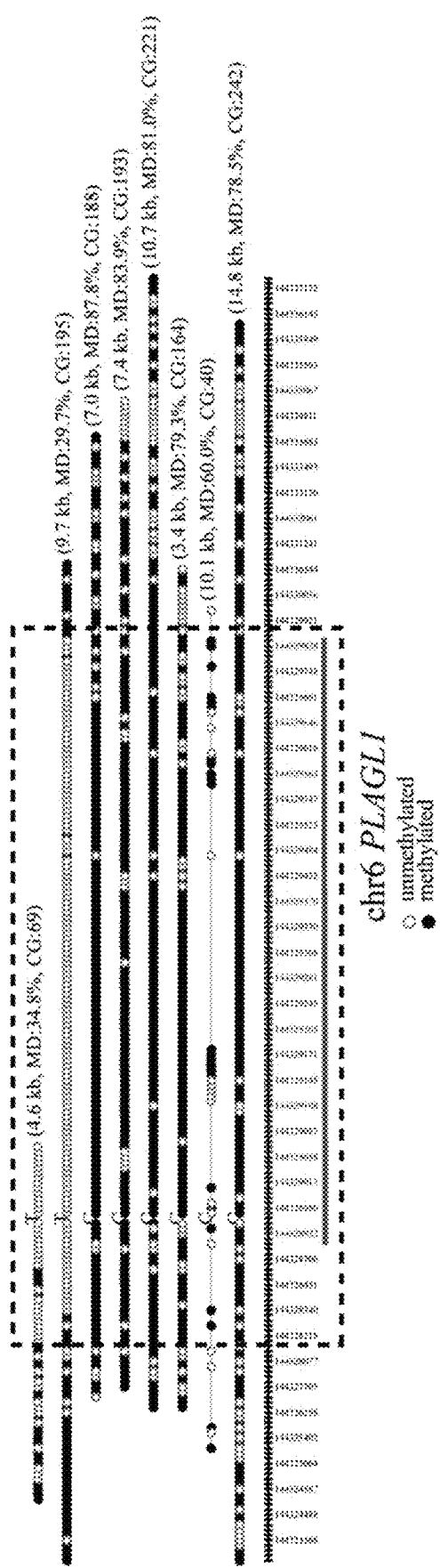
Figure 79C:
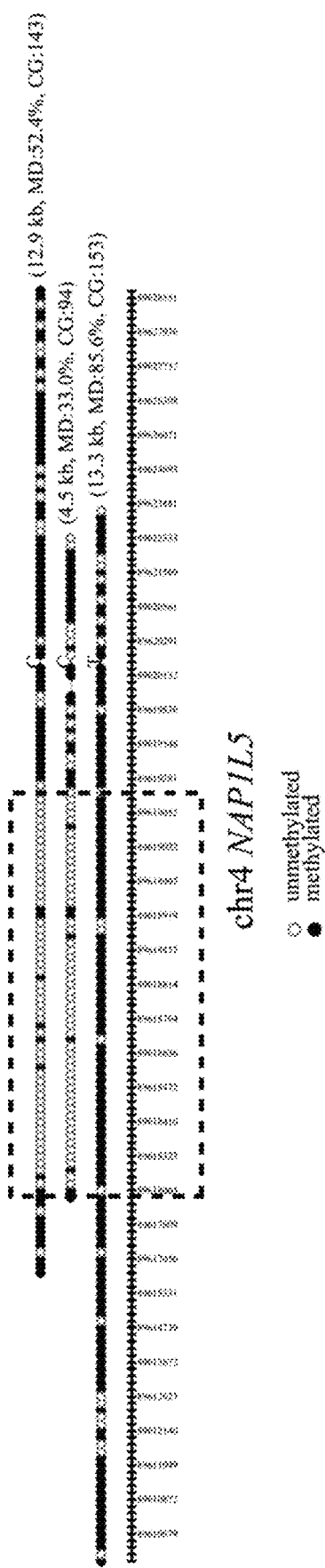
Figure 79D:
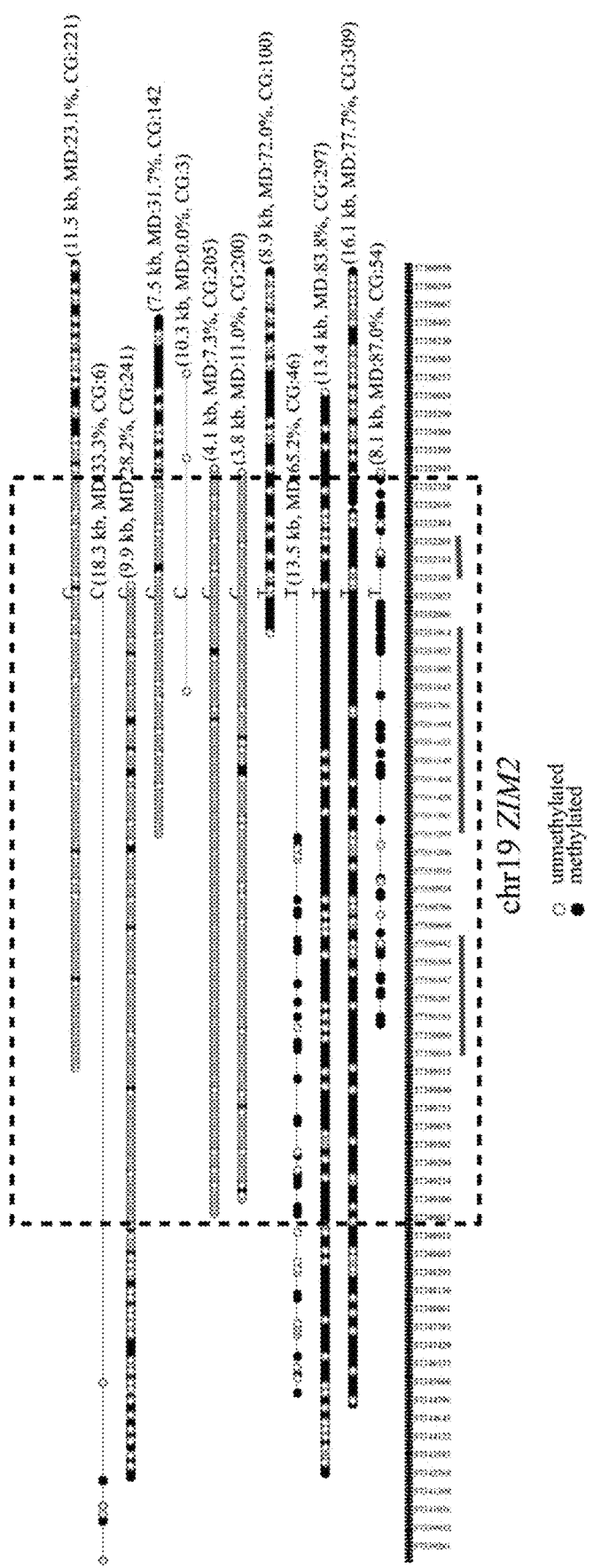

The allele-specific methylation patterns could be observed in other imprinted genes including PLAGL1 (FIG. 79B), NAPIL5 (FIG. 79C), and ZIM2 (FIG. 79D). FIG. 79B shows that with PLAGL1 the T allele associated fragments were highly unmethylated while the C allele associated fragments were highly methylated. FIG. 79C shows that with NAPIL5 the C allele associated fragments were highly unmethylated and that T allele associated fragments were highly methylated. FIG. 79D shows that with ZIM2 the C allele associated fragments were highly unmethylated and that T allele associated fragments were highly methylated.

Figure 80A:
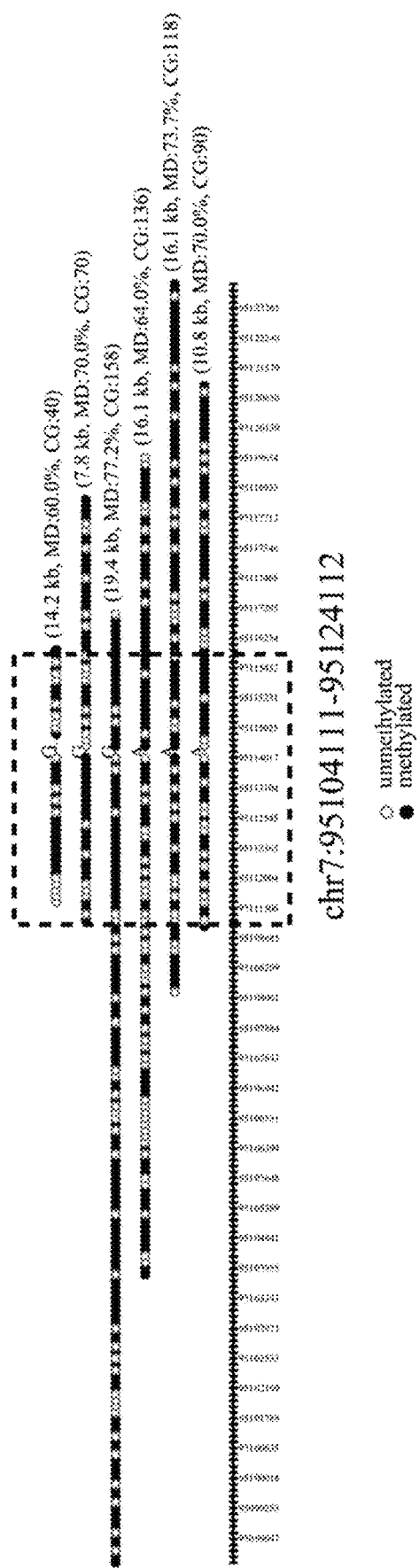
FIGS. 80A, 80B, 80C, and 80D show examples of allelic methylation patterns in non-imprinted regions according to embodiments of the present invention.
Figure 80B:
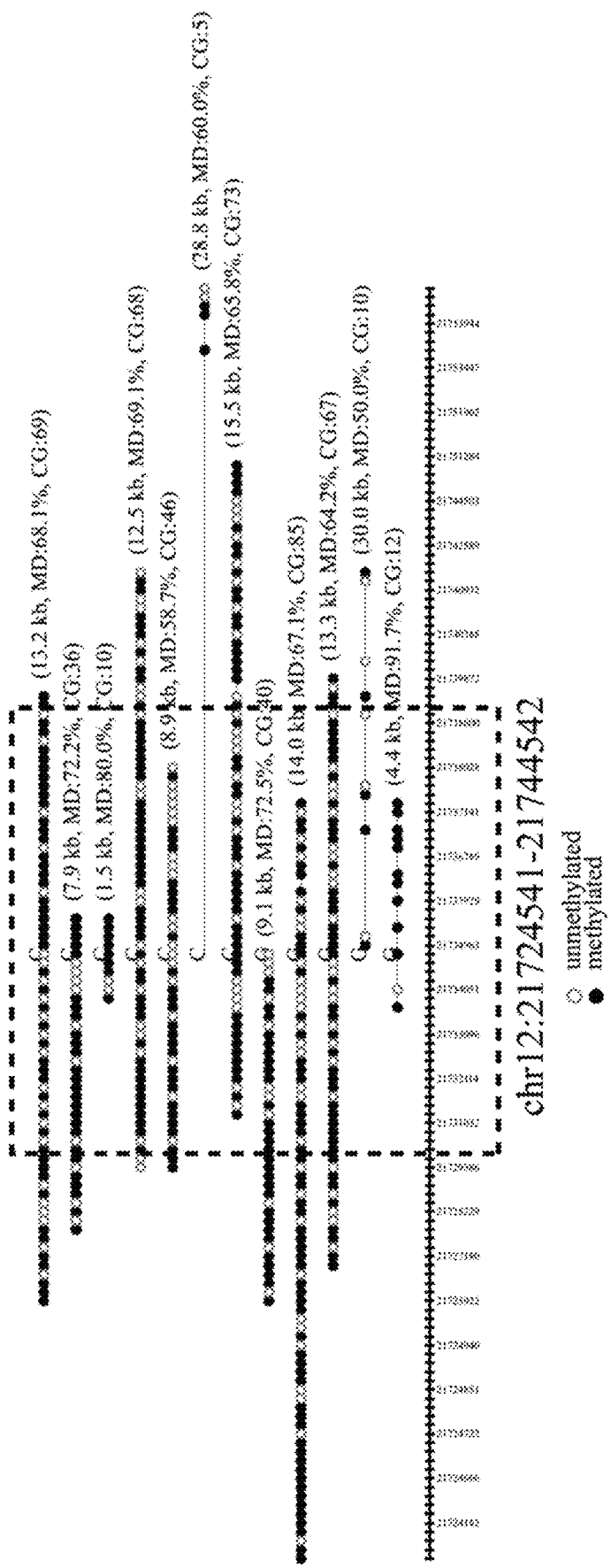
Figure 80C:
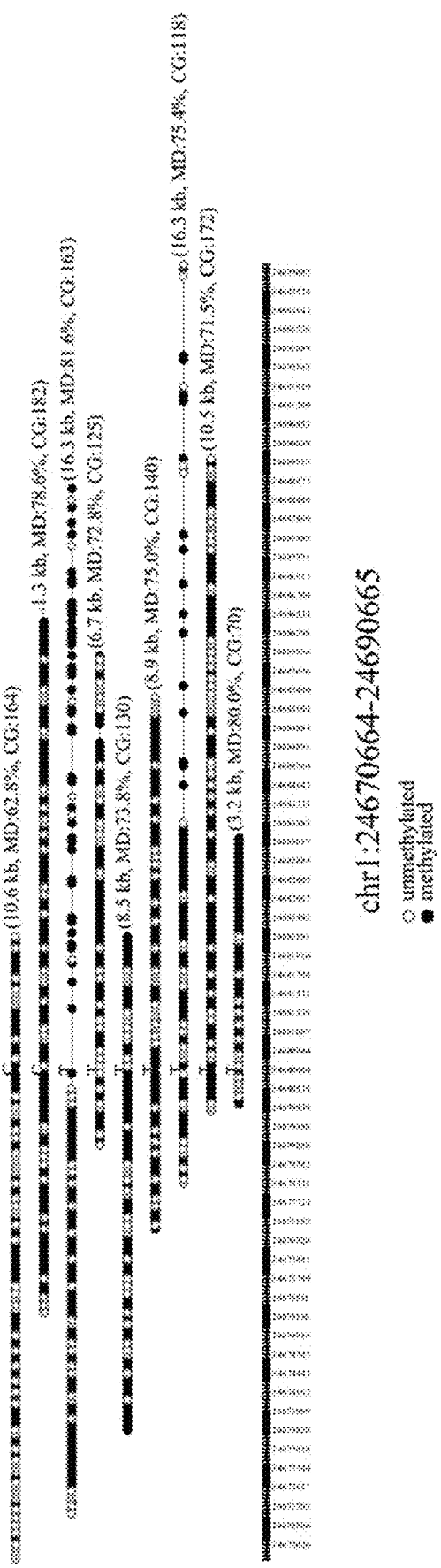
Figure 80D:
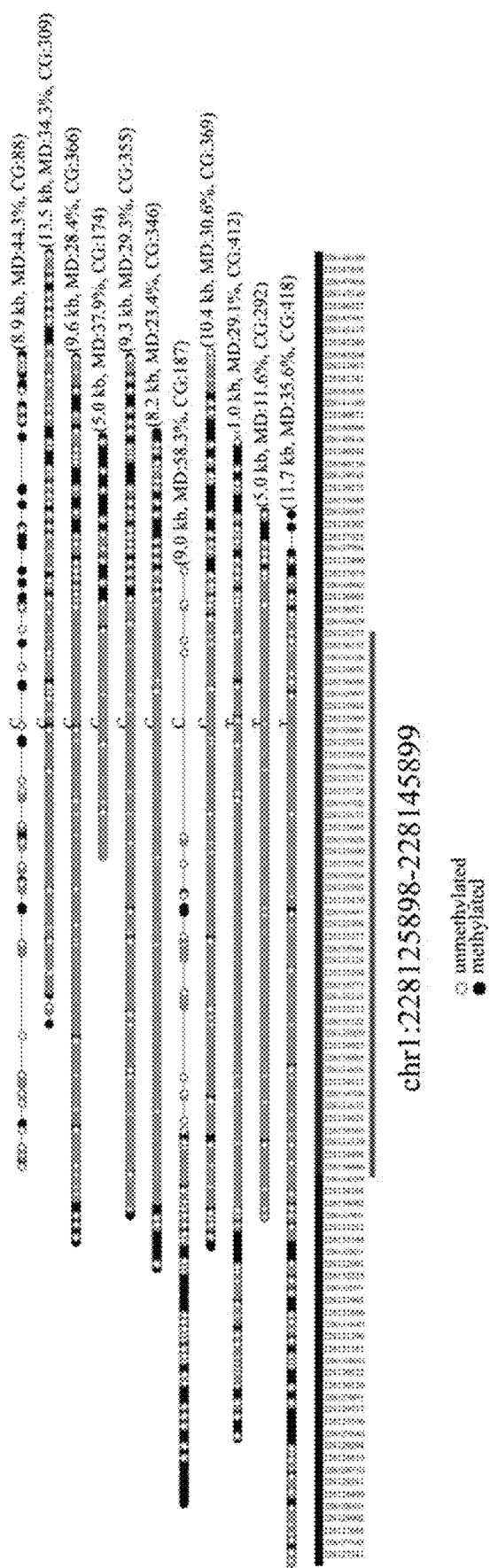

FIGS. 80A, 80B, 80C, and 80D show examples of allelic methylation patterns in non-imprinted regions. The x-axis indicates the coordinates of CpG sites. The coordinates highlighted in blue and underlined indicate CpG islands. Black filled dots indicate methylated CpG sites. Unfilled dots indicate unmethylated CpG sites. The alphabet embedded among each horizontal series of filled and unfilled dots (i.e. CpG sites) indicates the allele at the single nucleotide polymorphism (SNP) site. The numbers in parentheses on the right of each horizontal series of dots indicate the size of the fragment, fragment-level methylation density, and the number of CpG sites. The dashed rectangles indicate the randomly selected regions for calculating the methylation densities reported in the brackets. In contrast to the results in FIGS. 79A-79D, there were no such observable allelic methylation patterns present in the non-imprinted genes. FIG. 80A shows no different allelic methylation pattern in a chr7 region. FIG. 80B shows no different allelic methylation pattern in a chr12 region. FIG. 80C shows no different allelic methylation pattern in a chr1 region. FIG. 80D shows no different allelic methylation pattern in another chr1 region.

FIG. 81 shows a table with methylation levels of allele-specific fragments. The first column lists the categories of "Imprinted genes" and "Randomly selected regions." The second column lists the particular gene. The third column lists the first allele in a SNP in the gene. The fourth column lists the second allele in a SNP in the gene. The fifth column shows the methylation level for fragments linked to the first allele. The sixth column shows the methylation level for fragments linked to the second allele. The methylation levels of fragments linked to allele 2 (mean: 88.6%; range 84.6-91.1%) are much higher than those fragments linked to allele 1 (mean: 12.2%; range 7.6-15.7%) for those imprinted genes (P value=0.03), indicating the presence of allelic-specific methylation. In contrast, there are no significant changes in methylation levels between those randomly selected regions (P value=1), suggesting the absence of the allelic-specific methylation.

7. Cell-Free DNA Analysis in Pregnancy

In this exemplification, it is demonstrated that the methods hereby disclosed are applicable to the analysis of cell-free nucleic acids in plasma or serum obtained from women pregnant with at least one fetus. During pregnancy, cell-free DNA and cell-free RNA molecules from placental cells are found in maternal circulation. Such placenta-derived cell-free nucleic acid molecules are also referred as cell-free fetal nucleic acids in maternal plasma or circulating cell-free fetal nucleic acids. Cell-free fetal nucleic acids are present in maternal plasma among a background of maternal cell-free nucleic acids. For example, circulating cell-free fetal DNA molecules are present as a minor species among a background of cell-free maternal DNA in maternal plasma and serum.

To distinguish cell-free fetal DNA from cell-free maternal DNA in maternal plasma or serum, it is known that one could use genetic or epigenetic means or a combination. Genetically, the fetal genome may differ from the maternal genome by paternally inherited fetal-specific SNP alleles, paternally inherited mutations or de novo mutations. Epigenetically, the placental methylome is generally hypomethylated compared with the methylome of maternal blood cells (Lun et al. Clin Chem. 2013; 59:1583-94). Because the placenta is the main contributor of cell-free fetal DNA while maternal blood cells are the main contributor of cell-free maternal DNA in the maternal circulation (plasma or serum), cell-free fetal DNA molecules are generally hypomethylated compared with cell-free maternal DNA in plasma or serum. There are specific genomic loci where the placenta is hypermethylated compared with maternal blood cells. For example, the promoter and exon 1 region of RASSF1A is more methylated in the placenta than in the maternal blood cells (Chiu et al. Am J Pathol. 2007; 170:941-950). Thus, circulating cell-free fetal DNA derived from this RASSF1A locus would be hypermethylated compared with circulating cell-free maternal DNA from the same locus.

In embodiments, cell-free fetal DNA can be distinguished from the cell-free maternal DNA molecules based on the differential methylation status between the two pools of circulating nucleic acids. For example, CpG sites along a cell-free DNA molecule are found to be mostly unmethylated, this molecule is likely to be from the fetus. If CpG sites along a cell-free DNA molecule are found to be mostly methylated, this molecule is likely to be from the mother. There are several methods known to those skilled in the art to ascertain if such molecules are indeed from the fetus or mother. One approach is to compare the methylation pattern of the sequenced molecule with the known methylation profile of the corresponding locus in the placenta or maternal blood cells.

Figure 82:
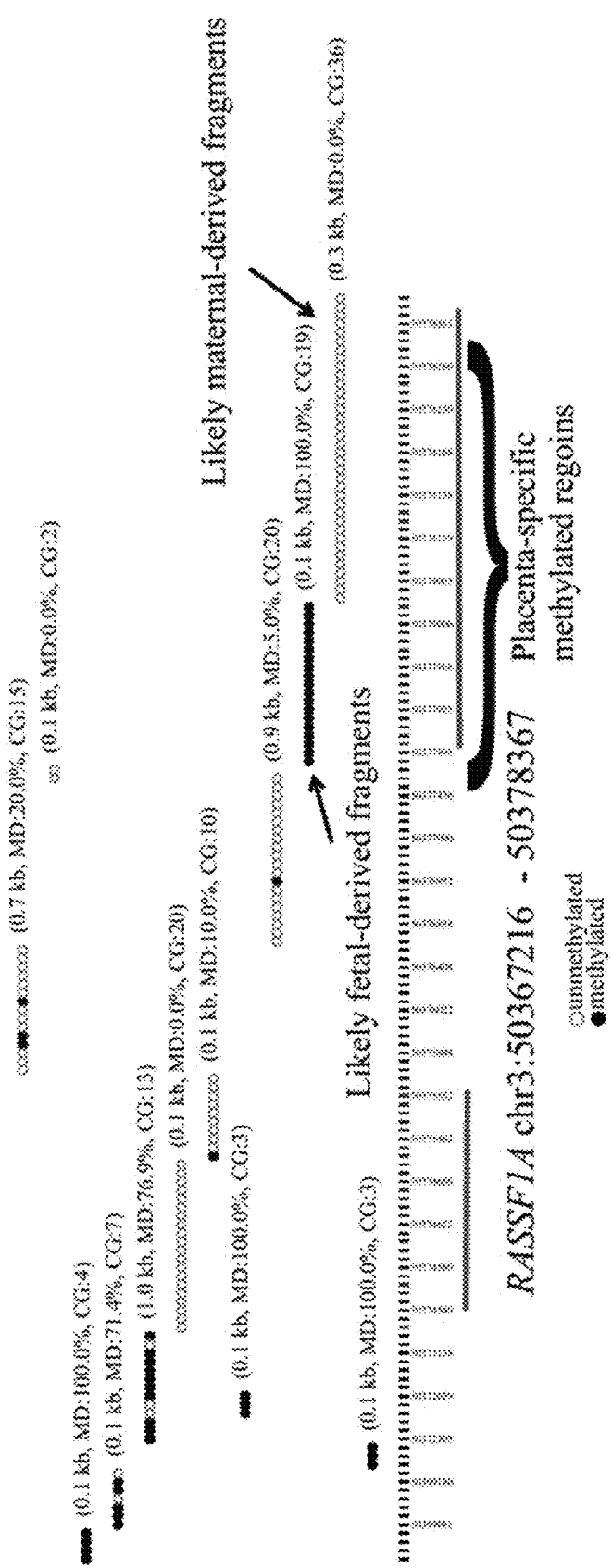
FIG. 82 shows an example for determining the placental origin of plasma DNA in pregnancy using methylation profiles according to embodiments of the present invention.

FIG. 82 shows an example for determining the placental origin of plasma DNA in pregnancy using methylation profiles. The coordinates highlighted in blue and underlined indicate CpG islands. Black filled dots indicate methylated sites. Unfilled dots indicate unmethylated sites. The numbers in parentheses near each horizontal line with dots indicate the size of the fragment, single molecular methylation density, and the number of CpG sites.

As shown in FIG. 82, if the maternal plasma cell-free DNA molecule aligns to the promoter region of RASSF1A (a region known to be specifically methylated in placental tissues) and the sequencing data generated using methods of this invention to be hypermethylated, this molecule is likely derived from the fetus or placenta. In contrast, the molecules showing hypomethylation is likely derived from the maternal background DNA (predominantly of hematopoietic origin).

Figure 83:
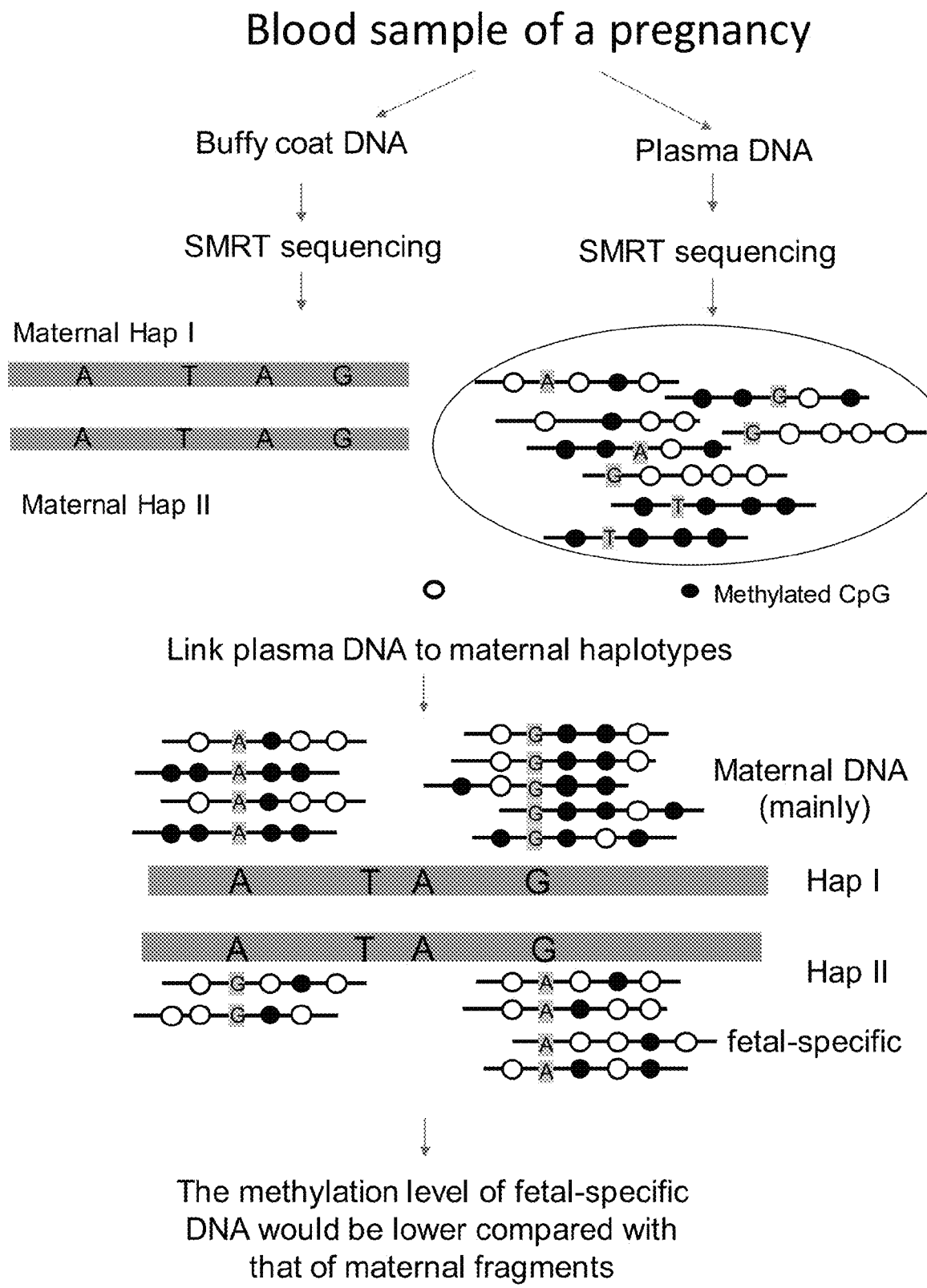
FIG. 83 illustrates fetal-specific DNA methylation analysis according to embodiments of the present invention.

FIG. 83 illustrates an approach for fetal-specific methylation analysis. The approach includes utilizing the sequenced molecule that contains a fetus-specific SNP allele or fetus-specific mutation (e.g., paternally inherited or de novo in nature). When such fetus-specific genetic features are identified, the methylation status of the bases present on the same cell-free DNA molecule reflect the methylation profile of the cell-free fetal DNA or the placental methylome. The fetus-specific genetic features can be uncovered when the plasma cell-free DNA sequencing reveals alleles or mutations not present in the maternal genome (e.g. by analyzing maternal genomic DNA), or by analyzing paternal DNA or known to be transmitted in the family (e.g. by analyzing DNA from a proband).

The methylation of fetal-specific DNA molecules can be determined by analyzing those DNA fragments carrying alleles that were different from the homozygous alleles in the maternal genome. The methylation of fetal DNA molecules may be expected to be lower than that of maternal DNA molecules.

As an example, the buffy coat DNA of one pregnant woman and its matched placental DNA were sequenced to obtain 59× and 58× haploid genome coverage, respectively. We identified a total of 822,409 informative SNPs for which the mother was homozygous and the fetus was heterozygous. We found 2,652 fetal-specific fragments and 24,837 shared fragments (i.e. the fragments carrying the shared allele; predominantly of maternal origin) in the maternal plasma (M13160) through single molecule, real-time sequencing. The fetal DNA fraction was 19.3%. According to the disclosure, the methylation profiles of those fetal-specific and shared fragments were deduced. As a result, the methylation level of fetal-specific fragments was found to be 57.4% while the methylation level of shared fragments was 69.9%. This finding was consistent with the current knowledge that the methylation level of the fetal DNA was lower than the maternal DNA in the plasma of a pregnant woman (Lun et al., Clin Chem. 2013; 59:1583-94).

Methylation patterns may be used for diagnostic or monitoring purposes. For example, the methylation profile of a maternal plasma sample has been used to determine the gestational age (https://www.ncbi.nlm.nih.gov/pubmed/27979959). One application is as a quality control step. Another potential application is to monitor the "biological" versus "chronological" age of a pregnancy. This application may be used in the detection or risk assessment of preterm birth. Other embodiments may be used for the analysis of fetal cells in maternal blood. In yet other embodiments, such fetal cells may be identified by antibody-based approaches or by selective staining using cellular markers (e.g., on the cell surface or in the cytoplasma), or enriched by flow cytometry or micromanipulation or microdissection or physical methods (e.g., differential flow speed through a chamber, surface or container).

C. Methylation Detection Using Different Reagents

This section shows that methylation techniques are not limited to a particular reagent system.

Methylation analysis was performed using different reagent systems to confirm that techniques can be applied. As an example, SMRT-seq was performed using the Sequel II System (Pacific Biosciences) to carry out single molecule, real-time sequencing. The sheared DNA molecules were subjected to single molecule real-time (SMRT) sequencing template construction using a SMRTbell Express Template Prep Kit 2.0 (Pacific Biosciences). Sequencing primer annealing and polymerase binding conditions were calculated with the SMRT Link v8.0 software (Pacific Biosciences). Briefly, sequencing primer v2 was annealed to the sequencing template, and then a polymerase was bound to templates using a Sequel II Binding and Internal Control Kit 2.0 (Pacific Biosciences). Sequencing was performed on a Sequel II SMRT Cell 8M. Sequencing movies were collected on the Sequel II system for 30 hours with a Sequel II Sequencing Kit 2.0 (Pacific Biosciences). In other embodiments, other chemical reagents and reaction buffers would be used for SMRT-seq. In one embodiment, a polymerase would have different kinetic features of incorporation of nucleotides along a DNA template strand depending on its methylation status (Huber et al. Nucleic Acids Res. 2016; 44:9881-9890). In this disclosure, results are generated using sequencing primer v1 unless otherwise noted.

To demonstrate the use of the invention in the disclosure described herein with the use of different reagents, we analyzed SMRT-seq data generated based on different sequencing kits, including, but not limited to Sequel I Sequencing Kit 3.0, RS II, Sequel II Sequencing Kit 1.0 and Sequel II Sequencing Kit 2.0. RS II includes 150,000 ZMWs per SMRT cell. Sequel uses 1,000,000 ZMWs per SMRT cell. Sequel II uses 8 million ZMWs per SMRT cell with two sequencing kits (1.0 And 2.0). This analysis involved two datasets. The first dataset was prepared based on DNA following whole genome amplification, representing unmethylated status. The second type dataset was prepared based on DNA after M.SsssI methyltransferase treatment, representing methylated status. These data were generated using the Sequel Sequencing Kit 3.0 in the Sequel sequencer; and the Sequel II Sequencing Kit 1.0, and Sequel II Sequencing Kit 2.0 in the Sequel II sequencer. Thus, we obtained three datasets with kinetic profiles generated with the different reagents (e.g. polymerases). Each dataset was split into a training dataset and a testing dataset for evaluating the performance using CNN models according to this disclosure.

1. Measurement Windows

Figure 84A:
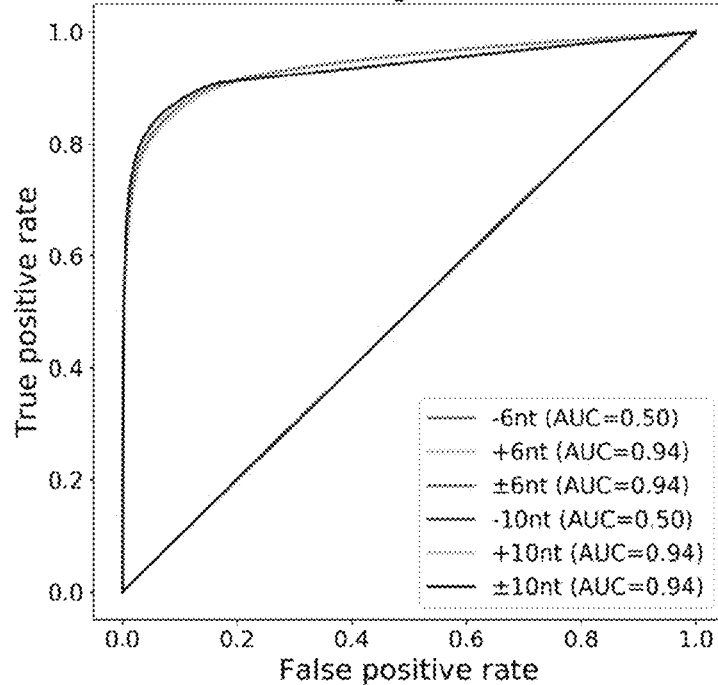
FIGS. 84A, 84B, and 84C show the performance of different measurement window sizes across different reagent kits for SMRT-seq according to embodiments of the present invention.
Figure 84B:
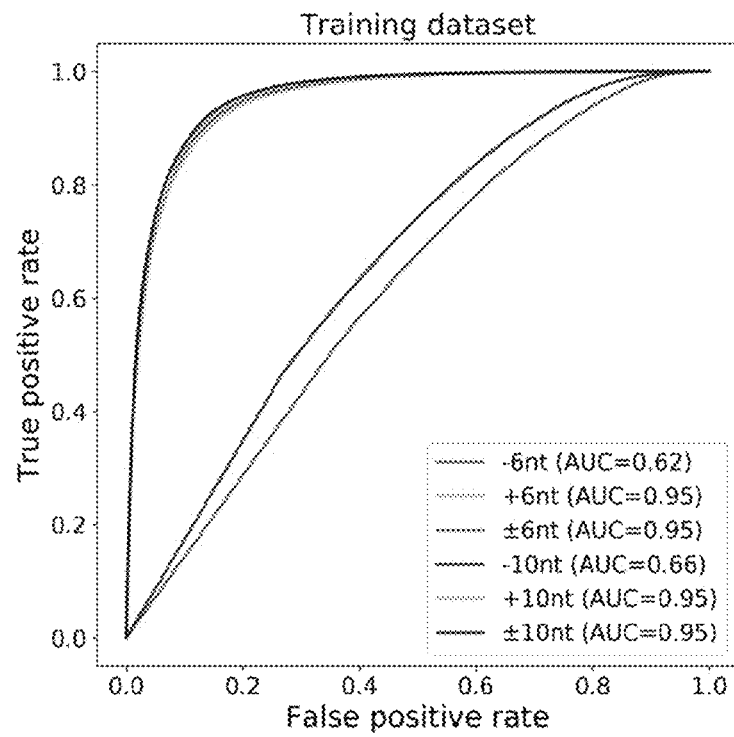
Figure 84C:
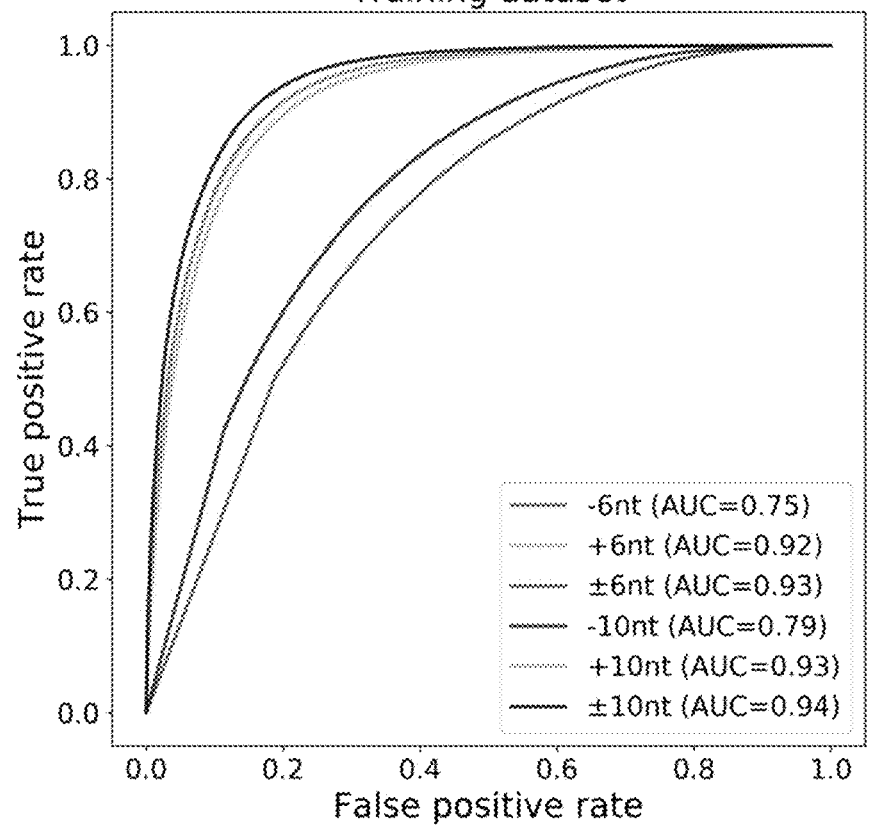

FIGS. 84A, 84B, and 84C show the performance of different measurement window sizes across different reagent kits for SMRT-seq in training datasets comprising whole genome amplified data (unmethylated CpG sites) and M.SsssI-treated data (methylated CpG sites). The true positive rate is plotted on the y-axis, and the false positive rate is plotted on the x-axis. FIG. 84A shows SMRT-seq data generated based on Sequel Sequencing Kit 3.0. FIG. 84B shows SMRT-seq data generated based on the Sequel II sequencing Kit 1.0. FIG. 84C shows SMRT-seq data generated based on the Sequel II Sequencing Kit 2.0. In the figures, '-' indicated upstream signals of a CpG cytosine site being analyzed. '+' indicated downstream signals of a CpG cytosine site being analyzed. For example, '−6 nt' represented the 6 nt upstream signals of a CpG cytosine site being analyzed. '+6 nt' represented the 6 nt downstream signals of a CpG cytosine site being analyzed. '6 nt' indicated including both 6 nt upstream signals and 6 nt downstream signals of a CpG cytosine site being analyzed (i.e. a total of 12 nt sequence flanking a CpG cytosine site).

For the training dataset based on the Sequel Sequencing Kit 3.0, as shown in FIG. 84A, using the measurement window comprising signals on a CpG cytosine being analyzed and 6 nt upstream signals (e.g. IPD, PW, relative positions and sequence compositions) of that cytosine site (denoted by −6 nt), the AUC value of 0.50 suggested no discriminative power in differentiating methylated CpG cytosines from unmethylated ones. However, for the training datasets based on Sequel II Sequencing Kit 1.0 and 2.0, the corresponding AUC values were 0.62 (FIG. 84B) and 0.75 (FIG. 84C). These data demonstrated that there were different kinetic profiles inherent in different reagents used in SMRT-seq. These data show that methods disclosed herein are readily adapted to the use of different reagents. Furthermore, the accuracy of detecting base modifications can potentially be improved with further developments in reagents, e.g. the use of different polymerases and other chemistry.

As another example, for training dataset based on the Sequel Sequencing Kit 3.0, as shown in FIG. 84A, using a measurement window comprising 10 bp upstream signals of a CpG cytosine site (denoted by −10 nt), the AUC value of 0.50 suggested no discriminative power in differentiating methylated CpG cytosines from unmethylated ones. However, for training datasets based on Sequel II Sequencing Kit 1.0 and 2.0, the corresponding AUC values were 0.66 (FIG. 84B) and 0.79 (FIG. 84C), which was shown to be improved compared with the measurement window comprising 6 nt upstream signals. These data confirmed that there were different kinetic profiles inherent in different reagents that were used for SMRT-seq. These data show that methods disclosed herein are readily adapted to the use of different reagents.

In contrast to the measurement window with upstream signals, the measurement window with downstream signals could lead to a greater improvement of the classification performance. For example, for training dataset based on Sequel Sequencing Kit 3.0, as shown in FIG. 84A, using measurement window comprising 6 nt downstream signals of a CpG cytosine site (+6 nt), the AUC value of 0.94 was much greater than that using 6 nt upstream signals (AUC: 0.5). For the training datasets based on Sequel II Sequencing Kit 1.0 and 2.0, the corresponding AUC values were 0.95 (FIG. 84B) and 0.92 (FIG. 84C), respectively, showing improvement compared with the measurement window comprising 6 nt upstream. These data suggested that the kinetic features linked to sequence context would improve the classification power using, but not limited to CNN models. These data also suggested that the disclosure herein would be applicable to datasets produced by different reagents and sequencing conditions (e.g. different polymerases, other chemical reagents, their concentrations and sequencing reaction parameters (e.g. duration)), through adjusting the measurement windows. A similar conclusion would be drawn from the analysis using the measurement window including 10 nt downstream signals of a CpG cytosine site (FIGS. 84A, 84B, and 84C).

In another embodiment, one could use a measurement window comprising signals on cytosine being analyzed, and both upstream and downstream signals of that cytosine. For example, as shown in FIGS. 84A, 84B, and 84C, using a measurement window comprising 6 nt upstream signals and 6 nt downstream signals (denoted by 6 nt), AUC values were found to be 0.94, 0.95, and 0.92 for the training dataset based on Sequel Sequencing Kit 3.0, Sequel II Sequencing Kit 1.0 and 2.0, respectively. Using a measurement window comprising 10 nt upstream signals and 10 nt downstream signals (denoted by 10 nt), AUC values were found to be 0.94, 0.95, and 0.94 for training dataset based on Sequel Sequencing Kit 3.0, Sequel II Sequencing Kit 1.0 and 2.0, respectively. These data suggested that the disclosure herein would be broadly applicable to datasets produced by different reagents and sequencing reaction parameters.

Figure 85A:
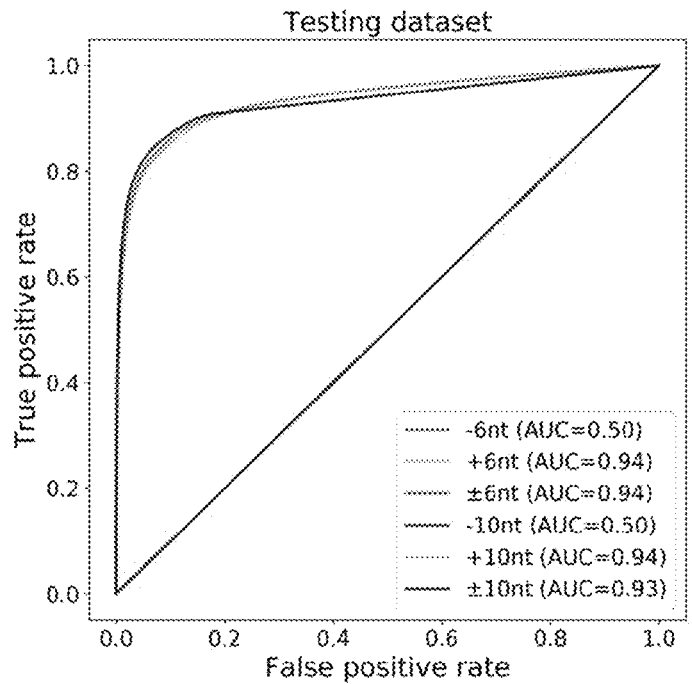
FIGS. 85A, 85B, and 85C show the performance of different measurement window sizes across different reagent kits for SMRT-seq according to embodiments of the present invention.
Figure 85B:
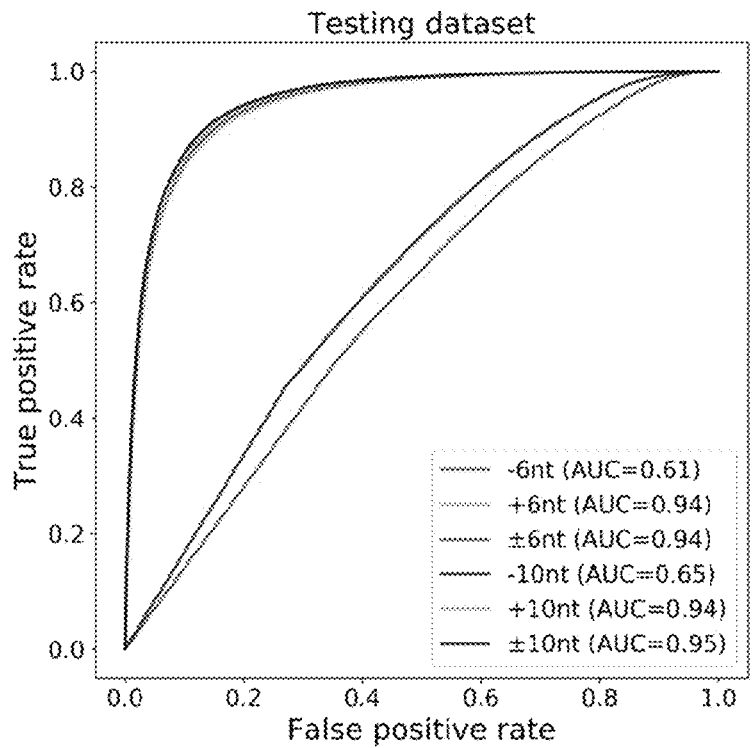
Figure 85C:
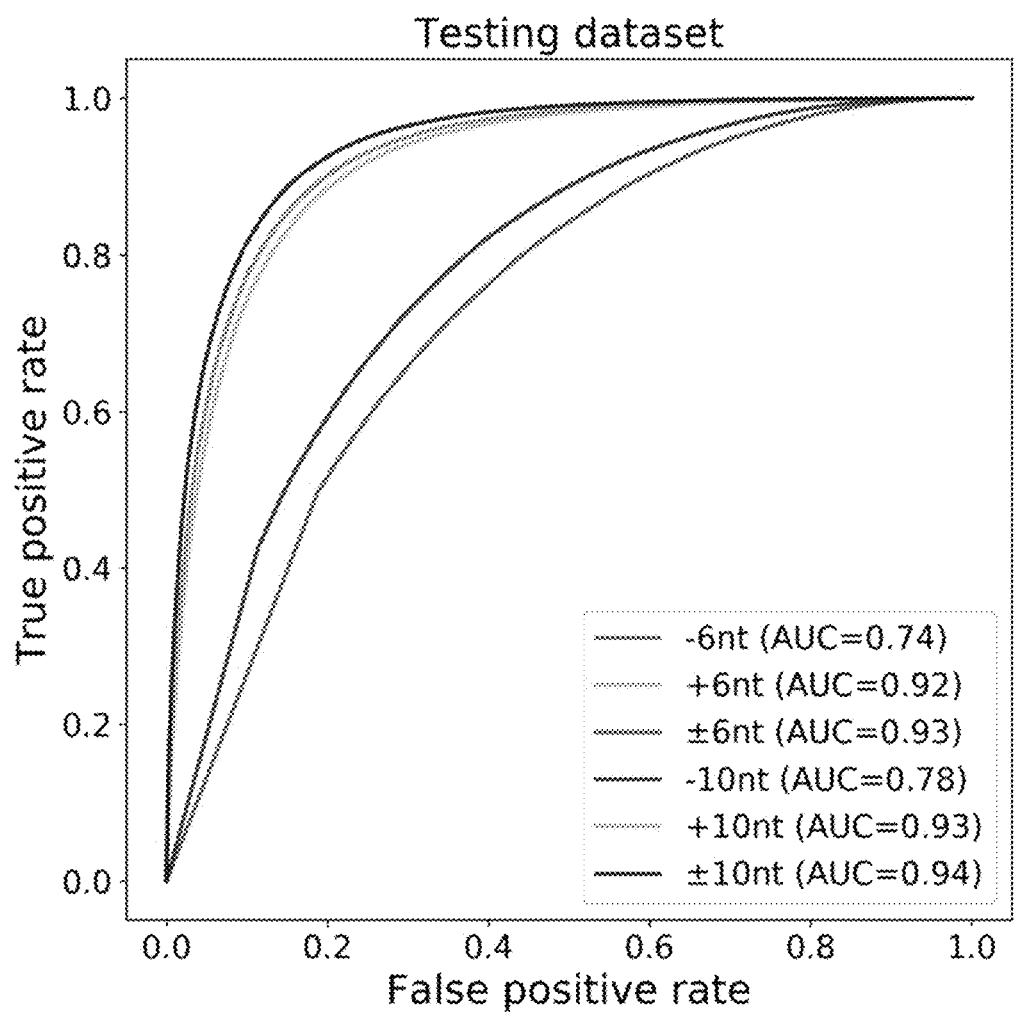

FIGS. 85A, 85B, and 85C showed that results were obtained from testing datasets with different measurement windows across different sequencing kits when applying CNN models trained from the training datasets. The true positive rate is plotted on the y-axis, and the false positive rate is plotted on the x-axis. The labeling in the legend is equivalent to the labeling used in FIGS. 84A, 84B, and 84C. FIG. 85A shows SMRT-seq data generated based on Sequel Sequencing Kit 3.0. FIG. 85B shows SMRT-seq data generated based on Sequel II sequencing Kit 1.0. FIG. 85C shows SMRT-seq generated based on Sequel II Sequencing Kit 2.0. All the conclusions drawn in the training datasets could be validated in these independent testing datasets that were not involved in the training process. Additionally, among three independent testing datasets, analyses for two datasets (⅔) involving Sequel II Sequencing Kit 1.0 and 2.0 showed that the use of measurement window including 10 nt upstream and downstream signals (denoted by 10 nt) outperformed the others.

2. Comparison with Bisulfite Sequencing

Figure 86A:
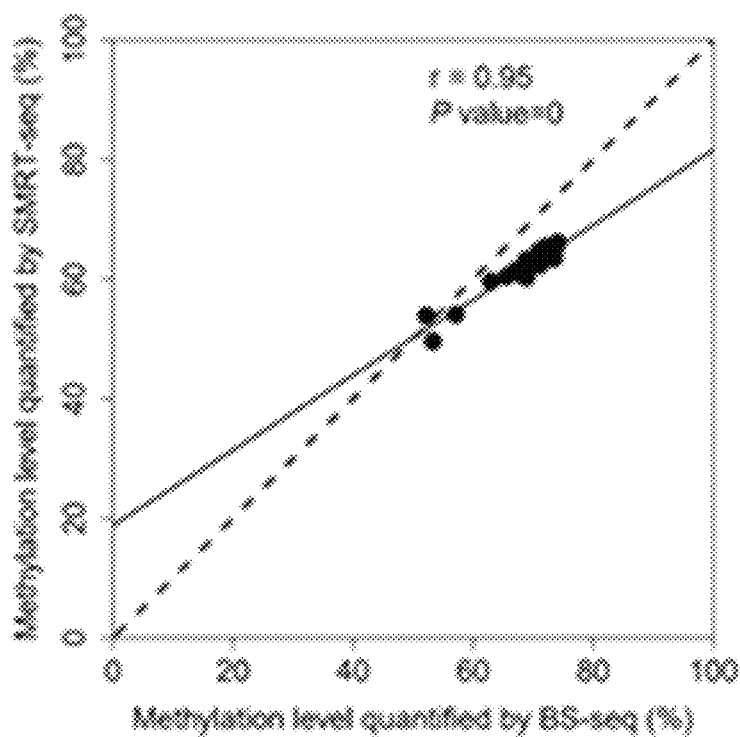
FIGS. 86A, 86B, and 86C show the correlation of overall methylation levels quantified by bisulfite sequencing and SMRT-seq (Sequel II Sequencing Kit 2.0) according to embodiments of the present invention.
Figure 86B:
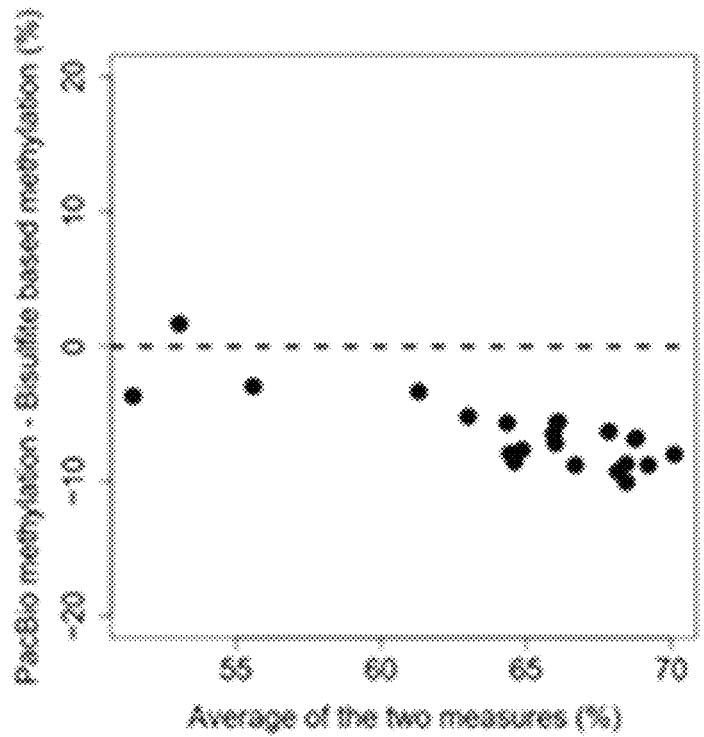
Figure 86C:
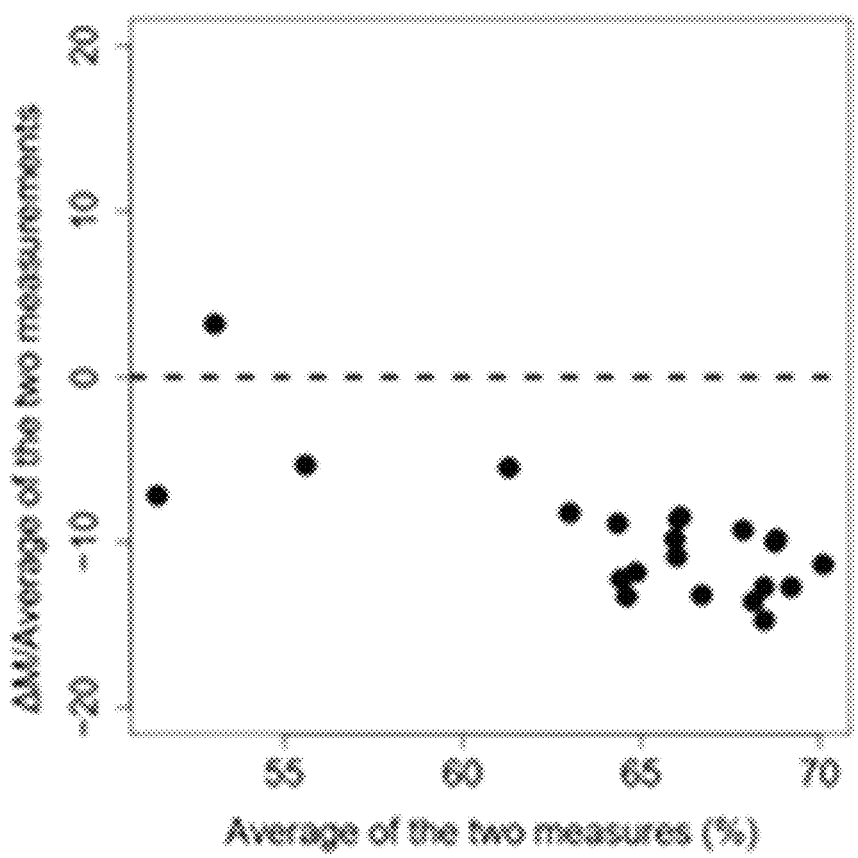

FIGS. 86A, 86B, and 86C show the correlation of overall methylation levels quantified by bisulfite sequencing and SMRT-seq (Sequel II Sequencing Kit 2.0). FIG. 86A shows methylation level as a percentage quantified by SMRT-seq on the y-axis. FIG. 86B shows methylation level as a percentage quantified by bisulfite sequencing on the x-axis. The black line is a fitted regression line. The dashed line is the diagonal line on which the two measures are equal. FIG. 86B shows a Bland-Altman plot. The x-axis indicates the average of methylation levels quantified by SMRT-seq according to the disclosure and bisulfite sequencing. The y-axis indicates the difference in methylation level between SMRT-seq according to the disclosure and bisulfite sequencing (i.e. Pacific Biosciences methylation—Bisulfite based methylation). The dashed line corresponds a line horizontally across zero on which there is no difference between two measures. Data points deviated from the dashed line suggest that the deviations between measures exist. FIG. 86C shows the percentage change relative to the value quantified by bisulfite sequencing. The x-axis indicates the average of methylation levels quantified by SMRT-seq according to the disclosure and bisulfite sequencing. The y-axis indicates the percentage that the difference in methylation levels between two measures relative to the average of the methylation levels. The dashed line corresponds to a line horizontally across zero on which there is no difference between two measures. Data points deviated from the dashed line suggest that the deviations between measures exist.

For FIG. 86A, the linear regression formula was $Y=aX+b$, where "Y" represents the methylation levels determined by SMRT-seq according to the disclosure; "X" represents the methylation levels determined by bisulfite sequencing; "a" represents the slope of the regression line (e.g. a=1.45); "b" represents the intercept in y-axis (e.g. b=−20.98). In this situation, the methylation values determined by SMRT-seq would be calculated by $(Y-b)/a$. This graph shows that methylation levels determined by SMRT-seq can be converted to methylation levels determined by bisulfite sequencing and vice versa for Sequel II Sequencing Kit 2.0 as with Sequel II Sequencing Kit 1.0.

FIG. 86B is a Bland-Altman plot that shows the bias of methylation quantification between SMRT-seq according to the disclosure and bisulfite sequencing, in which the x-axis indicates the average of methylation levels quantified by SMRT-seq according to the disclosure and bisulfite sequencing and y-axis indicates the difference in methylation levels quantified by SMRT-seq according to the disclosure and bisulfite sequencing. The median difference between the two measurements was −6.85% (range: −10.1-1.7%). The median percentage change of a methylation level quantified by the present disclosure relative to the value by bisulfite sequencing was −9.96% (range: −14.76-3.21%). The difference varied depending on the averaged values. The higher the average of two measures, the higher the bias is.

FIG. 86C shows the same data as FIG. 86B, but with the difference in methylation levels divided by the average of the two methylation levels. FIG. 86C also shows that with a higher average of the two measures, the higher the bias is.

The error may be with bisulfite sequencing and not related to the methods with SMRT-seq. It was reported that the conventional whole-genome bisulfite sequencing (Illumina) introduced a significantly biased sequence output and overestimated global methylation, with substantial variations in quantifying methylation levels between methods at specific genomic regions (Olova et al. Genome Biol. 2018; 19:33). The embodiments disclosed herein have a number of exemplary advantages whereby it can be performed without bisulfite conversion that would degrade DNA drastically and can be performed without PCR amplification.

3. Tissue Origin

We performed the methylation analysis across various cancer types according to the embodiments in this disclosure using single molecule, real-time sequencing (SMRT-seq, Pacific Biosciences). The cancer types used for SMRT-seq included, but not limited to, colorectal cancer (n=3), esophageal cancer (n=2), breast cancer (n=2), renal cell carcinoma (n=2), lung cancer (n=2), ovarian cancer (n=2), prostate cancer (n=2), stomach cancer (n=2), and pancreatic cancer (n=1). Their matched adjacent non-tumoral tissues were also included for SMRT-seq. The data set was generated from DNA prepared by the Sequel II Sequencing Kit 2.0.

Figure 87A:
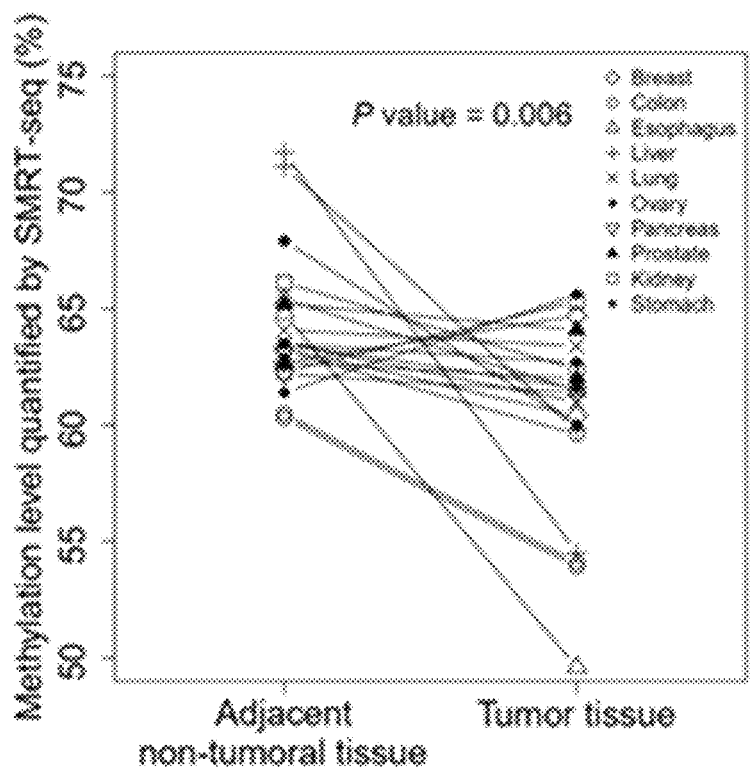
FIGS. 87A and 87B show a comparison of overall methylation level between various tumor tissues and paired adjacent non-tumoral tissues according to embodiments of the present invention.
Figure 87B:
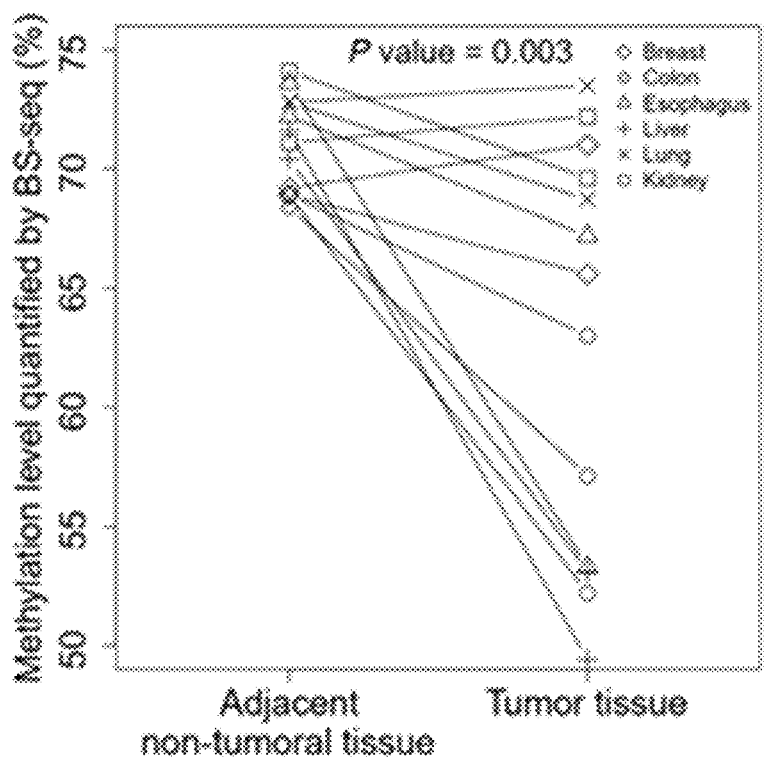

FIGS. 87A and 87B show a comparison of overall methylation level between various tumor tissues and paired adjacent non-tumoral tissues. The methylation level as a percentage is on the y-axis. In FIG. 87A, the methylation level is quantified by SMRT-seq. In FIG. 87B, the methylation levels quantified by bisulfite sequencing. The type of tissue (i.e., tumor tissue or adjacent non-tumoral tissue) is on the x-axis. The different symbols represent different tissues of origin.

FIG. 87A shows that the overall methylation levels of tumor tissues, including breast cancer, colorectal cancer, esophageal cancer, liver cancer, lung cancer, ovarian cancer, pancreatic cancer, renal cell carcinoma, and stomach cancer, were significantly lower than the corresponding non-tumoral tissues (P value=0.006, paired samples Wilcoxon signed-rank test), including breast, colon, esophagus, liver, lung, ovary, pancreas, prostate, kidney and stomach, respectively. The median difference in methylation level between tumor and paired non-tumoral tissues was −2.7% (IQR: −6.4-0.8%).

FIG. 84B confirms lower methylation levels in tumor tissues. Thus, these results suggested that the methylation patterns across various cancer types and tissues could be accurately determined by SMRT-seq according to the disclosure, implying a broad application of this disclosure for the early detection, prognosis, diagnosis and treatment of cancer, on the basis of tissue biopsy. The different degrees of methylation level reduction across various tumor types likely suggested that the methylation patterns were associated with cancer types, allowing for determining the tissue of origin of a cancer.

D. Enhancing Detection and Other Techniques

In some embodiments, analysis of base modification (e.g., methylation) can be performed using one or more of the following parameters: the sequence context, the IPD, and PW. IPD and PW can be determined from the sequencing reaction, without alignment to a reference genome. Aspects of the single molecule, real-time sequencing approach may further enhance the accuracy of determining the sequence context, the IPD, and PW. One aspect is the performance of circular consensus sequencing in which a particular portion of a sequencing template can be measured multiple times, hence allowing the sequence context, IPD, and PW to be measured based on the average or distribution of values through these multiple readouts. In certain embodiments, the analysis of base modification without an alignment process may increase computational efficiency, reduce the turn-around time and may reduce the costs of analysis. While embodiments can be performed without an alignment process, in yet other embodiments, an alignment process may be used and may be preferable, e.g., if the alignment process is used to ascertain the clinical or biological implications of the base modification detected (e.g., if a tumor suppressor is hypermethylated); or if the alignment process is used to select a subset of the sequencing data that corresponds to certain genomic regions of interest for further analysis. For embodiments in which data from selected genomic regions are desired, these embodiments may entail targeting such regions using one or more enzymes or enzyme-based methodologies that can cleave in regions of interest in the genome, e.g., a restriction enzyme or a CRISPR-Cas9 system. The CRISPR-Cas9 system may be preferable to PCR-based method as PCR amplification typically does not preserve information concerning base modifications of DNA. Methylation levels of such selected (either bioinformatically [e.g., through alignment] or via methods such as CRISPR-Cas9) regions can be analyzed to provide information on tissue origin, fetal disorders, pregnancy disorders, and cancer.

1. Methylation Analysis Using Subreads without Alignment to a Reference Genome

Figure 88:
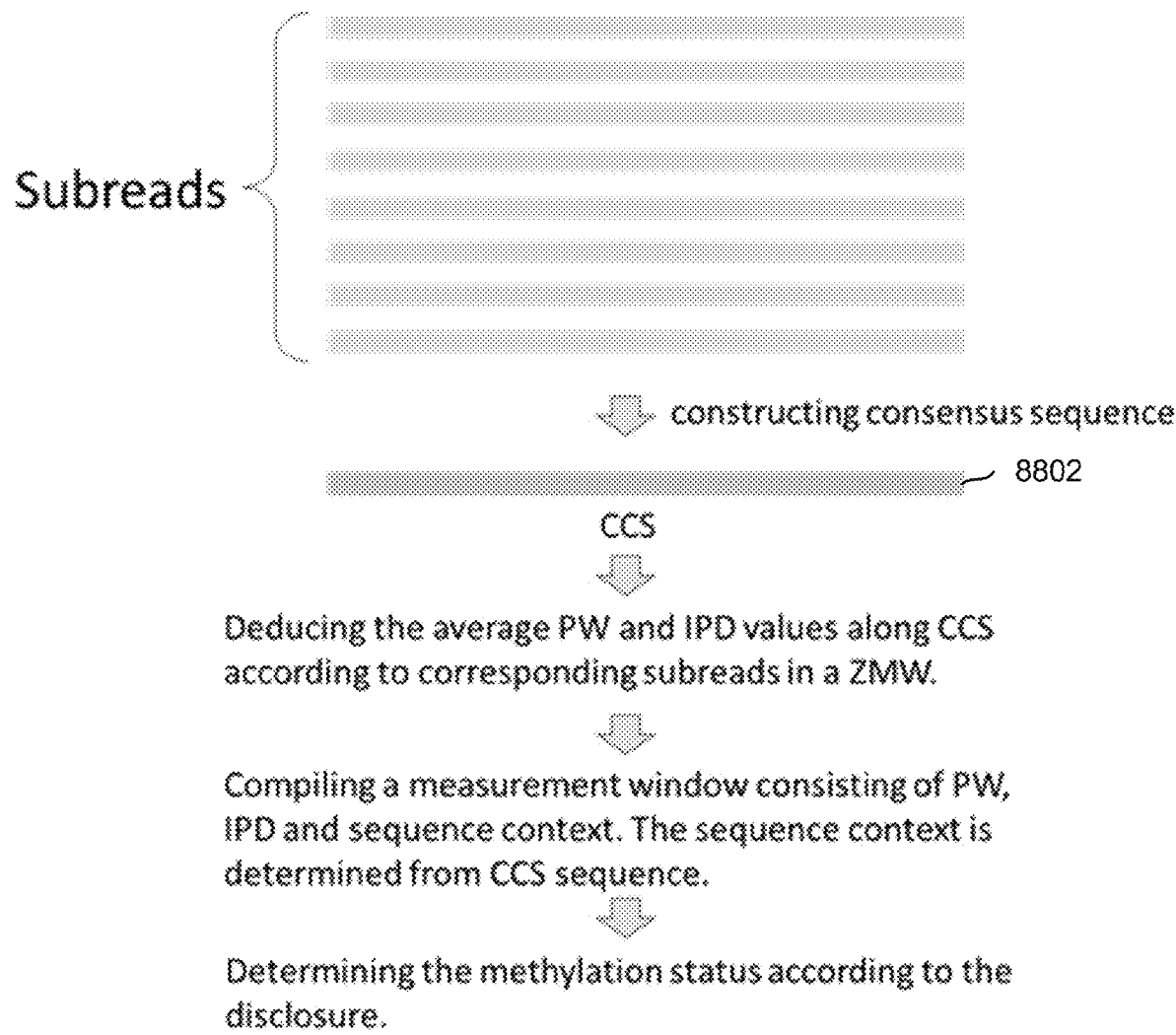
FIG. 88 shows determining the methylation status using a sequence context determined from a circular consensus sequence (CCS) according to embodiments of the present invention.

In embodiments, the methylation analysis could be performed using the measurement windows comprising kinetic features and sequence context from subreads without alignment to a reference genome. As shown in FIG. 88, subreads originating from a zero-mode waveguide (ZMW) were used to construct a consensus sequence 8802 (also known to be circular consensus sequence, CCS). Average kinetic values at each position in a CCS, including but not limited to PW and IPD values, were calculated. The sequence context surrounding a CpG site was determined from CCS based on the upstream and downstream sequences of that CpG site. Therefore, a measurement window as defined in this disclosure would be constructed for training, with the measurement window including PW, IPD values, and sequence context according to the subreads with kinetic features relative to CCS. This procedure obviates alignment of subreads to a reference genome.

To test the principle shown in FIG. 88, we used 601,942 unmethylated CpG sites which originated from the whole genome amplified DNA and 163,527 methylated CpG sites which originated from CpG Methyltransferase (e.g. M.SssI) treated DNA, forming the training dataset. We used 546,393 unmethylated CpG sites which originated from the whole genome amplified DNA and 193,641 methylated CpG sites which originated from CpG Methyltransferase (e.g. M.SssI) treated DNA, forming the testing dataset. The data set was generated from DNA prepared by the Sequel II Sequencing Kit 2.0.

Figure 89:
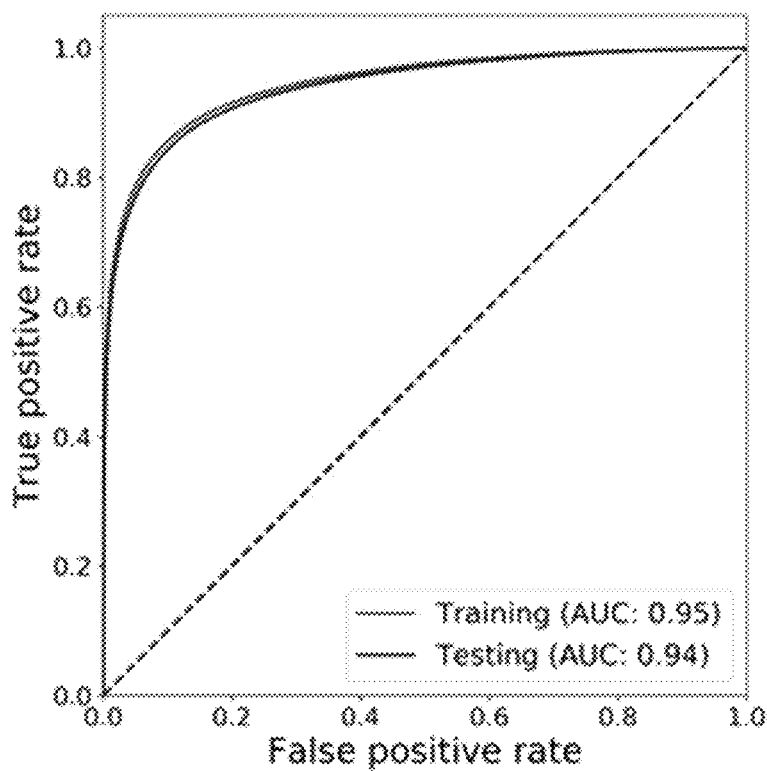
FIG. 89 shows an ROC curve for the detection of methylated CpG sites using a sequence context determined from CCS according to embodiments of the present invention.

As shown in FIG. 89, in one embodiment, using kinetic features and sequence context associated with subreads and CCS to train convolutional neural network (CNN) model for determining the methylation, one could achieve an AUC value of 0.94 and 0.95 for differentiating methylated CpG sites from unmethylated CpG sites in the testing and training datasets, respectively. In other embodiments, other neural network models, deep learning algorithms, artificial intelligence, and/or machine learning algorithms could be used.

If we set a cutoff of 0.2 for the probability of methylation, we could obtain 82.4% sensitivity and 91.7% specificity in detecting methylated CpG sites. These results illustrated that one could differentiate the methylated and unmethylated CpG sites using subreads with kinetic features without the prior alignment to a reference genome.

Figure 90:
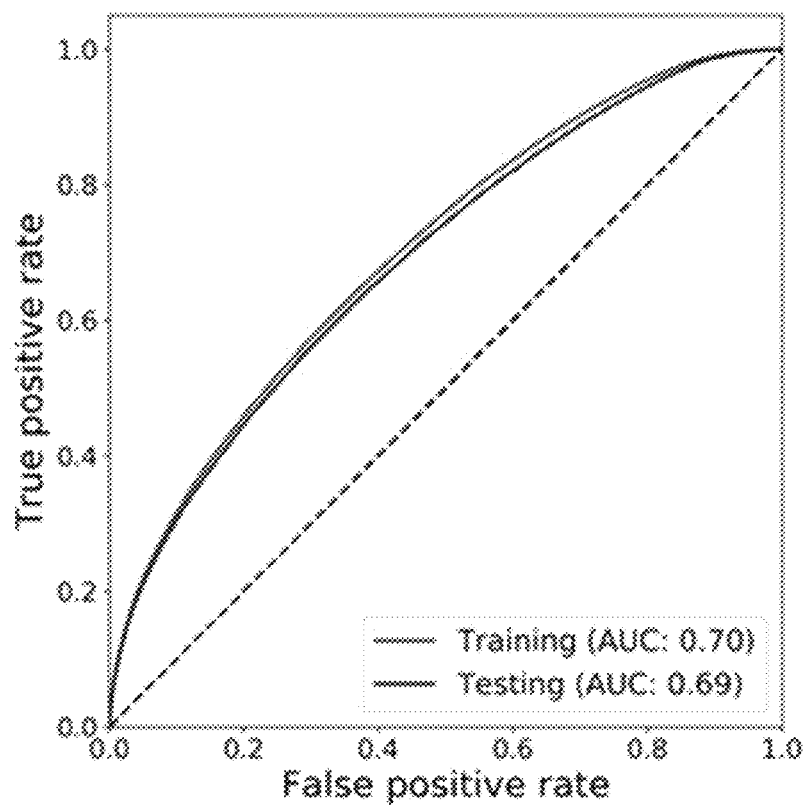
FIG. 90 shows an ROC curve for the detection of methylated CpG sites without CCS information and without prior alignment to a reference genome according to embodiments of the present invention.

In another embodiment, to determine the methylation status across CpG sites, one could also use the kinetic features together with sequence context directly from subreads without CCS information and prior alignment to a reference genome. We used kinetic features including PW and IPD values at positions spanning 20-nt upstream and 20-nt downstream of a CpG present in a subread to train a CNN model for determining methylation status. As shown in FIG. 90, according to the embodiments in this disclosure, an AUC of the ROC curve using kinetic features related to subreads was 0.70 and 0.69 for detecting methylated CpG sites in training and testing datasets, respectively. These data suggested that it would be feasible to use the embodiments in this disclosure to infer the methylation patterns for a DNA molecule using kinetic features associated with subreads but without a prior alignment and construction of consensus sequences. However, the performance of determining methylation in this embodiment was inferior to the embodiments combinatorially utilizing the alignment information or consensus sequences as described in this disclosure. One would envision that the enhanced precision in generating subreads and kinetic values would improve the performance of determining the base modifications using subreads and their associated kinetic features.

2. Methylation Analysis of Deleted Regions Using Targeted Single Molecule, Real-Time Sequencing Methods described herein can also be applied to analyze one or more selected genomic regions. In one embodiment, region(s) of interest can first be enriched by a hybridization method which allows hybridization of DNA molecules from the region(s) of interest to synthetic oligonucleotides with complementary sequences. For the analysis of base modifications using the methods described herein, the target DNA molecules cannot be amplified by PCR before subjected to sequencing because the base-modification information in the original DNA molecule would not be transferred to the PCR products. Several methods have been developed to enrich for these target regions without performing PCR amplification.

In another embodiment, the target region(s) can be enriched through the use of CRISPR-Cas9 system (Stevens et al. PLOS One 2019; 14(4):e0215441; Watson et al. Lab Invest 2020; 100:135-146). In one embodiment, the ends of DNA molecules in a DNA sample are first dephosphorylated so rendering them not susceptible to the ligation to sequencing adaptors directly. Then the region(s) of interest is directed by the Cas9 protein with guide RNAs (crRNA) to create double-stranded cuts. The region(s) of interested flanked by double-stranded cuts on both sides would then be ligated to the sequencing adaptors specified by the sequencing platform of choice. In another embodiment, the DNA can be treated with exonuclease so that the DNA molecules not bounded by Cas9 proteins would be degraded (Stevens et al. PLOS One 2019; 14(4):e0215441). As these methods do not involve PCR amplification, the original DNA molecules with base-modification can be sequenced and the base modification would be determined. In one embodiment, this method can be used to target a large number of regions sharing homologous sequences, for example the long interspersed nuclear element (LINE) repeats. In one example, such an analysis can be used for the analysis of circulating cell-free DNA in maternal plasma for the detection of fetal aneuploidies (Kinde et al. PLOS One 2012; 7(7):e41162.

Figure 91:
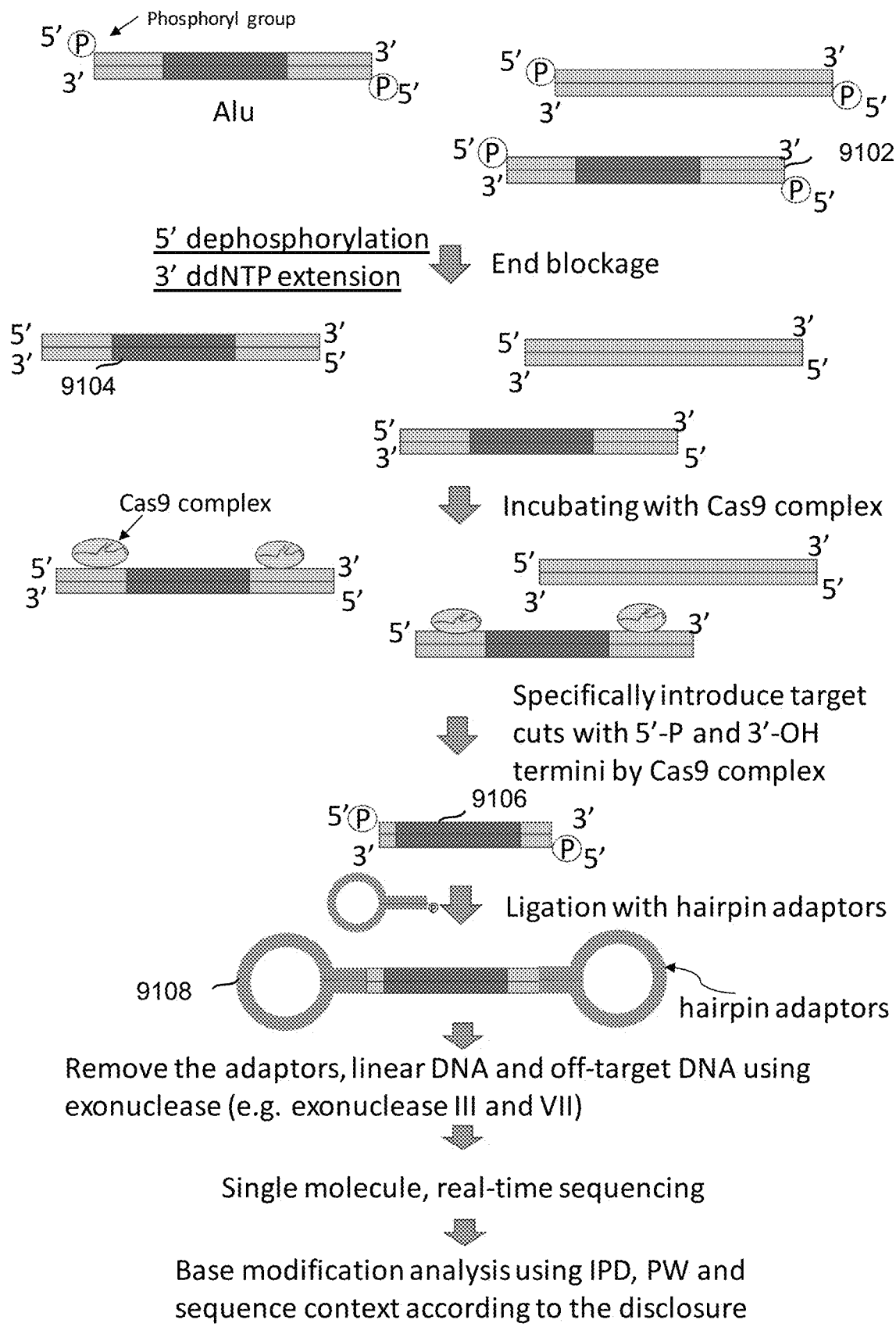
FIG. 91 shows an example of preparing molecules for single molecule, real-time sequencing according to embodiments of the present invention.

As shown in FIG. 91, the targeted single molecule, real-time sequencing can be implemented by using the CRISPR (clustered regularly interspaced short palindromic repeats)/Cas9 (CRISPR associated protein 9) system. The DNA fragments (e.g., molecule 9102) carrying 5' phosphoryl groups (i.e. 5'-P) and 3' hydroxyl groups (i.e. 3'-OH) were subjected to end blockage process by which the 5'-P was removed and 3'-OH was ligated with dideoxynucleotides (i.e. ddNTP). Hence, the resultant molecules (e.g., molecule 9104) whose ends have been modified were not able to be ligated with adaptors for subsequent DNA library preparation. However, the end-blocked molecules were subjected to target-specific cleavage mediated by CRISPR/Cas9 system, introducing 5'-P and 3'-OH termini to molecules of interest. Such newly-cleaved DNA molecules (e.g., molecule 9106) carrying 5'-P and 3'-OH termini acquired the capacity to be ligated with hairpin adaptors to form circular molecule 9108. The unligated adaptors, linear DNA, and molecules only carrying one cleavage were subjected to digestion with exonuclease III and VII. As a result, the molecules ligated with two hairpin adaptors were enriched and subjected to single molecule, real-time sequencing. These target molecules were suitable for base modification analysis according to the embodiments present in this disclosure (i.e. targeted single molecule, real-time sequencing).

Figure 92:
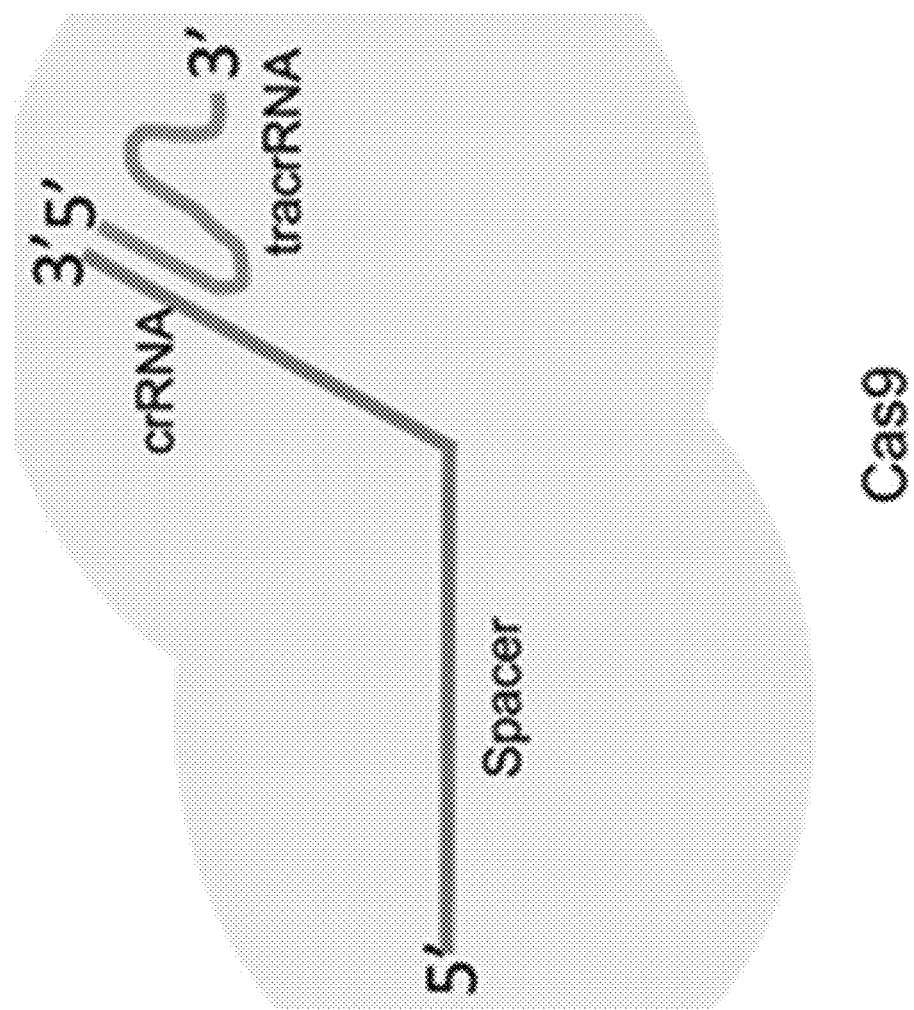
FIG. 92 shows an illustration of the CRISPR/Cas9 system according to embodiments of the present invention.

As shown in FIG. 92, Cas9 protein in CRISPR/Cas9 system interacted with the guide RNA (i.e. gRNA), which includes CRISPR RNA (crRNA, responsible for DNA targeting) and trans-activating crRNA (tracrRNA, responsible for forming the complex with Cas9) (Pickar-Oliver et al. Nat Rev Mol Cell biol. 2019; 20:490-507). The curved shape represents the Cas9 protein, which is an enzyme that uses CRISPR sequences as a guide to recognize and cut specific strands of DNA that are complementary to one part of CRISPR sequences. crRNA was annealed to tracrRNA. In one embodiment, a synthetic single RNA sequence contained both crRNA and tracrRNA sequences, called single-guide RNA (sgRNA). A segment in crRNA, named spacer sequence, would guide Cas9 protein to recognize and cut specific strands of double-stranded DNA (dsDNA), through complementary base pairing to the targeted region. In one embodiment, there were no mismatches involved in the complementarity between spacer sequence and targeted dsDNA. In another embodiment, the complementary base pairing between spacer sequence and targeted dsDNA would allow mismatches. For example, the number of mismatches is, but not limited to 1, 2, 3, 4, 5, 6, 7, 8, etc. In one embodiment, CRISPR sequences would be programmable, depending on the cutting efficiency, specificity, sensitivity, and the capability of multiplexing for different CRISPR/Cas complex designs.

Figure 93:
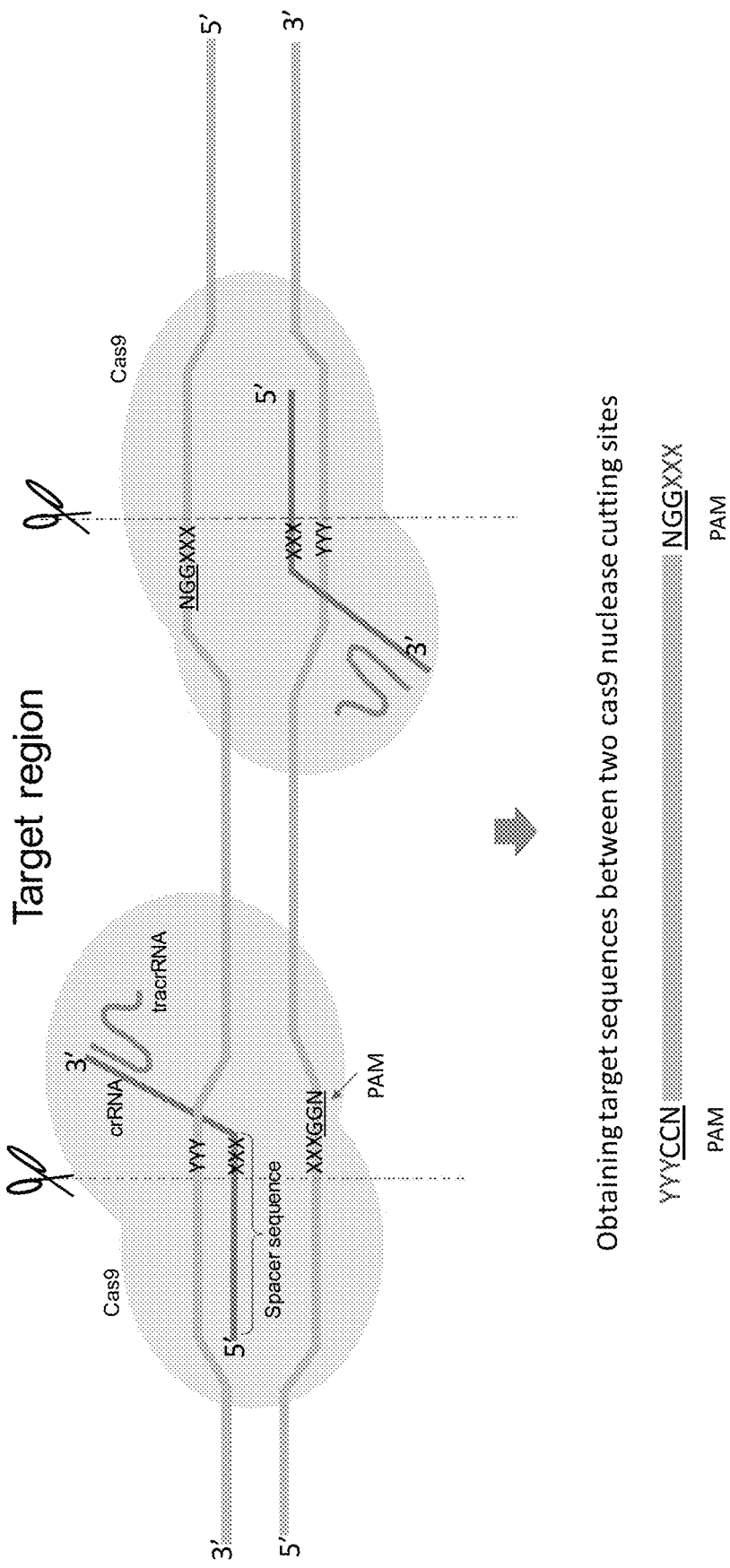
FIG. 93 shows an example of a Cas9 complex for introducing two cuts spanning an end-blocked molecule of interest according to embodiments of the present invention.

As illustrated in FIG. 93, we designed a pair of CRISPR/Cas9 complexes targeting two cuts spanning an Alu element in a human genome. 'XXX' indicates three nucleotides flanking Cas9 nuclease cutting site. 'YYY' indicates three corresponding nucleotides complementary to 'XXX'. 5'-NGG represents the protospacer adjacent motif (PAM) sequence. In other CRISPR/Cas systems, the PAM sequence can be different and the sequences flanking a Cas nuclease cutting site can be different. In this figure, an Alu region was 223 bp in size. There were 1,175,329 Alu regions, each containing homologs to such an Alu element in a human genome. A median of 5 CpG sites resided in this Alu element (range: 0-34). As an example, this design contained a 36-nt crRNA that contained a 20-nt spacer sequence. The detailed gRNA sequence information was shown as below:

A first CRISPR/Cas9 complex for introducing a first cut: (all sequences from 5' to 3')

```
crRNA:
                                    (SEQ ID NO: 1)
GCCUGUAAUCCCAGCACUUUGUUUUAGAGCUAUGCU tracrRNA:
                                    (SEQ ID NO: 2)
AGCAUAGCAAGUUAAAAUAAGGCUAGUCCGUUAUCAACU

UGAAAAAGUGGCACCGAGUCGGUGCUUU
```

A second CRISPR/Cas9 complex for introducing a second cut:

```
crRNA:
                                            (SEQ ID NO: 3)
AGGGUCUCGCUCUGUCGCCCGUUUUAGAGCUAUGCU tracrRNA:
                                            (SEQ ID NO: 2)
AGCAUAGCAAGUUAAAAUAAGGCUAGUCCGUUAUCAA

CUUGAAAAAGUGGCACCGAGUCGGUGCUUU
```

The crRNA molecules were annealed to a tracrRNA (e.g. 67-nt) to form the backbone of gRNA. The Cas9 nuclease with designed gRNA can cleave both strands of end-blocked molecules harboring the targeted cutting sites, with a certain level of specificity. There were 116,184 Alu regions of interest in a human genome which were supposed to be cut by the designed CRISPR/Cas9 complexes. Therefore, those Alu regions after the targeted cutting by Cas9 complexes can be ligated with hairpin adaptors. Those molecules ligated with hairpin adaptors can be sequenced by single molecule, real-time sequencing. The methylation patterns for those Alu regions can be determined in a targeted manner. In one embodiment, the spacer sequences from two Cas9 complexes can be base-paired to the same strand (e.g. Watson strand or Crick strand) of a double-stranded DNA substrate. In one embodiment, the spacer sequences in gRNA from two Cas9 complexes can be base-paired to the different strands of a double-stranded DNA substrate. For example, one spacer sequence in a Cas9 complex was complementary to the Watson strand of a double-stranded DNA substrate and the other spacer sequence in a Cas9 complex was complementary to the Crick strand of a double-stranded DNA substrate, or vice versus.

In one embodiment, the DNA molecules ligated with hairpin adaptors were in a circular form, which would be resistant to exonuclease digestion. Hence, one can treat the adaptor-ligated DNA product with exonuclease (e.g. exonuclease III and VII) to remove the linear DNA (e.g. off-targeted DNA molecules). This step with the use of exonucleases may further enrich the targeted molecules. The sizes of targeted molecules to be sequenced depended on the spanning size between two cutting sites introduced by one or more Cas9 nucleases, for example, including but not limited to, 10 bp, 20 bp, 30 bp, 40 bp, 50 bp, 100 bp, 200 bp, 300 bp, 400 bp, 500 bp, 1000 bp, 2000 bp, 3000 bp, 4000 bp, 5000 bp, 10 kb, 20 kb, 30 kb, 40 kb, 50 kb, 100 kb, 200 kb, 300 kb, 500 kb, and 1 Mb.

As an example, using Cas9 with gRNA targeting Alu regions, we sequenced 187,010 molecules from a human hepatocellular carcinoma (HCC) tumor tissue sample, using single molecule, real-time sequencing. Among them, 113, 491 molecules were carrying targeted cuts (i.e. on-target cleavage rate was around 60.7% of molecules). The data set was generated from DNA prepared by the Sequel II Sequencing Kit 2.0. In other words, the specificity of cutting sites introduced to the molecules of interest by Cas9 complexes in this example was 60.7%. In other embodiments, the specificity of cutting sites introduced to the molecules of interest by Cas9 or other Cas complexes would be varied, including but not limited to, 1%, 5%0, 10%, 20%, 30%, 40%, 50%, 60%, 70%, 80%, 90%, and 100%. The IPD, PW values, and sequence context derived from CCS and subreads without alignment to a reference genome were used for determining methylation status at CpG sites in Alu sequences.

Figure 94:
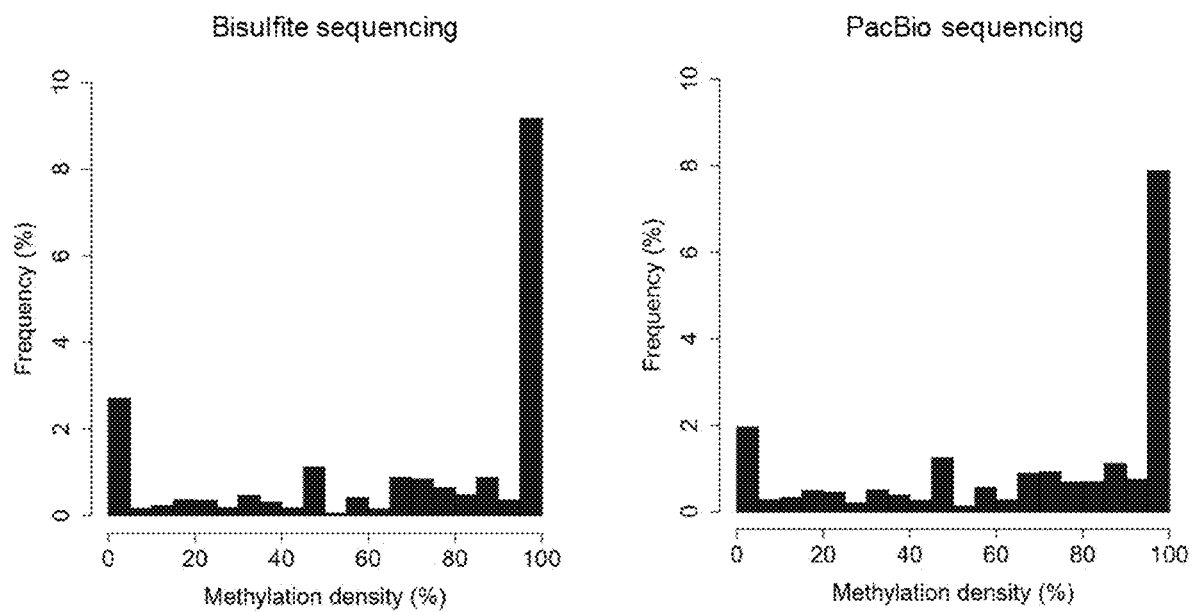
FIG. 94 shows methylation distribution of Alu regions determined by bisulfite sequencing and single molecule, real-time sequencing according to embodiments of the present invention.

As shown in FIG. 94, we observed a similar methylation distribution between methylation levels determined by bisulfite sequencing and single molecule, real-time sequencing according to the disclosure. FIG. 94 shows histograms of methylation densities (in percent) for bisulfite sequencing and single molecule, real-time sequencing (Pacific Biosciences). The y-axis indicates the proportion of molecules in the sample with the particular methylation density shown on the x-axis. This result suggested that it was feasible to determine the methylation patterns using Cas9 mediated targeted single molecule, real-time sequencing. This result also suggested that one could determine methylation using subreads associated kinetic features including PW and IPD values without alignment to a reference genome. As shown in FIG. 94, we observed a considerable amount of Alu regions showing hypomethylation, which was consistent with the prior knowledge for which the cancer genome would be demethylated in Alu repeat regions (Rodriguez et al. Nucleic Acids Res. 2008; 36:770-784).

Figure 95:
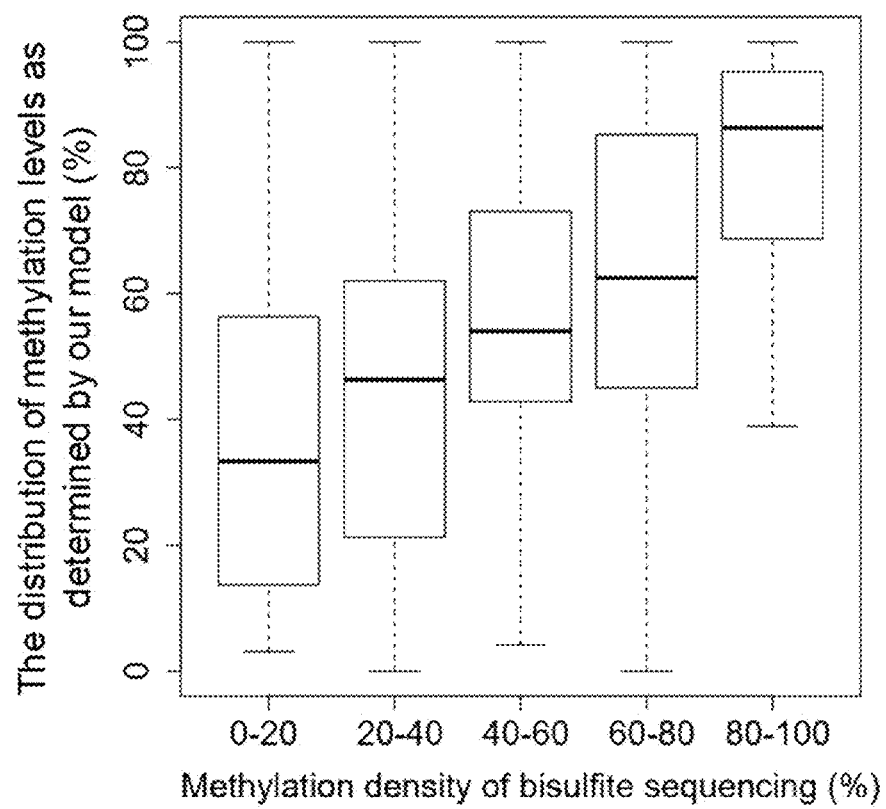
FIG. 95 shows the distribution of methylation levels of Alu regions determined by model using results from single molecule, real-time sequencing according to embodiments of the present invention.

FIG. 95 shows the distribution of methylation levels as determined by single molecule, real-time sequencing according to the disclosure on the y-axis and the methylation density as determined by bisulfite sequencing on the x-axis. As shown in FIG. 95, the methylation levels in Alu regions were binned into 5 categories, namely, 0-20%, 20-40%, 40-60%, 60-80%, and 80-100% according to the results of bisulfite sequencing. The methylation levels of the same set of Alu regions were further determined by our model using the measurement windows including kinetic features and sequence context (y-axis) for each category of Alu regions. The distribution of methylation levels determined by our model gradually increased according to the ascending orders of methylation levels across binned categories. Again, these results suggested that it is feasible to determine the methylation patterns using Cas9 mediated targeted single molecule, real-time sequencing. One can determine methylation using subreads associated kinetic features including PW and IPD values without alignment to a reference genome.

In yet another embodiment, one can use other types of CRISPR/Cas systems, for example but not limited to, Cas12a, Cas3, and other orthologs (e.g. *Staphylococcus aureus* Cas9) or engineered Cas proteins (enhanced *Acidaminococcus* spp Cas12a) to perform targeted single molecule, real-time sequencing.

In one embodiment, one can use the deactivated Cas9 (dCas9), without nuclease activity, for enriching the targeted molecules without cleavage. For example, the targeted DNA molecules were bound by the complex comprising biotinylated dCas9 and target sequence-specific gRNAs. Such targeted DNA molecules may not be cut by dCas9 because dCas9 was nuclease-deficient. Through the use of streptavidin-coated magnetic beads, the targeted DNA molecules can be enriched.

In one embodiment, one can use the exonucleases to digest the DNA mixture after incubating with Cas proteins. The exonucleases may degrade the Cas-protein-unbound DNA molecules while the exonucleases may not degrade or may be largely less efficient in degrading the Cas-protein-bound DNA molecules. Hence, the information concerning the target molecules bound by Cas proteins may be further enriched in the ultimate sequencing results.

FIG. 96 shows a table of tissues and the methylation levels of Alu regions in the tissues. Many tissues show methylation levels in the 85-92% range, including in the 88% to 92% range. HCC tumor tissue and placenta tissue showed methylation levels below 80%. As seen in FIG. 96, HCC tumor was shown to be frequently hypomethylated in the Alu regions that were targeted by our designs. Hence, the methylation determination of Alu regions present in this disclosure can be used for detecting, staging, and monitoring cancers during tumor progression or treatment using DNA extracted from tumor biopsies or other tissues or cells.

The hypomethylation of placental tissues across Alu regions may be used to perform noninvasive prenatal testing using the plasma DNA of pregnant women. For example, a higher degree of hypomethylation may indicate a higher fetal DNA fraction in a pregnant woman. In another example, if a woman is pregnant with a fetus with a chromosomal aneuploidy, the number of Alu fragments originating from an affected chromosome detected by this approach may be quantitatively different (i.e. either increased or decreased) than women pregnant with euploid fetuses. Hence, if a fetus has trisomy 21, then the number of Alu fragments originating from chromosome 21 detected by this approach may be increased when compared with women pregnant with euploid fetuses. On the other hand, if a fetus has a monosomic chromosome, then the number of Alu fragments originating from that chromosome detected by this approach may be decreased when compared with women pregnant with euploid fetuses. Compared with unaffected chromosomes, the determination of the presentation of extra hypomethylation of an affected chromosome (13, 18, or 21) in plasma may be used as a molecular indicator for differentiating women pregnant with normal and abnormal fetuses.

3. Methylation Analysis in the Alu Regions Targeted by Cas9 Complex for Different Types of Cancer Even though the Alu repeats we targeted were highly methylated in different tissues, we hypothesized that different cancer types would harbor different demethylation patterns across those Alu repeats. In one embodiment, one can use the Cas9 based targeted single molecule, real-time sequencing to analyze the methylation patterns to determine different cancer types according to the disclosure present herein.

Figure 97:
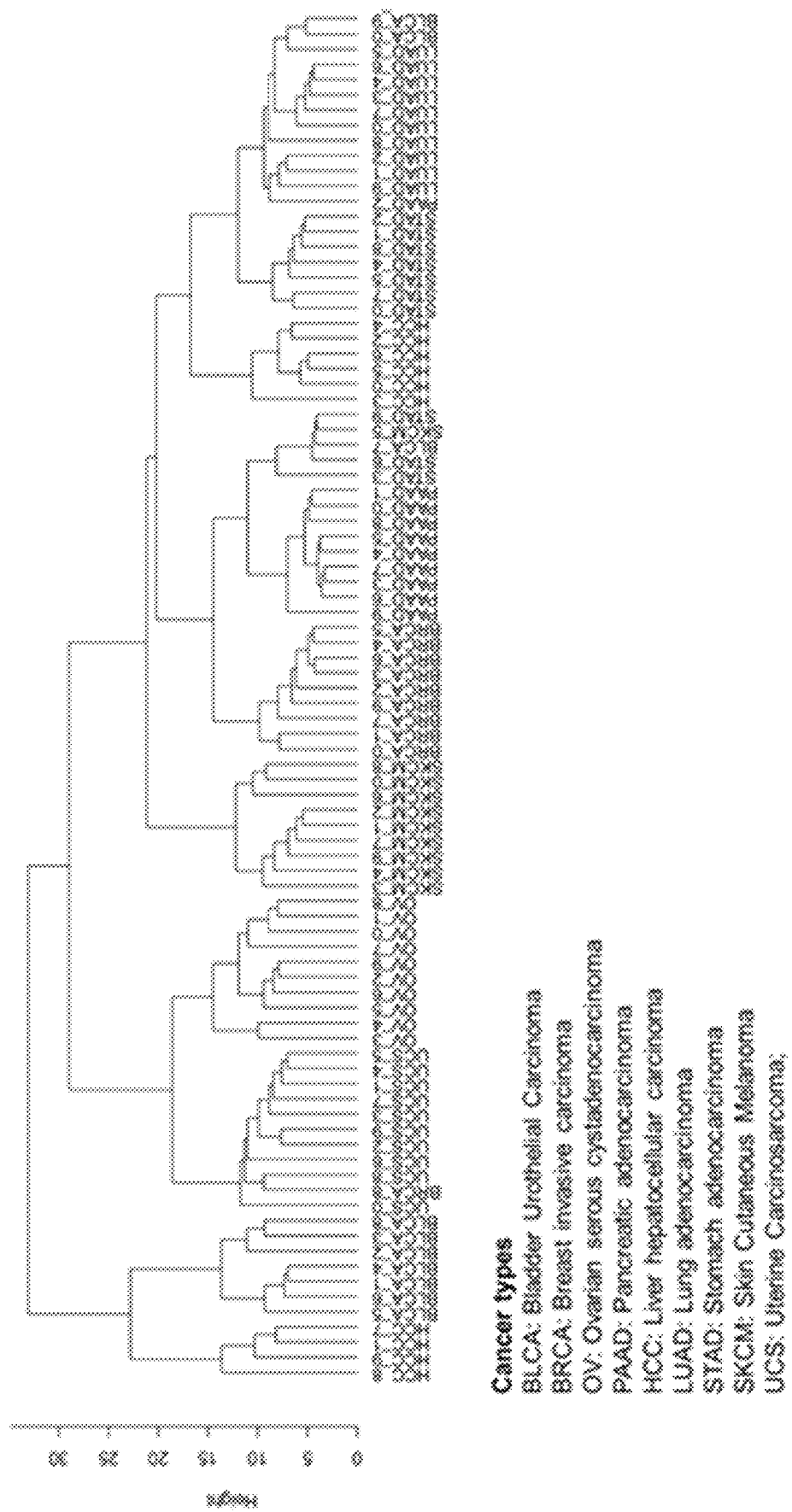
FIG. 97 shows clustering analysis for different cancer types using methylation signals related to Alu repeats according to embodiments of the present invention.

FIG. 97 shows clustering analysis of methylation signals related to Alu repeats for different cancer types. Cancer subjects from the TCGA database (www.cancer.gov/about-nci/organization/ccg/research/structural-genomics/tcga) had methylation status on CpG sites analyzed using microarray technology (Infinium HumanMethylation 450 BeadChip, Illumina Inc). The methylation statuses across 3,024 CpG sites present in microarray chip and overlapping with the Alu regions targeted by CRISPR/Cas9 complexes were analyzed. There are a number of CpGs originating from the Alu regions of interest in a patient. Methylation level of each CpG was quantified by microarray (also called methylation index, or beta value). We performed hierarchical clustering analysis based on a number of methylation levels at those CpG sites across patients. Therefore, patients with a similar pattern of methylation levels at those CpG sites would cluster together, forming a clade. The similarity of methylation patterns across different patients would be indicated by height values in the clustering dendrogram. The height was calculated according to Euclidean distances in this example. In other embodiments, other distance metrics would be used, including but not limited to Minkowski, Chebychev, Mahalanobism, Manhattan, Cosine, Correlation, Spearman, Hamming, Jaccard distances, etc. The height used herein represents the value of the distance metric between clusters, reflecting the relatedness between clusters. For example, if one observed two clusters merged at a height x, it suggested that the distance between those clusters was x (e.g. average distance between all inter-cluster patients).

With the use of the methylation statuses on CpG sites patients were clustered into different distinct groups depending on the cancer types in the results of clustering analysis. The cancer types included bladder urothelial carcinoma (BLCA), breast invasive carcinoma (BRCA), ovarian serous cystadenocarcinoma (OV), pancreatic adenocarcinoma (PAAD), HCC, lung adenocarcinoma (LUAD), stomach adenocarcinoma (STAD), skin cutaneous melanoma (SKCM), and uterine carcinosarcoma (UCS). The number after the cancer type in the figure denotes a patient. Hence, the clustering suggests that the methylation signals in Alu repeats we selected were informative for classifying cancer types, including cancer types not shown in FIG. 97. In one embodiment, one can differentiate the primary and secondary tumors based on the methylation patterns in a tissue biopsy. 4. Subread depth and size cutoffs This section shows that subread depth and/or size cutoffs may be used to improve accuracy and/or efficiency of methylation detection. Library preparation may be modified in order to test for certain subread depths or sizes.

On the basis of Sequel II Sequencing Kit 2.0, we analyzed the effect of read depth on the overall methylation level quantification in the testing datasets which were generated from samples following whole genome amplification or M.SsssI treatment. We studied genomic sites that were covered by subreads with at least a certain cutoff, for example but not limited to ≥1×, 10×, 20×, 30×, 40×, 50×, 60×, 70×, 80×, 90×, 100×, etc.

Figure 98B:
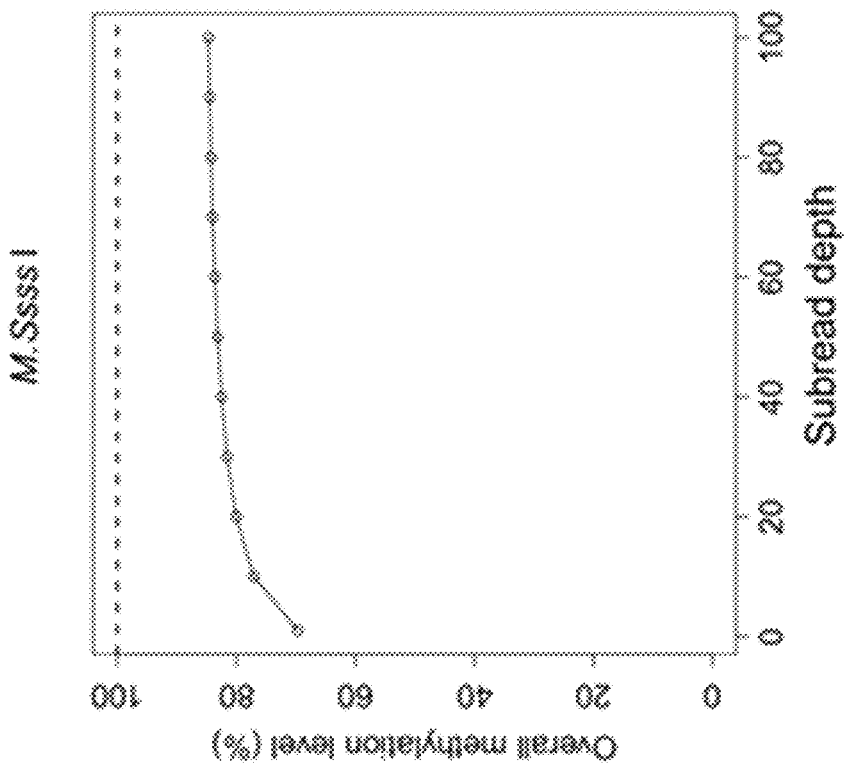
FIGS. 98A and 98B show the effect of read depth on the overall methylation level quantification in the testing datasets which were involved with the whole genome amplification and M.SsssI treatment according to embodiments of the present invention.
Figure 98A:
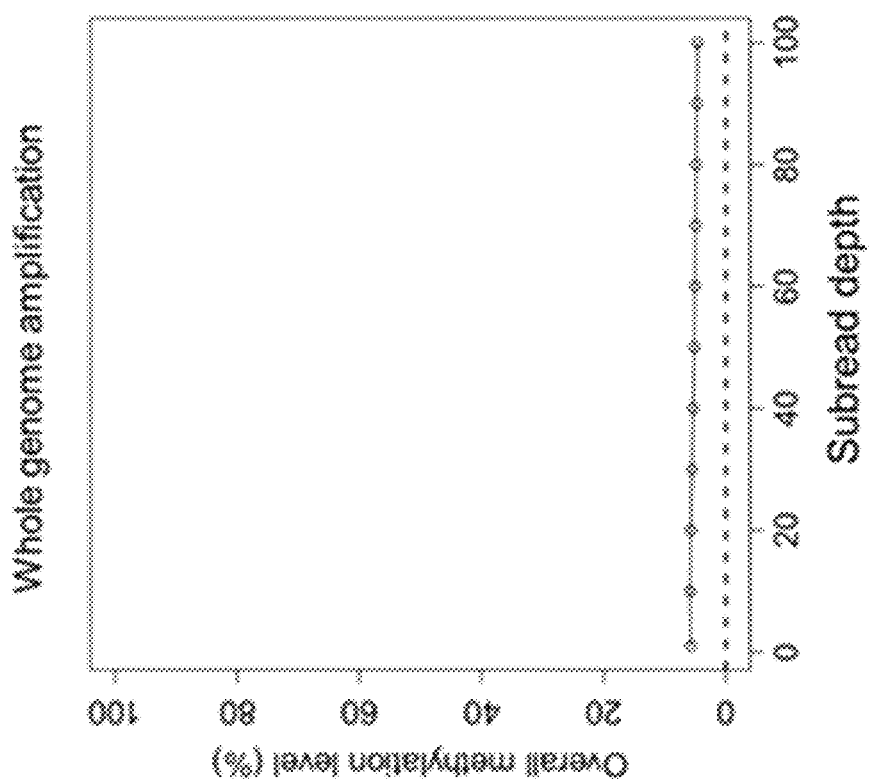

FIG. 98A shows the effect of read depth on the overall methylation level quantification in the testing datasets which were involved with the whole genome amplification. FIG. 98B shows the effect of read depth on the overall methylation level quantification in the testing datasets which were involved with M.SsssI treatment. The y-axis shows the overall methylation level as a percentage. The x-axis shows the subreads depth. The dashed lines indicate the expected values of overall methylation levels.

As shown in FIG. 98A, for the dataset involving whole genome amplification, the overall methylation declined in the initial few cutoffs such as but not limited to 1×, 10×, 20×, 40×, 50×, ranging from 5.7% to 5.2%. The methylation levels were progressively stabilized at around 5% at the cutoff of 50× or above.

On the other hand, in FIG. 98B, for the dataset generated from samples following M.SsssI treatment, the overall methylation increased in the initial few cutoffs such as but not limited to 1×, 10×, 20×, 40×, 50×, ranging from 70% to 83%. The methylation levels were progressively stabilized at around 83% at the cutoff of 50× or above.

In one embodiment, one could adjust subread depth cutoffs, making the performance of base modification analysis amenable across different applications. In other embodiments, one could use the less stringent subread depth cutoff to obtain more ZMWs (i.e. number of molecules) that were suited for downstream analysis. In yet another embodiment, one could calibrate the readout of methylation levels determined by SMRT-seq according to the disclosure to a second measurement, for example, but not limited to BS-seq, digital droplet PCR (on bisulfite converted samples), methylation-specific PCR, or methylated cytosine binding antibodies or other proteins. In another embodiment, a second measurement would be obtained by subjecting DNA molecules following 5mC-retained whole-genome amplification to BS-seq, digital droplet PCR (on bisulfite converted samples), methylation-specific PCR, or methyl-CpG binding domain (MBD) protein-enriched genome sequencing (MBD-seq). As an example, 5mC-retained whole-genome amplification could be mediated by DNA primase TthPrimPol, polymerase phi29, and DNMT1 (DNA Methyltransferase 1).

We analyzed the methylation levels across various cancer types and non-tumoral tissues for different subreads depths. The methylation levels determined by SMRT-seq according to the disclosure were also compared with BS-seq sequencing results. Using the Sequel II Sequencing Kit 2.0, we obtained a median of 43 million subreads (interquartile range (IQR): 30-52 million), which allowed the generation of a median of 4.6 million circular consensus sequences (CCS) that were aligned to a human reference genome (IQR: 2.8-5.8 million). Among those samples, 22 samples were also subjected to well-established massively parallel bisulfite sequencing (BS-seq) for determining the methylation patterns, providing a second measurement for comparison of methylation levels.

Figure 99:
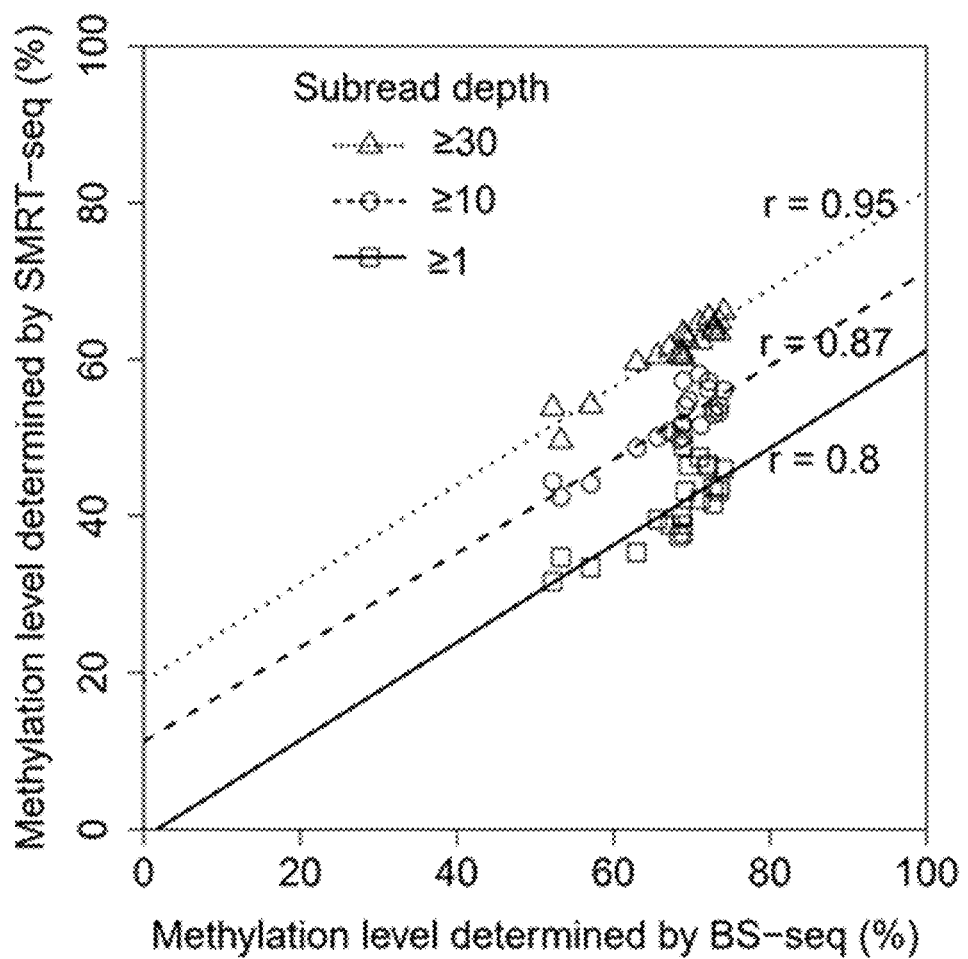
FIG. 99 shows a comparison between overall methylation levels determined by SMRT-seq (Sequel II Sequencing Kit 2.0) and BS-seq with the use of different subread depth cutoffs according to embodiments of the present invention.

FIG. 99 shows a comparison between overall methylation levels determined by SMRT-seq (Sequel II Sequencing Kit 2.0) according to the disclosure and BS-seq with the use of different subread depth cutoffs. The methylation level as a percentage determined by SMRT-seq is shown on the y-axis. The methylation level as a percentage determined by bisulfite sequencing is on the x-axis. The symbols indicate different subreads depths of 1×, 10×, and 30×. The three diagonal lines show fitted lines for the different subread depths.

FIG. 99 showed that methylation levels at CpG sites determined by SMRT-seq according to the disclosure were well correlated with (r=0.8; P value <0.0001) those determined by BS-seq, when analyzing genomic sites that were covered by subreads at least once (i.e. subread depth cutoff ≥1×). These results suggested that the embodiments present in this disclosure could be used for measuring the methylation levels for different tissue types, including, but not limited to colorectal cancer, colorectal tissues, esophageal cancer, esophagus tissues, breast cancer, non-cancerous breast tissues, renal cell carcinoma, kidney tissues, lung cancer, and lung tissues. We also observed that the correlation between these two measurements was improved to 0.87 (P value <0.0001) and 0.95 (P value <0.0001) as the subread depth cutoffs were increased to 10× and 30×, respectively. In some embodiments, the increase of subread depth or the selection of genomic regions with a coverage of more subreads would improve the performance of SMRT-seq based methylation determination according to the disclosure.

FIG. 100 is a table showing the effect of the subread depth on the correlation of methylation levels between two measurements by SMRT-seq (Sequel II Sequencing Kit 2.0) and BS-seq. The first column shows the subread depth cutoff. The second column shows Pearson's r, a correlation coefficient. The third column shows the number of CpG sites associated with the cutoff, with the range of the number of sites in parentheses.

As shown in FIG. 100, the correlation of methylation levels between two measurements by SMRT-seq and BS-seq varied according to different subread depth cutoffs. In one embodiment, one could make use of the relationship between subread depth cutoffs and correlation coefficients (e.g., Pearson's correlation coefficient) between two measurements to determine the optimal cutoff of subread depth for differentiating methylated cytosines from unmethylated cytosines. FIG. 100 showed that at a subread depth cutoff of 30× (i.e. ≥30×), the methylation levels measured by SMRT-seq according to this disclosure gave the highest correlation with the results produced by BS-seq (Pearson's r=0.952). In other embodiments, one may use, but not limited to, subread depth cutoffs of 1×, 10×, 30×, 40×, 50×, 60×, 70×, 80×, 900×, 100×, 200×, 300×, 400×, 500×, 600×, 700×, 800×, etc.

The number of CpG sites used for methylation analysis decreases with an increase of cutoff of subread depth, as shown in FIG. 100. With a subread depth cutoff of 100×, a lower correlation (Pearson's r=0.875) was observed between two measurements of methylation levels, compared with a subread depth cutoff of 30× (Pearson's r=0.952). The lower correlation for a higher subread cutoff may be attributed to the smaller number of CpG sites that fulfilled the more stringent subread depth cutoffs. In one embodiment, one may consider the trade-off between the requirement of subread depth and the number of molecules that can be used for methylation analysis. For example, if one aimed to scan a whole genome for methylation patterns, more molecules may be desirable. If one focused on a particular region with the use of targeted SMRT-seq, a higher subread depth may be desirable for obtaining methylation patterns for that region.

Figure 101:
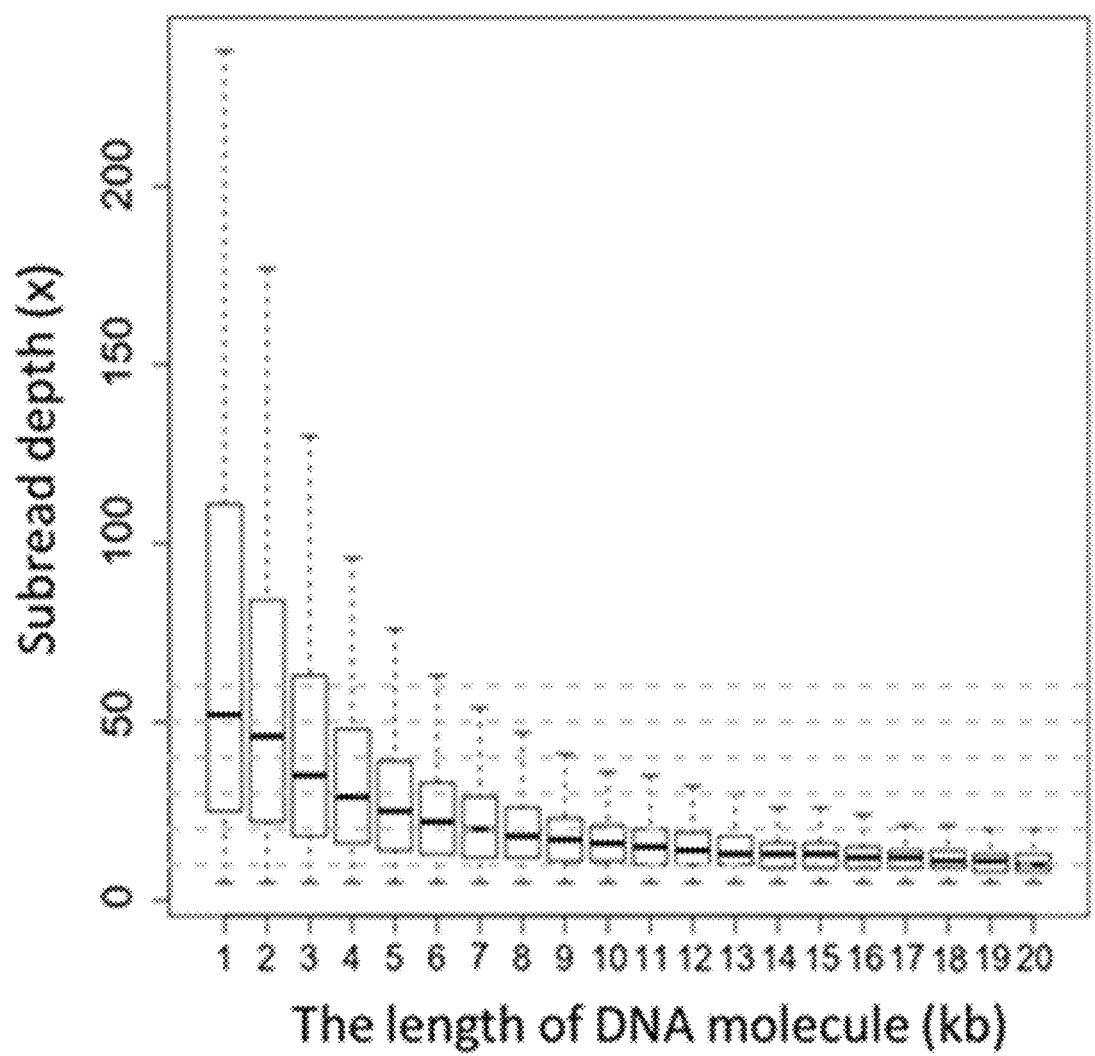
FIG. 101 shows the subread depth distribution with respect to fragment sizes in data generated by Sequel II Sequencing Kit 2.0 according to embodiments of the present invention.

FIG. 101 shows the subread depth distribution with respect to fragment sizes in data generated by Sequel II Sequencing Kit 2.0. The subreads depth is shown on the y-axis, and the length of the DNA molecule is shown on the x-axis. The lengths of DNA molecules were deduced from the size of circular consensus sequences (CCSs).

As the subread depth may affect the performance of the methylation determination using SMRT-seq data and the subread depth is a function of the length of a DNA molecule being sequenced, the sizes of DNA molecules may be crucial to obtaining an optimal subread depth for analyzing methylation patterns in a sample. As shown in FIG. 101, the longer the DNA, the lower the subread depth is. For instance, for the population of molecules with 1 kb in size, the median subread depth was 50×. For the population of molecules with 10 kb in size, the median subread depth was 15×.

In one embodiment, as shown in FIG. 100, the optimal cutoff of subread depth may be at least 30×, which results in the highest correlation coefficient. To further improve the throughput of molecules that would fulfill the optimal subread depth cutoff of 30×, one can make use of the relationship between subread depths and the lengths of DNA template molecules. For example, in FIG. 101, 30× is the median subread depth for molecules having a length of about 4 kb. One therefore can fractionate 4-kb DNA molecules prior to SMRT-seq library preparation and limit sequencing to the 4-kb DNA molecules. In other embodiments, other size cutoffs for DNA molecule fractionation could be used, including, but not limited to 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 9 kb, 10 kb, 20 kb, 30 kb, 40 kb, 50 kb, 60 kb, 70 kb, 80 kb, 90 kb, 100 kb, 500 kb, 1 Mb, or different combinations of size cutoffs.

5. Restriction Enzyme Based Targeted Single Molecule, Real-Time Sequencing

This section describes using restriction enzymes to improve the practicability and/or throughput and/or cost effectiveness of the detection of modifications. DNA fragments generated with restriction enzymes can be used to determine the origin of a sample.

a) Using Restriction Enzymes to Digest DNA Molecules

In embodiments, one may use one or more restriction enzymes to digest DNA molecules prior to single molecule, real-time sequencing (e.g. using the Pacific Biosciences system). Because the distribution of recognition sites of restriction enzymes would be unevenly present in a human genome, the DNA digested by restriction enzymes may generate a skewed size distribution. The genomic regions with more recognition sites of restriction enzymes can be digested into smaller fragments, while the genomic regions with fewer recognition sites of restriction enzymes may be digested into longer fragments. In embodiments, according to the size ranges, one may selectively obtain the DNA molecules originating from one or more regions that have similar cutting patterns of one or more restriction enzymes. The desired size ranges for size selection can be determined by in silico cutting analysis for one or more restriction enzymes. One can use a computer program to determine the number of recognition sites of restriction enzymes of interest in a reference genome (e.g. a human reference genome). Such a reference genome was sheared in silico into fragments according to those recognition sites, which provided the size information for genomic regions of interest.

FIG. 126 shows a method of MspI-based targeted single molecule, real-time sequencing with the use of DNA end repair and A-tailing. In embodiments, as shown in FIG. 126, one can use MspI, which recognizes 5'C^CGG3' sites, to digest a DNA sample of an organism, for example, but not limited to, a human DNA sample. The digested DNA fragments with 5' CG overhangs were subjected to size selection, enriching the DNA molecules originating from the CpG islands. Genomic regions that are enriched with G and C residues (also called the GC content) may generate shorter fragments. One can therefore determine the range of fragment sizes to perform selection based on the GC content of the regions of interest. A variety of DNA fragment size selection tools are available to one skilled in the art that include, but not limited to, gel electrophoresis, size exclusion electrophoresis, capillary electrophoresis, chromatography, mass spectrometry, filtration approaches, precipitation based approaches, microfluidics, and nanofluidics. The size-fractionated DNA molecules were subjected to DNA end repair and A-tailing such that the desired DNA product could be ligated with hairpin adapters which carried 5' T overhang, forming circular DNA templates.

After the removal of the unligated adapters, linear DNA, and uncomplete-circular DNA for example, but not limited to, using exonucleases (e.g. exonuclease III and VII), the DNA molecules ligated with hairpin adaptors can be used for single molecule, real time sequencing to determine the IPD, PW, and sequence context in determining methylation profiles as disclosed herein. By analyzing the genomic regions enriched with CpG, DNA obtained from different tissues or tissues with different diseases and/or physiological conditions or biological samples can be distinguished and classified by their methylation profile determined by the sequencing data analysis methods of this disclosure.

For the step involving size selection in FIG. 126, in embodiments, the desired size ranges can be determined by the in silico cutting analysis of MspI. We determined a total of 2,286,541 MspI cutting sites in a human reference. A human reference genome was sheared in silico into fragments according to those MspI cutting sites. We obtained a total of 2,286,565 fragments. Each individual fragment size was determined by the total number of nucleotides of that fragment.

FIGS. 127A and 127B show the size distribution of MspI-digested fragments. The y-axis for these figures is the frequency in percent for a particular size of fragment. FIG. 127A has a logarithmic scale for the x-axis ranging from 50 to 500,000 bp. FIG. 127B has a linear scale for the x-axis ranging from 50 to 1,000 bp.

As shown in FIGS. 127A and 127B, the MspI-digested DNA molecules have a skewed size distribution. The median size of MspI-digested fragments was 404 bp (IQR: 98-1,411 bp). About 53% of those MspI-digested fragments were less than 1 kb. There were a series of spiked peaks in the size profile that might be caused by repeat elements. Certain repeat elements may share similar patterns of MspI-cutting sites, leading to a set of molecules derived from MspI digestion that possessed similar fragment sizes. For example, the spiked peak with the highest frequency (i.e., a total of 49,079) corresponded to a size of 64 bp. Among them, 45,894 (94%) were overlapped with Alu repeats. One can select the DNA molecules with a size of 64 bp to enrich DNA molecules originating from Alu repeats. The data suggest that size selection can be used to enrich desired DNA molecules for downstream methylation analysis according to the disclosure.

FIG. 128 shows a table with the number of DNA molecules for certain selected size ranges. The first column shows size ranges in base pairs. The second column shows the percentage of molecules within a size range relative to total fragments. The third column shows the number of molecules within the size range overlapping CpG islands. The fourth column shows the percentage of molecules within a size range overlapping CpG islands. The fifth column shows the number of CpG sites being sequenced. The sixth column shows the number of CpG sites falling within CpG islands. The seventh column shows the percentage of CpG sites targeted by size selection and falling within CpG islands. As shown in FIG. 128, the amount of DNA molecules generated from a human genome subjected to MspI digestion varied according to different size ranges in question. The number of DNA molecules overlapping CpG islands varied with different size ranges.

As the CCGG motif occurred preferentially in CpG islands, the selection of molecules with a size of less than a certain cutoff can allow for enriching the DNA molecules originating from CpG islands. For example, for a size range of 50 to 200 bp, the number of molecules was 526,543, which accounted for 23.03% of total DNA fragments derived from a human genome subjected to MspI digestion. Among 526,543 DNA molecules, 104,079 (19.76%) were overlapped with CpG islands. For a size range of 600 to 800 bp, the number of molecules was 133,927, which accounted for 5.86% of total DNA fragments derived from a human genome subjected to MspI digestion. Among 133,927 molecules, 3,673 (2.74%) molecules were overlapped with CpG islands. As an example, one can select a size of 50 to 200 bp to enrich DNA fragments originating from CpG islands.

To calculate the degree of enrichment of CpG sites overlapping CpG islands via MspI-based targeted single molecule, real time sequencing, we performed a simulation for DNA sheared by sonication, we simulated 526,543 fragments generated from ZMW with a mean size of 200 bp and a standard deviation of 20 bp on the basis of normal distribution. There were only 0.88% DNA molecules overlapping CpG islands. A total of 71,495 CpG sites were overlapped with CpG islands. As shown in FIG. 128, the selection of MspI-digested fragments ranged from 50 to 200 bp would result in 19.8% fragments overlapping CpG islands. Thus, these data suggested that DNA prepared by MspI-digestion may have 22.5-fold enrichment of DNA fragments originating from CpG islands, compared with DNA prepared by sonication. Furthermore, we analyzed the CpG sites being enriched in CpG islands through the MspI-digestion. The selection of MspI-digested fragments ranging from 50 to 200 bp may give rise to 885,041 CpG sites overlapping CpG islands, accounting 37.5% of total CpG sites from sequenced fragments within that size range. There was a 12.3-fold (i.e. 885,041/71,495) enrichment of CpG sites overlapping CpG islands, in comparison with that of DNA prepared by sonication. Based on the information shown in FIG. 128, a suitable size range can be selected to include the desirable number of CpG sites and the desirable fold enrichment of CpG sites within CpG islands.

FIG. 129 is a graph of the percentage coverage of CpG sites within CpG islands versus size of DNA fragments after restriction enzyme digestion. The y-axis shows the percentage of CpG sites within CpG islands covered by fragments having the given sizes. The x-axis shows the upper limit of the size range of the DNA fragments after restriction enzyme digestion. FIG. 129 showed the percentage of CpG sites within CpG islands to be covered by widening the size selection range. In FIG. 129, the size range is from 50 bp to the size shown in the x-axis. In other embodiments, the lower limit of the size range can be customized, for example but not limited to 60 bp, 70 bp, 80 bp, 90 bp, 100 bp, 200 bp, 300 bp, 400 bp, and 500 bp. With the widening of the size range by increasing the upper size limit, we can observe that the percentage coverage of CpG sites within CpG islands increases gradually and plateaus at 65%. Some of the CpG sites are not covered because they are within DNA fragments below 50 bp or they are within fragments within extremely long molecules (e.g. >100,000 bp).

In some embodiments, a DNA sample can be analyzed using two or more different restriction enzymes (with different restriction sites) so as to increase the coverage of CpG sites within CpG islands. The digestion of the DNA sample by different enzymes may be carried out in individual reactions so that there is only one restriction enzyme in each reaction. For example, AccII which recognizes CGˆCG sites can be used to preferentially cut on CpG islands. In other embodiments, other restriction enzymes with CG dinucleotides as part of the recognition site can be used. Within the human genome, there were 678,669 AccII-cutting sites. We performed an in silico cutting of the human reference genome using AccII restriction and obtained a total of 678,693 fragments. Then we performed an in silico size selection of these fragments and calculated the percentage coverage of CpG sites within CpG islands according to the method described above for MspI digestion. We can observe a gradual increase in the percentage of CpG sites coverage with the widening of the size selection range. The percentage coverage plateaus at around 50%. The coverage of the CpG sites further increases within combining data from the two enzyme digestion experiments, namely MspI digestion and AccII digestion. 80% of the CpG sites within CpG islands are covered through selecting DNA fragments with size 50 bp to 400 bp. This percentage is higher than the respective numbers for the digestion experiments by any of the two enzymes alone. The coverage can further be increased through the analysis of the DNA sample using other restriction enzymes. If a DNA sample is divided into two aliquots. One aliquot is digested with MspI and the other is digested with AccII. The two digested DNA sample are mixed together in equal molar and sequenced using single molecule, real time sequencing with 5 million ZMWs. Based on in silico analysis, 83% of CpG sites within CpG islands (i.e. 1,734,345) would be sequenced by at least 4 times in terms of circular consensus sequences.

FIG. 130 shows MspI-based targeted single molecule, real time sequencing without the use of DNA end repair and A-tailing. In embodiments, the ligation between the digested DNA molecules and hairpin adapters may be performed without the process of DNA end repair and A-tailing. One can directly ligate the digested DNA molecules carrying 5' CG overhangs with hairpin adaptors carrying 5' CG overhangs, forming the circular DNA template for single molecule, real time sequencing. After the cleanup of the unligated adaptors and self-ligated adaptor dimers, and in some embodiments after the removal of the unligated adapters, linear DNA, and uncomplete-circular DNA, the DNA molecules ligated with hairpin adaptors may be suitable for single molecule, real time sequencing to obtain the IPD, PW, and sequence context. The methylation profile of a single molecule would be determined using IPD, PW, and sequence context according to the disclosure.

FIG. 131 shows MspI-based targeted single molecule, real time sequencing with a reduced probability of adapter self-ligation. The underlying cytosine base indicates a base without 5' phosphate groups. In some embodiments, to minimize the possibility of formation of self-ligated adaptor dimers that may occur during the process of adapter ligation, one can use dephosphorylated hairpin adapters to perform adapter ligation with those MspI-digested DNA molecules. Those dephosphorylated hairpin adapters may not form the self-ligated adapter dimers because of the lack of 5' phosphate groups. After the ligation, the product was subjected to the adapter cleanup step to purify the DNA molecules ligated with hairpin adapters. The DNA molecules ligated with hairpin adapters that may carry the nicks were further subjected to phosphorylation (e.g. T4 polynucleotide kinase) and nick sealing by DNA ligase (e.g. T4 DNA ligase). In embodiments, one may further perform the removal of the unligated adapters, linear DNA, and uncomplete-circular DNA. The DNA molecules ligated with hairpin adaptors were suitable for single molecule, real time sequencing to obtain the IPD, PW, and sequence context. The methylation profile of a single molecule would be determined using IPD, PW, and sequence context according to the disclosure.

In addition to MspI, other restriction enzymes, such SmaI, with a recognition site CCCGGG, can also be used.

In some embodiments, the desired size selection process can be performed following the DNA end-repair step. In some embodiments, the desired size selection process can be performed following the ligation of hairpin adapters, when the effect of hairpin adapters on the size selection outcome was determined. In these and other embodiments, the orders of procedural steps involving in MspI-based targeted single molecule, real time sequencing may change depending on the experimental situations.

In embodiments, the size selection would be carried out using gel electrophoresis based and/or magnetic bead based methods. In embodiments, the restriction enzymes may include, but 5 not limited to, BglII, EcoRI, EcoRII, BamHI, HindIII, TaqI, NotI, HinFI, PvuII, Sau3AI, SmaI, HaeIII, HgaI, HpaII, AluI, EcoRV, EcoP15I, KpnI, PstI, SacI, SalI, ScaI, SpeI, SphI, StuI, XbaI, and combinations thereof.

b) Distinguishing Biological Sample Types with Methylation

This section describes using methylation profiles determined using fragments generated by restriction enzyme digestion to facilitate distinguishing between different biological samples.

We assessed the differences in methylation profiles between biological samples using methylation profiles determined by MspI-based single molecule, real-time sequencing according to the embodiments in this disclosure. We took placental tissue DNA and buffy coat DNA samples as an example. We performed a computer simulation for generating the data regarding the placenta and buffy coat DNA sample on the basis of MspI-based targeted single molecule, real-time sequencing. The simulation was based on the kinetic values including IPD and PW for each nucleotide previously generated by SMRT sequencing placental tissue DNA and buffy coat DNA to whole genome coverage using Sequel II Sequencing Kit 1.0. We then simulated the condition whereby the placental DNA and buffy coat DNA samples were subjected to MspI digestion, followed by gel-based size selection using a size range of 50 to 200 bp. The selected DNA molecules were ligated with hairpin adapters to form circular DNA templates. The circular DNA templates were subjected to single molecule, real-time sequencing to obtain the information concerning IPD, PW, and sequence context.

Assuming there were 500,000 ZMWs generating SMRT sequencing subreads, those subreads followed the genomic distributions of MspI-digested fragments within a size range of 50 to 200 bp as shown in Table 1. The subread depth was assumed to be 30× for both placenta and buffy coat DNA samples. We repeated the simulation 10 times for the placenta DNA sample and buffy coat DNA sample, respectively. Thus, the dataset generated in silico by MspI-digested targeted single molecule, real-time sequencing comprised a total of 10 placenta DNA samples and 10 buffy coat DNA samples were obtained. The dataset was further analyzed by CNN, determining methylation profiles for each sample according to the disclosure. We obtained a median of 9,198 CpG sites from CpG islands (range: 5,497-13,928), which accounted for 13.6% of total sequenced CpG sites (range: 45,304-90,762). The methylate status for each CpG site in each molecule was determined by a CNN model according to the disclosure.

FIG. 132 is a graph of the overall methylation levels between placenta and buffy DNA samples determined by MspI-based targeted single molecule, real-time sequencing. The y-axis is the methylation level as a percent. The type of samples listed on the x-axis. FIG. 132 shows that the overall methylation levels (median: 57.6%; range: 56.9%-59.1%) were lower in placenta samples compared with buffy coat samples (median: 69.5%; range: 68.9%-70.4%) (P value <0.0001, Mann-Whitney U test). These results suggested that the methylation profiles determined by MspI-based single molecule, real-time sequencing can be used for differentiating tissue samples or biological samples based on their methylation differences. Because these data show that DNA from placenta can be distinguished from buffy coat DNA due to their methylation differences detected by MspI-based single molecule, real-time sequencing, one can apply this method to measurement of fetal DNA fraction in maternal plasma. The fetal DNA fraction can be measured using methylation because fetal DNA in maternal plasma or maternal serum is from the placenta while the remaining DNA molecules in the sample are mostly derived from maternal buffy coat cells. In embodiments, this technology would be a useful tool for differentiating different tissues or tissues with different diseases and/or physiological conditions or biological samples.

To perform clustering analysis between placenta DNA samples and buffy coat DNA sample using methylation profiles of CpG islands, we calculated the DNA methylation levels of a CpG island using the proportion of CpG sites classified as methylation among the total CpG sites of that CpG island. We used the methylation levels from CpG island regions to perform the clustering analysis for illustration purposes.

FIG. 133 shows a clustering analysis of placental and buffy coat samples using their DNA methylation profiles determined by MspI-based targeted single molecule, real-time sequencing. The similarity of methylation patterns from CpG islands across different patients is indicated by height values in the clustering dendrogram. The height is calculated according to Euclidean distances in this example. In one embodiment, one can use the height cutoff 100 to cut the clustering tree into two groups, allowing for differentiating placenta and buffy coat samples with 100% sensitivity and specificity. In other embodiments, one can use other height cutoffs including, but not limited to, 50, 60, 70, 80, 90, 120, 130, 140, and 150, etc. FIG. 133 showed that 10 placenta DNA samples and 10 buffy coat DNA samples were clearly clustered separately into two groups using the methylation profiles of CpG islands determined by MspI-based single molecule, real-time sequencing according to the disclosure.

V. Methods for Training and Detection

This section shows example methods of training a machine learning model for detection of a base modification and using the machine learning model to detect a base modification.

A. Model Training

FIG. 102 shows an example method 1020 of detecting a modification of a nucleotide in a nucleic acid molecule. Example method 1020 may be a method of training a model for detecting the modification. The modification may include a methylation. The methylation may include any methylation described herein. The modification can have discrete states, such as methylated and unmethylated, and potentially specifying a type of methylation. Thus, there may be more than two states (classifications) of a nucleotide.

At block 1022, a plurality of first data structures is received. Various examples of data structures are described here, e.g., in FIGS. 4-16. Each first data structure of the first plurality of first data structures can correspond to a respective window of nucleotides sequenced in a respective nucleic acid molecule of a plurality of first nucleic acid molecules. Each window associated with the first plurality of data structures may include 4 or more consecutive nucleotides, including 5, 6, 7, 8, 9, 10, 11, 12, 13, 14, 15, 16, 17, 18, 19, 20, 21, or more consecutive nucleotides. Each window may have the same number of consecutive nucleotides. The windows may be overlapping. Each window may include nucleotides on a first strand of the first nucleic acid molecule and nucleotides on a second strand of the first nucleic acid molecule. The first data structure may also include for each nucleotide within the window a value of a strand property. The strand property may indicate the nucleotide being present or either the first strand or the second strand. The window may include nucleotides in the second strand that are not complementary to a nucleotide at a corresponding position in the first strand. In some embodiments, all nucleotides on the second strand are complementary to the nucleotides on the first strand. In some embodiments, each window may include nucleotides on only one strand of the first nucleic acid molecule.

The first nucleic acid molecule may be a circular DNA molecule. The circular DNA molecule may be formed by cutting a double-stranded DNA molecule using a Cas9 complex to form a cut double-stranded DNA molecule. A hairpin adaptor may be ligated onto an end of the cut double-stranded DNA molecule. In embodiments, both ends of a double-stranded DNA molecule may be cut and ligated. For example, cutting, ligation, and subsequent analysis may proceed as described with FIG. 91.

The first plurality of first data structures may include 5,000 to 10,000, 10,000 to 50,000, 50,000 to 100,000, 100,000 to 200,000, 200,000 to 500,000, 500,000 to 1,000,000, or 1,000,000 or more first data structures. The plurality of first nucleic acid molecules may include at least 1,000, 10,000, 50,000, 100,000, 500,000, 1,000,000, 5,000,000, or more nucleic acid molecules. As a further example, at least 10,000 or 50,000 or 100,000 or 500,000 or 1,000,000 or 5,000,000 sequence reads can be generated.

Each of the first nucleic acid molecules is sequenced by measuring pulses in a signal corresponding to the nucleotides. The signal may be a fluorescence signal, or other type of optical signal (e.g. chemiluminescence, photometric). The signal may result from the nucleotides or tags associated with the nucleotides.

The modification has a known first state in the nucleotide at a target position in each window of each first nucleic acid molecule. The first state may be that the modification is absent in the nucleotide or may be that the modification is present in the nucleotide. The modification may be known to absent in the first nucleic acid molecules, or the first nucleic acid molecules may undergo a treatment such that the modification is absent. The modification may be known to present in the first nucleic acid molecules, or the first nucleic acid molecules may undergo a treatment such that the modification is present. If the first state is that the modification is absent, the modification may be absent in each window of each first nucleic acid molecule and not absent only at the target position. The known first states may include a methylated state for a first portion of the first data structures and an unmethylated state for a second portion of the first data structures.

The target position may be the center of the respective window. For a window having spanning an even number of nucleotides, the target position may be the position immediately upstream or immediately downstream of the center of the window. In some embodiments, the target position may be at any other position of the respective window, including the first position or the last position. For example, if the window spans n nucleotides of one strand, from the $1^{st}$ position to the $n^{th}$ position (either upstream or downstream), the target position may be at any from the $1^{st}$ position to the $n^{th}$ position.

Each first data structure includes values for properties within the window. The properties may be for each nucleotide within the window. The properties may include an identity of the nucleotide. The identity may include the base (e.g., A, T, C, or G). The properties may also include a position of the nucleotide with respect to the target position within the respective window. For example, the position may be a nucleotide distance relative to the target position. The position may be +1 when the nucleotide is one nucleotide away from the target position in one direction, and the position may be −1 when the nucleotide is one nucleotide away from the target position in the opposite direction.

The properties may include a width of the pulse corresponding to the nucleotide. The width of the pulse may be the width of the pulse at half the maximum value of the pulse. The properties may further include an interpulse duration (IPD) representing a time between the pulse corresponding to the nucleotide and a pulse corresponding to a neighboring nucleotide. The interpulse duration may be the time between the maximum value of the pulse associated with the nucleotide and the maximum value of the pulse associated with the neighboring nucleotide. The neighboring nucleotide may be the adjacent nucleotide. The properties may also include a height of the pulse corresponding to each nucleotide within the window. The properties may further include a value of a strand property, which indicates whether the nucleotide is present on the first strand or the second strand of the first nucleic acid molecule. The indication of the strand may be similar to the matrix shown in FIG. 6.

Each data structure of the plurality of first data structures may exclude first nucleic acid molecules with an IPD or width below a cutoff value. For example, only first nucleic acid molecules with an IPD value greater than a $10^{th}$ percentile (or a $1^{st}$, $5^{th}$, $15^{th}$, $20^{th}$, $30^{th}$, $40^{th}$, $50^{th}$, $60^{th}$, $70^{th}$, $80^{th}$, $90^{th}$, or 95th percentile) may be used. The percentile may be based on data from all nucleic acid molecules in a reference sample or reference samples. The cutoff value of the width may also correspond to a percentile.

At block 1024, a plurality of first training samples is stored. Each first training sample includes one of the first plurality of first data structures and a first label indicating the first state for the modification of the nucleotide at the target position.

At block 1026, a second plurality of second data structures is received. Block 1026 may be optional. Each second data structure of the second plurality of second data structures corresponds to a respective window of nucleotides sequenced in a respective nucleic acid molecule of a plurality of second nucleic acid molecules. The second plurality of nucleic acid molecules may be the same or different as the plurality of first nucleic acid molecules. The modification has a known second state in a nucleotide at a target position within each window of each second nucleic acid molecule. The second state is a different state than the first state. For example, if the first state is that the modification is present, then the second state is that the modification is absent, and vice versa. Each second data structure includes values for the same properties as the first plurality of first data structures.

The plurality of first training samples may be generated using multiple displacement amplification (MDA). In some embodiments, the plurality of first training samples may be generated by amplifying a first plurality of nucleic acid molecules using a set of nucleotides. The set of nucleotides may include a first type of methylation (e.g., 6 mA or any other methylation [e.g., CpG]) at a specified ratio. The specified ratio may include 1:10, 1:100, 1:1000, 1:10000, 1:100000, or 1:1000000 relative to unmethylated nucleotides. The plurality of second nucleic acid molecules may be generated using multiple displacement amplification with unmethylated nucleotides of the first type.

At block 1028, a plurality of second training samples is stored. Block 1028 may be optional. Each second training sample includes one of the second plurality of second data structures and a second label indicating the second state for the modification of the nucleotide at the target position.

At block 1029, a model is trained using the plurality of first training samples and optionally the plurality of second training samples. The training is performed by optimizing parameters of the model based on outputs of the model matching or not matching corresponding labels of the first labels and optionally the second labels when the first plurality of first data structures and optionally the second plurality of second data structures are input to the model. An output of the model specifies whether the nucleotide at the target position in the respective window has the modification. The method may include only the plurality of first training samples because the model may identify an outlier as being of a different state than the first state. The model may be a statistical model, also referred to as a machine learning model.

In some embodiments, the output of the model may include a probability of being in each of a plurality of states. The state with the highest probability can be taken as the state.

The model may include a convolutional neural network (CNN). The CNN may include a set of convolutional filters configured to filter the first plurality of data structures and optionally the second plurality of data structures. The filter may be any filter described herein. The number of filters for each layer may be from 10 to 20, 20 to 30, 30 to 40, 40 to 50, 50 to 60, 60 to 70, 70 to 80, 80 to 90, 90 to 100, 100 to 150, 150 to 200, or more. The kernel size for the filters can be 2, 3, 4, 5, 6, 7, 8, 9, 10, 11, 12, 13, 14, 15, from 15 to 20, from 20 to 30, from 30 to 40, or more. The CNN may include an input layer configured to receive the filtered first plurality of data structures and optionally the filtered second plurality of data structures. The CNN may also include a plurality of hidden layers including a plurality of nodes. The first layer of the plurality of hidden layers coupled to the input layer. The CNN may further include an output layer coupled to a last layer of the plurality of hidden layers and configured to output an output data structure. The output data structure may include the properties.

The model may include a supervised learning model. Supervised learning models may include different approaches and algorithms including analytical learning, artificial neural network, backpropagation, boosting (meta-algorithm), Bayesian statistics, case-based reasoning, decision tree learning, inductive logic programming, Gaussian process regression, genetic programming, group method of data handling, kernel estimators, learning automata, learning classifier systems, minimum message length (decision trees, decision graphs, etc.), multilinear subspace learning, naive Bayes classifier, maximum entropy classifier, conditional random field, Nearest Neighbor Algorithm, probably approximately correct learning (PAC) learning, ripple down rules, a knowledge acquisition methodology, symbolic machine learning algorithms, subsymbolic machine learning algorithms, support vector machines, Minimum Complexity Machines (MCM), random forests, ensembles of classifiers, ordinal classification, data pre-processing, handling imbalanced datasets, statistical relational learning, or Proaftn, a multicriteria classification algorithm The model may linear regression, logistic regression, deep recurrent neural network (e.g., long short term memory, LSTM), Bayes classifier, hidden Markov model (HMM), linear discriminant analysis (LDA), k-means clustering, density-based spatial clustering of applications with noise (DBSCAN), random forest algorithm, support vector machine (SVM), or any model described herein.

As part of training a machine learning model, the parameters of the machine learning model (such as weights, thresholds, e.g., as may be used for activation functions in neural networks, etc.) can be optimized based on the training samples (training set) to provide an optimized accuracy in classifying the modification of the nucleotide at the target position. Various form of optimization may be performed, e.g., backpropagation, empirical risk minimization, and structural risk minimization. A validation set of samples (data structure and label) can be used to validate the accuracy of the model. Cross-validation may be performed using various portions of the training set for training and validation. The model can comprise a plurality of submodels, thereby providing an ensemble model. The submodels may be weaker models that once combined provide a more accurate final model.

In some embodiments, chimeric or hybrid nucleic acid molecules may be used to validate the model. At least some of the plurality of first nucleic acid molecules each include a first portion corresponding to a first reference sequence and a second portion corresponding to a second reference sequence. The first reference sequence may be from a different chromosome, tissue (e.g., tumor or non-tumor), organism, or species than the second reference sequence. The first reference sequence may be human and the second reference sequence may be from a different animal. Each chimeric nucleic acid molecule may include the first portion corresponding to the first reference sequence and the second portion corresponding to the second reference sequence. The first portion may have a first methylation pattern and the second portion may have a second methylation pattern. The first portion may be treated with a methylase. The second portion may not be treated with the methylase and may correspond to an unmethylated portion of the second reference sequence.

B. Detection of Modifications

FIG. 103 shows a method 1030 for detecting a modification of a nucleotide in a nucleic acid molecule. The modification may be any modification described with method 1020 of FIG. 102.

At block 1032, an input data structure is received. The input data structure may correspond to a window of nucleotides sequenced in a sample nucleic acid molecule. The sample nucleic acid molecule may be sequenced by measuring pulses in an optical signal corresponding to the nucleotides. The window may be any window described with block 1022 in FIG. 102, and the sequencing may be any sequencing described with block 1022 in FIG. 102. The input data structure may include values for the same properties described with block 1022 in FIG. 102. Method 1030 may include sequencing the sample nucleic acid molecule.

The nucleotides within the window may or may not be aligned to a reference genome. The nucleotides within the window may be determined using a circular consensus sequence (CCS) without alignment of the sequenced nucleotides to a reference genome. The nucleotides in each window may be identified by the CCS rather than aligning to a reference genome. In some embodiments, the window may be determined without a CCS and without alignment of the sequenced nucleotides to a reference genome.

The nucleotides within the window may be enriched or filtered. The enrichment may be by an approach involving Cas9. The Cas9 approach may include cutting a double-stranded DNA molecule using a Cas9 complex to form a cut double-stranded DNA molecule, and ligating a hairpin adaptor onto an end of the cut double-stranded DNA molecule, similar to FIG. 91. The filtering may be by selecting double-stranded DNA molecules having a size within a size range.

The nucleotides may be from these double-stranded DNA molecules. Other methods that preserve the methylation status of the molecules may be used (e.g., methyl-binding proteins).

At block 1034, the input data structure is inputted into a model. The model may be trained by method 1020 in FIG. 102.

In some embodiments, chimeric nucleic acid molecules may be used to validate the model. At least some of the plurality of first nucleic acid molecules each include a first portion corresponding to a first reference sequence and a second portion corresponding to a second reference sequence that is disjoint from the first reference sequence. The first reference sequence may be from a different chromosome, tissue (e.g., tumor or non-tumor), organelles (e.g.

mitochondria, nucleus, chloroplasts), organism (mammals, viruses, bacteria, etc.), or species than the second reference sequence. The first reference sequence may be human and the second reference sequence may be from a different animal. Each chimeric nucleic acid molecule may include the first portion corresponding to the first reference sequence and the second portion corresponding to the second reference sequence. The first portion may have a first methylation pattern and the second portion may have a second methylation pattern. The first portion may be treated with a methylase. The second portion may not be treated with the methylase and may correspond to an unmethylated portion of the second reference sequence.

At block 1036, whether the modification is present in a nucleotide at the target position within the window in the input data structure is determined using the model.

The input data structure may be one input data structure of a plurality of input data structures. Each input data structure may correspond to a respective window of nucleotides sequenced in a respective sample nucleic acid molecule of the plurality of sample nucleic acid molecules. The plurality of sample nucleic acid molecules may be obtained from a biological sample of a subject. The biological sample may be any biological sample described herein. Method 1030 may be repeated for each input data structure. The method may include receiving the plurality of input data structures. The plurality of input data structures may be inputted into the model. Whether a modification is present in a nucleotide at the target location in the respective window of each input data structure may be determined using the model.

Each sample nucleic acid molecule of the plurality of sample nucleic acid molecules may have a size greater than a cutoff size. For example, the cutoff size may be 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 9 kb, 10 kb, 20 kb, 30 kb, 40 kb, 50 kb, 60 kb, 70 kb, 80 kb, 90 kb, 100 kb, 500 kb, or 1 Mb. Having a size cutoff may result in a higher subread depth, either of which may increase the accuracy of the modification detection. In some embodiments, the method may include fractionating the DNA molecules for certain sizes prior to sequencing the DNA molecules.

The plurality of sample nucleic acid molecules may align to a plurality of genomic regions. For each genomic region of the plurality of genomic regions, a number of sample nucleic acid molecules may be aligned to the genomic region. The number of sample nucleic acid molecules may be greater than a cutoff number. The cutoff number may be a subread depth cutoff. The subread depth cutoff number may be 1×, 10×, 30×, 40×, 50×, 60×, 70×, 80×, 900×, 100×, 200×, 300×, 400×, 500×, 600×, 700×, or 800×. The subread depth cutoff number may be determined to improve or to optimize accuracy. The subread depth cutoff number may be related to the number of the plurality of genomic regions. For example, a higher subread depth cutoff number, a lower number of the plurality of genomic regions.

The modification may be determined to be present at one or more nucleotides. A classification of a disorder may be determined using the presence of the modification at one or more nucleotides. The classification of the disorder may include using the number of modifications. The number of modifications may be compared to a threshold. Alternatively or additionally, the classification may include the location of the one or more modifications. The location of the one or more modifications may be determined by aligning sequence reads of a nucleic acid molecule to a reference genome. The disorder may be determined if certain locations known to be correlated with the disorder are shown to have the modification. For example, a pattern of methylated sites may be compared to a reference pattern for a disorder, and the determination of the disorder may be based on the comparison. A match with the reference pattern or a substantial match (e.g., 80%, 90%, or 95% or more) with the reference pattern may indicate the disorder or a high likelihood of the disorder. The disorder may be cancer or any disorder (e.g., pregnancy-associated disorder, autoimmune disease) described herein.

A statistically significant number of nucleic acid molecules can be analyzed so as to provide an accurate determination for a disorder, tissue origin, or clinically-relevant DNA fraction. In some embodiments, at least 1,000 nucleic acid molecules are analyzed. In other embodiments, at least 10,000 or 50,000 or 100,000 or 500,000 or 1,000,000 or 5,000,000 nucleic acid molecules, or more, can be analyzed. As a further example, at least 10,000 or 50,000 or 100,000 or 500,000 or 1,000,000 or 5,000,000 sequence reads can be generated.

The method may include determining that the classification of the disorder is that the subject has the disorder. The classification may include a level of the disorder, using the number of modifications and/or the sites of the modifications.

A clinically-relevant DNA fraction, a fetal methylation profile, a maternal methylation profile, a presence of an imprinting gene region, or a tissue of origin (e.g., from a sample containing a mixture of different cell types) may be determined using the presence of the modification at one or more nucleotides. Clinically-relevant DNA fraction includes, but is not limited to, fetal DNA fraction, tumor DNA fraction (e.g., from a sample containing a mixture of tumor cells and non-tumor cells), and transplant DNA fraction (e.g., from a sample containing a mixture of donor cells and recipient cells).

The method may further include treating the disorder. Treatment can be provided according to a determined level of the disorder, the identified modifications, and/or the tissue of origin (e.g., of tumor cells isolated from the circulation of a cancer patient). For example, an identified modification can be targeted with a particular drug or chemotherapy. The tissue of origin can be used to guide a surgery or any other form of treatment. And, the level of disorder can be used to determine how aggressive to be with any type of treatment.

Embodiments may include treating the disorder in the patient after determining the level of the disorder in the patient. Treatment may include any suitable therapy, drug, chemotherapy, radiation, or surgery, including any treatment described in a reference mentioned herein. Information on treatments in the references are incorporated herein by reference.

VI. Haplotype Analysis

Differences in the methylation profiles between two haplotypes were found in samples of tumor tissue. Methylation imbalances between haplotypes may therefore be used to determine a classification of a level of cancer or other disorder. Imbalances in haplotypes may also be used to identify the inheritance of a haplotype by a fetus. Fetal disorders may also be identified through analyzing methylation imbalances between haplotypes. Cellular DNA may be used for analyzing methylation levels of haplotypes.

A. Haplotype-Associated Methylation Analysis

Single molecule, real-time sequencing technology allows the identification of individual SNPs. The long reads produced from single molecule, real-time sequencing wells (e.g., up to several kilobases) would allow for phasing variants in genomes by leveraging the haplotype information present in each consensus read (Edge et al. Genome Res. 2017; 27:801-812; Wenger et al. Nat Biotechnol. 2019; 37:1155-1162). The methylation profile of the haplotype could be analyzed from the methylation levels of the CpG sites linked by the CCS to the alleles on respective haplotypes, as illustrated in FIG. 77. This phased methylation haplotype analysis could be used to solve a question as to whether two copies of homologous chromosomes share the similar or different methylation patterns in different clinical-relevant conditions, such as cancer. In one embodiment, the haplotype methylation would be the aggregated methylation levels contributed from a number of DNA fragments assigned to that haplotype. The haplotype could be blocks in different sizes, including but not limited to, 50 nt, 100 nt, 200 nt, 300 nt, 400 nt, 500 nt, 1 knt, 2 knt, 3 knt, 4 knt, 5 knt, 10 knt, 20 knt, 30 knt, 40 knt, 50 knt, 100 knt, 200 knt, 300 knt, 400 knt, 500 knt, 1 Mnt, 2 Mnt, and 3 Mnt.

B. Relative Haplotype-Based Methylation Imbalance Analysis

Figure 104:
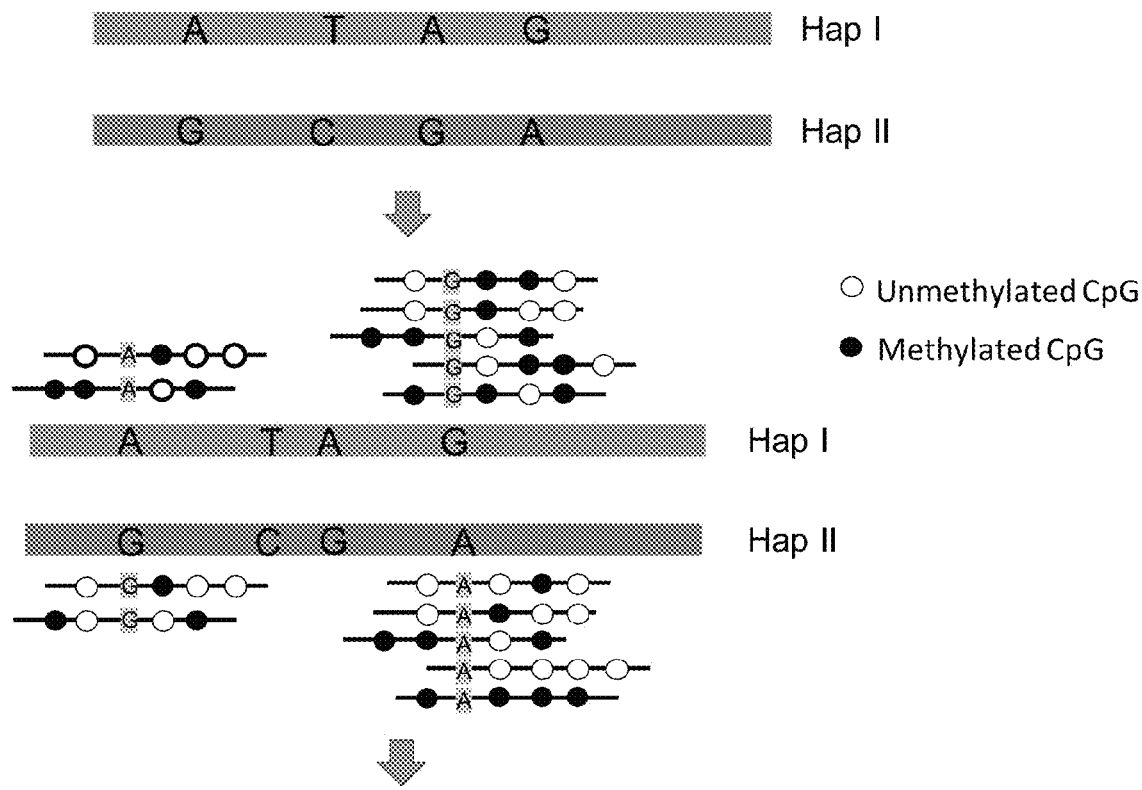
FIG. 104 illustrates relative haplotype-based methylation imbalance analysis according to embodiments of the present invention.

FIG. 104 illustrates relative haplotype-based methylation imbalance analysis. The haplotypes (i.e., Hap I and Hap II) were determined by analyzing single molecule, real-time sequencing results. The methylation patterns linked to each haplotype could be determined using those haplotype-associated fragments whose methylation profiles were determined according to the approach described in FIG. 77. Thereby, the methylation patterns between Hap I and Hap II could be compared.

To quantify the difference in methylation between Hap I and Hap II, the difference of methylation levels (ΔF) between Hap I and Hap II were calculated. The difference ΔF is calculated as:

$$\Delta F = M_{HapI} - M_{HapII}$$

where ΔF represents the difference in the methylation level between the Hap I and Hap II, and $M_{HapI}$ and $M_{HapII}$ represent the methylation levels of Hap I and Hap II, respectively. A positive value of ΔF suggested a higher methylation level of DNA for Hap I compared with the Hap II.

C. Relative Haplotype-Based Methylation Imbalance Analysis for HCC Tumor DNA

In one embodiment, the haplotype methylation analysis may be useful to detect methylation aberrations in cancer genomes. For example, the methylation change between two haplotypes within a genomic region would be analyzed. A haplotype within a genomic region is defined as a haplotype block. A haplotype block could be considered as a set of alleles on a chromosome that have been phased. In some embodiments, a haplotype block would be extended as long as possible according to a set of sequence information which supports two alleles physically linked on a chromosome. For case 3033, we obtained 97,475 haplotype blocks from the sequencing results of adjacent normal tissue DNA. The median size of haplotype blocks was 2.8 kb. 25% of haplotype blocks were greater than 8.2 kb in size. The maximal size of haplotype blocks was 282.2 kb. The data set was generated from DNA prepared by the Sequel II Sequencing Kit 1.0.

For illustration purposes, we used a number of criteria to identify the potential haplotype blocks which exhibited the differential methylation between Hap I and Hap II in the tumor DNA compared with the adjacent non-tumoral tissue DNA. The criteria were: (1) the haplotype block being analyzed contained at least 3 three CCS sequences which were produced from three sequencing wells, respectively; (2) the absolute difference in methylation level between Hap I and Hap II in the adjacent non-tumoral tissue DNA was less than 5%; (3) the absolute difference in methylation level between Hap I and Hap II in the tumor tissue DNA was greater than 30%. We identified 73 haplotype blocks fulfilling the above criteria.

FIGS. 105A and 105B are tables of the 73 haplotype blocks showing differential methylation levels between Hap I and Hap II in the HCC tumor DNA compared with the adjacent non-tumoral tissue DNA for the case TBR3033. The first column shows the chromosome associated with the haplotype block. The second column shows the starting coordinate of the haplotype block within the chromosome. The third column shows the ending coordinate of the haplotype block. The fourth column shows the length of the haplotype block. The fourth column lists the haplotype block id. The fifth column shows the methylation level of Hap I in non-tumoral tissue adjacent to tumor tissue. The sixth column shows the methylation level of Hap II in the non-tumoral tissue. The seventh column shows the methylation level of Hap I in tumor tissue. The eighth column shows the methylation level of Hap II in tumor tissue.

In contrast to the 73 haplotype blocks showing a greater than 30% difference in methylation level between haplotypes for tumor tissue DNA, only one haplotype block showed a greater than 30% difference for non-tumoral tissue DNA but less than 5% difference in tumoral tissue DNA. In some embodiments, another set of criteria could be used to identify the haplotype blocks displaying differential methylations. Other maximum and minimum threshold differences may be used. For example, minimum threshold differences may be 10%, 15%, 20%, 25%, 30%, 35%, 40%, 45%, 50%, or more. Maximum threshold differences may be 1%, 5%, 10%, 15%, 20%, or 30%, as examples. These results suggested that the variation of methylation difference between haplotypes may serve as a new biomarker for cancer diagnosis, detection, monitoring, prognostication and guidance for treatment.

In some embodiments, a long haplotype block would be, in silico, partitioned into smaller blocks when studying the methylation patterns.

For case 3032, we obtained 61,958 haplotype blocks from the sequencing results of adjacent non-tumoral tissue DNA. The median size of haplotype blocks was 9.3 kb. 25% of haplotype blocks were greater than 27.6 kb in size. The maximal size of haplotype blocks was 717.8 kb. As an illustration, we used the same three criteria described above to identify the potential haplotype blocks which exhibited the differential methylation between Hap I and Hap II in the tumor DNA compared with the adjacent normal tissue DNA. We identified 20 haplotype blocks fulfilling the above criteria. The data set was generated from DNA prepared by the Sequel II Sequencing Kit 1.0.

FIG. 106 is a table of the 20 haplotype blocks showing differential methylation levels between Hap I and Hap II in the tumor DNA compared with the adjacent normal tissue DNA for the case TBR3032. The first column shows the chromosome associated with the haplotype block. The second column shows the starting coordinate of the haplotype block within the chromosome. The third column shows the ending coordinate of the haplotype block. The fourth column shows the length of the haplotype block. The fourth column lists the haplotype block id. The fifth column shows the methylation level of Hap I in non-tumoral tissue adjacent to tumor tissue. The sixth column shows the methylation level of Hap II in the non-tumoral tissue. The seventh column shows the methylation level of Hap I in tumor tissue. The eighth column shows the methylation level of Hap II in tumor tissue.

In contrast to the 20 haplotype blocks showing the difference in HCC tumor tissue in FIG. 106, only one haplotype block showed a difference of greater than 30% in non-tumoral tissue but less than 5% in tumoral tissue. These results further suggest that the variation of methylation difference between haplotypes would serve as a new biomarker for cancer diagnosis, detection, monitoring, prognostication and guidance for treatment. For other embodiments, other criteria could be used to identify the haplotype blocks displaying differential methylations.

D. Relative Haplotype-Based Methylation Imbalance Analysis for DNA from Other Tumor Types As stated above, the analysis of methylation levels between haplotype revealed that HCC tumor tissues harbored more haplotype blocks displaying methylation imbalance in comparison with paired adjacent non-tumoral tissues. As one example, the criteria for a haplotype block showing methylation imbalance in a tumor tissue were: (1) the haplotype block being analyzed contained at least three CCS sequences which were produced from three sequencing wells; (2) the absolute difference in methylation level between Hap I and Hap II in the adjacent non-tumoral tissue DNA or normal tissue DNA based on historical data was less than 5%; (3) the absolute difference in methylation level between Hap I and Hap II in the tumor tissue DNA was greater than 30%. Criterion (2) was included because non-tumoral/normal tissues showing haplotype imbalance in methylation levels may indicate imprinted regions rather than tumor regions. The criteria for a haplotype block showing methylation imbalance in a non-tumor tissue were: (1) the haplotype block being analyzed contained at least three CCS sequences which were produced from three sequencing wells; (2) the absolute difference in methylation level between Hap I and Hap II in the adjacent non-tumoral tissue DNA or normal tissue DNA based on historical data was greater than 30%; (3) the absolute difference in methylation level between Hap I and Hap II in the tumor tissue DNA was less than 5%.

In other embodiments, other criteria can be used. For example, to identify the imbalance haplotype I cancer genome, the difference in methylation level between Hap I and Hap II may be less than 1%, 5%, 10%, 20%, 40%, 50%, or 60%, etc., in non-tumoral tissues, whereas the difference in methylation level between Hap I and Hap II may be greater than 1%, 5%, 10%, 20%, 40%, 50%, or 60%, etc., in tumoral tissues. To identify the imbalance haplotype I non-cancer genome, the difference in methylation level between Hap I and Hap II may be greater than 1%, 5%, 10%, 20%, 40%, 50%, or 60%, etc., in non-tumoral tissues, whereas the difference in methylation level between Hap I and Hap II may be less than 1%, 5%, 10%, 20%, 40%, 50%, or 60%, etc., in tumoral tissues.

FIG. 107A is a table summarizing the number of haplotype blocks showing methylation imbalance between two haplotypes between tumor and adjacent nontumoral tissues on the basis of data generated by Sequel II Sequencing Kit 2.0. The first column lists the tissue type. The second column lists the number of haplotype blocks showing methylation imbalance between two haplotypes in tumor tissues. The third column lists the number of haplotype blocks showing methylation imbalance between two haplotypes in paired adjacent non-tumoral tissues. The rows show tumor tissue with more haplotype blocks showing methylation imbalance between two haplotypes than the paired adjacent non-tumoral tissue.

The median length of haplotype blocks involved in this analysis was 15.7 kb (IQR: 10.3-26.1 kb). Including HCC results for liver, the data show 7 tissue types for which tumor tissue harbored more haplotype blocks with methylation imbalance. In addition to liver, the other tissues include colon, breast, kidney, lung, prostate and stomach tissues. Thus, in some embodiments, one could use the number of haplotype blocks harboring methylation imbalance to detect whether a patient had a tumor or cancer.

FIG. 107B is a table summarizing the number of haplotype blocks showing methylation imbalance between two haplotypes in tumor tissues for different tumor stages on the basis of data generated by Sequel II Sequencing Kit 2.0. The first column shows the tissue type with a tumor. The second column shows the number of haplotype blocks with a methylation imbalance between two haplotypes in tumor tissues. The third column lists the tumor staging information using the TNM classification of malignant tumors. T3 and T3a are larger sizes of tumor than T2.

The table shows more haplotype blocks showing methylation imbalance for larger tumors for both breast and kidney. For example, for breast tissue, tissue categorized as tumor grade T3 (TNM staging), ER positive, and exhibiting ERBB2 amplification had more haplotype blocks (57) showing a methylation imbalance than haplotype blocks (18) for tissue categorized as tumor grade T2 (TNM staging), PR (progesterone receptor)/ER (estrogen receptor) positive, and no ERBB2 amplification. For kidney tissue, tissue categorized as tumor grade T3a had more haplotype blocks (68) showing methylation imbalance than haplotype blocks (0) for tissue categorized as tumor grade T2.

In some embodiments, one can make use of haplotype blocks showing methylation imbalance for the classification of tumors and to correlate with their clinical behavior (e.g. progression, prognosis, or treatment response). These data suggested that the degree of haplotype-based methylation imbalance can serve as a classifier of tumors and can be incorporated in clinical studies or trials or eventual clinical services. Classification of tumors may include size and severity.

E. Haplotype-Based Methylation Analysis of Maternal Plasma Cell-Free DNA

Haplotypes of both parents or either parent can be determined. Haplotyping methods can include long read single-molecule sequencing, linked short-read sequencing (e.g. 10× genomics), long range single-molecule PCR, or population inference. If the paternal haplotypes are known, the cell-free fetal DNA methylome can be assembled by linking the methylation profiles of multiple cell-free DNA molecules each containing at least one paternal specific SNP allele that are present along the paternal haplotype. In other words, the paternal haplotype is used as a scaffold to link the fetal-specific read sequences.

Figure 108:
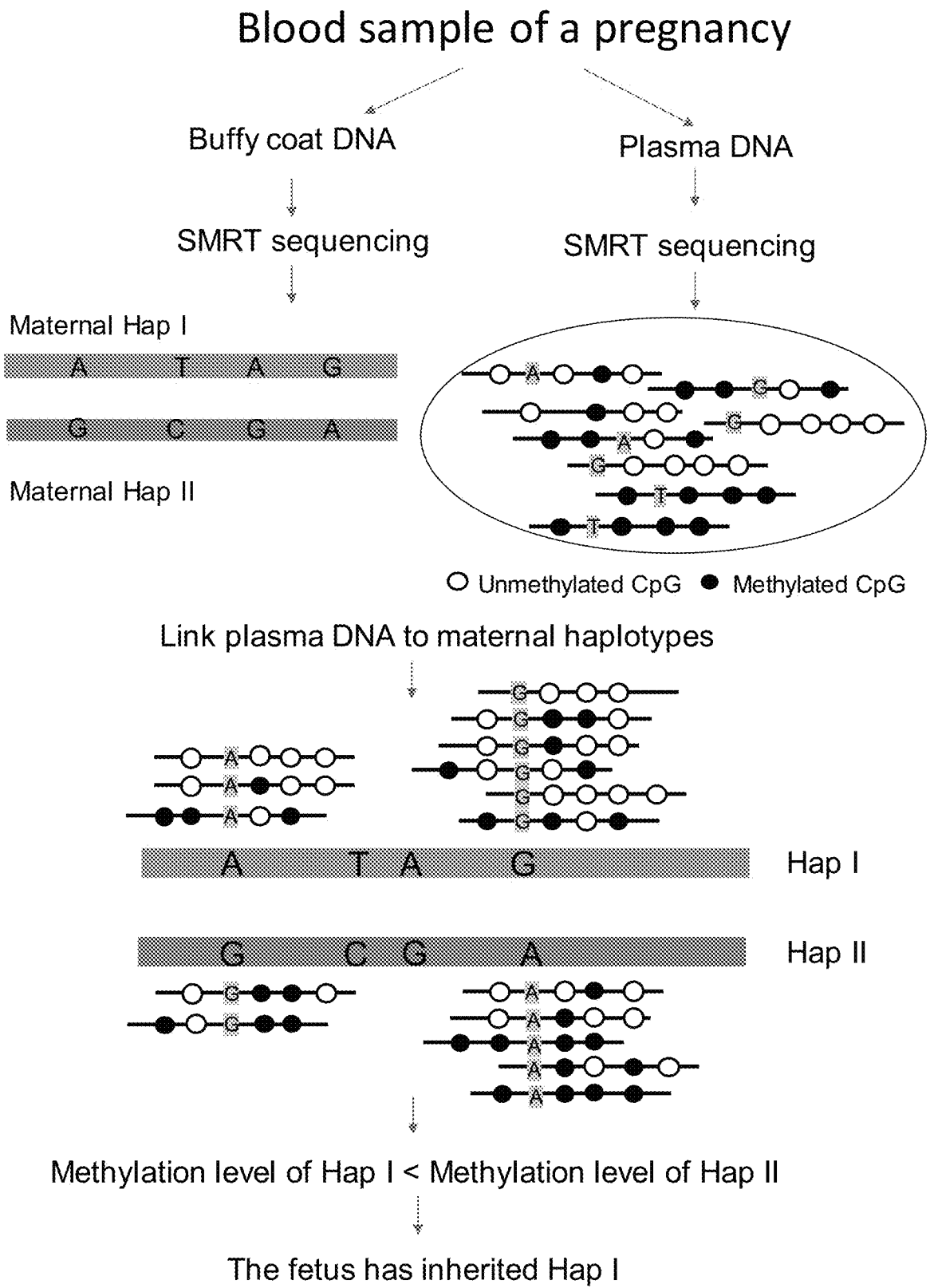
FIG. 108 illustrates relative haplotype-based methylation imbalance analysis according to embodiments of the present invention.

FIG. 108 illustrates analysis of haplotypes for relative methylation imbalance. If the maternal haplotypes are known, methylation imbalance between the two haplotypes (i.e. Hap I and Hap II) can be used to determine the fetally inherited maternal haplotype. As shown in FIG. 108, plasma DNA molecules from a pregnant woman are sequenced using single molecule, real-time sequencing technology. The methylation and allelic information can be determined according to the disclosure herein. In one embodiment, the SNPs linked to a disease-causing gene are assigned as Hap I. If the fetus has inherited Hap I, more fragments carrying alleles of Hap I would be present in maternal plasma in comparison with those carrying alleles of Hap II. The hypomethylation of DNA fragments derived from the fetus would lower the methylation level of Hap I compared to that of Hap II. As a result, if the methylation of Hap I shows a lower methylation level than Hap II, the fetus is more likely to inherit maternal Hap I. Otherwise, the fetus is more likely to inherit maternal Hap II. In clinical practice, haplotype-based methylation imbalance analysis can be used to determine whether an unborn fetus has inherited a maternal haplotype associated with genetic disorders, for example, but not limited to, single-gene disorders including fragile X syndrome, muscular dystrophy, Huntington disease, or beta-thalassemia.

F. Example Disorder Classification Method

Figure 109:
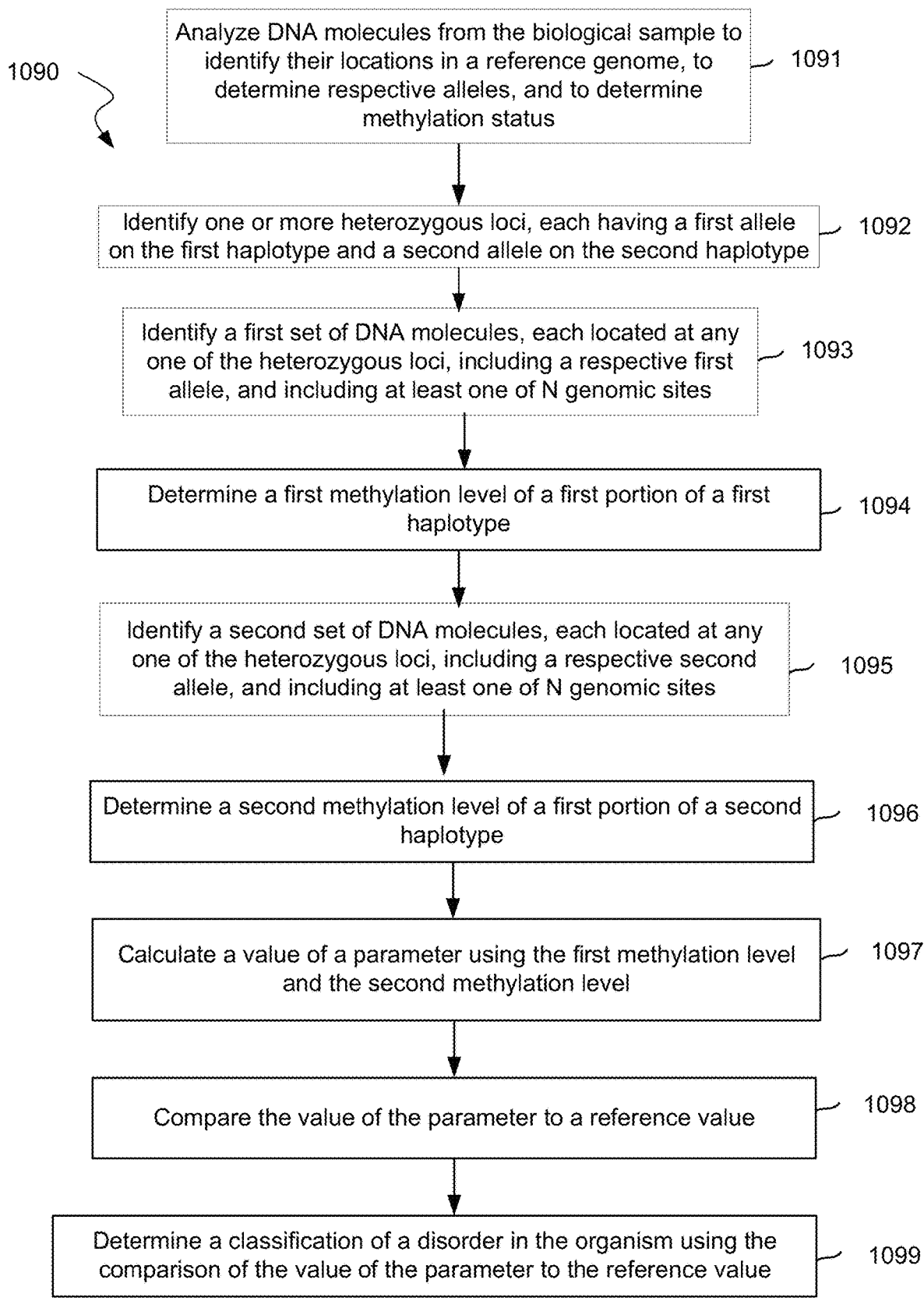
FIG. 109 shows a method of classifying a disorder in an organism having a first haplotype and a second haplotype according to embodiments of the present invention.

FIG. 109 shows an example method 1090 of classifying a disorder in an organism having a first haplotype and a second haplotype. Method 1090 involves comparing the relative methylation levels between two haplotypes.

At block 1091, DNA molecules from the biological sample are analyzed to identify their locations in a reference genome corresponding to the organism. The DNA molecules may be cellular DNA molecules. For example, the DNA molecules can be sequenced to obtain sequence reads, and the sequence reads can be mapped (aligned) to the reference genome. If the organism was a human, then the reference genome would be a reference human genome, potentially from a particular subpopulation. As another example, the DNA molecules can be analyzed with different probes (e.g., following PCR or other amplification methods), where each probe corresponds to a genomic location, which may cover a heterozygous and one or more CpG sites, as is described below.

Further, the DNA molecules can be analyzed to determine a respective allele of the DNA molecule. For example, an allele of a DNA molecule can be determined from a sequence read obtained from sequencing or from a particular probe that hybridizes to the DNA molecule, where both techniques can provide a sequence read (e.g., the probe can be treated as the sequence read when there is hybridization). A methylation status at each of one or more sites (e.g., CpG sites) can be determined for the DNA molecules.

At block 1092, one or more heterozygous loci of a first portion of the first chromosomal region are identified. Each heterozygous locus can include a corresponding first allele in the first haplotype and a corresponding second allele in the second haplotype. The one or more heterozygous loci may be a first plurality of heterozygous loci, where a second plurality of heterozygous loci can correspond to a different chromosomal region.

At block 1093, a first set of the plurality of DNA molecules is identified. Each of the plurality of DNA molecules is located at any one of the heterozygous loci from block 1096 and includes a corresponding first allele, so that the DNA molecule can be identified as corresponding to the first haplotype. It is possible for a DNA molecule to be located at more than one of the heterozygous loci, but typically a read would only include one heterozygous locus. Each of the first set of DNA molecules also includes at least one of N genomic sites, where the genomic sites are used to measure the methylation levels. N is an integer, e.g., greater than or equal to 1, 2, 3, 4, 5, 10, 20, 50, 100, 200, 500, 1,000, 2,000, or 5,000. Thus, a read of a DNA molecule can indicate coverage of 1 site, 2 sites, etc. The 1 genomic site may include a site at which a CpG nucleotide is present.

At block 1094, a first methylation level of the first portion of the first haplotype is determined using the first set of the plurality of DNA molecules. The first methylation level may be determined by any method described herein. The first portion can correspond to a single site or include many sites. The first portion of the first haplotype may be longer than or equal to 1 kb. For example, the first portion of the first haplotype may be longer than or equal to 1 kb, 5 kb, 10 kb, 15 kb, or 20 kb. The methylation data may be data from cellular DNA.

In some embodiments, a plurality of first methylation levels may be determined for a plurality of portions of the first haplotype. Each portion may have a length of greater than or equal to 5 kb or any size disclosed herein for the first portion of the first haplotype.

At block 1095, a second set of the plurality of DNA molecules is identified. Each of the plurality of DNA molecules is located at any one of the heterozygous loci from block 1096 and includes a corresponding second allele, so that the DNA molecule can be identified as corresponding to the second haplotype. Each of the second set of DNA molecules also includes at least one of the N genomic sites, where the genomic sites are used to measure the methylation levels.

At block 1096, a second methylation level of the first portion of a second haplotype is determined using the second set of the plurality of DNA molecules. The second methylation level may be determined by any method described herein. The first portion of the second haplotype may be longer than or equal to 1 kb or any size for the first portion of the first haplotype. The first portion of the first haplotype may be complementary to the first portion of the second haplotype. The first portion of the first haplotype and the first portion of the second haplotype may form a circular DNA molecule. The first methylation level of the first portion of the first haplotype may be determined using data from the circular DNA molecule. For example, the analysis of the circular DNA may include analysis described with FIG. 1, FIG. 2, FIG. 4, FIG. 5, FIG. 6, FIG. 7, FIG. 8, FIG. 50, or FIG. 61.

The circular DNA molecule may be formed by cutting a double-stranded DNA molecule using a Cas9 complex to form a cut double-stranded DNA molecule. A hairpin adaptor may be ligated onto an end of the cut double-stranded DNA molecule. In embodiments, both ends of a double-stranded DNA molecule may be cut and ligated. For example, cutting, ligation, and subsequent analysis may proceed as described with FIG. 91.

In some embodiments, a plurality of second methylation levels may be determined for a plurality of portions of the second haplotype. Each portion of the plurality of portions of the second haplotype may be complementary to a portion of the plurality of portions of the first haplotype.

At block 1097, a value of a parameter is calculated using the first methylation level and the second methylation level. The parameter may by a separation value. The separation value may be a difference between the two methylation levels or a ratio of the two methylation levels.

If a plurality of portions of the second haplotype are used, then for each portion of the plurality of portions of the second haplotype, a separation value may be calculated using the second methylation level of the portion of the second haplotype and the first methylation level using the complementary portion of the first haplotype. The separation value may be compared to a cutoff value.

The cutoff value may be determined from tissues not having the disorder. The parameter may be the number of portions of the second haplotype where the separation value exceeds the cutoff value. For example, the number of portions of the second haplotype where the separation value exceeds the cutoff value may be similar to the number of regions shown having a difference of greater than 30% in FIG. 105A, FIG. 105B, and FIG. 106. With FIG. 105A, FIG. 105B, and FIG. 106, the separation value is a ratio, and the cutoff value is 30%. In some embodiments, the cutoff value may be determined from tissues having the disorder.

In another example, the separation value for each portion can be aggregated, e.g., summed, which may be done by a weighted sum or a sum of functions of the respect separation values. Such aggregation can provide the value of the parameter.

At block 1098, the value of the parameter is compared to a reference value. The reference value may be determined using a reference tissue without the disorder. The reference value may be a separation value. For example, the reference value may represent that there should be no significant difference between methylation levels of the two haplotypes. For example, the reference value may be a statistical difference of 0 or a ratio of about 1. When a plurality of portions is used, the reference value may be a number of portions in a healthy organism where the two haplotypes show a separation value exceeding the cutoff value. In some embodiments, the reference value may be determined using a reference tissue with the disorder.

At block 1099, the classification of the disorder in the organism is determined using the comparison of the value of the parameter to the reference value. The disorder may be determined to be present or more likely if the value of the parameter exceeds the reference value. The disorder may include cancer. The cancer may be any cancer described herein. The classification of the disorder may be a likelihood of the disorder. The classification of the disorder may include a severity of the disorder. For example, a larger parameter value indicating a larger number of portions with a haplotype imbalance may indicate a more severe form of cancer.

While the method described with FIG. 109 involves a classification of a disorder, similar methods may be used to determine any condition or characteristic that may result from an imbalance in methylation levels between haplotypes. For example, the methylation level of a haplotype from fetal DNA may be lower than the methylation of a haplotype from maternal DNA. Methylation levels may be used to classify nucleic acids as being maternal or fetal.

When the disorder is cancer, different chromosomal regions of a tumor may exhibit such differences in methylation. Depending on which regions are affected, different treatment may be provided. Further, subject having different regions exhibiting such differences in methylation can have different prognoses.

Chromosomal regions (portions) that have a sufficient separation (e.g., greater than a cutoff value) can be identified as being aberrant (or having aberrant separation). A pattern of aberrant region (potentially accounting for which haplotype is higher than the other) can be compared to a reference pattern (e.g., as determined from a subject having cancer, potentially a particular type of cancer, or a healthy subject). If the two patterns are the same within a threshold (e.g., less than a specified number of regions/portions that differ) than a reference pattern having a particular classification, the subject can be identified as having that classification for the disorder. Such a classification can include an imprinting disorder, e.g., as described herein.

VII. Single-Molecule Methylation Analysis for Hybrid Molecules

To further evaluate the performance and utility of the embodiments disclosed herein regarding the determination of base modifications of nucleic acids, we artificially created human and mouse hybrid DNA fragments for which the human part was methylated and the mouse part was unmethylated, or vice versa. Determining junctions of hybrid or chimeric DNA molecules may allow for detecting gene fusions for various disorders or diseases, including cancer.

A. Methods to Create Human and Mouse Hybrid DNA Fragments

This section describes creating hybrid DNA fragments and then a procedure for determining methylation profiles of the fragments.

In one embodiment, the human DNA was amplified through whole genome amplification such that the original methylation signature in the human genome would be eliminated because whole genome amplification would not preserve the methylation states. The whole genome amplification could be performed using exonuclease-resistant thiophosphate-modified degenerate hexamers as primers which could bind at random over a genome, allowing the polymerase (e.g. Phi29 DNA polymerase) to amplify the DNA without thermal cycling. The amplified DNA product would be unmethylated. The amplified human DNA molecules were further treated with M.SssI, a CpG methyltransferase, which would in theory completely methylate all cytosines at the CpG context in double-stranded, non-methylated or hemimethylated DNA. Thus, such amplified human DNA treated by M.SssI would become methylated DNA molecules.

By contrast, the mouse DNA was subjected to whole genome amplification so that the unmethylated mouse DNA fragments would be produced.

Figure 110:
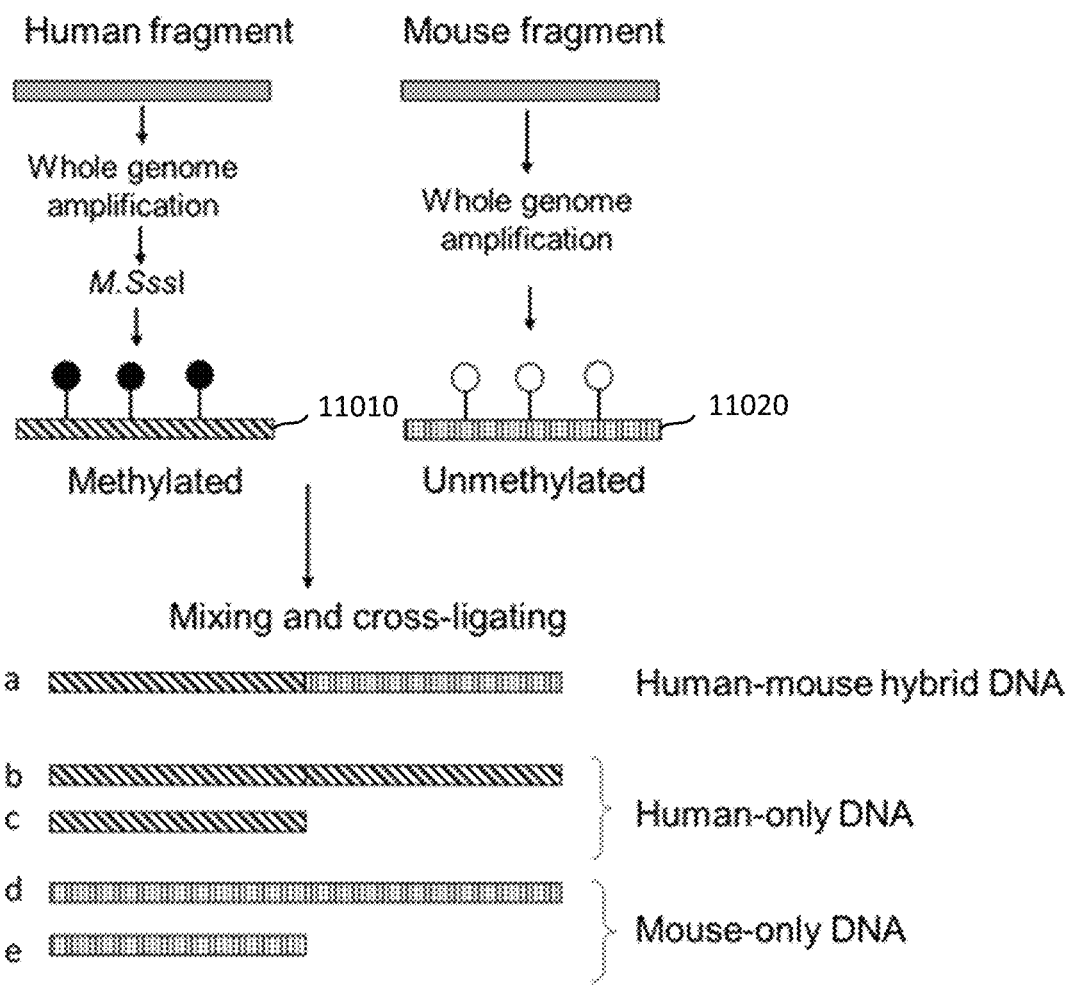
FIG. 110 illustrates creating human-mouse hybrid fragments for which the human part is methylated while the mouse part is unmethylated according to embodiments of the present invention.

FIG. 110 illustrates creating human-mouse hybrid DNA fragments for which the human part is methylated while the mouse part is unmethylated. The filled lollipops represent methylated CpG sites. The unfilled lollipops represent unmethylated CpG sites. The thick bar 11010 with diagonal stripes represents the methylated human part. The thick bar 11020 with vertical stripes represents the unmethylated mouse part.

For generation of hybrid human-mouse DNA molecules, in one embodiment, the whole-genome amplified and M.SssI-treated DNA molecules were further digested with HindIII and NcoI to generate sticky ends for facilitating downstream ligation. In one embodiment, the methylated human DNA fragments were further mixed with the unmethylated mouse DNA fragments in an equimolar ratio. Such a human-mouse DNA mixture was subjected to a ligation process, which in one embodiment was mediated by DNA ligase at 20° C. for 15 minutes. As shown in FIG. 110, this ligation reaction would produce 3 types of resultant molecules, including human-mouse hybrid DNA molecules (a: human-mouse hybrid fragments); human-only DNA molecules (b: human-human ligation, and c: human DNA without ligation); and mouse-only DNA molecules (d: mouse-mouse ligation and e: mouse DNA without ligation). The DNA product after ligation was subjected to single molecule, real-time sequencing. The sequencing results were analyzed according to the disclosure provided herein for determining the methylation states.

Figure 111:
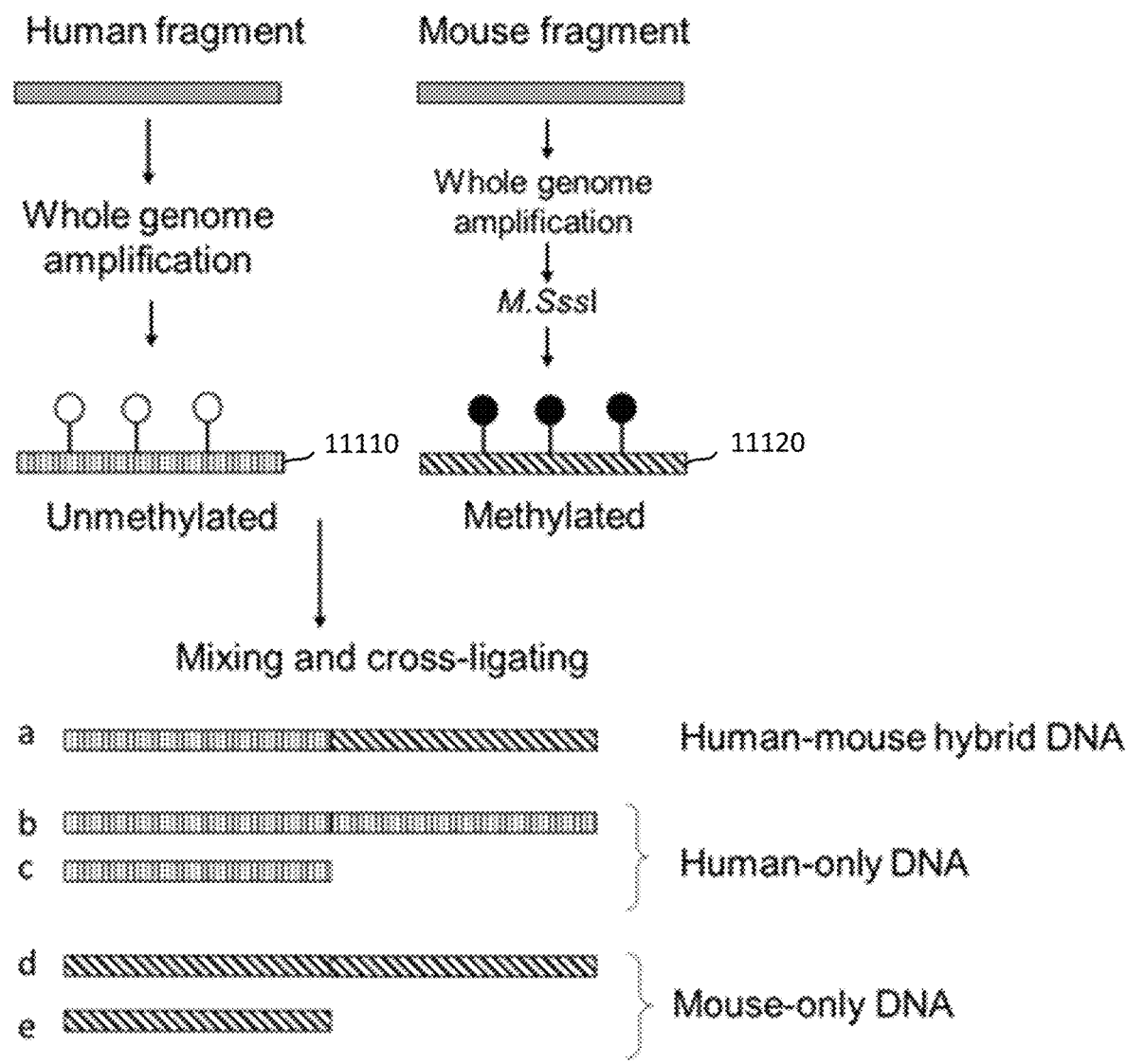
FIG. 111 illustrates creating human-mouse hybrid fragments for which the human part is unmethylated while the mouse part is methylated according to embodiments of the present invention.

FIG. 111 illustrates creating human-mouse hybrid DNA fragments for which the human part is unmethylated while the mouse part is methylated. The filled lollipops represent methylated CpG sites. The unfilled lollipops represent unmethylated CpG sites. The thick bar 11110 with diagonal stripes represents the methylated mouse part. The thick bar 11120 with vertical stripes represents the unmethylated human part.

For the embodiment in FIG. 111, the mouse DNA molecules were amplified through whole genome amplification such that the original methylation in the mouse genome would be eliminated. The amplified DNA product would be unmethylated. The amplified mouse DNA would be further treated with M.SssI. Thus, such amplified mouse DNA treated by M.SssI would become methylated DNA molecules. In contrast, the human DNA fragments were subjected to whole genome amplification so that the unmethylated human fragments would be obtained. In one embodiment, the methylated human fragments were further mixed with the unmethylated fragments in an equimolar ratio. Such a human-mouse DNA mixture was subjected to a ligation process mediated by DNA ligase. As shown in FIG. 111, this ligation reaction would produce 3 types of resultant molecules, including human-mouse hybrid DNA molecules (a: human-mouse hybrid fragments); human-only DNA molecules (b: human-human ligation, and c: human DNA without ligation); and mouse-only DNA molecules (d: mouse-mouse ligation and e: mouse DNA without ligation). The DNA product after ligation was subjected to single molecule, real-time sequencing. The sequencing results were analyzed according to the disclosure provided herein for determining the methylation states.

According to the embodiment shown in FIG. 110, we prepared an artificial DNA mixture (named sample MIX01) comprising human-mouse hybrid DNA molecules, human-only DNA and mouse-only DNA for which the human-associated DNA molecules were methylated whereas the mouse DNA molecules were unmethylated. For the sample MIX01, we obtained 166 million subreads which could be aligned either to a human or mouse reference genome, or partially to a human genome and partially to a mouse genome. These subreads were generated from approximately 5 million Pacific Biosciences Single Molecular Real-Time (SMRT) sequencing wells. Each molecule in a single molecule real-time sequencing well was sequenced on average 32 times (range: 1-881 times).

To determine the human DNA and mouse DNA part in a hybrid fragment, we first constructed consensus sequences by combining the nucleotide information from all relevant subreads in a well. In total, we obtained 3,435,657 consensus sequences for sample MIX01. The data set was generated from DNA prepared by the Sequel II Sequencing Kit 1.0.

The consensus sequences were aligned to the reference genomes comprising both the human and mouse references. We obtained 3.2 million aligned consensus sequences. Among them, 39.6% of them were classified as human-only DNA type; 26.5% of them were classified as mouse-only DNA type, and 30.2% of them were classified as human-mouse hybrid DNA.

Figure 112:
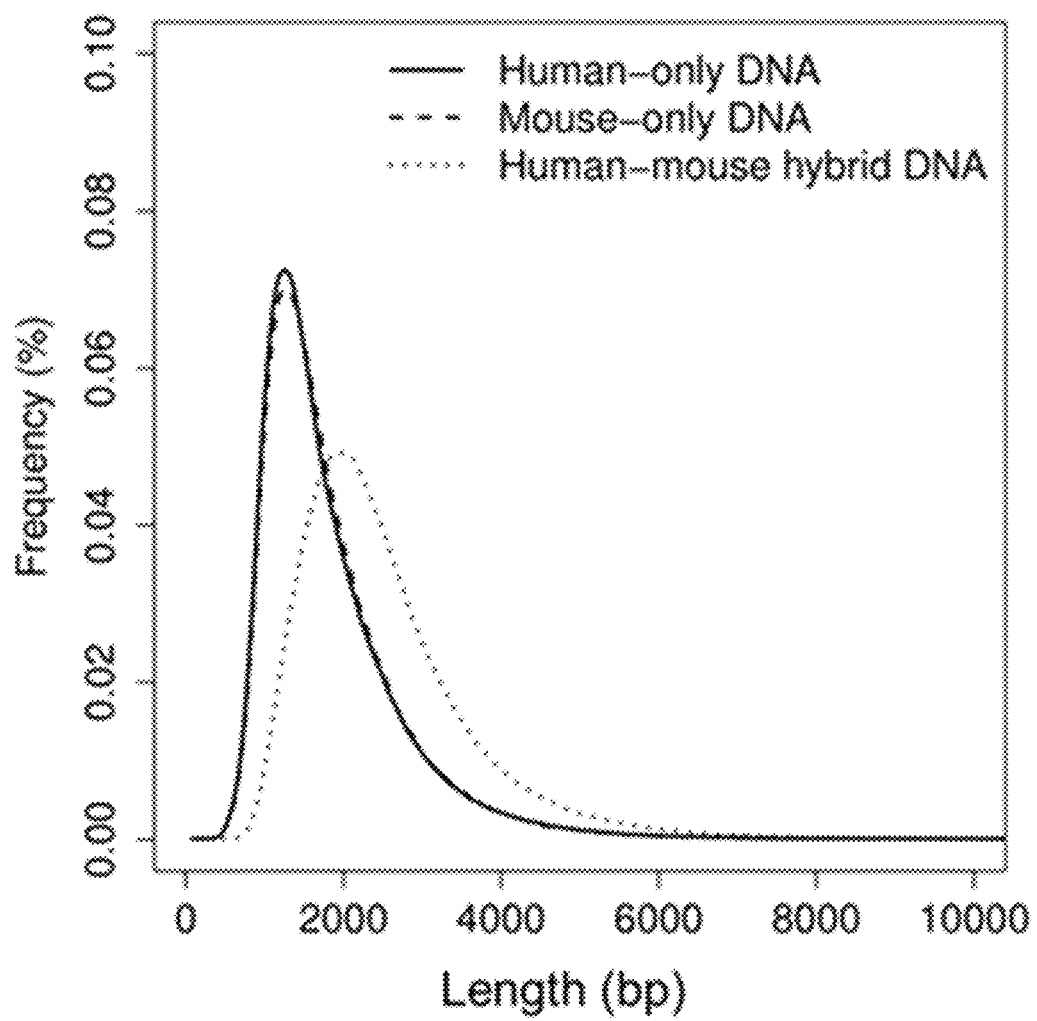
FIG. 112 shows the length distribution of DNA molecules in a DNA mixture (sample MIX01) after ligation according to embodiments of the present invention.

FIG. 112 shows the length distribution of DNA molecules in the DNA mixture after ligation (sample MIX01). The x-axis shows the length of a DNA molecule. The y-axis shows the frequency associated with the length of the DNA molecule. As shown in FIG. 112, the human-mouse hybrid DNA molecules had a longer length distribution which was consistent with the fact that they were a combination of at least two types of molecules.

Figure 113:
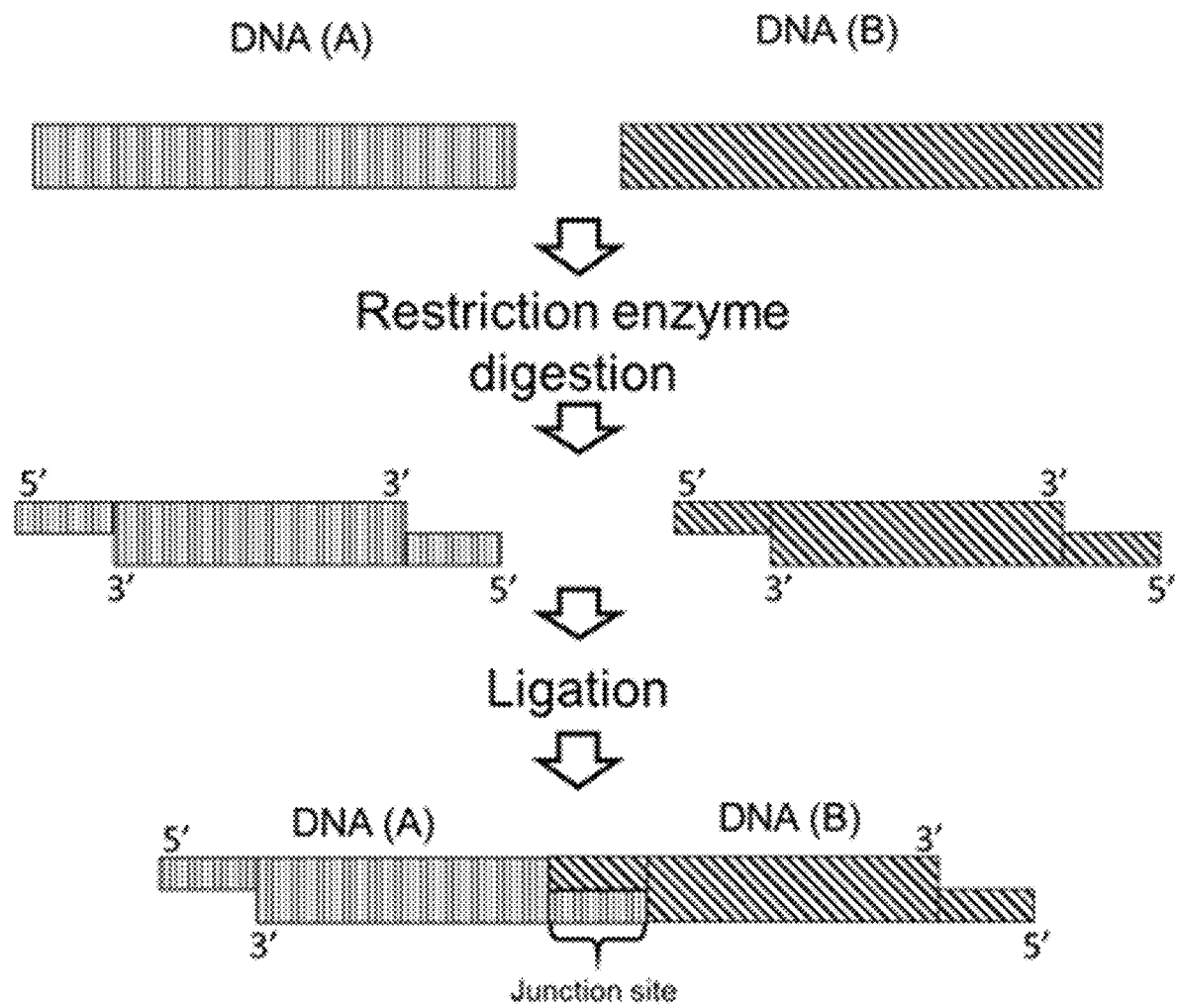
FIG. 113 illustrates a junction region by which a first DNA (A) and a second DNA (B) are joined together according to embodiments of the present invention.

FIG. 113 illustrates a junction region by which a first DNA (A) and a second DNA (B) are joined together. DNA (A) and DNA (B) may be digested with a restriction enzyme. In one embodiment, to improve the efficiency of ligation using the staggered ends, we used the restriction enzyme HindIII and NcoI, recognizing A^AGCTT and C^CATGG sites respectively, to digest the human and mouse DNA prior to the step of ligation. DNA (A) and DNA (B) may then be ligated. Among 698,492 human-mouse hybrid DNA molecules harboring junction regions, we found that 88% of human-mouse hybrid DNA molecules carrying the enzyme recognition site of A^AGCTT and C^CATGG, further suggesting the ligation between human and mouse DNA fragments had occurred. The said junction region is defined as a region or site by which a first DNA fragment and a second DNA fragment were physically joined together. Because the junction includes sequences common to both DNA (A) and DNA (B), the portion of one strand corresponding to the junction cannot be determined to be part of either DNA (A) or DNA (B) by sequence alone. Analyzing methylation pattern or density of the portion of one strand corresponding to the junction may be used to determine whether the portion is from DNA (A) or DNA (B). As an example, DNA (A) may be viral DNA and DNA (B) may be human DNA. The determination of the exact junction may inform whether and how such integrated DNA disrupt protein structures.

Figure 114:
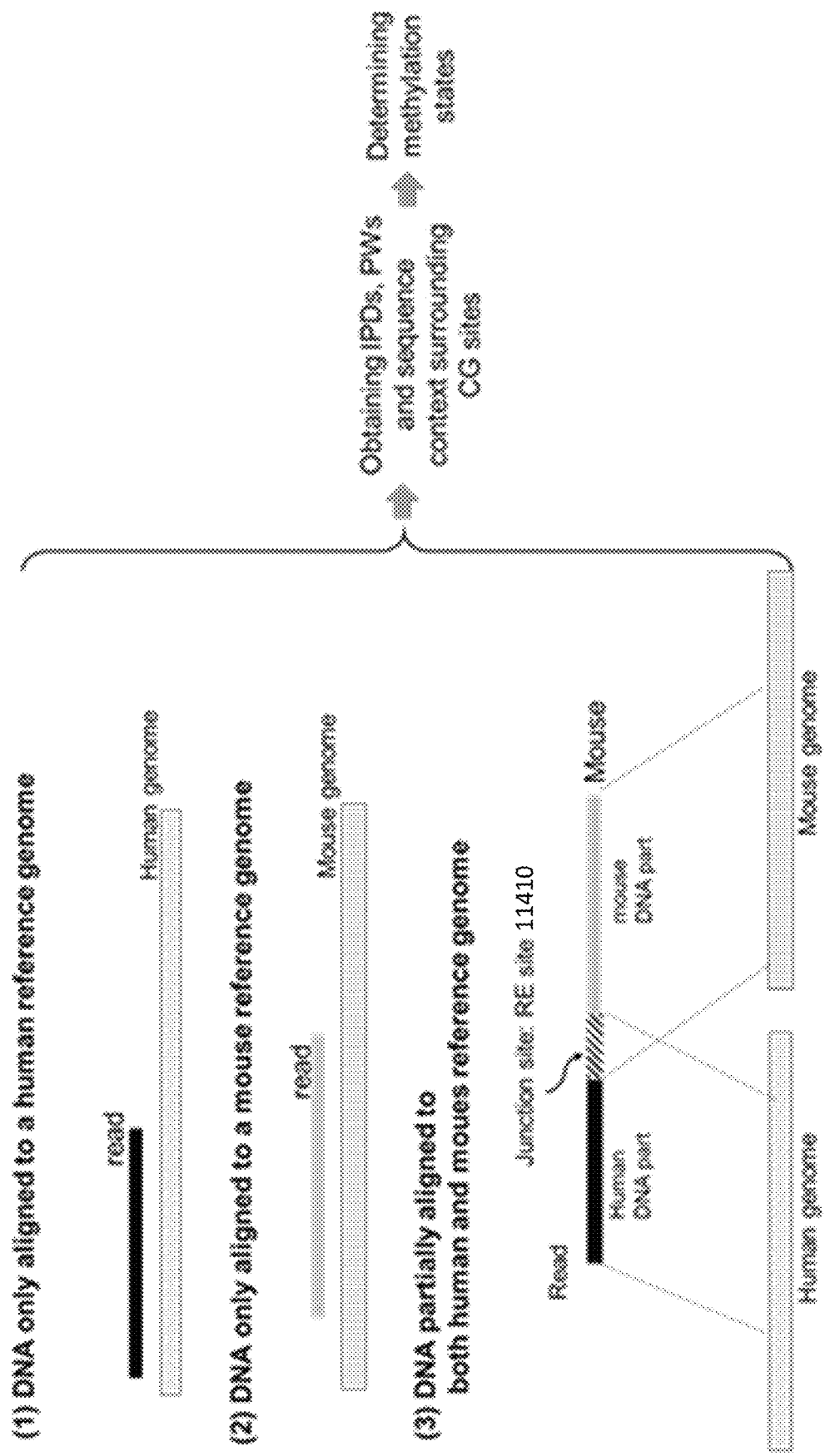

FIG. 114 illustrates methylation analysis for the DNA mixture. The bar 11410 with diagonal stripes indicates a junction region observed in the alignment analysis that would be introduced by a restriction enzyme treatment prior to the ligation. "RE site" denotes restriction enzyme (RE) recognition site.

As shown in FIG. 114, in one embodiment, the aligned consensus sequences were grouped into three categories as follows:

(1) A sequenced DNA was only aligned to a human reference genome but not aligned to a mouse reference genome, in reference to one or more alignment criteria. In one embodiment, one alignment criterion could be defined as, but not limited to, 100%, 95%, 90%, 80%, 70%, 60%, 50% 40%, 30%, or 20% of contiguous nucleotides of a sequenced DNA could be aligned to a human reference. In one embodiment, one alignment criterion would be that the remaining part of the sequenced fragment that did not align to the human reference could not be aligned to a mouse reference genome. In one embodiment, one alignment criterion was that the sequenced DNA could be aligned to a single region in a reference human genome. In one embodiment, the alignment could be perfect. Yet in other embodiment, the alignment could accommodate nucleotide discrepancies, including insertions, mismatches, and deletions, provided that such discrepancies were less than certain thresholds, such as but not limited to 1%, 2%, 3%, 4%, 5%, 10%, 20%, or 30% of the length of the aligned sequences. In another embodiment, the aligned could be to more than one location in a reference genome. Yet in other embodiments, the alignment to one or more sites in a reference genome could be stated in a probabilistic manner (e.g. indicating the chance of an erroneous alignment), and the probabilities measurement could be used in subsequent processing.

(2) A sequenced DNA was only aligned to a mouse reference genome but not aligned to a human reference genome, in reference to one or more alignment criteria. In one embodiment, one alignment criterion could be defined as, but not limited to, 100%, 95%, 90%, 80%, 70%, 60%, 50% 40%, 30%, or 20% of contiguous nucleotides of a sequenced DNA could be aligned to a mouse reference. In one embodiment, one alignment criterion would be that the remaining part could not be aligned to a human reference genome. In one embodiment, one alignment criterion was that the sequenced DNA could be aligned to a single region in a reference mouse genome. In one embodiment, the alignment could be perfect. Yet in other embodiments, the alignment could accommodate nucleotide discrepancies, including insertions, mismatches, and deletions, provided that such discrepancies were less than certain thresholds, such as but not limited to 1%, 2%, 3%, 4%, 5%, 10%, 20%, or 30% of the length of the aligned sequences. In another embodiment, the aligned could be to more than one location in a reference genome. Yet in other embodiments, the alignment to one or more sites in a reference genome could be stated in a probabilistic manner (e.g. indicating the chance of an erroneous alignment), and the probabilities measurement could be used in subsequent processing.

(3) One part of a sequenced DNA was uniquely aligned to a human reference genome, whereas another part was uniquely aligned to a mouse reference genome. In one embodiment, if a restriction enzyme was used prior to the ligation, a junction region would be observed in the alignment analysis, corresponding to the restriction enzyme cutting site. In some embodiments, the junctional regions between human and mouse DNA parts could only be approximately determined within a certain region because of sequencing and alignment errors. In some embodiments, the restriction enzyme recognition sites would not be observable in the junction regions of human-mouse hybrid DNA fragments if the ligation involved molecules without the cutting of restriction enzymes (e.g. if there was blunt end ligation).

The inter-pulse durations (IPDs), pulse widths (PWs), and sequence context surrounding CpG sites were obtained from those subreads corresponding to the consensus sequences. Thereby, the methylation for each DNA molecule, including human-only, mouse-only and human-mouse hybrid DNA, could be determined according to embodiments present in this disclosure.

B. Methylation Results

This section describes the methylation results for hybrid DNA fragments. Methylation densities can be used to identify the origins of different parts of hybrid DNA fragments.

Figure 115:
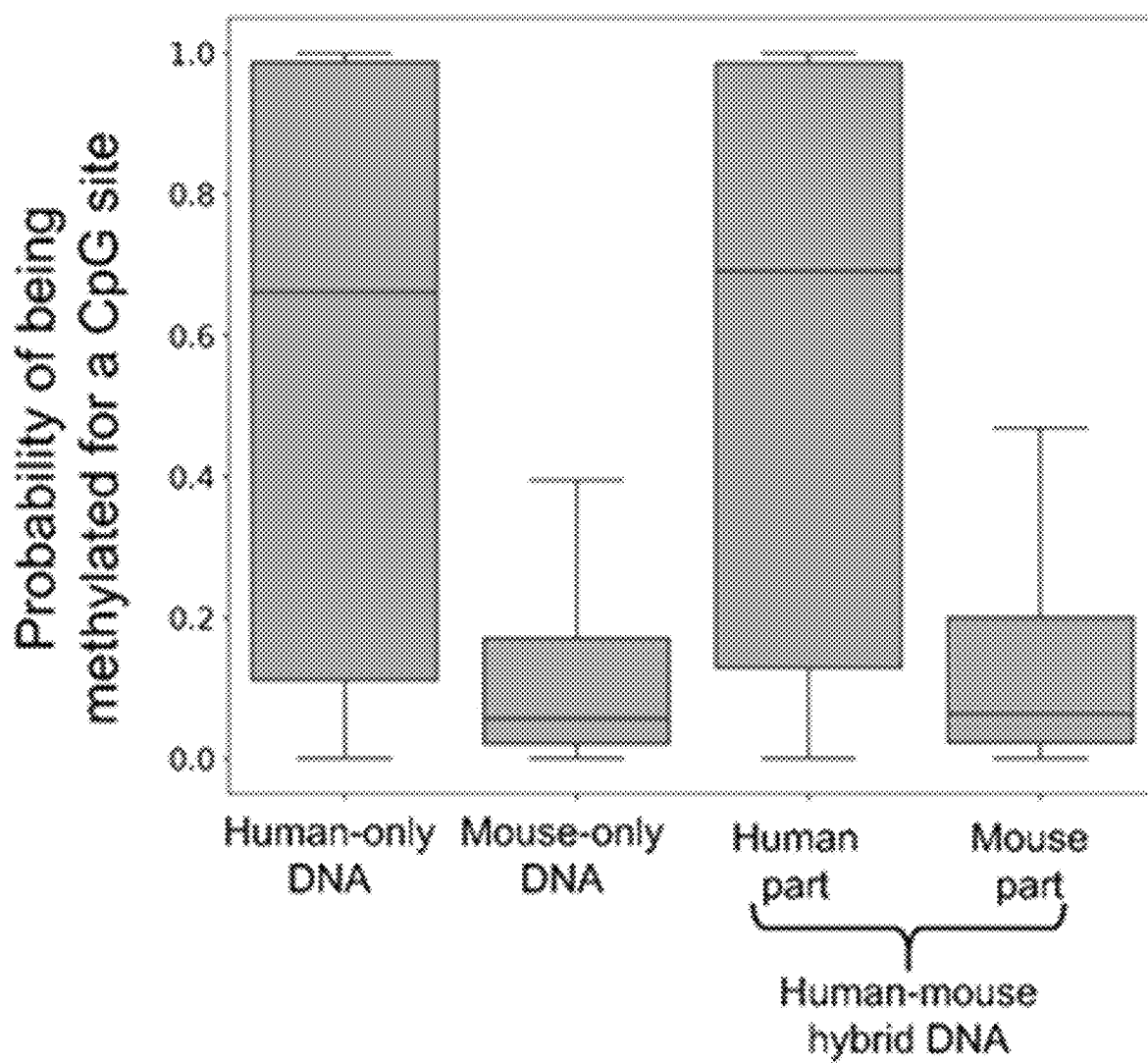

FIG. 115 shows a boxplot of the probabilities of being methylated for CpG sites in the sample MIX01. The x-axis shows the three different molecules present in sample MIX01: human-only DNA, mouse-only DNA, and human-mouse hybrid DNA (includes both a human part and a mouse part). The y-axis shows the probability of a CpG site of a particular single DNA molecule being methylated. This assay was performed in a way that the human DNA was more methylated while the mouse DNA was more unmethylated.

As shown in FIG. 115, the probability of being methylated for a CpG site in the human-only DNA (median: 0.66; range: 0-1) was significantly higher than that for mouse-only DNA (median: 0.06; range: 0-1) (P-value <0.0001). These results were in line with the assay design for which the human DNA was more methylated because of the treatment of the CpG Methyltransferase M.SssI, whereas the mouse DNA was more unmethylated because the methylation could not be preserved during whole genome amplification. Moreover, CpG sites within the human DNA part in a human-mouse hybrid DNA molecule showed a higher probability of being methylated (median: 0.69; range: 0-1) in comparison with those within the mouse DNA part (median: 0.06; range: 0-1) (P-value <0.0001). These data indicate that the disclosed method could accurately determine the methylation status of DNA molecules as well as segments within a DNA molecule.

The probability of methylation refers to the estimated probability of a particular CpG site within a single molecule based on the statistical model used. A probability of 1 indicates that, based on the statistical model, 100% of the CpG sites using the measured parameters (including IPD, PW, and sequence context) would be methylated. A probability of 0 indicates that, based on the statistical model, 0% of the CpG sites using the measured parameters (including IPD, PW, and sequence context) would be methylated. In other words, all CpG sites using the measured parameters would be unmethylated. FIG. 115 shows a distribution of methylation probabilities, with a wider distribution for the human-only DNA and human part than the mouse counterparts. Bisulfite sequencing is used to measure methylation of similar samples to confirm that methylation was not complete, and results are shown below. FIG. 115 shows a significant difference between methylation in human versus mouse DNA.

According to the embodiment shown in FIG. 111, we prepared an artificial DNA mixture (named sample MIX02) comprising human-mouse hybrid DNA molecules, human-only DNA and mouse-only DNA for which the human part is unmethylated and the moues part was methylated. For the sample MIX02, we obtained 140 million subreads which could be aligned either to a human or mouse reference genome, or partially to a human genome and partially to a mouse genome. These subreads were generated from approximately 5 million Pacific Biosciencees Single Molecule, Real-Time (SMRT) sequencing wells. Each molecule in a single-molecule real-time sequencing well was sequenced on average 27 times (range: 1-1028 times).

We also constructed consensus sequences by combining the nucleotide information from all relevant subreads in a well. In total, we obtained 3,265,487 consensus sequences for the sample MIX02. The consensus sequences were aligned to the reference genomes comprising both the human and mouse references using BWA (Li H et al., Bioinformatics. 2010; 26(5):589-595). We obtained 3.0 million aligned consensus sequences. Among them, 30.5% were classified as human-only DNA type; 32.2% were classified as mouse-only DNA type, and 33.8% were classified as human-mouse hybrid DNA. The data set was generated from DNA prepared by the Sequel II Sequencing Kit 1.0.

Figure 116:
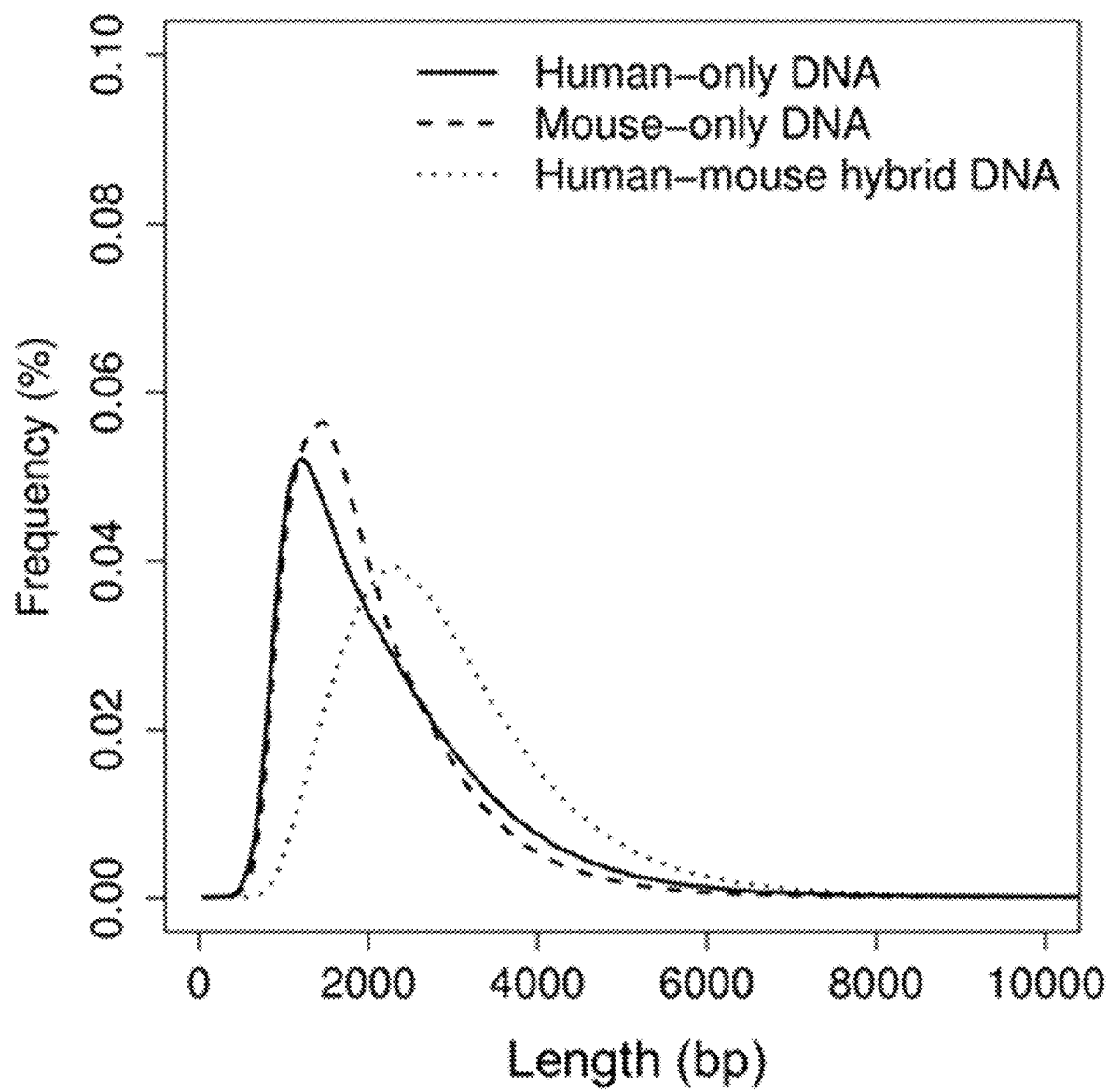

FIG. 116 shows length distribution of DNA molecules in the DNA mixture after cross-ligation of sample MIX02. The x-axis shows the length of a DNA molecule. The y-axis shows the frequency associated with the length of the DNA molecule. As shown in FIG. 116, the human-mouse hybrid DNA molecules had a longer length distribution, consistent with the fact that they were produced through the ligation of more than one molecule.

Figure 117:
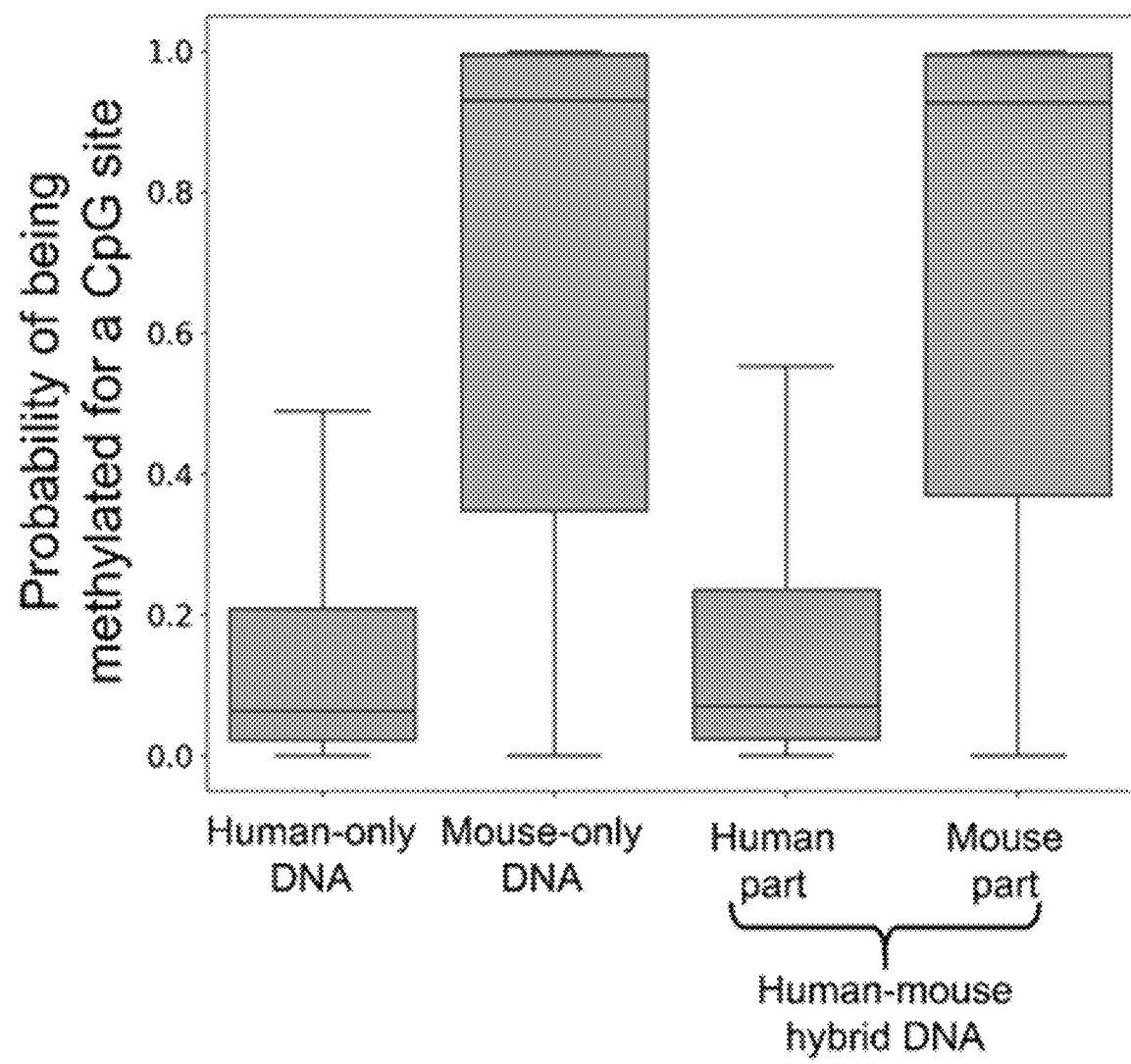

FIG. 117 shows a boxplot of the probabilities of being methylated for CpG sites in the sample MIX02. The methylation status was determined according to methods described herein. The x-axis shows the three different molecules present in sample MIX01: human-only DNA, mouse-only DNA, and human-mouse hybrid DNA (includes both a human part and a mouse part). The y-axis shows the probability of a CpG site being methylated. This assay was performed in a way that the human DNA was unmethylated while the mouse DNA was methylated.

As shown in FIG. 117, the probability of being methylated for CpG sites in the human-only DNA (median: 0.06; range: 0-1) was significantly lower than that for mouse-only DNA (median: 0.93; range: 0-1) (P-value <0.0001). These results were in line with the assay design for which the human DNA was more unmethylated because the methylation could not be preserved during whole genome amplification, whereas the mouse DNA was more methylated because of the treatment of the CpG Methyltransferase M.SssI. Moreover, CpG sites within the human DNA part in a human-mouse hybrid DNA molecule showed lower probabilities of being methylated (median: 0.07; range: 0-1) in comparison with those within the mouse DNA part (median: 0.93; range: 0-1) (P-value <0.0001). These data indicate that the disclosed method could accurately determine the methylation status of DNA molecules as well as segments within a DNA molecule.

Bisulfite sequencing was used to measure methylation of human-mouse hybrid fragments whose methylation patterns were determined by single molecule, real-time sequencing according to embodiments in this disclosure. The sample MIX01 (human DNA was methylated and mouse DNA was unmethylated) and MIX02 (human DNA was unmethylated and mouse DNA was methylated) were sheared resulting in a mixture with a median DNA fragment size of 196 bp (interquartile range: 161-268) via sonication. Paired-end bisulfite sequencing (BS-Seq) in MiSeq platform (Illumina) with read length 300 bp×2 was then performed. We obtained 3.7 million and 2.9 million sequenced fragments for MIX01 and MIX02, respectively, which were aligned to human or mouse reference genome, or partially to a human genome and partially to a mouse genome. For MIX01, 41.6% of aligned fragments were classified as human-only DNA, 56.6% as mouse-only DNA, and 1.8% as human-mouse hybrid DNA. For MIX02, 61.8% of aligned fragments were classified as human-only DNA, 36.3% as mouse-only DNA, and 1.9% as human-mouse hybrid DNA. The percentage of sequenced fragments determined to be human-mouse hybrid DNA in BS-Seq (<2%) was much lower than that observed in the Pacific Biosciences sequencing results (>30%). Notably, the long fragments (a median of ~2 kb) were sequenced by Pacific Biosciences sequencing, while the long fragments were shared into short fragments (a median of ~196 bp) that were suited for MiSeq. Such a shearing process would greatly dilute the human-mouse hybrid fragments.

FIG. 118 shows a table comparing methylation determined by bisulfite sequencing and Pacific Biosciences sequencing for MIX01. The left-most section of the table shows the type of DNA: 1) human-only; 2) mouse-only; and 3) human-mouse hybrid, divided into the human part and the mouse part. The middle section of the table shows details from bisulfite sequencing, including the number of CG sites and the methylation density. The right-most section of the table shows details from Pacific Biosciences sequencing, including the number of CG sites and the methylation density.

As shown in FIG. 118, the human-only DNA consistently displayed a higher methylation density than mouse-only DNA for MIX01 in both bisulfite sequencing and the Pacific Biosciences sequencing results. For the human-mouse hybrid fragments, the methylation levels of the human part and mouse part were determined to be 46.8% and 2.3%, respectively, in bisulfite sequencing results. These results confirmed the higher methylation densities for the human part compared to the mouse part as determined by Pacific Biosciences sequencing according to the disclosure. With Pacific Biosciences sequencing, a methylation density of 57.4% was observed in the human part and a lower methylation density of 12.1% was observed in the mouse part. These results suggest that methylation determined by Pacific Biosciences sequencing according to this disclosure could be feasible. In particular, Pacific Biosciences sequencing may be used to determine different methylation densities, including in DNA having a section with a higher methylation density than another section. We observed that the methylation density determined by Pacific Biosciences sequencing according to the disclosure was higher relative to bisulfite sequencing. Such an estimation may be adjusted using the difference between results determined by these two technologies in order to compare results across the technologies.

FIG. 119 shows a table comparing methylation determined by bisulfite sequencing and Pacific Biosciences sequencing for MIX02. The left-most section of the table shows the type of DNA: 1) human-only; 2) mouse-only; and 3) human-mouse hybrid, divided into the human part and the mouse part. The middle section of the table shows details from bisulfite sequencing, including the number of CG sites and the methylation density. The right-most section of the table shows details from Pacific Biosciences sequencing, including the number of CG sites and the methylation density.

As shown in FIG. 119, the human-only DNA consistently displayed a lower methylation density than mouse-only DNA for MIX02 in both bisulfite sequencing and Pacific Biosciences sequencing results. For the human-mouse hybrid fragments, the methylation levels of the human part and mouse part were determined to be 1.8% and 67.4%, respectively, in bisulfite sequencing results. These results further confirmed the lower methylation densities for the human part compared to the mouse part as determined by Pacific Biosciences sequencing according to the disclosure. With Pacific Biosciences sequencing, a methylation density of 13.1% was observed in the human part and a higher methylation density of 72.2% was observed in the mouse part as determined by Pacific Biosciences sequencing according to this disclosure. It also suggested that determining methylation by Pacific Biosciences sequencing according to this disclosure was feasible. In particular, Pacific Biosciences sequencing may be used to determine different methylation densities, including in DNA having a section with a lower methylation density than another section. We also observed that the methylation density determined by Pacific Biosciences sequencing according to the disclosure was higher relative to bisulfite sequencing. Such an estimation may be adjusted using the difference between results determined by these two technologies in order to compare results across the technologies.

Figure 120A:
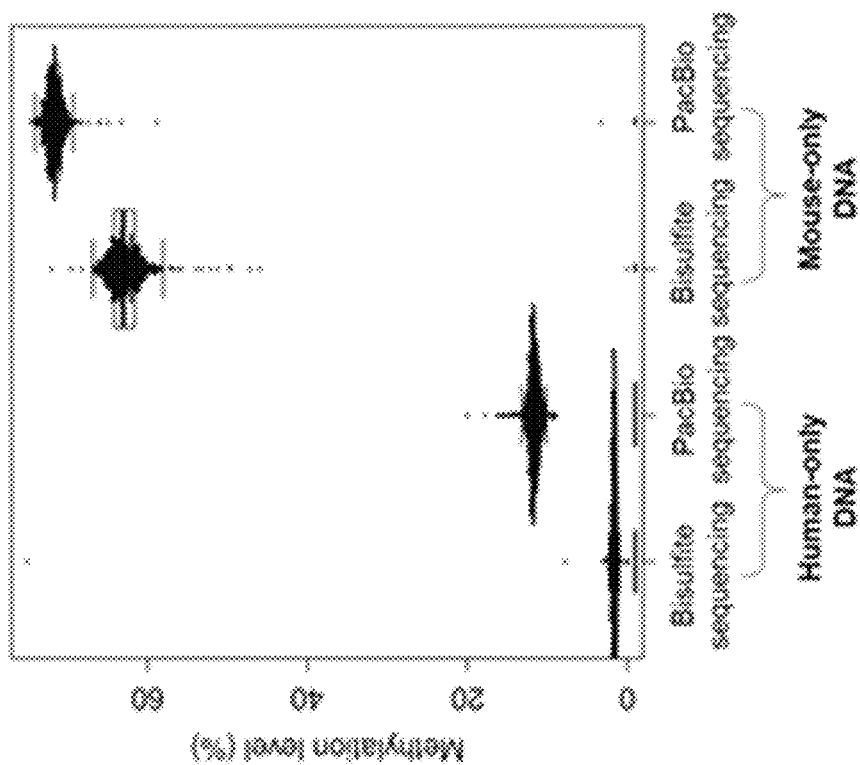
Figure 120B:
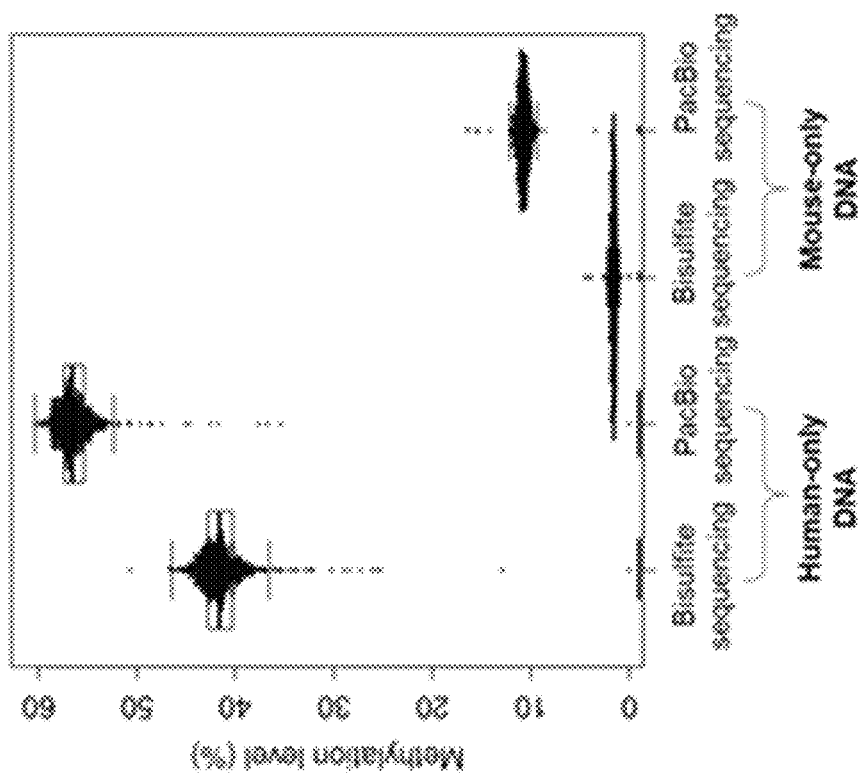

FIG. 120A shows the methylation levels in 5-Mb bins for human-only and mouse-only DNA for MIX01. FIG. 120B shows the methylation levels in 5-Mb bins for human-only and mouse-only DNA for MIX02. In both figures, the methylation level in percent is shown on the y-axis. Bisulfite sequencing and Pacific Biosciences sequencing for each of human-only DNA and mouse-only DNA are shown on the x-axis.

The results in FIG. 120A and FIG. 120B determined by Pacific Biosciences sequencing according to the disclosure were found to be systemically higher across bins in both sample MIX01 and MIX02.

Figure 121A:
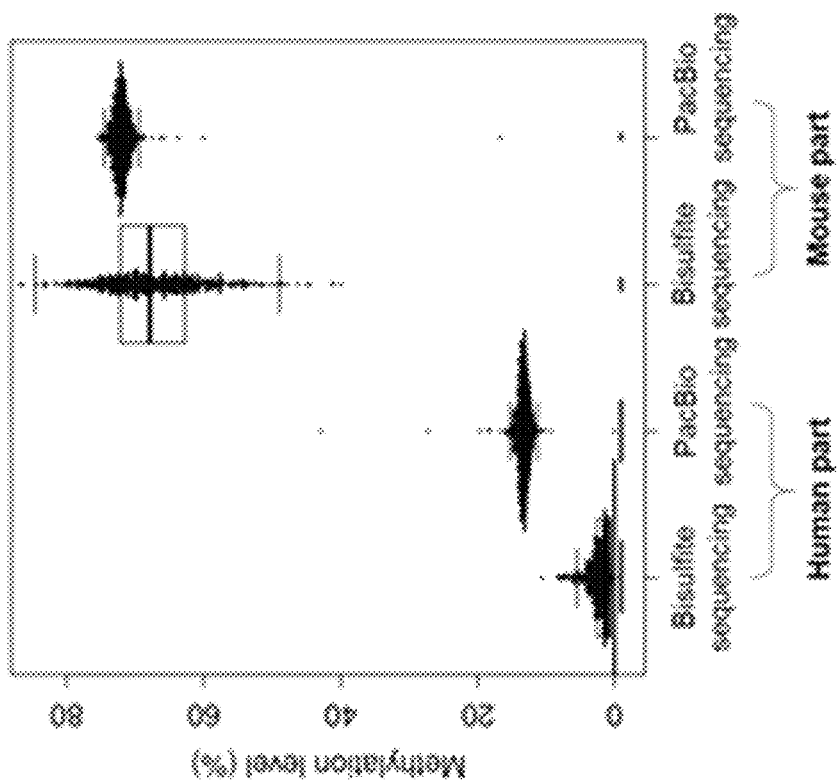
Figure 121B:
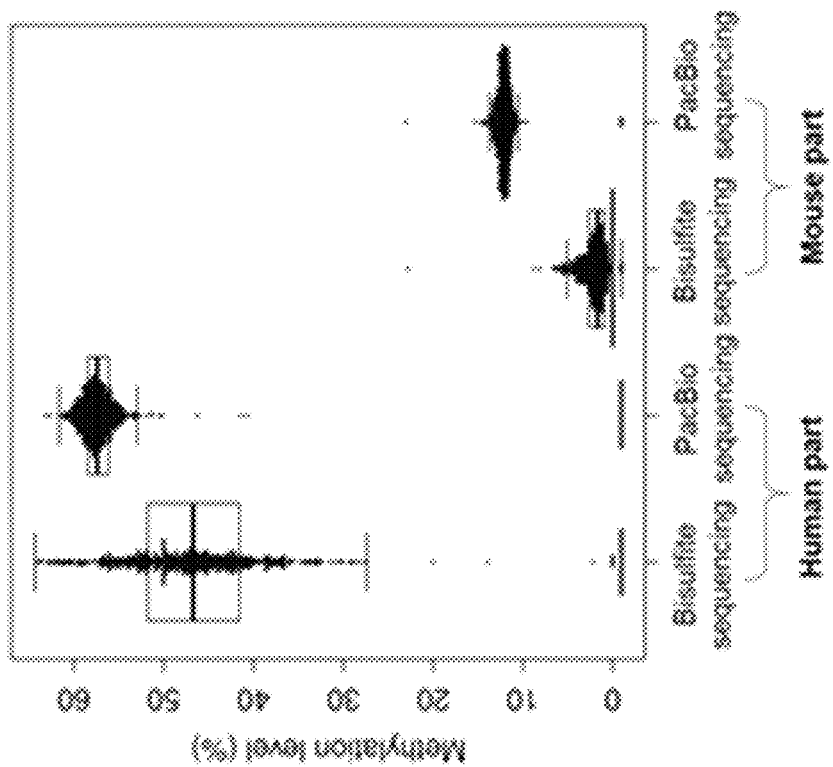

FIG. 121A shows the methylation levels in 5-Mb bins for the human part and the mouse part of human-mouse hybrid DNA fragments for MIX01. FIG. 121B shows the methylation levels in 5-Mb bins for the human part and the mouse part of human-mouse hybrid DNA fragments for MIX02. In both figures, the methylation level in percent is shown on the y-axis. Bisulfite sequencing and Pacific Biosciences sequencing for each of human part DNA and mouse part DNA are shown on the x-axis.

FIG. 121A and FIG. 121B both shown an increase in methylation level when Pacific Biosciences sequencing is used compared to bisulfite sequencing. This increase is similar to the increase in methylation levels by Pacific Biosciences sequencing seen with human-only DNA and mouse-only DNA in FIG. 120A and FIG. 120B. The increased variability in methylation levels across 5-Mb bins present in bisulfite sequencing results for hybrid fragments was likely because of the lower number of CpG sites used for analysis.

Figure 122A:
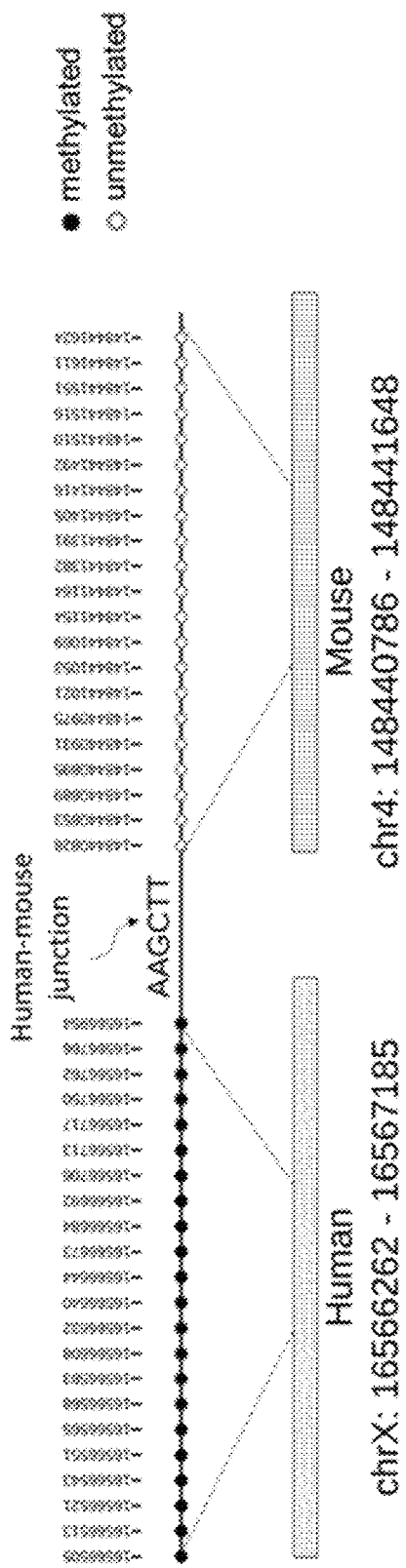
Figure 122B:
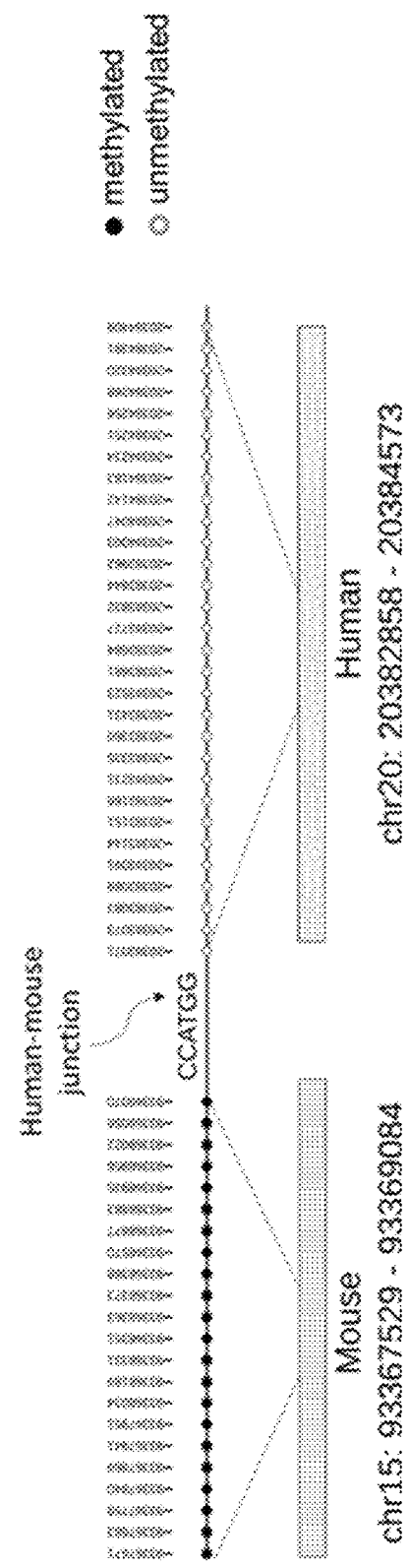

FIGS. 122A and 122B are representative graphs showing methylation states in a single human-mouse hybrid molecule. FIG. 122A shows a human-mouse hybrid fragment in the sample MIX01. FIG. 122B shows a human-mouse hybrid fragment in the sample MIX02. A filled circle indicates a methylated site, and an unfilled circle indicates an unmethylated site. Methylation states in these fragments were determined according to embodiments described herein.

As shown in FIG. 122A, the human part of a hybrid molecule from the sample MIX01 was determined to be more methylated. In contrast, the mouse DNA part was determined to be more hypomethylated. By contrast, FIG. 122B shows that the human part of a hybrid molecule from the sample MIX02 was determined to be more hypomethylated, whereas the mouse DNA part was determined to be more methylated.

These results demonstrated that the embodiments present in this disclosure allowed one to determine the methylation changes in a single DNA molecule with different methylation patterns in different parts of the molecule. In one embodiment, the methylation status of a gene or other genomic regions in which different parts of the gene or genomic regions would exhibit different methylation status (e.g. the promoter versus gene body) can be measured. In another embodiment, the methods presented herein can detect the human-mouse hybrid fragments, providing a generic approach to detect DNA molecules containing non-contiguous fragments (i.e. chimeric molecules) with respect to a reference genome and to analyze their methylation states. For example, we could use this approach to analyze, but not limited to, gene fusions, genomic rearrangements, translations, inversions, duplications, structure variations, viral DNA integrations, meiotic recombinations, etc.

In some embodiments, these hybrid fragments could be enriched prior to sequencing using probe-based hybridization methods or CRISPR-Cas systems or their variant approaches for target DNA enrichment. Recently, it was reported that a CRISPR-associated transposase from the cyanobacteria, *Scytonema hofmanni*, was able to insert DNA segments into a region nearby the targeted site of interest (Strecker et al. Science. 2019; 365:48-53). CRISPR-associated transposase could function like Tn7-mediated transposition. In one embodiment, we could adapt this CRISPR-associated transposase to insert comment sequences labeled, for example, with biotin to one or more genomic regions of interest, guided by gRNAs. We could use magnetic beads coated with, for example, streptavidin to capture the comment sequences, thereby simultaneously pulling down targeted DNA sequences for sequencing and methylation analysis according to the embodiments in this disclosure.

In some embodiments, fragments may be enriched by using restriction enzymes, which may include any restriction enzyme disclosed herein.

C. Example Chimeric Molecule Detection Method

FIG. 123 shows a method 1230 of detecting chimeric molecules in a biological sample. Chimeric molecules may include sequences from two different genes, chromosomes, organelles (e.g. mitochondria, nucleus, chloroplasts), organisms (mammals, bacteria, viruses, etc), and/or species. The method 1230 may be applied to each of a plurality of DNA molecules from the biological sample. In some embodiments, the plurality of DNA molecules may be cellular DNA. In other embodiments, the plurality of DNA molecules may be cell-free DNA molecules from the plasma of a pregnant woman.

At block 1232, single molecule sequencing of a DNA molecule may be performed to obtain a sequence read that provides a methylation status at each of N sites. N may be 5 or more, including 5 to 10, 10 to 15, 15 to 20, or more than 20. The methylation statuses of the sequence read may form a methylation pattern. The DNA molecule may be one DNA molecule of the plurality of DNA molecules, and method 1230 may be performed on the plurality of DNA molecules. The methylation pattern may take various forms. For example, the pattern could be N (e.g., 2, 3, 4, etc.) methylated sites followed by N unmethylated sites, or vice versa. Such a change in methylation can indicate a junction. The number of contiguous sites that are methylated can be different from the number of contiguous sites that are unmethylated.

At block 1234, the methylation pattern may be slid over one or more reference patterns that correspond to chimeric molecules that have two portions from two parts of a reference human genome. A reference pattern can act as a filter to identify a matching pattern that is indicative of a junction. The number of sites that match the reference pattern can be tracked so that a match position corresponding to a maximum number of matching sites (i.e., number where methylation status matches the reference pattern). The two parts of the reference human genome may be discontinuous parts of the reference human genome. The two parts of the reference human genome may be separated by over 1 kb, 5 kb, 10 kb, 100 kb, 1 Mb, 5 Mb, or 10 Mb. The two parts may be from two different chromosomal arms or chromosomes. The one or more reference patterns may include a change between methylated statuses and unmethylated statuses.

At block 1236, a match position may be identified between the methylation pattern and a first reference pattern of the one or more reference patterns. The match position may identify a junction between the two parts of the reference human genome in the sequence read. The match position can correspond to a maximum in an overlap function between a reference pattern and the methylation pattern. The overlap function can use multiple reference patterns, with the output possibly being a maximum over an aggregate function (i.e., each reference pattern contributing to an output value) or a single maximum that is identified across the reference patterns.

At block 1238, the junction may be outputted as a location of a gene fusion in a chimeric molecule. The location of the gene fusion may be compared to reference locations of gene fusions for various disorders or diseases, including cancer. The organism from which the biological sample is obtained may be treated for the disorder or disease.

The match position may be output to an alignment function. The location of the gene fusion may be refined. Refining the location of the gene fusion may include aligning a first portion of the sequence read to a first part of the reference human genome. The first portion may be before the junction. Refining the location of the gene fusion may include aligning a second portion of the sequence read to a second part of the reference human genome. The second portion may be after the junction. The first part of the reference human genome may be at least 1 kb apart from the second part of the human reference genome. For example, the first part of the reference human genome and the second part of the human reference genome may be 1.0 to 1.5 kb, 1.5 to 2.0 kb, 2.0 to 2.5 kb, 2.5 to 3.0 kb, 3 to 5 kb, or more than 5 kb apart.

The junctions of multiple chimeric molecules may be compared to each other to confirm the location of a gene fusion.

VIII. Conclusion

We have developed an efficient approach to predict the base modification (e.g. methylation) levels of nucleic acids at single-base resolution. This new approach implements a new scheme for concurrently capturing polymerase kinetics surrounding the base being interrogated, sequence context and strand information. Such a new transformation of kinetics enabled the subtle interruption occurring in kinetics pulses could be identified and modeled. Compared with previous methods used IPD only, the new approach present in this patent application has much improved the resolution and accuracy in methylation analysis. This new scheme could be easily extended for other purposes, for example, detecting 5hmC (5-hydroxymethylcytosine), 5fC (5-formylcytyosine), 5caC (5-carboxylcytosine), 4mC (4-methylcytosine), 6 mA (N6-methyladenine), 8oxoG (7,8-dihydro-8-oxoguanine), 8oxoA (7,8-dihydro-8-oxoadenine) and other forms of base modifications as well as DNA damages. In another embodiment, this new scheme (e.g. kinetics transformation analogous to 2-D digital matrix present in this application) could be used for base modification analysis with the use of a nanopore sequencing system.

This implementation of detection of methylation could be used for nucleic acid samples from different sources, e.g., cellular nucleic acids, nucleic acids from environmental sampling (e.g. cell contaminants), nucleic acids from pathogens (e.g. bacteria, and fungi), and cfDNA in the plasma of pregnant women. It would open many new possibilities for genomic research and molecular diagnostics, such as non-invasive prenatal testing, cancer detection and transplantation monitoring. For cfDNA-based noninvasive prenatal diagnostics, this new invention has made it feasible the simultaneous use of copy number aberrations, sizes, mutations, fragment ends and base modification for each molecule in diagnostics without PCR and experimental conversion prior to sequencing, thus enhancing the sensitivity. Imbalances in methylation levels between haplotypes can be detected using methods described herein. Such imbalances may indicate the origin of a DNA molecule (e.g., extracted from or a disorder, such as cancer cell isolated from the blood of a cancer patient) or a disorder.

IX. Example Systems

Figure 124:
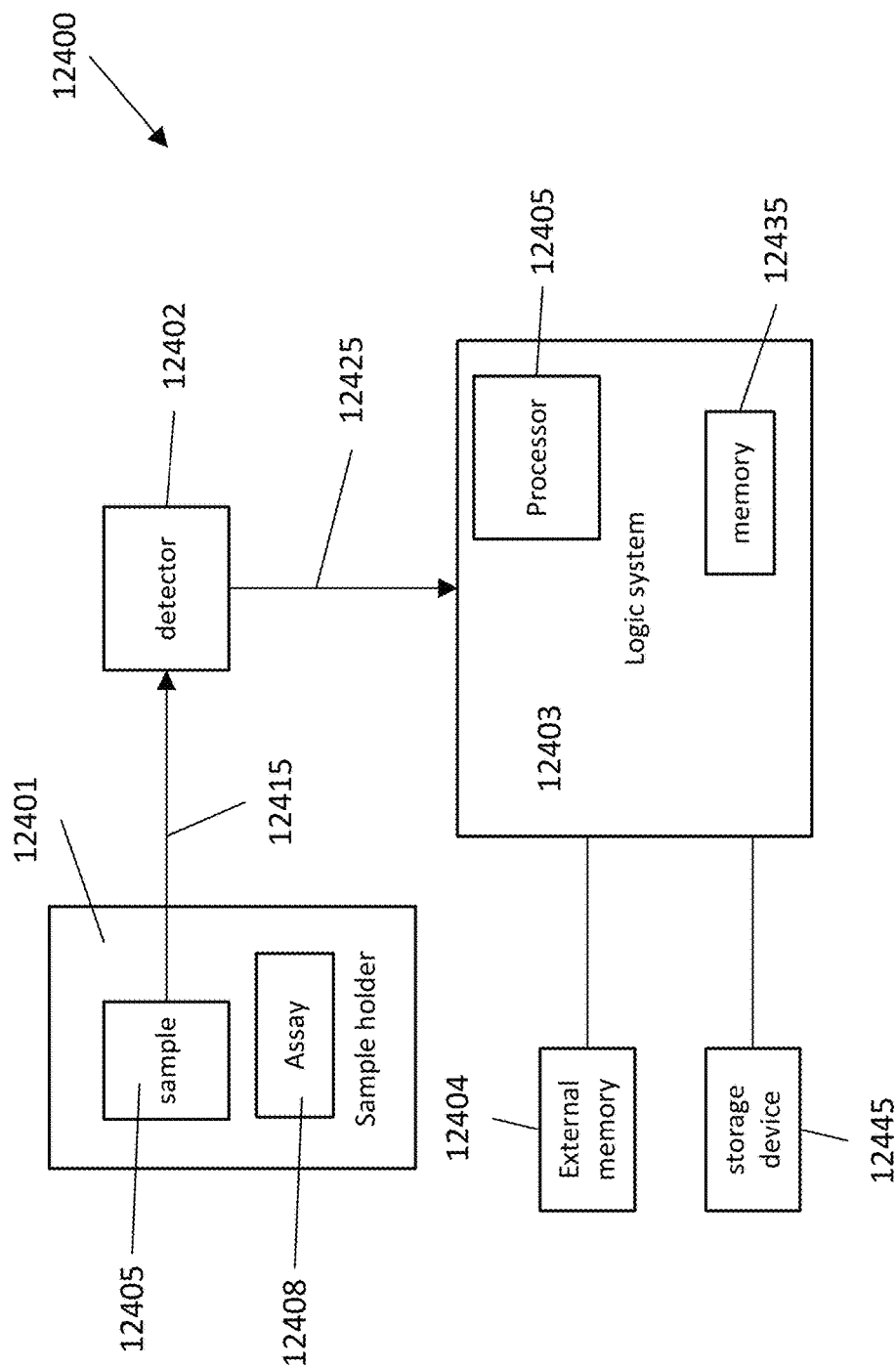

FIG. 124 illustrates a measurement system 12400 according to an embodiment of the present invention. The system as shown includes a sample 12405, such as DNA molecules within a sample holder 12410, where sample 12405 can be contacted with an assay 12408 to provide a signal of a physical characteristic 12415. An example of a sample holder can be a flow cell that includes probes and/or primers of an assay or a tube through which a droplet moves (with the droplet including the assay). Physical characteristic 12415 (e.g., a fluorescence intensity, a voltage, or a current), from the sample is detected by detector 12420. Detector 12402 can take a measurement at intervals (e.g., periodic intervals) to obtain data points that make up a data signal. In one embodiment, an analog-to-digital converter converts an analog signal from the detector into digital form at a plurality of times. Sample holder 12401 and detector 12402 can form an assay device, e.g., a sequencing device that performs sequencing according to embodiments described herein. A data signal 12425 is sent from detector 12402 to logic system 12403. Data signal 12425 may be stored in a local memory 12435, an external memory 12404, or a storage device 12445.

Logic system 12403 may be, or may include, a computer system, ASIC, microprocessor, etc. It may also include or be coupled with a display (e.g., monitor, LED display, etc.) and a user input device (e.g., mouse, keyboard, buttons, etc.). Logic system 12403 and the other components may be part of a stand-alone or network connected computer system, or they may be directly attached to or incorporated in a device (e.g., a sequencing device) that includes detector 12402 and/or sample holder 12401. Logic system 12403 may also include software that executes in a processor 12405. Logic system 12403 may include a computer readable medium storing instructions for controlling system 12400 to perform any of the methods described herein. For example, logic system 12403 can provide commands to a system that includes sample holder 12401 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Figure 125:
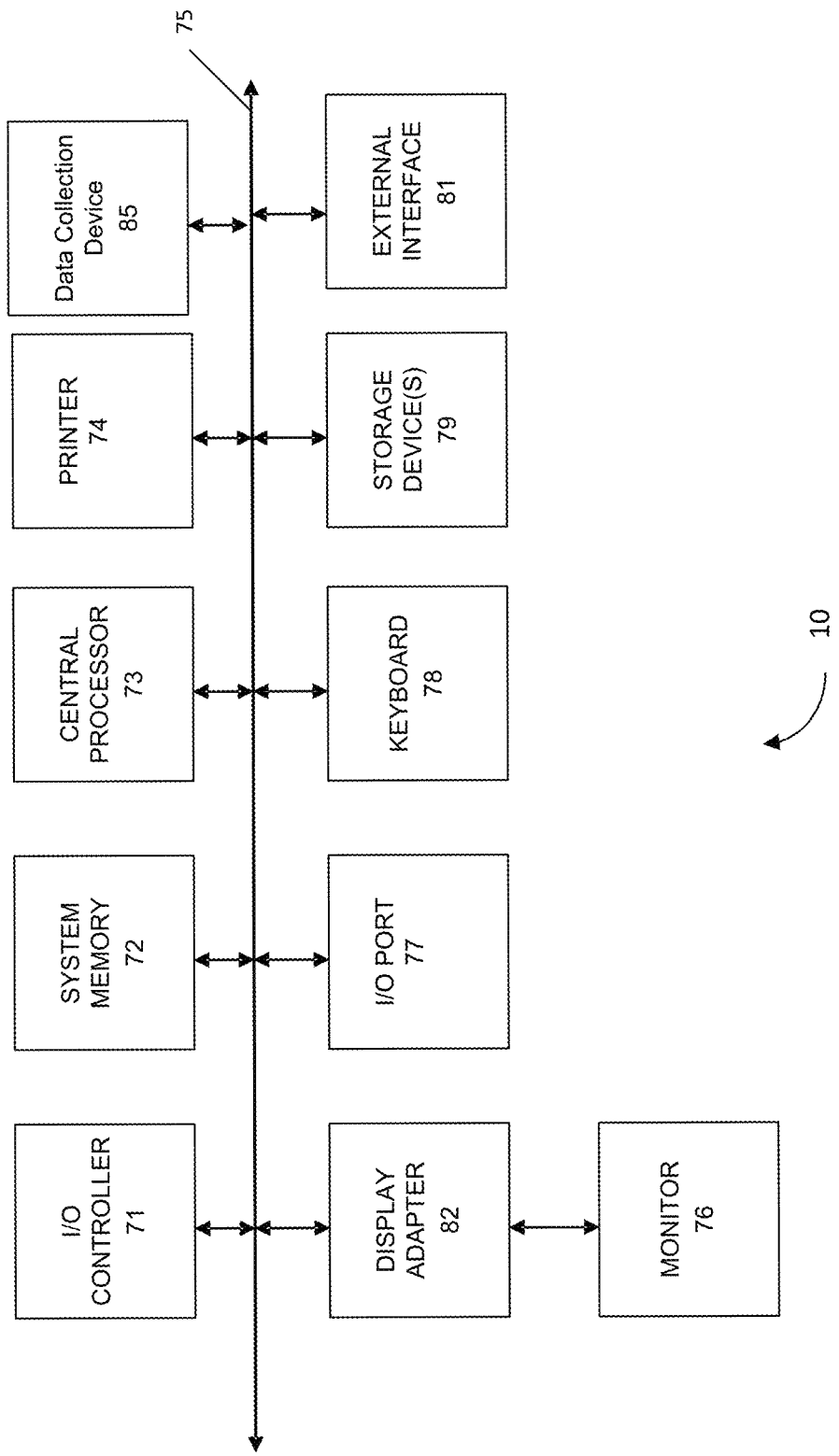

Any of the computer systems mentioned herein may utilize any suitable number of subsystems. Examples of such subsystems are shown in FIG. 125 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones, other mobile devices, and cloud-based systems.

The subsystems shown in FIG. 125 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an", or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

REFERENCES

Albert, T. J. et al. (2007) Direct selection of human genomic loci by microarray hybridization. *Nat. Methods*, 4, 903-905.

Beckmann et al. (2014) Detecting epigenetic motifs in low coverage and metagenomics settings. *BMC Bioinformatics*, 15(Suppl9): S16.

Beaulaurier, J. et al. (2019) Deciphering bacterial epigenomes using modern sequencing technologies. *Nature Reviews Genetics*, 20:157-172.

Blow, M. J. et al. (2016) The Epigenomic Landscape of Prokaryotes. *PLOS Genet.*, 12, e1005854.

Breiman, L. (2001) Random Forests. *Mach. Learn.*, 45, 5-32.

Chan, K. C. A. et al. (2013) Noninvasive detection of cancer-associated genome-wide hypomethylation and copy number aberrations by plasma DNA bisulfite sequencing. *Proc. Nat. Acad. Sci. U.S.A.*, 110, 18761-8.

Clark, T. A. et al. (2013) Enhanced 5-methylcytosine detection in single-molecule, real-time sequencing via Tet1 oxidation. *BMC Biol.*, 11, 4.

Clark, T. A. et al. (2012) Characterization of DNA methyltransferase specificities using single-molecule, real-time DNA sequencing. *Nucleic Acids Res.*, 40:e29.

Eid, J. et al. (2009) Real-Time DNA Sequencing from Single Polymerase Molecules. *Science* 323, 133-138.

Feinberg, A. P. and Irizarry, R. A. (2010) Stochastic epigenetic variation as a driving force of development, evolutionary adaptation, and disease. *Proc. Nat. Acad. Sci.*, 107, 1757-1764.

Feng, Z. et al. (2013) Detecting DNA modifications from SMRT sequencing data by modeling sequence context dependence of polymerase kinetic. *PLoS Comput Biol.*, 9:e1002935.

Flusberg, B. A. et al. (2010) Direct detection of DNA methylation during single-molecule, real-time sequencing. *Nat. Methods*, 7, 461-465.

Frommer, M. et al. (1992) A genomic sequencing protocol that yields a positive display of 5-methylcytosine residues in individual DNA strands. *Proc. Nat. Acad. Sci.,* 89, 1827-1831.

Gai, W. et al. (2018) Liver- and colon-specific DNA methylation markers in plasma for investigation of colorectal cancers with or without liver metastases. *Clin. Chem.,* 64, 1239-1249.

Gouil, Q. et al. (2019) Latest techniques to study DNA methylation. *Essays Biochem.* 63(6):639-648.

Grunau, C. (2001) Bisulfite genomic sequencing: systematic investigation of critical experimental parameters. *Nucleic Acids Res.,* 29, 65e-65.

Herman, J. G. et al. (1996) Methylation-specific PCR: a novel PCR assay for methylation status of CpG islands. *Proc. Nat. Acad. Sci. U.S.A.,* 93, 9821-9826.

Jiang, P. et al. (2014) Methy-Pipe: An Integrated Bioinformatics Pipeline for Whole Genome Bisulfite Sequencing Data Analysis. *PLoS One,* 9, e100360.

LeCun, Y. et al. (1989) Backpropagation Applied to Handwritten Zip Code Recognition. *Neural Comput.,* 1, 541-551.

Lee, E.-J. et al. (2011) Targeted bisulfite sequencing by solution hybrid selection and massively parallel sequencing. *Nucleic Acids Res.,* 39, e127-e127.

Lehmann-Werman, R. et al. (2016) Identification of tissue-specific cell death using methylation patterns of circulating DNA. *Proc. Nat. Acad. Sci.,* 113, E1826-E1834.

Lister, R. et al. (2009) Human DNA methylomes at base resolution show widespread epigenomic differences. *Nature,* 462, 315-322.

Liu, Q. et al. (2019) Detection of DNA base modifications by deep recurrent neural network on Oxford Nanopore sequencing data. *Nature Commun.,* 10, 2449.

Liu, Y. et al. (2019) Bisulfite-free direct detection of 5-methylcytosine and 5-hydroxymethylcytosine at base resolution. *Nat. Biotechnol.,* 37, 424-429.

Lun, F. M. F. et al. (2013) Noninvasive prenatal methylomic analysis by genomewide bisulfite sequencing of maternal plasma DNA. *Clin. Chem.,* 59, 1583-1594.

Nattestad, M. et al. (2018) Complex rearrangements and oncogene amplifications revealed by long-read DNA and RNA sequencing of a breast cancer cell line. *Genome Res.,* 28, 1126-1135.

Ng, A. Y. (2004) Feature selection, $L_1$ vs. $L_2$ regularization, and rotational invariance. In, *Twenty-first International Conference on Machine Learning—ICML '04.* ACM Press, New York, N.Y., USA, p. 78.

Ni, P. et al. (2019) DeepSignal: detecting DNA methylation state from Nanopore sequencing reads using deep-learning. *Bioinformatics,* 35, 4586-4595

Okou, D. T. et al. (2007) Microarray-based genomic selection for high-throughput resequencing. *Nat. Methods,* 4, 907-909.

Olova, N. et al. (2018) Comparison of whole-genome bisulfite sequencing library preparation strategies identifies sources of biases affecting DNA methylation data. *Genome Biol.,* 19, 33.

Robertson, K. D. (2005) DNA methylation and human disease. *Nat. Rev. Genet.,* 6, 597-610.

Smith, Z. D. and Meissner, A. (2013) DNA methylation: roles in mammalian development. *Nat. Rev. Genet.,* 14, 204-20.

Schadt, E. E. et al. (2013) Modeling kinetic rate variation in third generation DNA sequencing data to detect putative modifications to DNA bases. *Genome Res.,* 23(1):129-41.

Sun, K. et al. (2015) Plasma DNA tissue mapping by genome-wide methylation sequencing for noninvasive prenatal, cancer, and transplantation assessments. *Proc. Natl. Acad. Sci.,* 112, E5503-E5512.

Suzuki, Y. et al. (2016) AgIn: measuring the landscape of CpG methylation of individual repetitive elements. *Bioinformatics,* 32, 2911-2919.

Watson, C. M. et al. (2019) Cas9-based enrichment and single-molecule sequencing for precise characterization of genomic duplications. *Lab. Investig,* 100, 135-146.

Zhang, W. et al. (2015) Predicting genome-wide DNA methylation using methylation marks, genomic position, and DNA regulatory elements. *Genome Biol.,* 16, 14.

---

What is claimed is:

1. A method for detecting a modification of a nucleotide in a nucleic acid molecule, the method comprising:
   (a) receiving data acquired by measuring pulses in an optical signal corresponding to nucleotides sequenced in a sample nucleic acid molecule and obtaining, from the data, values for the following properties:
      for each nucleotide:
         an identity of the nucleotide,
         a position of the nucleotide within the sample nucleic acid molecule,
         a width of the pulse corresponding to the nucleotide, and
         an interpulse duration representing a time between the pulse corresponding to the nucleotide and a pulse corresponding to a neighboring nucleotide;
   (b) creating an input data structure, the input data structure comprising a window of the nucleotides sequenced in the sample nucleic acid molecule, wherein the input data structure includes, for each nucleotide within the window, the properties:
      the identity of the nucleotide,
      a position of the nucleotide with respect to a target position within the window,
      the width of the pulse corresponding to the nucleotide, and
      the interpulse duration;
   (c) inputting the input data structure into a model, the model trained by:
      receiving a first plurality of first data structures, each first data structure of the first plurality of data structures corresponding to a respective window of nucleotides sequenced in a respective nucleic acid molecule of a plurality of first nucleic acid molecules, wherein each of the first nucleic acid molecules is sequenced by measuring pulses in the optical signal corresponding to the nucleotides, wherein the modification has a known first state in a nucleotide at a target position in each window of each first nucleic acid molecule, each first data structure comprising values for the same properties as the input data structure,
      storing a plurality of first training samples, each including one of the first plurality of first data structures and a first label indicating the first state of the nucleotide at the target position, and
      optimizing, using the plurality of first training samples, parameters of the model based on outputs of the model matching or not matching corresponding labels of the first labels when the first plurality of first data structures is input to the model, wherein an output of the model specifies whether the nucleotide at the target position in the respective window has the modification,
   (d) determining, using the model, whether the modification is present in a nucleotide at the target position within the window in the input data structure.

2. The method of claim 1, wherein:
   the input data structure is one input data structure of a plurality of input data structures,
   the sample nucleic acid molecule is one sample nucleic acid molecule of a plurality of sample nucleic acid molecules, the plurality of sample nucleic acid molecules are obtained from a biological sample of a subject, and each input data structure corresponds to a respective window of nucleotides sequenced in a respective sample nucleic acid molecule of the plurality of sample nucleic acid molecules, and the method further comprising:

receiving the plurality of input data structures, inputting the plurality of input data structures into the model, and determining, using the model, whether a modification is present in a nucleotide at a target location in the respective window of each input data structure.

3. The method of claim 2, further comprising:

determining the modification is present at one or more nucleotides, and determining a classification of a disorder using the presence of the modification at one or more nucleotides.

4. The method of claim 3, wherein the disorder comprises cancer.

5. The method of claim 4, further comprising:

determining that the classification of the disorder is that the subject has the disorder, and treating the subject for the disorder by chemotherapy, radiation, or surgery.

6. The method of claim 3, wherein determining the classification of the disorder uses the number of modifications or the sites of the modifications.

7. The method of claim 2, wherein the modification is a methylation, the method further comprising:

determining the modification is present at one or more nucleotides, and determining a clinically-relevant DNA fraction, a fetal methylation profile, a maternal methylation profile, a presence of an imprinting gene region, or a tissue of origin using the presence of the modification at one or more nucleotides.

8. The method of claim 2, wherein each sample nucleic acid molecule of the plurality of sample nucleic acid molecules has a size greater than a cutoff size.

9. The method of claim 2, wherein:

the plurality of sample nucleic acid molecules align to a plurality of genomic regions, for each genomic region of the plurality of genomic regions:

a number of sample nucleic acid molecules is aligned to the genomic region, the number of sample nucleic acid molecules is greater than a cutoff number.

10. The method of claim 1, further comprising sequencing the sample nucleic acid molecule.

11. The method of claim 1, wherein the model includes a machine learning model, a principal component analysis, a convolutional neural network, or a logistic regression.

12. The method of claim 1, wherein:

the window of nucleotides corresponding to the input data structure comprises nucleotides on a first strand of the sample nucleic acid molecule and nucleotides on a second strand of the sample nucleic acid molecule, and the input data structure further comprises for each nucleotide within the window a value of a strand property, the strand property indicating the nucleotide being present on either the first strand or the second strand.

13. The method of claim 12, wherein the sample nucleic acid molecule is a circular DNA molecule formed by:

cutting a double-stranded DNA molecule using a Cas9 complex to form a cut double-stranded DNA molecule, and ligating a hairpin adaptor onto an end of the cut double-stranded DNA molecule.

14. The method of claim 1, wherein the nucleotides within the window are determined using a circular consensus sequence and without alignment of the sequenced nucleotides to a reference genome.

15. The method of claim 1, wherein each nucleotide within the window is enriched or filtered.

16. The method of claim 15, wherein each nucleotide within the window is enriched by:

cutting a double-stranded DNA molecule using a Cas9 complex to form a cut double-stranded DNA molecule, and ligating a hairpin adaptor onto an end of the cut double-stranded DNA molecule, or filtered by:

selecting double-stranded DNA molecules having a size with a size range.

17. The method of claim 1, wherein nucleotides within the window are determined without using a circular consensus sequence and without alignment of the sequenced nucleotides to a reference genome.

18. The method of claim 1, wherein the optical signal is a fluorescence signal from a dye-labeled nucleotide.

19. The method of claim 1, wherein each window associated with the first plurality of data structures comprises 4 consecutive nucleotides on a first strand of each first nucleic acid molecule.

* * * * *

UNITED STATES PATENT AND TRADEMARK OFFICE
CERTIFICATE OF CORRECTION

PATENT NO.         : 11,091,794 B2
APPLICATION NO.    : 16/995607
DATED              : August 17, 2021
INVENTOR(S)        : Yuk-Ming Dennis Lo et al.

It is certified that error appears in the above-identified patent and that said Letters Patent is hereby corrected as shown below:

In the Claims

In Column 115, Line 67 and Column 116, Line 36 of Claim 1, please delete "of the first plurality of data structures corresponding to" and insert --of the first plurality of first data structures corresponding to--

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*